US009669108B2

(12) United States Patent
Williams et al.

(10) Patent No.: US 9,669,108 B2
(45) Date of Patent: Jun. 6, 2017

(54) MEDITOPES AND MEDITOPE-BINDING ANTIBODIES AND USES THEREOF

(71) Applicant: City of Hope, Duarte, CA (US)

(72) Inventors: John C. Williams, Monrovia, CA (US); David A. Horne, Duarte, CA (US); Yuelong Ma, Duarte, CA (US); Heng Wei Chang, Foster City, CA (US); Joshua M. Donaldson, Lumberton, NJ (US); Cindy Zer, Duarte, CA (US); Krzysztof Bzymek, Pasadena, CA (US); Kendra N. Avery, Pasadena, CA (US); Jun Xie, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 14/453,586

(22) Filed: Aug. 6, 2014

(65) Prior Publication Data

US 2015/0030535 A1    Jan. 29, 2015

Related U.S. Application Data

(60) Division of application No. 13/443,804, filed on Apr. 10, 2012, now Pat. No. 8,962,804, which is a continuation-in-part of application No. 13/270,207, filed on Oct. 10, 2011, now Pat. No. 8,658,774.

(60) Provisional application No. 61/391,558, filed on Oct. 8, 2010, provisional application No. 61/597,708, filed on Feb. 10, 2012.

(51) Int. Cl.
C07K 16/18    (2006.01)
C07K 7/00     (2006.01)
A61K 47/48    (2006.01)
A61K 38/00    (2006.01)
A61K 39/00    (2006.01)
A61K 51/10    (2006.01)
C07K 16/28    (2006.01)
C07K 16/32    (2006.01)
B82Y 5/00     (2011.01)

(52) U.S. Cl.
CPC .. *A61K 47/48746* (2013.01); *A61K 47/48346* (2013.01); *A61K 47/48669* (2013.01); *A61K 51/1087* (2013.01); *B82Y 5/00* (2013.01); *C07K 16/18* (2013.01); *C07K 16/2863* (2013.01); *C07K 16/32* (2013.01); *C07K 2299/00* (2013.01); *C07K 2317/34* (2013.01); *C07K 2317/40* (2013.01); *C07K 2317/55* (2013.01); *C07K 2317/567* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| 7,754,853 B2 | 7/2010 | Hellendoorn et al. |
| 8,592,149 B2 | 11/2013 | Ramakrishnan |
| 8,658,774 B2 | 2/2014 | Williams et al. |
| 2004/0001842 A1* | 1/2004 | Michaeli ........... A61K 39/0005 424/185.1 |
| 2004/0067503 A1 | 4/2004 | Tan et al. |
| 2005/0042664 A1 | 2/2005 | Wu et al. |
| 2005/0069549 A1 | 3/2005 | Herman |
| 2005/0260711 A1 | 11/2005 | Datta et al. |
| 2008/0038260 A1 | 2/2008 | Ponath et al. |
| 2009/0005257 A1 | 1/2009 | Jespers et al. |
| 2009/0074780 A1 | 3/2009 | Urech et al. |
| 2009/0202568 A1 | 8/2009 | Eriksson et al. |
| 2010/0068135 A1 | 3/2010 | Rock |
| 2010/0076178 A1 | 3/2010 | Ghayur et al. |

FOREIGN PATENT DOCUMENTS

| WO | WO-96/40210 | 12/1996 | |
| WO | WO 0132207 A1 * | 5/2001 | ........... A61K 39/385 |
| WO | WO-02/072832 | 9/2002 | |
| WO | WO-2004/101790 | 11/2004 | |
| WO | WO-2005/056606 | 6/2005 | |
| WO | WO-2007/019541 | 2/2007 | |
| WO | WO-2009/062051 | 5/2009 | |
| WO | WO 2009099651 A1 * | 8/2009 | ............. A61K 31/44 |
| WO | WO-2010/114940 | 10/2010 | |

OTHER PUBLICATIONS

Riemer et al.,Journal of the National Cancer Institute, 2005, 97(22):1663-1670.*
Carter et al., Endocrine-Related Cancer, 2004, 11:659-687.*
Albanell et al., "Trastuzumab, a humanized anti-HER2 monoclonal antibody, for the treatment of breast cancer," Drugs Today (Barc) (1999) 35(12):931-946.
International Preliminary Report on Patentability for PCT/US2011/55656 issued Jun. 4, 2013, 8 pages.
Notice of the First Office Action (including translation) for CN 201280060888.7, mailed Jul. 17, 2015, 24 pages.
Smith et al., Sequence of the full-length immunoglobulin kappa-chain of mouse myeloma MPC 11, Biochem. J. (1978) 171:337-347.
Supplementary European Search Report for EP 11831753.6, mailed May 12, 2015, 9 pages.
Supplementary European Search Report for EP 12839868.2, mailed May 12, 2015, 10 pages.
Accardi et al., "Antibodies in single-chain format against tumour-associated antigens: present and future applications," Curr Med Chem (2010) 17(17):1730-1755.
Adams et al., "High affinity restricts the localization and tumor penetration of single-chain fv antibody molecules," Cancer Res (2001) 61(12):4750-4755.

(Continued)

*Primary Examiner* — Hong Sang
(74) *Attorney, Agent, or Firm* — Sheppard Mullin Richter & Hampton LLP

(57) ABSTRACT

Antibodies and meditopes that bind to the antibodies are provided, as well as complexes, compositions and combinations containing the meditopes and antibodies, and methods of producing, using, testing, and screening the same, including therapeutic and diagnostic methods and uses.

8 Claims, 76 Drawing Sheets

(56) References Cited

OTHER PUBLICATIONS

Adams et al., "PHENIX: Building new software for automated crystallographic structure determination," Acta Crystallogr D Biol Crystallogr (2002) 58:1948-1954.

Adams et al., "Potent and selective inhibitors of the proteasome: dipeptidyl boronic acids," Bioorg Med Chem Lett (1998) 8(4):333-338.

Adessi et al., "Converting a peptide into a drug: strategies to improve stability and bioavailability," Curr Med Chem (2002) 9(9):963-978.

Akamatsu et al., "Whole IgG surface display on mammalian cells: Application to isolation of neutralizing chicken monoclonal anti-IL-12 antibodies," J Immunol Methods (2007) 3271(1-2):40-52.

Alley et al., "Antibody-drug conjugates: targeted drug delivery for cancer," Curr Opin Chem Biol (2010) 14(4):529-537.

Auffinger et al., "Halogen bonds in biological molecules," Proc Natl Acad Sci USA (2004) 101(48):16789-16794.

Beck et al., "Trends in glycosylation, glycoanalysis and glycoengineering of therapeutic antibodies and Fc-fusion proteins," Curr Pharm Biotechnol (2008) 9(6):482-501.

Beck et al., "Strategies and challenges for the next generation of therapeutic antibodies," Nat Rev Immunol (2010) 10(5):345-352.

Bendig, "Humanization of rodent monoclonal antibodies by CDR grafting" Methods: A Companion to Methods in Enzymology (1995) 8:83-93.

Bilgicer et al., "A non-chromatographic method for the purification of a bivalently active monoclonal IgG antibody from biological fluids," J Am Chem Soc (2009) 131(26):9361-9367.

Bilgicer et al., "A synthetic trivalent hapten that aggregates anti-2,4-DNP IgG into bicyclic trimers," J Am Chem Soc (2007) 129(12):3722-3728.

Bokemeyer et al., "Fluorouracil, leucovorin, and oxaliplatin with and without cetuximab in the first-line treatment of metastatic colorectal cancer," J Clin Oncol (2009) 27(5):663-671.

Bowie et al., "Deciphering the message in protein sequences: tolerance to amino acid substitutions," Science (1990) 247(4948):1306-1310.

Bretscher et al., "Structural characterization and kinetics of nitric-oxide synthase inhibition by novel N5-(iminoalkyl)- and N5-(iminoalkenyl)-ornithines," J Biol Chem (2003) 278(47):46789-46797.

Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol (1990) 111(5 Pt 1):2129-2138.

Butlin et al., "Antibodies with infinite affinity: origins and applications," Acc Chem Res (2006) 39(10):780-787.

Cardarelli et al., "Binding to CD20 by anti-B1 antibody or F(ab')(2) is sufficient for induction of apoptosis in B-cell lines," Cancer Immunol Immunother (2002) 51(1):15-24.

Carson et al., "Monoclonal antibody-associated progressive multifocal leucoencephalopathy in patients treated with rituximab, natalizumab, and efalizumab: a Review from the Research on Adverse Drug Events and Reports (RADAR) Project," Lancet Oncol (2009) 10(8):816-824.

Chen et al., "MolProbity: all-atom structure validation for macromolecular crystallography," Acta Crystallogr D Biol Crystallogr (2010) 66(Pt 1):12-21.

Chih et al., "Identification of amino acid residues responsible for the release of free drug from an antibody-drug conjugate utilizing lysine-succinimidyl ester chemistry," J Pharm Sci (2011) 100(7):2518-2525.

Chmura et al., "Antibodies with infinite affinity," Proc Natl Acad Sci USA (2001) 98(15):8480-8484.

Cho et al., "Structure of the extracellular region of HER2 alone and in complex with the Herceptin Fab," Nature (2003) 421(6924):756-760.

Chung et al., "Cetuximab-induced anaphylaxis and IgE specific for galactose-alpha-1,3-galactose," N Eng J Med (2008) 358(11):1109-1117.

Collis et al., "Analysis of the antigen combining site: correlations between length and sequence composition of the hypervariable loops and the nature of the antigen," J Mol Biol (2003) 325(2):337-354.

Colman, "Effects of amino acid sequence changes on antibody-antigen interactions," Res Immunol (1994) 145:33-36.

Dechant et al., "Complement-dependent tumor cell lysis triggered by combinations of epidermal growth factor receptor antibodies," Cancer Res (2008) 68(13):4998-5003.

Demarest et al., "Antibody therapeutics, antibody engineering, and the merits of protein stability," Curr Opin Drug Discov Devel (2008) 11(5):675-687.

Denardo et al., "Dose intensified molecular targeted radiotherapy for cancer-lymphoma as a paradigm," Semin Nucl Med (2010) 40(2):136-144.

Derksen et al., "Antimicrobial leucocin analogues with a disulfide bridge replaced by a carbocycle or by noncovalent interactions of allyl glycine residues," J Am Chem Soc (2006) 128(44):14252-14253.

Donaldson et al., "Design and development of masked therapeutic antibodies to limit off-target effects: application to anti-EGFR antibodies," Cancer Biol Ther (2009) 8(22):2147-2152.

Donaldson et al., "Identification and grafting of a unique peptide-binding site in the Fab framework of monoclonal antibodies," Proc Natl Acad Sci USA (2013) 110(43):17456-17461 (Published online before print Oct. 7, 2013, doi: 10.1073/pnas.1307309110, supplemental information included, 38 pages).

Doppalapudi et al., "Chemical generation of bispecific antibodies," Proc Natl Acad Sci USA (2010) 107(52):22611-22616.

Doppalapudi et al., "Chemically programmed antibodies: endothelin receptor targeting CovX-Bodies," Bioorg Med Chem Lett (2007) 17(2):501-506.

Dornan et al., "Therapeutic potential of an anti-CD79b antibody-drug conjugate, anti-CD79b-vc-MMAE, for the treatment of non-Hodgkin lymphoma," Blood (2009) 114(13):2721-2729.

Du et al., "Structural basis for recognition of CD20 by therapeutic antibody Rituximab," J Biol Chem (2007) 282(20):15073-15080.

Emsley et al., "Coot: model-building tools for molecular graphics," Acta Crystallogr D Biol Crystallogr (2004) 60(Pt 12 Pr 1):2126-2132.

Erlanson et al., "Discovery of a potent and highly selective PDK1 inhibitor via fragment-based drug discovery," Bioorg Med Chem Lett (2011) 21(10):3078-3083.

Ferenczy et al., "Thermodynamics guided lead discovery and optimization," Drug Discov Today (2010) 15:919-932.

Gencoglan et al., "Two cases of acneiform eruption induced by inhibitor of epidermal growth factor receptor," Skin Pharmacol Physiol (2007) 20(5):260-262.

Goodwin et al., "Pretargeted peptide imaging and therapy," Cancer Biother Radiopharm (1999) 14(3):145-152.

Graille et al., "Complex between Peptostreptococcus magnus protein L and a human antibody reveals structural convergence in the interaction modes of Fab binding proteins," Structure (2001) 9(8):679-687.

Graille et al., "Crystal structure of a *Staphylococcus aureus* protein A domain complexed with the Fab fragment of a human IgM antibody: structural basis for recognition of B-cell receptors and superantigen activity," Proc Natl Acad Sci USA (2000) 97(10):5399-5404.

Graille et al., "Evidence for plasticity and structural mimicry at the immunoglobulin light chain-protein L interface," J Biol Chem (2002) 277(49):47500-47506.

Green et al., "Pretargeted radioimmunotherapy for B-cell lymphomas," Clin Cancer Res (2007) 13(18 Pt 2):5598s-5603s.

Guay et al., "Therapeutic utility and medicinal chemistry of cathepsin C inhibitors," Curr Top Med Chem (2010) 10(7):708-716.

Hansel et al., "The safety and side effects of monoclonal antibodies," Nat Rev Drug Discov (2010) 9(4):325-338.

Hardegger et al., "Systematic investigation of halogen bonding in protein-ligand interactions," Angew Chem Int Ed Engl (2011) 50(1):314-318.

(56) References Cited

OTHER PUBLICATIONS

Hartmann et al., "Peptide mimotopes recognized by antibodies cetuximab and matuzumab induce a functionally equivalent anti-EGFR immune response," Oncogene (2010) 29(32):4517-4527.
Hernandes et al., "Halogen atoms in the modern medicinal chemistry: hints for the drug design," Curr Drug Targets (2010) 11(3):303-314.
Horiuchi et al., "Transmembrane TNF-alpha: structure, function and interaction with anti-TNF agents," Rheumatology (Oxford) (2010) 49(7):1215-1228.
Hughes et al., "Fragment based discovery of a novel and selective PI3 kinase inhibitor," Bioorg Med Chem Lett (2011) 21(21):6586-6590.
Hutchins et al., "Site-specific coupling and sterically controlled formation of multimeric antibody fab fragments with unnatural amino acids," J Mol Biol (2011) 406(4):595-603.
International Search Report and Written Opinion for PCT/US2012/032938, dated Oct. 17, 2012.
International Search Report and Written Opinion for PCT/US2011/55656, dated May 10, 2012, 8 pages.
Junutula et al., "Site-specific conjugation of a cytotoxic drug to an antibody improves the therapeutic index," Nat Biotechnol (2008) 26(8):925-932.
Kamat et al., "Enhanced EGFR inhibition and distinct epitope recognition by EGFR antagonistic mAbs C225 and 425," Cancer Biol Ther (2008) 7(5):726-733.
Kiessling et al., "Chemical approaches to glycobiology," Annu Rev Biochem (2010) 79:619-653.
Ladbury et al., "Adding calorimetric data to decision making in lead discovery: a hot tip," Nat Rev Drug Discov (2010) 9(1):23-27.
Lazar et al., "Engineered antibody Fc variants with enhanced effector function," Proc Natl Acad Sci USA (2006) 103(11):4005-4010.
Lazar et al., "Transforming Growth Factor α: Mutation of Aspartic Acid 47 and Leucine 48 Results in Different Biological Activities," Molecular and Cellular Biology (1988) 8(3):1247-1252.
Lesch et al., "Avidin-biotin technology in targeted therapy," Expert Opin Drug Deliv (2010) 7(5):551-564.
Li et al., "Mimotope vaccination for epitope-specific induction of anti-CD20 antibodies," Cell Immunol (2006) 239(2):136-143.
Li et al., "Structural basis for inhibition of the epidermal growth factor receptor by cetuximab," Cancer Cell (2005) 7(4):301-311.
Liu et al., "Adding new chemistries to the genetic code," Annu Rev Biochem (2010) 79:413-444.
Lofgren et al., "Comparing ELISA and surface plasmon resonance for assessing clinical immunogenicity of panitumumab," J. Immunology (2007) 178(11):7467-7472.
Lomash et al., "An antibody as surrogate receptor reveals determinants of activity of an innate immune peptide antibiotic," J Biol Chem (2010) 285(46):35750-35758.
Lowe et al., "New developments in affinity chromatography with potential application in the production of biopharmaceuticals," J Biochem Biophys Methods (2001) 49(1-3):561-574.
Mammen et al., "Polyvalent interactions in biological systems: implications for design and use of multivalent ligands and inhibitors," Angew Chem Int Ed (1998) 37:2754-2794.
McCoy et al., "Phaser crystallographic software," J Appl Crystallogr (2007) 40(Pt 4):658-674.
Meares, "The chemistry of irreversible capture," Adv Drug Deliv Rev (2008) 60(12):1383-1388.
Meira et al., "Different antiproliferative effects of matuzumab and cetuximab in A431 cells are associated with persistent activity of the MAPK pathway," Eur J Cancer (2009) 45(7):1265-1273.
Melosky et al., "Management of skin rash during EGFR-targeted monoclonal antibody treatment for gastrointestinal malignancies: Canadian recommendations," Curr Oncol (2009) 16(1):16-26.
Meredith et al., "Pretargeted radioimmunotherapy," Int J Radiat Oncol Biol Phys (2006) 66(2 Supp):S57-S59.
Milo et al., "Chemical and biological evaluation of dipeptidyl boronic acid proteasome inhibitors for use in prodrugs and pro-soft drugs targeting solid tumors," J Med Chem (2011) 54(13):4365-4377.
Molloy et al., "Therapy: Targeted but not trouble-free: efalizumab and PML," Nat Rev Rheumatol (2009) 5(8):418-419.
Morse et al., "EGFR-targeted therapy and related skin toxicity," Semin Oncol Nurs (2006) 22(3):152-162.
Moss et al., "Trastuzumab-induced cardiotoxicity," Oncol Nurs Forum (2009) 36(6):676-685.
Mossessova et al., "Ulp1-SUMO crystal structure and genetic analysis reveal conserved interactions and a regulatory element essential for cell growth in yeast," Mol Cell (2000) 5(5):865-876.
Muller et al., "Bispecific antibodies for cancer immunotherapy: Current perspectives," BioDrugs (2010) 24(2):89-98.
Muller et al., "Rigid conformation of an immunoglobulin domain tandem repeat in the A-band of the elastic muscle protein titin," J Mol Biol (2007) 371(2):469-480.
Ngo et al., in: The Protein Folding Problem and Tediary Structure Prediction, Merz et al. (eds.), Birkhauser, Boston, MA (1994) pp. 433 and 492-495.
Nicola et al., "Crystal structure of *Escherichia coli* penicillin-binding protein 5 bound to a tripeptide boronic acid inhibitor: a role for Ser-110 in deacylation," Biochemistry (2005) 44(23):8207-8217.
Nilson et al., "Purification of antibodies using protein L-binding framework structures in the light chain variable domain," J Immunol Methods (1993) 164(1):33-40.
Nygaard et al., Uniprot Accession No. F4WN58, dated Jun. 28, 2011, retrieved online from <URL:http://www.uniprot.org/uniprot/F4WN58.txt?version=1>.
Pagel et al., "Comparison of a tetravalent single-chain antibody-streptavidin fusion protein and an antibody-streptavidin chemical conjugate for pretargeted anti-CD20 radioimmunotherapy of B-cell lymphomas," Blood (2006) 108:328-336.
Pakkala et al., "Mimetics of the disulfide bridge between the N- and C-terminal cysteines of the KLK3-stimulating peptide B-2," Amino Acids (2010) 39:233-242.
Paul, Fundamental Immunology, 3rd Edition, Raven Press, New York (1993) pp. 292-295.
Pugashetti et al., "Efalizumab discontinuation: a practical strategy," J Dermatolog Treat (2009) 20(3):132-136.
Rao et al., "A trivalent system from vancomycin.D-ala-D-Ala with higher affinity than avidin.biotin," Science (1998) 280(5364):708-711.
Riemer et al., "Generation of Peptide mimics of the epitope recognized by trastuzumab on the oncogenic protein Her-2/neu," J Immunol (2004) 173:394-401.
Riemer et al., "Vaccination with cetuximab mimotopes and biological properties of induced anti-epidermal growth factor receptor antibodies," J Natl Cancer Inst (2005) 97(22):1663-1670.
Rivera et al., "Cetuximab in metastatic or recurrent head and neck cancer: the EXTREME trial," Expert Rev Anticancer Ther (2009) 9(10):1421-1428.
Robert et al., "Phase I study of anti-epidermal growth factor receptor antibody cetuximab in combination with radiation therapy in patients with advanced head and neck cancer," J Clin Oncol (2001) 19(13):3234-3243.
Roe et al., "Description and management of cutaneous side effects during cetuximab or erlotinib treatments: a prospective study of 30 patients," J Am Acad Dermatol (2006) 55(3):429-437.
Rosenberg et al., "Apolipoprotein J/clusterin prevents a progressive glomerulopathy of aging," Mol Cell Biol (2002) 22(6):1893-1902.
Rossi et al., "Stably tethered multifunctional structures of defined composition made by the dock and lock method for use in cancer targeting," Proc Natl Acad Sci USA (2006) 103(18):6841-6846.
Rudikoff et al., "Single amino acid substitution altering antigen-binding specificity," Proc Natl Acad Sci USA (1982) 79(6):1979-1983.
Rudnick et al., "Affinity and avidity in antibody-based tumor targeting," Cancer Biother Radiopharm (2009) 24(2):155-161.

(56) References Cited

OTHER PUBLICATIONS

Scheuer et al., "Strongly enhanced antitumor activity of trastuzumab and pertuzumab combination treatment on HER2-positive human xenograft tumor models," Cancer Res (2009) 69(24):9330-9336.
Schrag et al., "Cetuximab therapy and symptomatic hypomagnesemia," J Natl Cancer Inst (2005) 97(16):1221-1224.
Seeman, "DNA in a material world," Nature (2003) 421(6921):427-431.
Shan et al., "Apoptosis of malignant human B cells by ligation of CD20 with monoclonal antibodies," Blood (1998) 91(5):1644-1652.
Sharav et al., "Mimotope vaccines for cancer immunotherapy," Vaccine (2007) 25(16):3032-3037.
Sharkey et al., "Recombinant bispecific monoclonal antibodies prepared by the dock-and-lock strategy for pretargeted radioimmunotherapy," Semin Nucl Med (2010) 40(3):190-203.
Sheedy et al., "Isolation and affinity maturation of hapten-specific antibodies," Biotechnol Adv (2007) 25(4):333-352.
Shirasaki et al., "Exploration of orally available calpain inhibitors 2: peptidyl hemiacetal derivatives," J Med Chem (2006) 49(13):3926-3932.
Shuker et al., "Discovering high-affinity ligands for proteins: SAR by NMR," Science (1996) 274(5292):1531-1534.
Skolnick and Fetrow, "From genes to protein structure and function: novel applications of computational approaches in the genomic era," Trends Biotechnol (2000) 18(1):34-39.
Spangler et al., "Combination antibody treatment down-regulates epidermal growth factor receptor by inhibiting endosomal recycling," Proc Natl Acad Sci USA (2010) 107(30):13252-13257.
Stymiest et al., "Synthesis of oxytocin analogues with replacement of sulfur by carbon gives potent antagonists with increased stability," J Org Chem (2005) 70(20):7799-7809.
Tamura et al., "Structural correlates of an anticarcinoma antibody: identification of specificity-determining residues (SDRs) and development of a minimally immunogenic antibody variant by retention of SDRs only," J Immunol (2000) 164(3):1432-1441.
Teillaud et al., "Engineering of monoclonal antibodies and antibody-based fusion proteins: successes and challenges," Expert Opin Biol Ther (2005) 5(Suppl 1):S15-S27.
Thakur et al., "Cancer therapy with bispecific antibodies: Clinical experience," Curr Opin Mol Ther (2010) 12(3):340-349.
Van Cutsem et al., "Cetuximab and chemotherapy as initial treatment for metastatic colorectal cancer," N Engl J Med (2009) 360(14):1408-1417.
Wakankar et al., "Physicochemical stability of the antibody-drug conjugate Trastuzumab-DM1: changes due to modification and conjugation processes," Bioconjug Chem (2010) 21(9):1588-1595.
Young Jr. et al., "Staphylococcal protein A binding to the Fab fragments of mouse monoclonal antibodies," J Immunol (1984) 133(6):3163-3166.
International Preliminary Report on Patentability for PCT/US2012/032938, dated Aug. 21, 2013, 13 pages.
First Office Action and Search Report in Chinese Patent Application No. 201180059323.2, issued Jul. 6, 2014.

* cited by examiner

Figure 1
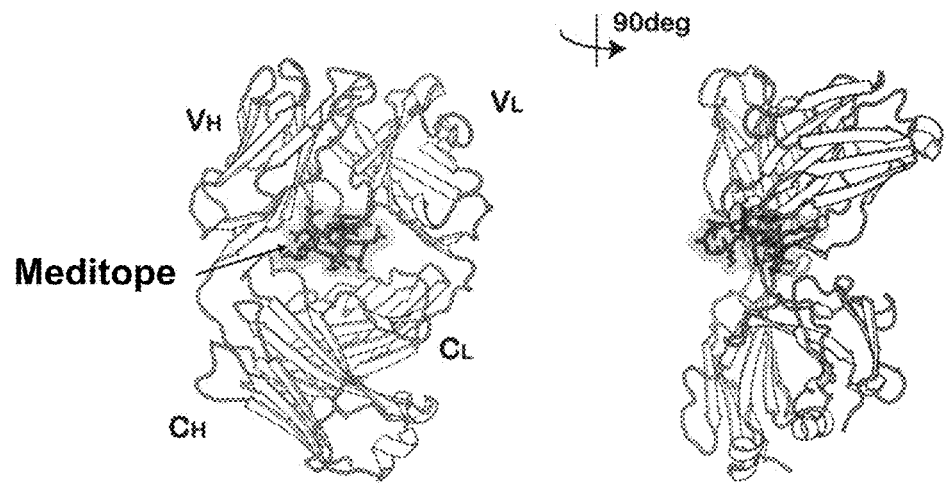
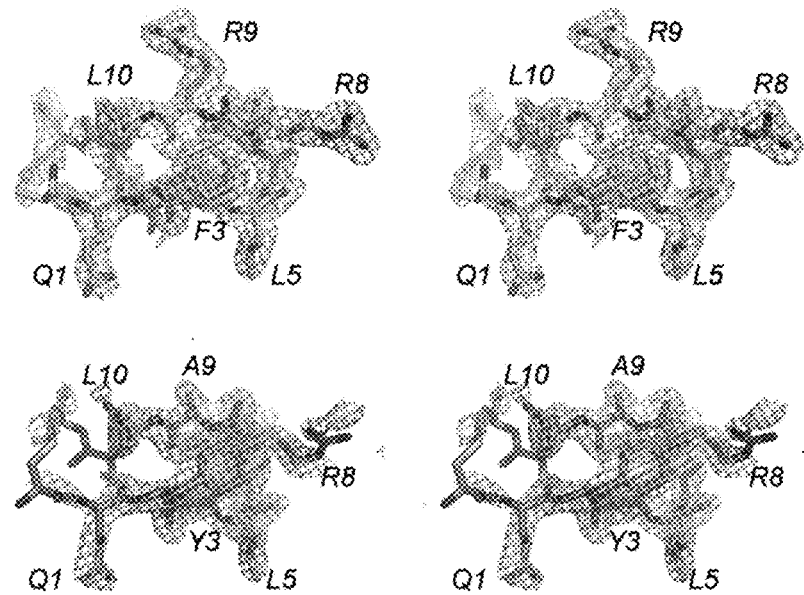

A)

Light Chain
| Kabat Number | 10 | 38-------43 | 83----87 | 100----105 | 165 |
|---|---|---|---|---|---|
| cetuximab | I | QRTNGS | IADYY | AGTKLE | E |
| ch 14.18 | S | QKPGQS | LGVYF | AGTKLE | E |
| trastuzumab | S | QKPGKA | FATYY | QGTKVE | E |

Heavy Chain
| Kabat Number | 39-------44 | 87-89 | 105-108 | 150 | 175-176 |
|---|---|---|---|---|---|
| cetuximab | QSPGKG | TAI | QGTL | E | PA |
| ch 14.18 | QNIGKS | SAV | QGTS | E | PA |
| trastuzumab | QAPGKG | TAV | QGTL | E | PA |

B)

Figure 4 A-C
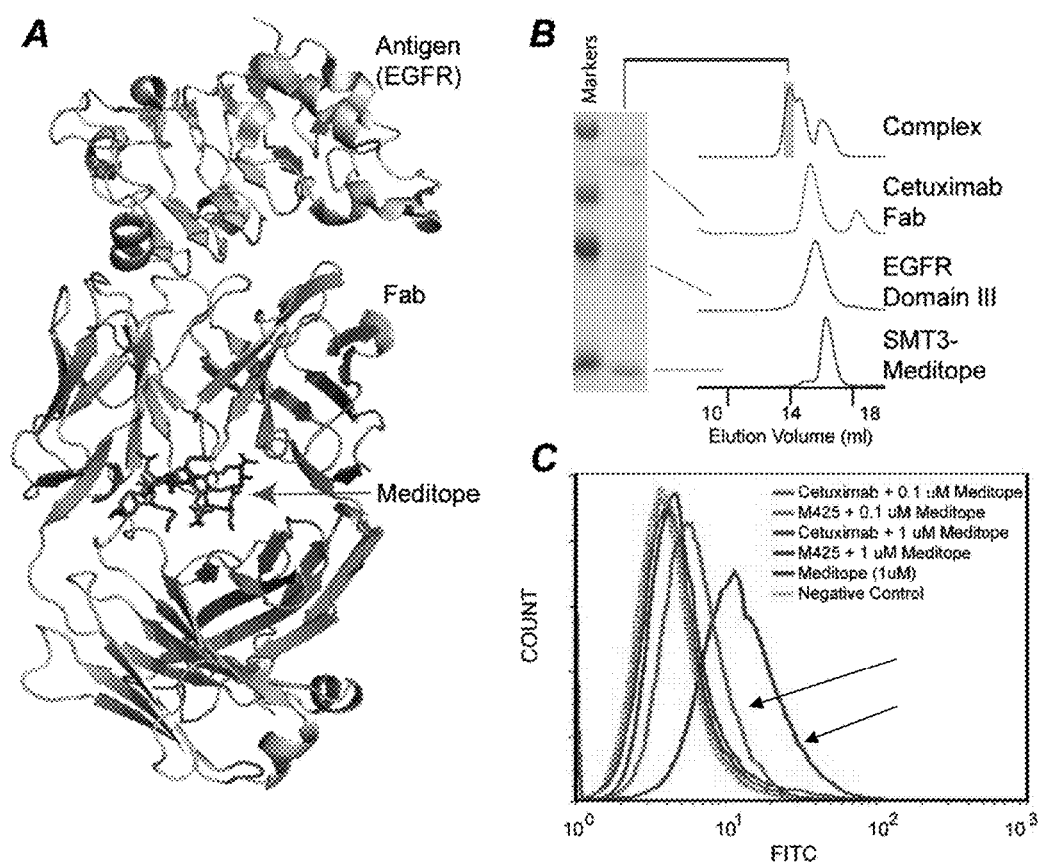

Figure 15

Meditope-Fc (SEQ ID NO:3 nucleic acid and SEQ ID NO: 4 amino acid)

```
                          tgccagtttgacctgtcaactcggcgactgaaatgcggt
                           C  Q  F  D  L  S  T  R  R  L  K  C  G
gggggctccggttcaggctcggcggttcatcggaggaggggagggaacctaagtca
 G  G  S  G  S  G  S  G  G  S  S  G  G  G  G  E  P  K  S
tgcgataagacgcacacctgtcctccatgcccagcccccgagttgcttggtgggcctca
 C  D  K  T  H  T  C  P  P  C  P  A  P  E  L  L  G  G  P  S
gtattcctcttccctccaaaacccaaagacaccttgatgatttccgcacgccggaagtc
 V  F  L  F  P  P  K  P  K  D  T  L  M  I  S  R  T  P  E  V
acgtgtgtggtcgtggatgtgagccatgaggatcccgaggtgaagttcaattggtacgtg
 T  C  V  V  V  D  V  S  H  E  D  P  E  V  K  F  N  W  Y  V
gatggagtagaggtacacaacgcgaaaacgaagcccaggaggaacagtacaattccaca
 D  G  V  E  V  H  N  A  K  T  K  P  R  E  E  Q  Y  N  S  T
tatcgcgtggtgtccgtgcttactgtgttgcatcaagactggctgaatgggaaggagtat
 Y  R  V  V  S  V  L  T  V  L  H  Q  D  W  L  N  G  K  E  Y
aagtgcaaagtatcaaacaaggcgctgcctgctccaatcgaaaagaccatctcgaaggcg
 K  C  K  V  S  N  K  A  L  P  A  P  I  E  K  T  I  S  K  A
aaaggacaacccagagaaccccaagtctacacgcttccgccctcgcgggatgagctcacc
 K  G  Q  P  R  E  P  Q  V  Y  T  L  P  P  S  R  D  E  L  T
aaaaaccaggtatccctcacttgtttggtaaaaggattctacccgtcggacattgcagtc
 K  N  Q  V  S  L  T  C  L  V  K  G  F  Y  P  S  D  I  A  V
gagtgggagtcgaatgggcagccggaaaacaactacaaaacaacaccgcccgtcttggac
 E  W  E  S  N  G  Q  P  E  N  N  Y  K  T  T  P  V  L  D
tccgatggttcgttcttctctattcgaagctcaccgtagacaagtcgaggtggcagcag
 S  D  G  S  F  F  L  Y  S  K  L  T  V  D  K  S  R  W  Q  Q
ggcaacgtcttttcgtgctcagtgatgcatgaggcccttcacaatcactatacgcagaaa
 G  N  V  F  S  C  S  V  M  H  E  A  L  H  N  H  Y  T  Q  K
agcctgagcctgtccgggggaagtaa
 S  L  S  L  S  P  G  K  -
```

Figure 22
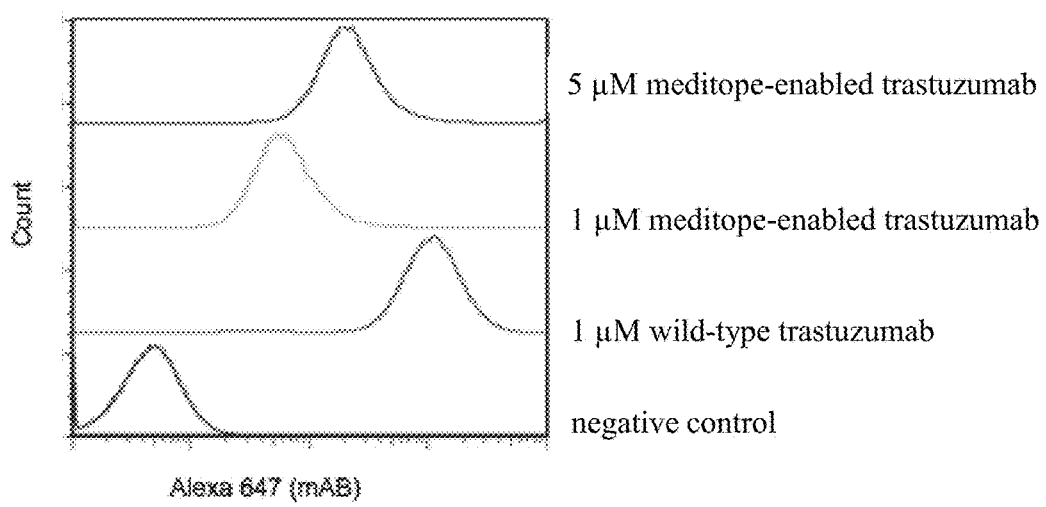
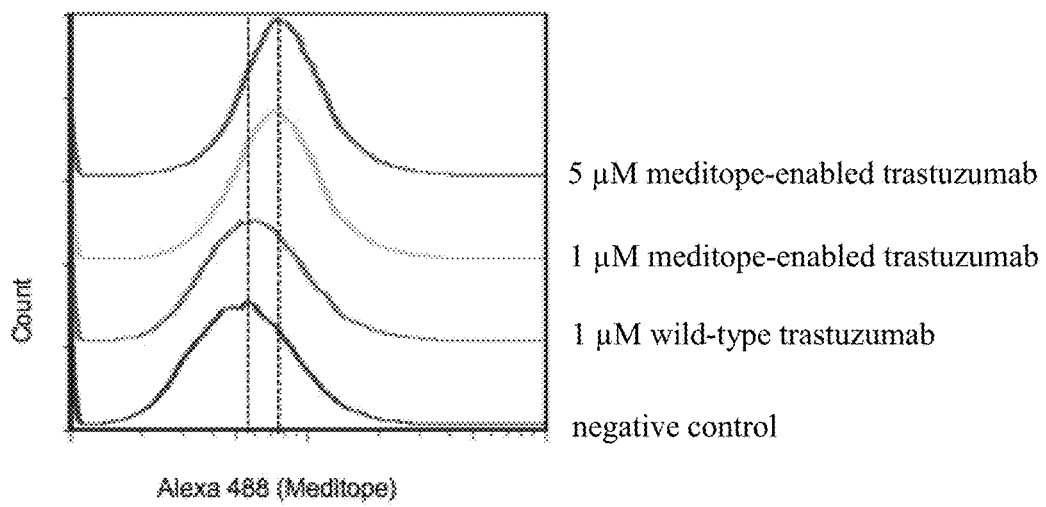

Figure 23A

```
ATGAAATGCT GGTGGGTCAT GTTTTCCCTT ATGGCGGTAC TAACCGGAGT AAACTCCGAG GTCCAGCTCG
TCGAATCCGG TGGCGGCTTG GTGCAGCCGG GTGGGTCGTT GCGACTGTCG TGCGCAGCGT CGGGGTTTAA
CATCAAAGAC ACCTATATCC ACTGGGTGAG GCAATCGCCC GGAAAGGGGC TCGAATGGGT AGCCAGAATC
TACCCTACGA ATGGTTATAC TCGATATGCG GACTCCGTGA AAGGAAGATT CACCATCAGC GCAGATACGT
CCAAAAACAC TGCATACCTC CAGATGAATA GCCTTCGGGC GGAGGACACG GCGATCTACT ACTGTAGCCG
GTGGGGTGGG GACGGGTTCT ATGCGATGGA CTACTGGGGA CAGGGGACGC TTGTAACGGT CAGCTCGGCG
TCAACAAAGG GACCTAGCGT GTTTCCCTTG GCTCCCTCAT CGAAATCAAC GTCCGGTGGG ACGGCGGCAT
TGGGGTGTCT TGTCAAGGAC TATTTCCCCG AGCCCGTGAC AGTCTCGTGG AACTCGGGTG CCCTTACAAG
CGGCGTACAT ACGTTTCCCG CCGTGCTCCA ATCATCCGGA CTGTATTCCC TTTCATCCGT CGTGACTGTG
CCGTCCTCGT CACTCGGAAC GCAAACTTAC ATTTGCAATG TCAACCACAA ACCGTCAAAT ACAAAGGTCG
ATAAGAAGGT CGAGCCAAAG TCGTGTGATA AGACCCACAC ATGCCCTCCC TGTCCAGCGC GGAGCTGTT
GGGAGGGCCT TCAGTGTTCC TCTTCCCGCC CAAACCCAAG GACACCCTGA TGATTAGCCG CACACCCGAG
GTGACGTGTG TCGTCGTCGA TGTCTCACAT GAGGACCCGG AGGTAAAGTT CAACTGGTAC GTGGATGGAG
TCGAAGTGCA CAACGCAAAA ACAAAACCTC GGGAAGAGCA GTACAATAGC ACGTACGAGA TAGTCAGCGT
GCTCACCGTG CTGCACCAGG ATTGGCTCAA TGGAAAGGAG TACAAGTGTA AAGTGTCGAA TAAGGCGCTG
CCTGCCCCCA TCGAAAAGAC AATTTCCAAA GCTAAAGGCC AACCCCGCGA GCCGCAAGTA TACACCCTCC
CACCCTCGCG CGATGAACTG ACCAAGAACC AGGTGTCATT GACGTGCTC GTCAAGGGCT TCTATCCGAG
CGACATTGCA GTAGAATGGG AAAGCAACGG ACAGCCGGAA AACAACTACA AGACTACACC GCCTGTCCTT
GATTCGGATG GTTCCTTCTT TCTTTACTCA AAACTTACAG TCGACAAATC GAGGTGGCAG CAGGGAAATG
TGTTTTCGTG CAGCGTGATG CACGAGGCCT TGCATAATCA CTATACACAG AAGTCGTTGT CACTGTCGCC
GGGAAAGTAA
```

Figure 23B

```
Medi   EVQLVESGGGLVQPGGSLRLSCAASGFNIKDTYIHWVRQSPGKGLEWVARIYPTNGYTRYADSV
       ::::::::::::::::::::::::::::::::::::::: ::::::::::::::::::::::::
WT     EVQLVESGGGLVQPGGSLRLSCAASGFNIKDTYIHWVRQAPGKGLEWVARIYPTNGYTRYADSV Medi   KGRFTISADTSKNTAYLQMNSLRAEDTA YYCSRWGGDGFYAMDYWGQGTLVTVSSASTK
       :::::::::::::::::::::::::::: :::::::::::::::::::::::::::::::
WT     KGRFTISADTSKNTAYLQMNSLRAEDTA YYCSRWGGDGFYAMDYWGQGTLVTVSSASTK Medi   GPSVFPLAPSSKSTSGGTAALGCLVKDYFPEPVTVSWNSGALTSGVHTFPAVLQSSGLYS
       :::::::::::::::::::::::::::::::::::::::::::::::::::::::::::
WT     GPSVFPLAPSSKSTSGGTAALGCLVKDYFPEPVTVSWNSGALTSGVHTFPAVLQSSGLYS
```

Figure 23C

```
░░░░░░░░░░ ░░░░░░░░░░ ░░░░░░░░░░ ░░░░░░░░░░ ░░░░░░░░░░ ░░░░░░░░░░ GATATTCAGA
TGACCCAGTC ACCGATCCTT CTCTCGGCGA GCGTGGGGGA TAGAGTAACG ATCACGTGTA GAGCGTCCCA
AGACGTCAAC ACAGCTGTCG CGTGGTATCA GCAGCGGACA AATGGATCGC CGAGGCTCCT GATCTACAGC
GCATCATTTC TCTATTCGGG AGTCCCCTCC CGATTTTCCG GATCGCGCAG CGGTACTGAC TTCACCCTCA
CGATTTCCTC CCTTCAACCG GAAGATATCG CTGATTACTA CTGTCAGCAG CACTATACAA CACCTCCCAC
TTTCGGAGCA GGGACAAAAG TGGAGATTAA GCGCACTGTA GCAGCCCCCT CGGTCTTTAT CTTCCCTCCT
AGCGACGAAC AATTGAAGTC AGGGACCGCC TCGGTGGTAT GCCTGCTTAA CAACTTTTAC CCACGGGAAG
CCAAAGTACA GTGGAAGGTG GATAATGCGC TCCAGAGCGG AAACTCCCAA GAGAGCGTGA CAGAACAGGA
CTCGAAGGAT TCGACGTACT CACTCAGCTC AACGCTGACC CTGTCGAAAG CGGACTATGA GAAACACAAG
GTCTACGCGT GCGAGGTGAC CCATCAGGGC CTGAGCTCCC CCGTAACTAA GTCATTCAAC CGGGGTGAAT
GCTAA
```

Figure 23D

```
             10         20         30         40         50         60
medi    DIQMTQSP░░LSASVGDRVTITCRASQDVNTAVAWYQQ░░░░PRLLIYSASFLYSGVPS
        ::::::::  :::::::::::::::::::::::::::::   :  ::::::::::::::::
WT      DIQMTQSP░░LSASVGDRVTITCRASQDVNTAVAWYQQ░░░░PKLLIYSASFLYSGVPS
             10         20         30         40         50         60

70         80         90        100        110        120
medi    RFSGSRSGTDFTLTISSLQPED░A░YYCQQHYTTPPTFG░GTKVEIKRTVAAPSVFIFPP
        :::::::::::::::::::::::  :  ::::::::::::  :::::::::::::::::::
WT      RFSGSRSGTDFTLTISSLQPED░A░YYCQQHYTTPPTFG░GTKVEIKRTVAAPSVFIFPP
             70         80         90        100        110        120

130        140        150        160        170        180
medi    SDEQLKSGTASVVCLLNNFYPREAKVQWKVDNALQSGNSQESVTEQDSKDSTYSLSSTLT
        ::::::::::::::::::::::::::::::::::::::::::::::::::::::::::::
WT      SDEQLKSGTASVVCLLNNFYPREAKVQWKVDNALQSGNSQESVTEQDSKDSTYSLSSTLT
            130        140        150        160        170        180

190        200        210
medi    LSKADYEKHKVYACEVTHQGLSSPVTKSFNRGEC
        :::::::::::::::::::::::::::::::::
WT      LSKADYEKHKVYACEVTHQGLSSPVTKSFNRGEC
            190        200        210
```

Figure 25A

```
tcactatagggcaagcttgccgccaccatgaaatgctcgtggtgatcttttccttatg
 S  L  -  G  K  L  A  A  T  M  K  C  S  W  V  I  F  F  L  M
gcggtagtaaccggagttaactccgaggtccagctcgtcgaatccggtggcggcttggtg
 A  V  V  T  G  V  N  S  E  V  Q  L  V  E  S  G  G  G  L  V
cagccgggtgggtcgttgcgactgtcgtgcgcagcgtcggggtttaacatcaaagacacc
 Q  P  G  G  S  L  R  L  S  C  A  A  S  G  F  N  I  K  D  T
tatatccactgggtgaggcaagcgcccggaaagggctcgaatgggtagccagaatctac
 Y  I  H  W  V  R  Q  A  P  G  K  G  L  E  W  V  A  R  I  Y
cctacgaatggttatactcgatatgcggactccgtgaaggaagattcaccatcagcgca
 P  T  N  G  Y  T  R  Y  A  D  S  V  K  G  R  F  T  I  S  A
gatacgtccaaaaacactgcatacctccagatgaatagccttcgggcggaggacacggcg
 D  T  S  K  N  T  A  Y  L  Q  M  N  S  L  R  A  E  D  T  A
gtctactactgtagccggtggggtggggacgggttctatgcgatggactactggggacag
 V  Y  Y  C  S  R  W  G  G  D  G  F  Y  A  M  D  Y  W  G  Q
gggacgcttgtaacggtcagctcggctagcacaaagggacctagcgtgtttcccttggct
 G  T  L  V  T  V  S  S  A  S  T  K  G  P  S  V  F  P  L  A
ccctcatcgaaatcaacgtccggtgggacggcggcattggggtgtcttgtcaaggactat
 P  S  S  K  S  T  S  G  G  T  A  A  L  G  C  L  V  K  D  Y
ttccccgagcccgtgacagtctcgtggaactcgggtgcccttacaagcggcgtacatacg
 F  P  E  P  V  T  V  S  W  N  S  G  A  L  T  S  G  V  H  T
tttccgccgtgctccaatcatccggactgtattcccttcatccgtcgtgactgtgccg
 F  P  A  V  L  Q  S  S  G  L  Y  S  L  S  S  V  V  T  V  P
tcctcgtcactcggaacgcaaacttacatttgcaatgtcaaccacaaaccgtcaaataca
 S  S  S  L  G  T  Q  T  Y  I  C  N  V  N  H  K  P  S  N  T
aaggtcgataagaaggtcgagccaaagtcgtgtgataagacccacacatgccctccctgt
 K  V  D  K  K  V  E  P  K  S  C  D  K  T  H  T  C  P  P  C
ccagcgccggagctgttgggagggccttcagtgttcctcttcccgcccaaacccaaggac
 P  A  P  E  L  L  G  G  P  S  V  F  L  F  P  P  K  P  K  D
accctgatgattagccgcacacccgaggtgacgtgtgtcgtcgtcgatgtctcacatgag
 T  L  M  I  S  R  T  P  E  V  T  C  V  V  V  D  V  S  H  E
gacccggaggtaaagttcaactggtacgtggatggagtcgaagtgcacaacgcaaaaaca
 D  P  E  V  K  F  N  W  Y  V  D  G  V  E  V  H  N  A  K  T
aaacctcgggaagagcagtacaatagcacgtacagagtagtcagcgtgctcaccgtgctg
 K  P  R  E  E  Q  Y  N  S  T  Y  R  V  V  S  V  L  T  V  L
caccaggattggctcaatggaaaggagtacaagtgtaaagtgtcgaataaggcgctgcct
 H  Q  D  W  L  N  G  K  E  Y  K  C  K  V  S  N  K  A  L  P
gcccccatcgaaagacaatttccaaagctaaagggcaaccccgcgagccgcaagtatac
 A  P  I  E  K  T  I  S  K  A  K  G  Q  P  R  E  P  Q  V  Y
accctcccaccctcgcgcgatgaactgaccaagaaccaggtgtcattgacgtgtctcgtc
 T  L  P  P  S  R  D  E  L  T  K  N  Q  V  S  L  T  C  L  V
aagggcttctatccgagcgacattgcagtagaatggaaagcaacggacagccggaaaac
 K  G  F  Y  P  S  D  I  A  V  E  W  E  S  N  G  Q  P  E  N
aactacaagactacaccgcctgtccttgattcggatggttccttctttctttactcaaaa
 N  Y  K  T  T  P  P  V  L  D  S  D  G  S  F  F  L  Y  S  K
cttacagtcgacaaatcgaggtggcagcagggaaatgtgttttcgtgcagcgtgatgcac
 L  T  V  D  K  S  R  W  Q  Q  G  N  V  F  S  C  S  V  M  H
gaggccttgcataatcactatacacagaagtcgttgtcactgtcgccgggaaagtaatga
 E  A  L  H  N  H  Y  T  Q  K  S  L  S  L  S  P  G  K  -  -
```

Figure 25B

```
ataggggaagcttgccgccaccatggagacagacacgcttttgctttgggtgttgttgttg
         -  G  K  L  A  A  T  M  E  T  D  T  L  L  L  W  V  L  L  L
tgggtccccggttcgaccggtgatattcagatgacccagtcaccgtcatccctttcggcg
 W  V  P  G  S  T  G  D  I  Q  M  T  Q  S  P  S  S  L  S  A
agcgtggggatagagtaacgatcacgtgtagagcgtcccaagacgtcaacacagctgtc
 S  V  G  D  R  V  T  I  T  C  R  A  S  Q  D  V  N  T  A  V
gcgtggtatcagcagaagccaggaaaaagcgccgaagctcctgatctacagcgcatcattt
 A  W  Y  Q  Q  K  P  G  K  A  P  K  L  L  I  Y  S  A  S  F
ctctattcgggagtcccctcccgattttccggatcgcgcagcggtactgacttcaccctc
 L  Y  S  G  V  P  S  R  F  S  G  S  R  S  G  T  D  F  T  L
acgatttcctcccttcaaccggaagatttgctacttactactgtcagcagcactataca
 T  I  S  S  L  Q  P  E  D  F  A  T  Y  Y  C  Q  Q  H  Y  T
acacctcccactttcggacaggggacaaaagtggagattaagcggaccgtagcagccccc
 T  P  P  T  F  G  Q  G  T  K  V  E  I  K  R  T  V  A  A  P
tcggtctttatcttccctcctagcgacgaacaattgaagtcagggaccgcctcggtggta
 S  V  F  I  F  P  P  S  D  E  Q  L  K  S  G  T  A  S  V  V
tgcctgcttaacaacttttacccacgggaagccaaagtacagtggaaggtggataatgcg
 C  L  L  N  N  F  Y  P  R  E  A  K  V  Q  W  K  V  D  N  A
ctccagagcggaaactcccaagagagcgtgacagaacaggactcgaaggattcgacgtac
 L  Q  S  G  N  S  Q  E  S  V  T  E  Q  D  S  K  D  S  T  Y
tcactcagctcaacgctgaccctgtcgaaagcggactatgagaaacacaaggtctacgcg
 S  L  S  S  T  L  T  L  S  K  A  D  Y  E  K  H  K  V  Y  A
tgcgaggtgacccatcagggcctgagctcccccgtaactaagtcattcaaccggggtgaa
 C  E  V  T  H  Q  G  L  S  S  P  V  T  K  S  F  N  R  G  E
tgctaatga
 C  -  -
```

Figure 26

```
1YY9_D|PDBID|CHAIN|SEQUENCE    QVQLKQSGPGLVQPSQSLSITCTVSGFSLTNYGVHWV      GLEWLG-  49
2R56_H|PDBID|CHAIN|SEQUENCE    QVSLRESGGGLVQPGRSLRLSCTASGFTFRHHGMTWVRQAPGKGLEWVAS  50
                               **.*::** *****.:**  :;**.***:: ::*: ****;*******:.

1YY9_D|PDBID|CHAIN|SEQUENCE    VIWSGGNTDYNTPFTSRLSINKDNSKSQVFFKMNSLQSNDTAIYYCARAL  99
2R56_H|PDBID|CHAIN|SEQUENCE    LSGSGTKTHFADSVKGRFTISRDNSNNTLYLQMDNVRDEDTAIYYCAKAK 100
                               : ** :*.:   ....*::*.:***:.  ::::*:.::.:********;*

1YY9_D|PDBID|CHAIN|SEQUENCE    TYYDY-EFAYWGQGTLVTVSAASTKGPSVFPLAPSSKSTSGGTAALGCLV 148
2R56_H|PDBID|CHAIN|SEQUENCE    RVGATGYFDLWGRGTLVTVSSASTKGPSVFPLAPSSKSTSGGTAALGCLV 150
                                *  **.******:***********************************

1YY9_D|PDBID|CHAIN|SEQUENCE    KDYFPEPVTVSWNSGALTSGVHTFPAVLQSSGLYSLSSVVTVPSSSLGTQ 198
2R56_H|PDBID|CHAIN|SEQUENCE    KDYFPEPVTVSWNSGALTSGVHTFPAVLQSSGLYSLSSVVTVPSSSLGTQ 200
                               **************************************************

1YY9_D|PDBID|CHAIN|SEQUENCE    TYICNVNHKPSNTKVDKRVEPKS 221
2R56_H|PDBID|CHAIN|SEQUENCE    TYICNVNHKPSNTKVDKKAEP-- 221
                               *****************;.**
```

Modified Arg8

R = alkyl, substituted alkyl, aromatic or NHR'''
where R''' = alkyl, substituted alkyl, aromatic Figure 38
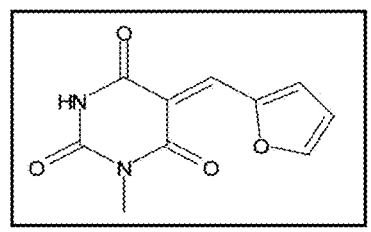
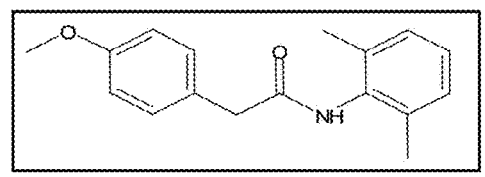
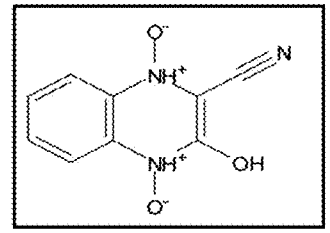
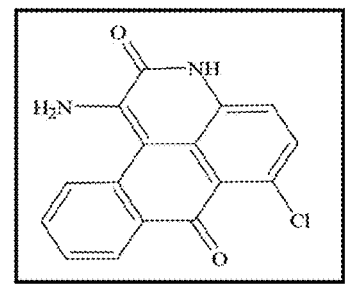
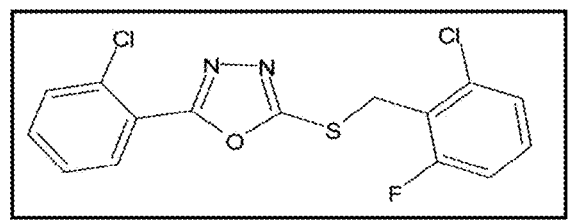

Figure 39 (cont'd)
G
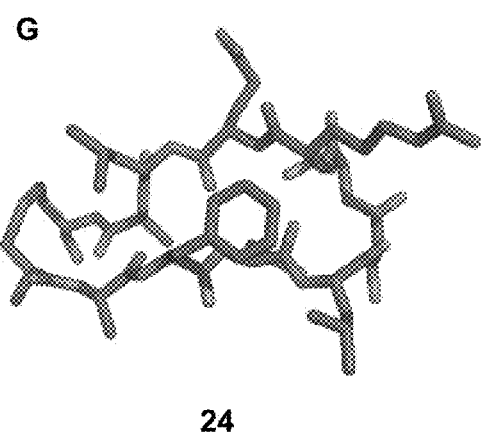
24
H
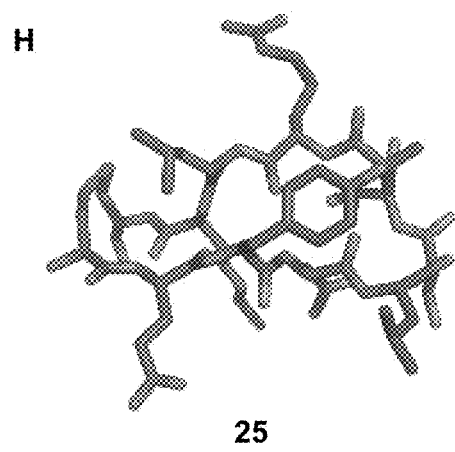
25
I
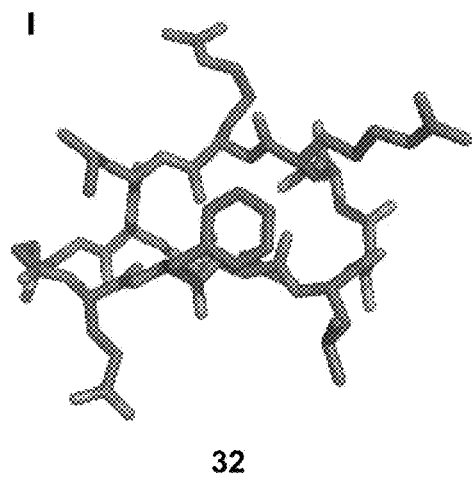
32
J
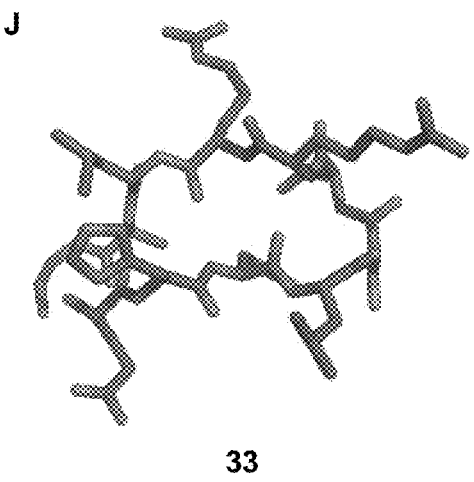
33
K
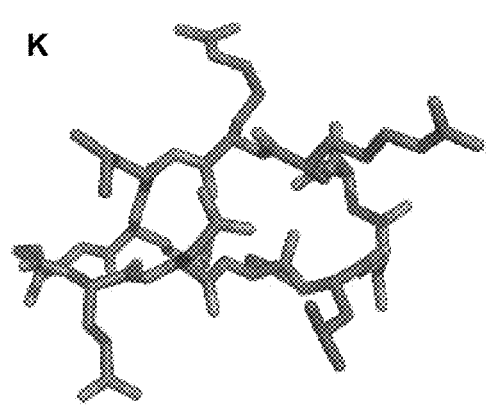
34
L
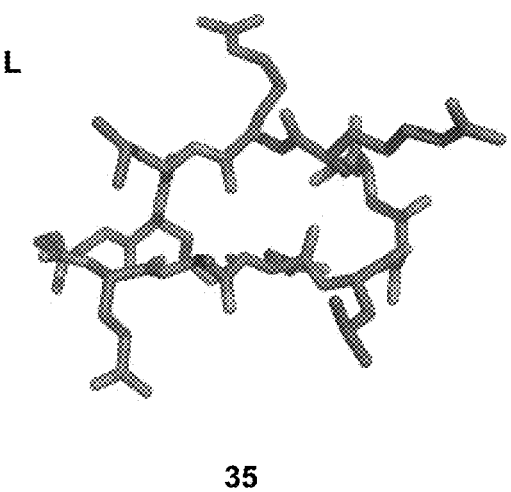
35

Figure 39 (cont'd)
M
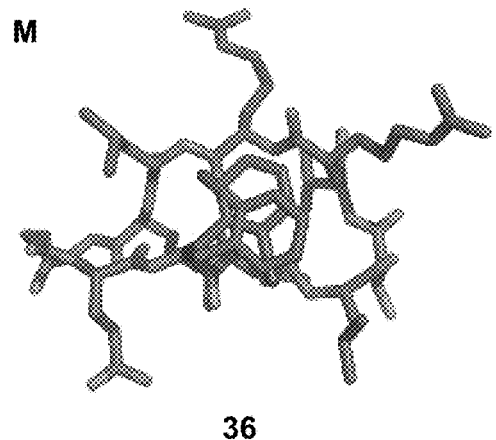
36
N
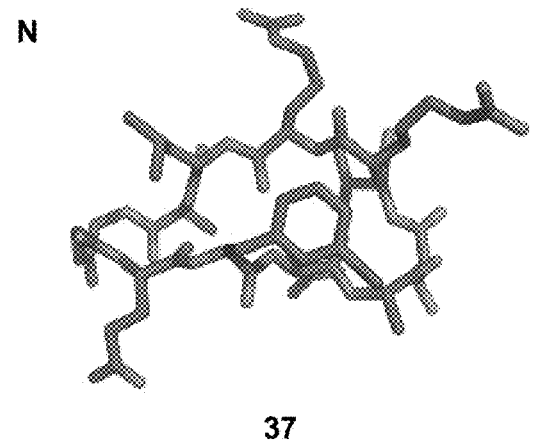
37
O
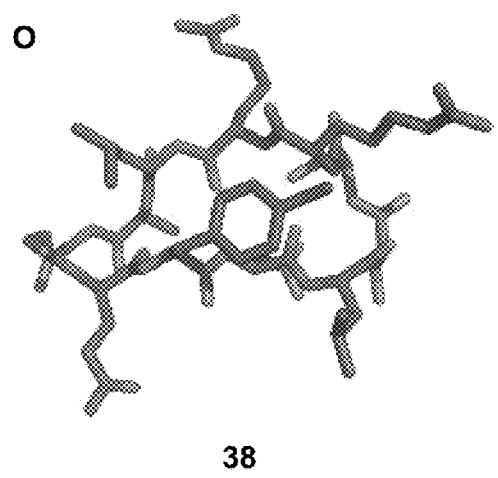
38
P
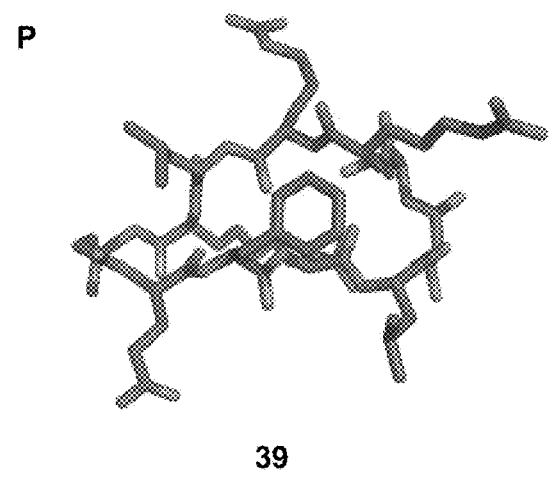
39
Q
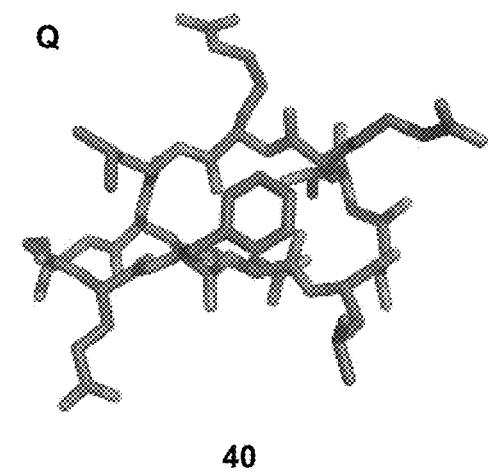
40
R
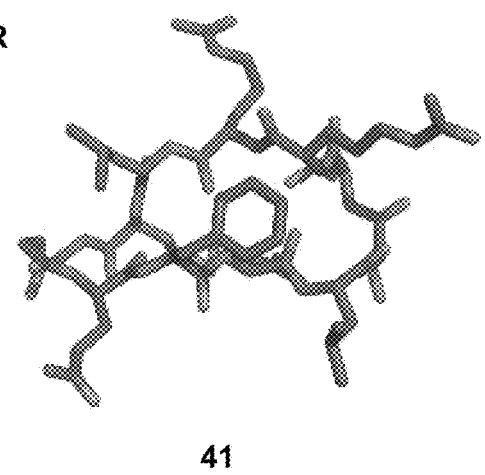
41

Figure 40

| SEQ ID NO: | 15 | 16 | 17 | 18 |
|---|---|---|---|---|
| Data Collection | | | | |
| Space group | P2₁2₁2₁ | P2₁2₁2₁ | P2₁2₁2₁ | P2₁2₁2₁ |
| Cell dimensions | | | | |
| a, b, c (Å) | 64.33, 82.84, 212.32 | 64.20, 82.50, 212.49 | 64.02, 82.83, 212.10 | 64.28, 83.25, 212.30 |
| α, β, γ (°) | 90.0, 90.0, 90.0 | 90.0, 90.0, 90.0 | 90.0, 90.0, 90.0 | 90.0, 90.0, 90.0 |
| Resolution (Å) | 30.00-2.24 (2.45-2.24) | 32.99-2.53 (2.60-2.53) | 34.36-2.48 (2.54-2.48) | 33.19-2.48 (2.54-2.48) |
| $R_{mrgd-F}$ | 0.070 (0.281) | 0.066 (0.334) | 0.065 (0.312) | 0.072 (0.331) |
| I/σ(I) | 19.05 (5.92) | 24.74 (5.21) | 24.88 (4.97) | 23.52 (4.68) |
| Completeness (%) | 99.1 (99.1) | 97.6 (91.3) | 99.4 (92.6) | 99.1 (90.3) |
| Redundancy | 5.2 (5.4) | 4.9 (4.5) | 6.19 (4.27) | 4.61 (3.16) |
| Refinement | | | | |
| Resolution (Å) | 2.24 | 2.53 | 2.48 | 2.48 |
| No. reflections | 55,026 | 37,650 | 40,641 | 41,098 |
| $R_{work}/R_{free}$ | 18.0/22.6 | 17.2/23.6 | 17.6/22.0 | 17.4/22.9 |
| No. atoms | | | | |
|   Protein | 6526 | 6514 | 6551 | 6541 |
|   Meditope | 174 | 291 (198)* | 212 | 218 |
|   Water | 507 | 392 | 511 | 469 |
| B-factors | | | | |
|   Protein | | | | |
|   Fab | 38.16 | 27.79 | 25.74 | 25.23 |
|   Meditope | 49.08 | 43.40 (27.51)* | 31.78 | 31.52 |
|   Water | 41.78 | 28.05 | 28.32 | 29.65 |
| r.m.s.d | | | | |
|   Bond lengths (Å) | 0.007 | 0.005 | 0.007 | 0.008 |
|   Bond angles (°) | 1.093 | 0.903 | 1.091 | 1.106 |
| Ramachandran favored/allowed/disallowed | 96.9/3.1/0.0 | 96.8/3.2/0.0 | 97.6/2.4/0.0 | 97.2/2.7/0.1 |

* 3 meditopes in asymmetric unit. Data in parenthesis refer to the meditopes in the meditope binding pocket characteristic for the WT meditope

Figure 40 (cont'd)

| SEQ ID NO: | 21 | 22 | 23 | 24 |
|---|---|---|---|---|
| Data Collection | | | | |
| Space group | $P2_12_12_1$ | $P2_12_12_1$ | $P2_12_12_1$ | $P2_12_12_1$ |
| Cell dimensions | | | | |
| a, b, c (Å) | 64.38, 82.87, 213.00 | 64.24, 83.14, 211.94 | 64.30, 83.39, 212.73 | 64.46, 83.21, 212.44 |
| α, β, γ (°) | 90.0, 90.0, 90.0 | 90.0, 90.0, 90.0 | 90.0, 90.0, 90.0 | 90.0, 90.0, 90.0 |
| Resolution (Å) | 32.65-2.53 (2.60-2.53) | 33.15-2.48 (2.55-2.48) | 33.23-2.49 (2.55-2.49) | 34.96-2.62 (2.69-2.62) |
| $R_{mrgd-F}$ | 0.129 (0.637) | 0.044 (0.153) | 0.056 (0.219) | 0.125 (0.470) |
| I/σ(I) | 23.46 (7.34) | 25.24 (9.23) | 19.83 (6.03) | 15.21 (3.87) |
| Completeness (%) | 99.6 (98.1) | 95.1 (72.3) | 99.6 (95.4) | 98.6 (97.7) |
| Redundancy | 3.91 (3.41) | 5.2 (4.6) | 5.0 (3.66) | 4.95 (5.05) |
| Refinement | | | | |
| Resolution (Å) | 2.53 | 2.48 | 2.49 | 2.62 |
| No. reflections | 38,821 | 39,080 | 40,816 | 34,738 |
| $R_{work}/R_{free}$ | 19.1/24.7 | 17.9/22.6 | 17.1/22.3 | 18.4/23.5 |
| No. atoms | | | | |
|   Protein | 6535 | 6554 | 6525 | 6529 |
|   Meditope | 202 | 208 | 198 | 174 |
|   Water | 327 | 493 | 511 | 380 |
| B-factors | | | | |
|   Protein | | | | |
|     Fab | 26.57 | 24.08 | 24.69 | 25.47 |
|     Meditope | 31.61 | 27.64 | 30.40 | 26.45 |
|     Water | 28.48 | 29.37 | 29.15 | 28.75 |
| r.m.s.d | | | | |
|   Bond lengths (Å) | 0.008 | 0.003 | 0.007 | 0.002 |
|   Bond angles (°) | 1.185 | 0.742 | 1.103 | 0.618 |
| Ramachandran favored/allowed/disallowed | 97.2/2.7/0.1 | 96.9/3.1/0.0 | 97.1/2.9/0.0 | 96.3/3.7/0.0 |

Figure 40 (cont'd)

| SEQ ID NO: | 25 | 31 | 32 | 33 |
|---|---|---|---|---|
| Data Collection | | | | |
| Space group | $P2_12_12_1$ | $P2_12_12_1$ | $P2_12_12_1$ | $P2_12_12_1$ |
| Cell dimensions | | | | |
| a, b, c (Å) | 64.10, 83.16, 212.32 | 64.22, 82.53, 212.53 | 64.28, 82.64, 212.50 | 64.16, 82.46, 212.05 |
| α, β, γ (°) | 90.0, 90.0, 90.0 | 90.0, 90.0, 90.0 | 90.0, 90.0, 90.0 | 90.0, 90.0, 90.0 |
| Resolution (Å) | 33.14-2.55 (2.62-2.55) | 33.00-2.60 (2.67-2.60) | 30.00-2.55 (2.62-2.55) | 32.51-2.49 (2.55-2.49) |
| $R_{mrgd\text{-}F}$ | 0.094 (0.374) | 0.093 (0.385) | 0.085 (0.365) | 0.039 (0.163) |
| $I/\sigma(I)$ | 19.13 (4.60) | 16.79 (4.65) | 20.27 (4.54) | 31.38 (9.58) |
| Completeness (%) | 99.4 (94.1) | 95.8 (93.7) | 96.7 (91.5) | 99.6 (96.1) |
| Redundancy | 4.33 (3.96) | 4.35 (4.36) | 5.1 (5.1) | 5.01 (3.61) |
| Refinement | | | | |
| Resolution (Å) | 2.55 | 2.60 | 2.55 | 2.49 |
| No. reflections | 37701 | 34,156 | 36,560 | 40,266 |
| $R_{work}/R_{free}$ | 17.8/22.5 | 18.8/23.1 | 18.7/22.7 | 16.9/22.0 |
| No. atoms | | | | |
|   Protein | 6517 | 6527 | 6545 | 6509 |
|   Meditope | 190 | 192 | 188 | 174 |
|   Water | 404 | 338 | 332 | 471 |
| B-factors | | | | |
|   Protein | | | | |
|     Fab | 25.98 | 21.36 | 27.94 | 25.70 |
|     Meditope | 26.64 | 24.70 | 29.73 | 53.33 |
|     Water | 28.08 | 22.78 | 29.40 | 31.55 |
| r.m.s.d | | | | |
|   Bond lengths (Å) | 0.008 | 0.003 | 0.002 | 0.003 |
|   Bond angles (°) | 1.122 | 0.777 | 0.631 | 0.771 |
| Ramachandran favored/allowed/disallowed | 96.5/3.4/0.1 | 97.4/2.6/0.0 | 96.2/3.8/0.0 | 97.2/2.8/0.0 |

Figure 40 (cont'd)

| SEQ ID NO: | 34 | 35 | 36 | 37 |
|---|---|---|---|---|
| Data Collection | | | | |
| Space group | P2₁2₁2₁ | P2₁2₁2₁ | P2₁2₁2₁ | P2₁2₁2₁ |
| Cell dimensions | | | | |
| a, b, c (Å) | 64.18, 82.66, 211.91 | 63.97, 82.50, 211.88 | 64.01, 82.21, 211.90 | 64.04, 82.51, 211.54 |
| α, β, γ (°) | 90.0, 90.0, 90.0 | 90.0, 90.0, 90.0 | 90.0, 90.0, 90.0 | 90.0, 90.0, 90.0 |
| Resolution (Å) | 33.02-2.50 (2.56-2.50) | 32.95-2.50 (2.62-2.55) | 34.14-2.51 (2.58-2.51) | 34.22-2.48 (2.55-2.48) |
| $R_{mrgd-F}$ | 0.047 (0.177) | 0.094 (0.405) | 0.046 (0.238) | 0.039 (0.144) |
| I/σ(I) | 30.78 (9.25) | 17.76 (3.68) | 25.22 (6.50) | 30.13 (8.86) |
| Completeness (%) | 99.8 (99.0) | 99.0 (90.1) | 98.5 (92.3) | 99.4 (92.5) |
| Redundancy | 6.02 (4.70) | 4.00 (3.70) | 4.12 (3.52) | 5.77 (4.14) |
| Refinement | | | | |
| Resolution (Å) | 2.50 | 2.55 | 2.51 | 2.48 |
| No. reflections | 39,848 | 37,028 | 38,565 | 40,290 |
| $R_{work}/R_{free}$ | 16.9/22.5 | 16.9/21.4 | 19.0/23.9 | 17.9/23.5 |
| No. atoms | | | | |
|   Protein | 6507 | 6555 | 6528 | 6535 |
|   Meditope | 182 | 190 | 218 | 187 |
|   Water | 503 | 285 | 338 | 454 |
| B-factors | | | | |
|   Protein | | | | |
|     Fab | 21.62 | 32.02 | 34.24 | 26.67 |
|     Meditope | 40.13 | 38.42 | 47.05 | 48.78 |
|   Water | 27.78 | 33.79 | 32.96 | 31.14 |
| r.m.s.d | | | | |
|   Bond lengths (Å) | 0.004 | 0.005 | 0.003 | 0.008 |
|   Bond angles (°) | 0.876 | 0.904 | 0.749 | 1.120 |
| Ramachandran favored/allowed/disallowed | 97.3/2.7/0.0 | 96.4/3.6/0.0 | 96.4/3.5/0.1 | 96.0/4.0/0.0 |

Figure 40 (cont'd)

| SEQ ID NO: | 38 | 39 | 40 | 41 |
|---|---|---|---|---|
| Data Collection | | | | |
| Space group | $P2_12_12_1$ | $P2_12_12_1$ | $P2_12_12_1$ | $P2_12_12_1$ |
| Cell dimensions | | | | |
|   a, b, c (Å) | 64.05, 83.16, 212.26 | 64.14, 83.19, 212.46 | 64.21, 83.04, 212.26 | 64.34, 82.57, 212.05 |
|   α, β, γ (°) | 90.0, 90.0, 90.0 | 90.0, 90.0, 90.0 | 90.0, 90.0, 90.0 | 90.0, 90.0, 90.0 |
| Resolution (Å) | 33.13–2.50 (2.56-2.50) | 33.16-2.48 (2.55-2.48) | 34.40-2.48 (2.54-2.48) | 34.29-2.48 (2.54-2.48) |
| $R_{mrgd-F}$ | 0.084 (0.375) | 0.054 (0.186) | 0.051 (0.184) | 0.035 (0.147) |
| $I/\sigma(I)$ | 20.51 (4.31) | 29.15 (8.34) | 30.80 (7.93) | 38.15 (11.37) |
| Completeness (%) | 99.2 (92.2) | 99.3 (93.2) | 99.4 (93.6) | 98.2 (91.1) |
| Redundancy | 6.26 (4.94) | 5.79 (4.10) | 5.40 (3.86) | 6.17 (4.25) |
| Refinement | | | | |
| Resolution (Å) | 2.50 | 2.48 | 2.48 | 2.48 |
| No. reflections | 39,826 | 40,872 | 40,869 | 40,195 |
| $R_{work}/R_{free}$ | 19.1/24.0 | 18.1/23.3 | 17.8/22.4 | 18.6/23.8 |
| No. atoms | | | | |
|   Protein | 6524 | 6539 | 6499 | 6539 |
|   Meditope | 190 | 192 | 192 | 192 |
|   Water | 361 | 485 | 466 | 475 |
| B-factors | | | | |
|   Protein | | | | |
|     Fab | 26.19 | 19.15 | 20.04 | 20.24 |
|     Meditope | 33.05 | 26.02 | 26.61 | 27.05 |
|   Water | 28.90 | 24.13 | 24.30 | 24.57 |
| r.m.s.d | | | | |
|   Bond lengths (Å) | 0.004 | 0.003 | 0.007 | 0.007 |
|   Bond angles (°) | 0.822 | 0.760 | 1.071 | 1.125 |
| Ramachandran favored/allowed/disallowed | 96.6/3.4/0.0 | 96.8/3.1/0.1 | 97.0/2.9/0.1 | 96.9/3.0/0.1 |

Figure 40 (cont'd)

| SEQ ID NO: | 42 | 43 | 44 | 46 |
|---|---|---|---|---|
| Data Collection | | | | |
| Space group | P2$_1$2$_1$2$_1$ | P2$_1$2$_1$2$_1$ | P2$_1$2$_1$2$_1$ | P2$_1$2$_1$2$_1$ |
| Cell dimensions | | | | |
| a, b, c (Å) | 64.06, 82.71, 212.39 | 64.14, 82.57, 212.07 | 64.28, 83.05, 212.37 | 63.95, 82.38, 211.54 |
| α, β, γ (°) | 90.0, 90.0, 90.0 | 90.0, 90.0, 90.0 | 90.0, 90.0, 90.0 | 90.0, 90.0, 90.0 |
| Resolution (Å) | 34.74-2.48 (2.54-2.48) | 34.26-2.55 (2.61-2.55) | 32.71-2.55 (2.62-2.55) | 34.17-2.50 (2.56-2.50) |
| R$_{mrgd-F}$ | 0.045 (0.209) | 0.101 (0.482) | 0.078 (0.313) | 0.066 (0.337) |
| I/σ(I) | 28.89 (7.15) | 20.57 (3.85) | 21.03 (4.48) | 20.98 (4.11) |
| Completeness (%) | 98.7 (89.6) | 99.2 (93.0) | 97.6 (95.1) | 99.1 (90.6) |
| Redundancy | 5.85 (4.14) | 5.49 (4.89) | 4.47 (4.69) | 3.92 (3.01) |
| Refinement | | | | |
| Resolution (Å) | 2.48 | 2.55 | 2.55 | 2.50 |
| No. reflections | 40,599 | 37,507 | 37,078 | 39,231 |
| R$_{work}$/R$_{free}$ | 17.2/21.8 | 19.8/25.2 | 18.2/22.3 | 18.2/22.9 |
| No. atoms | | | | |
|   Protein | 6539 | 6531 | 6522 | 6520 |
|   Meditope | 185 | 182 | 190 | 198 |
|   Water | 490 | 338 | 459 | 412 |
| *B*-factors | | | | |
|   Protein | | | | |
|     Fab | 21.04 | 31.73 | 23.90 | 27.12 |
|     Meditope | 26.53 | 39.04 | 37.29 | 37.46 |
|     Water | 24.76 | 31.88 | 28.49 | 29.83 |
| r.m.s.d | | | | |
|   Bond lengths (Å) | 0.007 | 0.004 | 0.003 | 0.004 |
|   Bond angles (°) | 1.136 | 0.755 | 0.767 | 0.921 |
| Ramachandran favored/allowed/disallowed | 97.1/2.9/0.0 | 96.6/3.4/0.0 | 96.5/3.5/0.0 | 96.9/3.1/0.0 |

Figure 40 (cont'd)

| SEQ ID NO: | 49 | 51 | 52 | 53 |
|---|---|---|---|---|
| Data Collection | | | | |
| Space group | $P2_12_12_1$ | $P2_12_12_1$ | $P2_12_12_1$ | $P2_12_12_1$ |
| Cell dimensions | | | | |
| a, b, c (Å) | 64.24, 82.94, 212.4 | 64.11, 82.47, 212.49 | 64.27, 82.74, 212.37 | 64.15, 82.75, 211.67 |
| α, β, γ (°) | 90.0, 90.0, 90.0 | 90.0, 90.0, 90.0 | 90.0, 90.0, 90.0 | 90.0, 90.0, 90.0 |
| Resolution (Å) | 34.38-2.52 (2.59-2.52) | 34.23-2.48 (2.54-2.48) | 34.79-2.49 (2.55-2.49) | 33.03-2.50 (2.56-2.50) |
| $R_{mrgd-F}$ | 0.057 (0.196) | 0.087 (0.374) | 0.067 (0.308) | 0.059 (0.238) |
| I/σ(I) | 26.03 (7.14) | 18.64 (4.04) | 27.61 (5.79) | 21.92 (5.96) |
| Completeness (%) | 97.4 (91.4) | 99.1 (90.3) | 99.1 (94.2) | 98.4 (91.0) |
| Redundancy | 4.60 (3.89) | 4.76 (3.19) | 4.54 (3.53) | 4.30 (3.12) |
| Refinement | | | | |
| Resolution (Å) | 2.52 | 2.48 | 2.49 | 2.50 |
| No. reflections | 38,211 | 40,649 | 40,191 | 39,261 |
| $R_{work}/R_{free}$ | 18.6/22.9 | 18.1/22.9 | 17.3/22.9 | 18.0/23.4 |
| No. atoms | | | | |
|   Protein | 6587 | 6544 | 6529 | 6549 |
|   Meditope | 196 | 197 | 185 | 206 |
|   Water | 363 | 438 | 454 | 361 |
| B-factors | | | | |
|   Protein | | | | |
|     Fab | 23.36 | 23.05 | 21.47 | 25.78 |
|     Meditope | 27.69 | 33.77 | 27.91 | 47.45 |
|   Water | 25.75 | 26.89 | 25.45 | 28.54 |
| r.m.s.d | | | | |
|   Bond lengths (Å) | 0.006 | 0.008 | 0.007 | 0.005 |
|   Bond angles (°) | 1.079 | 1.164 | 1.076 | 0.970 |
| Ramachandran favored/allowed/disallowed | 96.9/3.1/0.0 | 97.3/2.7/0.0 | 96.9/3.1/0.0 | 96.9/3.0/0.1 |

Figure 40 (cont'd)

| SEQ ID NO: | 54 | 55 |
|---|---|---|
| Data Collection | | |
| Space group | $P2_12_12_1$ | $P2_12_12_1$ |
| Cell dimensions | | |
| a, b, c (Å) | 64.58, 83.06, 211.83 | 64.18, 82.89, 212.90 |
| α, β, γ (°) | 90.0, 90.0, 90.0 | 90.0, 90.0, 90.0 |
| Resolution (Å) | 33.17-2.48 (2.55-2.48) | 34.82-2.50 (2.57-2.50) |
| $R_{mrgd-F}$ | 0.036 (0.169) | 0.064 (0.245) |
| I/σ(I) | 34.78 (9.23) | 20.15 (5.87) |
| Completeness (%) | 98.0 (85.0) | 99.6 (96.1) |
| Redundancy | 5.47 (4.28) | 4.68 (3.53) |
| Refinement | | |
| Resolution (Å) | 2.48 | 2.50 |
| No. reflections | 40,269 | 40,034 |
| $R_{work}/R_{free}$ | 19.0/23.0 | 16.8/21.6 |
| No. atoms | | |
|   Protein | 6577 | 6569 |
|   Meditope | 184 | 194 |
|   Water | 294 | 501 |
| B-factors | | |
|   Protein | | |
|     Fab | 37.76 | 20.94 |
|     Meditope | 50.14 | 28.28 |
|     Water | 36.97 | 25.34 |
| r.m.s.d | | |
|   Bond lengths (Å) | 0.004 | 0.007 |
|   Bond angles (°) | 0.864 | 1.095 |
| Ramachandran favored/allowed/disallowed | 97.1/2.8/0.1 | 96.9/3.1/0.0 |

Figure 41
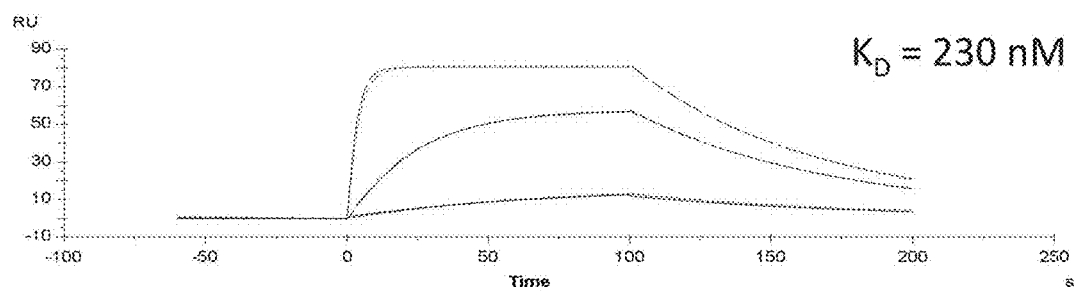
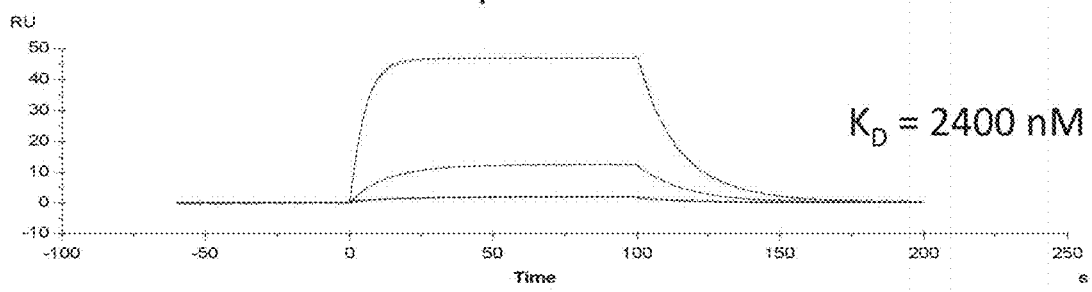

Figure 47A

A) Light chain nucleic acid (SEQ ID NO: 60) and amino acid (SEQ ID NO: 61) sequences

```
aagcttgccgccaccatggagacagacacgcttttgcttgggtgttgttgttgtgggtc
cccgttcgacccgtaccggtgacatcttgttgacgcagtccccgtcattctgagcgtg
                       D  I  L  L  T  Q  S  P  V  I  L  S  V
tccccggagagcgggtatcgttttcctgccgagcctcgcaagatatcaacactgcgatt
 S  P  G  E  R  V  S  F  S  C  R  A  S  Q  D  I  N  T  A  I
gcatggtatcaacagcgcacaaacgggtcgccgagactgctcatctactcagcctcgttc
 A  W  Y  Q  Q  R  T  N  G  S  P  R  L  L  I  Y  S  A  S  F
ctttatagcggtgtgccttcgaggttctcgggatcacggtcaggaacggattttacactc
 L  Y  S  G  V  P  S  R  F  S  G  S  R  S  G  T  D  F  T  L
agcatcaattccgtggaatcagaggacattgcggactactattgtcagcagcactacacc
 S  I  N  S  V  E  S  E  D  I  A  D  Y  Y  C  Q  Q  H  Y  T
acaccaccgaccttcggcgctgggacgaaagtcgaaatcaagcggaccgtagcagcccc
 T  P  P  T  F  G  A  G  T  K  V  E  I  K  R  T  V  A  A  P
tcggtcttatcttccctctagcgacgaacaattgaagtcagggaccgcctcggtggta
 S  V  F  I  F  P  P  S  D  E  Q  L  K  S  G  T  A  S  V  V
tgcctgcttaacaactttaccccacgggaagccaaagtacagtggaaggtggataatgcg
 C  L  L  N  N  F  Y  P  R  E  A  K  V  Q  W  K  V  D  N  A
ctccagagcggaaactcccaagagagcgtgacagaacaggactcgaaggattcgacgtac
 L  Q  S  G  N  S  Q  E  S  V  T  E  Q  D  S  K  D  S  T  Y
tcactcagctcaacgctgacctgtcgaaagcggactatgagaaacacaaggtctacgcg
 S  L  S  S  T  L  T  L  S  K  A  D  Y  E  K  H  K  V  Y  A
tgcgaggtgacccatcagggcctgagctcccccgtaactaagtcattcaaccggggtgaa
 C  E  V  T  H  Q  G  L  S  S  P  V  T  K  S  F  N  R  G  E
tgctaa
 C  -
```

Figure 47B

B) Heavy chain nucleic acid (SEQ ID NO: 62) and amino acid (SEQ ID NO: 63) sequences

```
aagcttgccgccaccatgaaatgctcgtgggtgatcttttccttatggcggtagtaacc
ggagttaactcccaagtacagcttaagcagtcggtccggggctggtgcagccatcgcag
            Q  V  Q  L  K  Q  S  G  P  G  L  V  Q  P  S  Q
tcgttgtcaatcacatgcacggtgtcgggattcaacattaaagacacctatatccactgg
 S  L  S  I  T  C  T  V  S  G  F  N  I  K  D  T  Y  I  H  W
gtccgacaatcccctggtaaagggctggagtggctcggtcggatctaccccacgaacgga
 V  R  Q  S  P  G  K  G  L  E  W  L  G  R  I  Y  P  T  N  G
tacaccaggtataacacgccctttacatcgagactttcaattaacgcggataatagcaag
 Y  T  R  Y  N  T  P  F  T  S  R  L  S  I  N  A  D  N  S  K
aatcaggtgttcttcaagatgaatagcctccagtcaaatgacactgcaatctactactgt
 N  Q  V  F  F  K  M  N  S  L  Q  S  N  D  T  A  I  Y  Y  C
gcccgctggggaggggatggcttttatgcgatggactattgggggcagggaactttggtc
 A  R  W  G  G  D  G  F  Y  A  M  D  Y  W  G  Q  G  T  L  V
acagtaagctccgctagcacaaagggacctagcgtgtttcccttggctcctcatcgaaa
 T  V  S  S  A  S  T  K  G  P  S  V  F  P  L  A  P  S  S  K
tcaacgtccggtgggacggcggcattgggtgtcttgtcaaggactatttccccgagccc
 S  T  S  G  G  T  A  A  L  G  C  L  V  K  D  Y  F  P  E  P
gtgacagtctcgtggaactcgggtgcccttacaagcgggcgtacatacgtttccgccgtg
 V  T  V  S  W  N  S  G  A  L  T  S  G  V  H  T  F  P  A  V
ctccaatcatccggactgtattcctttcatccgtcgtgactgtgccgtcctcgtcactc
 L  Q  S  S  G  L  Y  S  L  S  S  V  V  T  V  P  S  S  L
ggaacgcaaacttacatttgcaatgtcaaccacaaaccgtcaaatacaaaggtcgataag
 G  T  Q  T  Y  I  C  N  V  N  H  K  P  S  N  T  K  V  D  K
aaggtcgagccaaagtcgtgtgataagacccacacatgccctccctgtccagcgccggag
 K  V  E  P  K  S  C  D  K  T  H  T  C  P  P  C  P  A  P  E
ctgttgggagggccttcagtgttcctcttcccgcccaaacccaaggacaccctgatgatt
 L  L  G  G  P  S  V  F  L  F  P  P  K  P  K  D  T  L  M  I
agccgcacacccgaggtgacgtgtgtcgtcgtcgatgtctcacatgaggacccggaggta
 S  R  T  P  E  V  T  C  V  V  V  D  V  S  H  E  D  P  E  V
aagttcaactggtacgtggatggagtcgaagtgcacaacgcaaaaacaaaacctcgggaa
 K  F  N  W  Y  V  D  G  V  E  V  H  N  A  K  T  K  P  R  E
gagcagtacaatagcacgtacagagtagtcagcgtgctcaccgtgctgcaccaggattgg
 E  Q  Y  N  S  T  Y  R  V  V  S  V  L  T  V  L  H  Q  D  W
ctcaatggaaaggagtacaagtgtaaagtgtcgaataaggcgctgcctgccccatcgaa
 L  N  G  K  E  Y  K  C  K  V  S  N  K  A  L  P  A  P  I  E
aagacaatttccaaagctaaagggcaacccgcgagccgcaagtatacacctcccacc
 K  T  I  S  K  A  K  G  Q  P  R  E  P  Q  V  Y  T  L  P  P
tcgcgcgatgaactgaccaagaaccaggtgtcattgacgtgtctcgtcaagggcttctat
 S  R  D  E  L  T  K  N  Q  V  S  L  T  C  L  V  K  G  F  Y
ccgagcgacattgcagtagaatgggaaagcaacggacagccggaaaacaactacaagact
 P  S  D  I  A  V  E  W  E  S  N  G  Q  P  E  N  N  Y  K  T
acaccgcctgtccttgattcggatggttccttctttcttactcaaaacttacagtcgac
 T  P  P  V  L  D  S  D  G  S  F  F  L  Y  S  K  L  T  V  D
aaatcgaggtggcagcagggaaatgtgttttcgtgcagcgtgatgcacgaggccttgcat
 K  S  R  W  Q  Q  G  N  V  F  S  C  S  V  M  H  E  A  L  H
aatcactatacacagaagtcgttgtcactgtcgccgggaaagtaa
 N  H  Y  T  Q  K  S  L  S  L  S  P  G  K  -
```

White Sticks: 5-dipheylalanine meditope bound to trastuzumab MeMab;
Dark Grey Sticks: 5-diphenylalanine meditope bound to cetuximab;
Outlined Sticks show Fab residues.

```
IgG2|P01859|1-98    ASTKGPSVFPLAPCSRSTSESTAALGCLVKDYFPEPVTVSWNSGALTSGVHTFPAVLQSS 60
IgG4|P01861|1-98    ASTKGPSVFPLAPCSRSTSESTAALGCLVKDYFPEPVTVSWNSGALTSGVHTFPAVLQSS 60
IgG3|P01860|1-98    ASTKGPSVFPLAPCSRSTSGGTAALGCLVKDYFPEPVTVSWNSGALTSGVHTFPAVLQSS 60
IgG1|P01857|1-98    ASTKGPSVFPLAPSSKSTSGGTAALGCLVKDYFPEPVTVSWNSGALTSGVHTFPAVLQSS 60
                    *************.*;*  .**************************** **** sp|P01859|1-98      GLYSLSSVVTVPSSNFGTQTYTCNVDHKPSNTKVDKTV 98  (SEQ ID NO: 64)
sp|P01861|1-98      GLYSLSSVVTVPSSSLGTKTYTCNVDHKPSNTKVDKRV 98  (SEQ ID NO: 65)
sp|P01860|1-98      GLYSLSSVVTVPSSSLGTQTYTCNVNHKPSNTKVDKRV 98  (SEQ ID NO: 66)
sp|P01857|1-98      GLYSLSSVVTVPSSSLGTQTYICNVNHKPSNTKVDKKV 98  (SEQ ID NO: 67)
                    **************.**.******.*********.*
```

B.

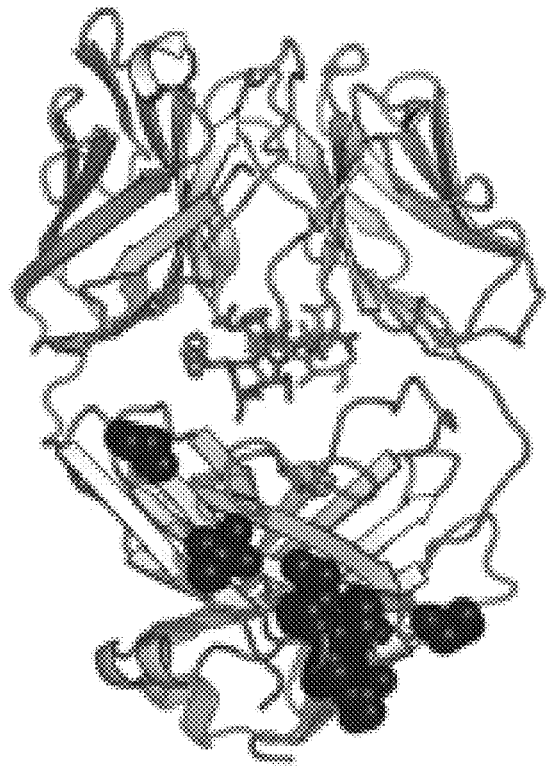

Figure 56

```
             10         20         30         40         50         60
WT      METDTLLLWVLLLWVPGSTGDIQLTQSPSSLSASVGDRVTITCRAGESVDIFGVGFLHWY
        ::::::::::::::::::::::::::::::::  :::::::::::::::::::::::::
Medi    METDTLLLWVLLLWVPGSTGDIQLTQSPVILSASVGDRVTITCRAGESVDIFGVGFLHWY
             10         20         30         40         50         60

70         80         90        100        110        120
WT      QQKPGKAPKLLIYRASNLESGVPSRFSGSGSRTDFTLTISSLQPEDFATYYCQQTNEDPY
        :::   .::::::::::::::::::::::::::::::::::::::: :::::::::::::
Medi    QQKTNGSPKLLIYRASNLESGVPSRFSGSGSRTDFTLTISSLQPEDIADYYCQQTNEDPY
             70         80         90        100        110        120

130        140        150        160        170        180
WT      TFGQGTKVEIKRTVAAPSVFIFPPSDEQLKSGAASVVCLLNNFYPREAKVQWKVDNALQS
        ::::::::::::::::::::::::::::::::::::::::::::::::::::::::::::
Medi    TFGQGTKVEIKRTVAAPSVFIFPPSDEQLKSGAASVVCLLNNFYPREAKVQWKVDNALQS
            130        140        150        160        170        180

190        200        210        220        230
WT      GNSQESVTEQDSKDSTYSLSSTLTLSKADYEKHKVYACEVTHQGLSSPVTKSFNRGEC
        :::::::::::::::::::::::::::::::::::::::::::::::::::::::::
Medi    GNSQESVTEQDSKDSTYSLSSTLTLSKADYEKHKVYACEVTHQGLSSPVTKSFNRGEC
            190        200        210        220        230
```

Figure 59
HPLC
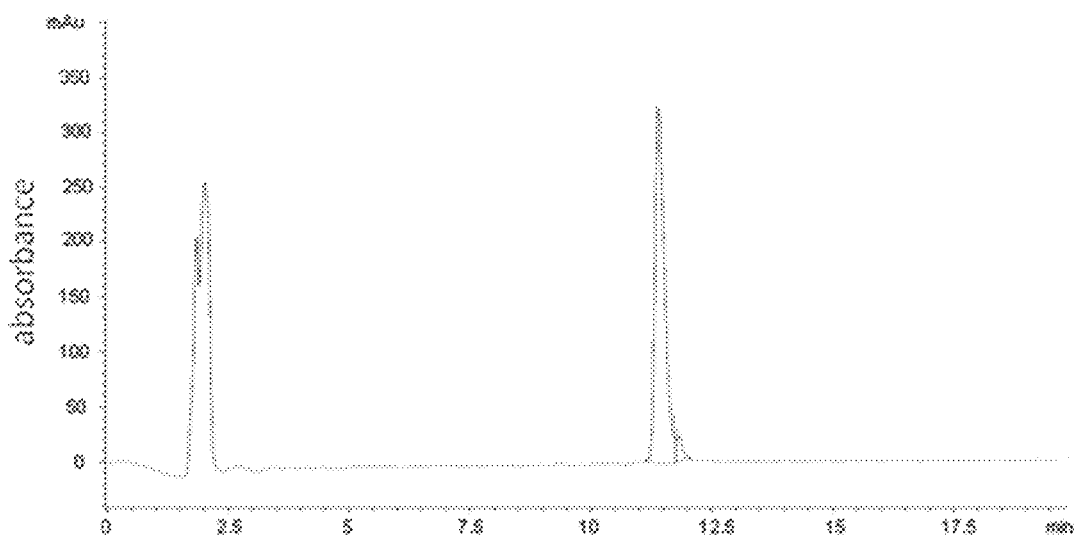
Mass Spectrum
$C_{66}H_{113}N_{19}O_{16}$, ESI-MS, calculated m/z 714.94 $[M+2H]^{2+}$, found 714.94 $[M+2H]^{2+}$.
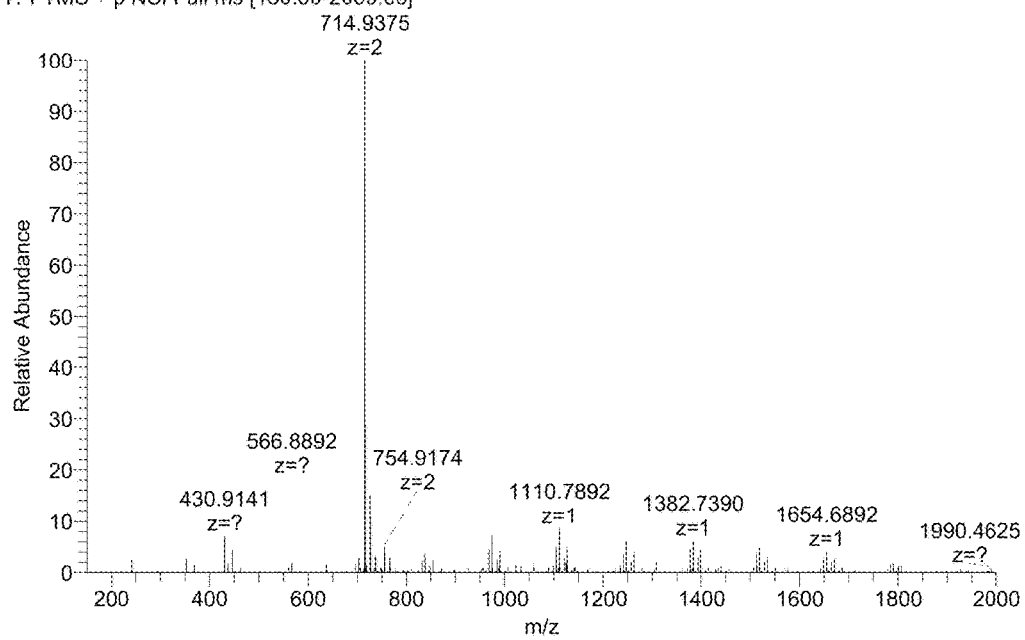

SEQUENCE LISTING

<160> NUMBER OF SEQ ID NOS: 189

<210> SEQ ID NO 1
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 1

Cys Gln Phe Asp Leu Ser Thr Arg Arg Leu Lys Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 2

Cys Gln Tyr Asn Leu Ser Ser Arg Ala Leu Lys Cys
1               5                   10

<210> SEQ ID NO 3
<211> LENGTH: 747
<212> TYPE: DNA
<213> ORGANISM: Artificial Sequence
<220> FEATURE:
<223> OTHER INFORMATION: synthetically constructed peptide-Fc fusion
      protein

<400> SEQUENCE: 3
gggggctccg gttcaggctc gggcggttca tcgggaggag ggggagggga acctaagtca      60
tgcgataaga cgcacacctg tcctccatgc ccagccccccg agttgcttgg tgggccctca    120
gtattcctct tccctccaaa acccaaagac accttgatga tttcccgcac gccggaagtc    180
acgtgtgtgg tcgtggatgt gagccatgag gatcccgagg tgaagttcaa ttggtacgtg    240
gatggagtag aggtacacaa cgcgaaaacg aagcccaggg aggaacagta caattccaca    300
tatcgcgtgg tgtccgtgct tactgtgttg catcaagact ggctgaatgg aaggagtat    360 aagtgcaaag tatcaaacaa ggcgctgcct gctccaatcg aaaagaccat ctcgaaggcg    420
aaaggacaac ccagagaacc ccaagtctac acgcttccgc cctcgcggga tgagctcacc    480
aaaaaccagg tatccctcac ttgtttggta aaaggattct acccgtcgga cattgcagtc    540
gagtgggagt cgaatgggca gccggaaaac aactacaaaa caacaccgcc cgtcttggac    600
tccgatggtt cgttctttct ctattcgaag ctcaccgtag acaagtcgag gtggcagcag    660
ggcaacgtct tttcgtgctc agtgatgcat gaggcccttc acaatcacta tacgcagaaa    720
agcctgagcc tgtcaccggg gaagtaa                                       747

<210> SEQ ID NO 4
<211> LENGTH: 261
<212> TYPE: PRT
<213> ORGANISM: Artificial Sequence
<220> FEATURE:
<223> OTHER INFORMATION: synthetically constructed peptide-Fc fusion
      protein

<400> SEQUENCE: 4

Cys Gln Phe Asp Leu Ser Thr Arg Arg Leu Lys Cys Gly Gly Gly Ser
1               5                   10                  15

Gly Ser Gly Ser Gly Gly Ser Ser Gly Gly Gly Gly Glu Pro Lys
            20                  25                  30

Ser Cys Asp Lys Thr His Thr Cys Pro Pro Cys Pro Ala Pro Glu Leu
            35                  40                  45

Leu Gly Gly Pro Ser Val Phe Leu Phe Pro Pro Lys Pro Lys Asp Thr
        50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260

<210> SEQ ID NO 5
<211> LENGTH: 1410
<212> TYPE: DNA
<213> ORGANISM: Homo sapiens

<400> SEQUENCE: 5
atgaaatgct cgtgggtgat cttttccctt atggcggtag taaccggagt aaactccgag      60
gtccagctcg tcgaatccgg tggcggcttg gtgcagccgg gtgggtcgtt gcgactgtcg     120
tgcgcagcgt cggggtttaa catcaaagac acctatatcc actgggtgag caatcgccc      180
ggaaagggc tcgaatgggt agccagaatc taccctacga atggttatac tcgatatgcg     240
gactccgtga aggaagatt caccatcagc gcagatacgt ccaaaaacac tgcataccctc    300
cagatgaata gccttcgggc ggaggacacg gcgatctact actgtagccg gtggggtggg     360
gacgggttct atgcgatgga ctactgggga caggggacgc ttgtaacggt cagctcggcg     420
tcaacaaagg gacctagcgt gtttcccttg gctccctcat cgaaatcaac gtccggtggg     480
acggcggcat tggggtgtct tgtcaaggac tatttccccg agcccgtgac agtctcgtgg     540
aactcgggtg cccttacaag cggcgtacat acgtttcccg ccgtgctcca atcatccgga     600
ctgtattccc tttcatccgt cgtgactgtg ccgtcctcgt cactcggaac gcaaacttac     660
atttgcaatg tcaaccacaa accgtcaaat acaaaggtcg ataagaaggt cgagccaaag     720
tcgtgtgata gacccacac atgccctccc tgtccagcgc cggagctgtt gggagggcct     780
tcagtgttcc tcttcccgcc caaacccaag gacaccctga tgattagccg cacacccgag     840
gtgacgtgtg tcgtcgtcga tgtctcacat gaggacccgg aggtaaagtt caactggtac     900
gtggatggag tcgaagtgca aacgcaaaaa acaaaacctc gggaagagca gtacaatagc     960
acgtacagag tagtcagcgt gctcaccgtg ctgcaccagg attggctcaa tggaaaggag    1020
tacaagtgta aagtgtcgaa taaggcgctg cctgccccca tcgaaaagac aatttccaaa    1080
gctaaagggc aaccccgcga gccgcaagta tacaccctcc caccctcgcg cgatgaactg    1140

-continued

```
accaagaacc aggtgtcatt gacgtgtctc gtcaagggct tctatccgag cgacattgca      1200
gtagaatggg aaagcaacgg acagccggaa acaactaca agactacacc gcctgtcctt      1260
gattcggatg gttccttctt tctttactca aaacttacag tcgacaaatc gaggtggcag     1320
cagggaaatg tgttttcgtg cagcgtgatg cacgaggcct tgcataatca ctatacacag     1380
aagtcgttgt cactgtcgcc gggaaagtaa                                      1410
```

<210> SEQ ID NO 6
<211> LENGTH: 184
<212> TYPE: PRT
<213> ORGANISM: Homo sapiens

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ser Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser
            180

<210> SEQ ID NO 7
<211> LENGTH: 184
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys

```
                    85                  90                  95
Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser
                180
```

<210> SEQ ID NO 8
<211> LENGTH: 705
<212> TYPE: DNA
<213> ORGANISM: Homo sapiens

<400> SEQUENCE: 8

```
atggagacag acacgctttt gctttgggtg ttgttgttgt gggtccccgg ttcgacgggg    60
gatattcaga tgacccagtc accgatcctt ctctcggcga gcgtggggga tagagtaacg   120
atcacgtgta gagcgtccca agacgtcaac acagctgtcg cgtggtatca gcagcggaca   180
aatggatcgc cgaggctcct gatctacagc gcatcatttc tctattcggg agtcccctcc   240
cgattttccg gatcgcgcag cggtactgac ttcaccctca cgatttcctc ccttcaaccg   300
gaagatatcg ctgattacta ctgtcagcag cactatacaa cacctcccac tttcggagca   360
gggacaaaag tggagattaa gcgcactgta gcagcccccct cggtctttat cttccctcct   420
agcgacgaac aattgaagtc agggaccgcc tcggtggtat gcctgcttaa caacttttac   480
ccacgggaag ccaaagtaca gtggaaggtg gataatgcgc tccagagcgg aaactcccaa   540
gagagcgtga cagaacagga ctcgaaggat tcgacgtact cactcagctc aacgctgacc   600
ctgtcgaaag cggactatga gaaacacaag gtctacgcgt gcgaggtgac ccatcagggc   660
ctgagctccc ccgtaactaa gtcattcaac cggggtgaat gctaa                   705
```

<210> SEQ ID NO 9
<211> LENGTH: 214
<212> TYPE: PRT
<213> ORGANISM: Homo sapiens

<400> SEQUENCE: 9

```
Asp Ile Gln Met Thr Gln Ser Pro Ile Leu Leu Ser Ala Ser Val Gly
  1               5                  10                  15

Asp Arg Val Thr Ile Thr Cys Arg Ala Ser Gln Asp Val Asn Thr Ala
             20                  25                  30

Val Ala Trp Tyr Gln Gln Arg Thr Asn Gly Ser Pro Arg Leu Leu Ile
         35                  40                  45

Tyr Ser Ala Ser Phe Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Ile Ala Asp Tyr Tyr Cys Gln Gln His Tyr Thr Thr Pro Pro
                 85                  90                  95

Thr Phe Gly Ala Gly Thr Lys Val Glu Ile Lys Arg Thr Val Ala Ala
```

```
                100             105             110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135             140

Lys Val Gln Trp Lys Val Asp Asn Ala Leu Gln Ser Gly Asn Ser Gln
145             150                 155                 160

Glu Ser Val Thr Glu Gln Asp Ser Lys Asp Ser Thr Tyr Ser Leu Ser
        165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 10
<211> LENGTH: 214
<212> TYPE: PRT
<213> ORGANISM: Homo sapiens

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135             140

Lys Val Gln Trp Lys Val Asp Asn Ala Leu Gln Ser Gly Asn Ser Gln
145             150                 155                 160

Glu Ser Val Thr Glu Gln Asp Ser Lys Asp Ser Thr Tyr Ser Leu Ser
        165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 11
<211> LENGTH: 1440
<212> TYPE: DNA
<213> ORGANISM: Homo sapiens

<400> SEQUENCE: 11

```
tcactatagg ggaagcttgc cgccaccatg aaatgctcgt gggtgatctt tttccttatg      60
gcggtagtaa ccggagttaa ctccgaggtc cagctcgtcg aatccggtgg cggcttggtg     120
cagccgggtg ggtcgttgcg actgtcgtgc gcagcgtcgg ggtttaacat caaagacacc     180
tatatccact gggtgaggca agcgcccgga aaggggctcg aatgggtagc cagaatctac     240
cctacgaatg gttatactcg atatgcggac tccgtgaaag gaagattcac catcagcgca     300
gatacgtcca aaacactgc ataccctccag atgaatagcc ttcgggcgga ggacacggcg     360
gtctactact gtagccggtg gggtggggac gggttctatg cgatggacta ctggggacag     420
gggacgcttg taacggtcag ctcggctagc acaaagggac ctagcgtgtt tcccttggct     480
ccctcatcga atcaacgtc cggtgggacg gcggcattgg ggtgtcttgt caaggactat     540
ttccccgagc ccgtgacagt ctcgtggaac tcgggtgccc ttacaagcgg cgtacatacg     600
tttcccgccg tgctccaatc atccggactg tattcccttt catccgtcgt gactgtgccg     660
tcctcgtcac tcggaacgca aacttacatt tgcaatgtca accacaaacc gtcaaataca     720
aaggtcgata agaaggtcga gccaaagtcg tgtgataaga cccacacatg ccctccctgt     780
ccagcgccgg agctgttggg agggccttca gtgttcctct tcccgcccaa acccaaggac     840
accctgatga ttagccgcac acccgaggtg acgtgtgtcg tcgtcgatgt ctcacatgag     900
gacccggagg taaagttcaa ctggtacgtg gatggagtcg aagtgcacaa cgcaaaaaca     960
aaacctcggg aagagcagta caatagcacg tacagagtag tcagcgtgct caccgtgctg    1020
caccaggatt ggctcaatgg aaaggagtac aagtgtaaag tgtcgaataa ggcgctgcct    1080
gcccccatcg aaaagacaat ttccaaagct aaagggcaac cccgcgagcc gcaagtatac    1140
accctcccac cctcgcgcga tgaactgacc aagaaccagg tgtcattgac gtgtctcgtc    1200
aagggcttct atccgagcga cattgcagta gaatgggaaa gcaacggaca gccggaaaac    1260
aactacaaga ctacaccgcc tgtccttgat tcggatggtt ccttctttct ttactcaaaa    1320
cttacagtcg acaaatcgag gtggcagcag ggaaatgtgt tttcgtgcag cgtgatgcac    1380
gaggccttgc ataatcacta tacacagaag tcgttgtcac tgtcgccggg aaagtaatga    1440
```

<210> SEQ ID NO 12
<211> LENGTH: 477
<212> TYPE: PRT
<213> ORGANISM: Homo sapiens

<400> SEQUENCE: 12

```
Ser Leu Gly Lys Leu Ala Ala Thr Met Lys Cys Ser Trp Val Ile Phe
  1               5                  10                  15

Phe Leu Met Ala Val Val Thr Gly Val Asn Ser Glu Val Gln Leu Val
             20                  25                  30

Glu Ser Gly Gly Gly Leu Val Gln Pro Gly Gly Ser Leu Arg Leu Ser
         35                  40                  45

Cys Ala Ala Ser Gly Phe Asn Ile Lys Asp Thr Tyr Ile His Trp Val
     50                  55                  60

Arg Gln Ala Pro Gly Lys Gly Leu Glu Trp Val Ala Arg Ile Tyr Pro
 65                  70                  75                  80

Thr Asn Gly Tyr Thr Arg Tyr Ala Asp Ser Val Lys Gly Arg Phe Thr
                 85                  90                  95

Ile Ser Ala Asp Thr Ser Lys Asn Thr Ala Tyr Leu Gln Met Asn Ser
            100                 105                 110
```

```
Leu Arg Ala Glu Asp Thr Ala Val Tyr Tyr Cys Ser Arg Trp Gly Gly
            115                 120                 125

Asp Gly Phe Tyr Ala Met Asp Tyr Trp Gly Gln Gly Thr Leu Val Thr
        130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 13
<211> LENGTH: 730
<212> TYPE: DNA
<213> ORGANISM: Homo sapiens

<400> SEQUENCE: 13 atagggaag cttgccgcca ccatggagac agacacgctt ttgctttggg tgttgttgtt      60
```

-continued

```
gtgggtcccc ggttcgaccg gtgatattca gatgacccag tcaccgtcat cccttcggc     120
gagcgtgggg gatagagtaa cgatcacgtg tagagcgtcc caagacgtca acacagctgt    180
cgcgtggtat cagcagaagc caggaaaagc gccgaagctc ctgatctaca gcgcatcatt    240
tctctattcg ggagtcccct cccgattttc cggatcgcgc agcggtactg acttcaccct    300
cacgatttcc tcccttcaac cggaagattt tgctacttac tactgtcagc agcactatac    360
aacacctccc actttcggac aggggacaaa agtggagatt aagcggaccg tagcagcccc    420
ctcggtcttt atcttccctc ctagcgacga acaattgaag tcaggaccg cctcggtggt     480
atgcctgctt aacaactttt acccacggga agccaaagta cagtggaagg tggataatgc    540
gctccagagc ggaaactccc aagagagcgt gacagaacag gactcgaagg attcgacgta    600
ctcactcagc tcaacgctga ccctgtcgaa agcggactat gagaaacaca aggtctacgc    660
gtgcgaggtg acccatcagg gcctgagctc ccccgtaact aagtcattca accggggtga    720
atgctaatga                                                           730
```

<210> SEQ ID NO 14
<211> LENGTH: 240
<212> TYPE: PRT
<213> ORGANISM: Homo sapiens

<400> SEQUENCE: 14

Gly Lys Leu Ala Ala Thr Met Glu Thr Asp Thr Leu Leu Trp Val
1               5                   10                  15

Leu Leu Leu Trp Val Pro Gly Ser Thr Gly Asp Ile Gln Met Thr Gln
            20                  25                  30

Ser Pro Ser Ser Leu Ser Ala Ser Val Gly Asp Arg Val Thr Ile Thr
        35                  40                  45

Cys Arg Ala Ser Gln Asp Val Asn Thr Ala Val Ala Trp Tyr Gln Gln
    50                  55                  60

Lys Pro Gly Lys Ala Pro Lys Leu Leu Ile Tyr Ser Ala Ser Phe Leu
65                  70                  75                  80

Tyr Ser Gly Val Pro Ser Arg Phe Ser Gly Ser Arg Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln His Tyr Thr Thr Pro Pro Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 15

```
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 2
<223> OTHER INFORMATION: Xaa =D-glutamine

<400> SEQUENCE: 15

Cys Xaa Phe Asp Leu Ser Thr Arg Arg Leu Lys Cys
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 16

Cys Gln Tyr Asp Leu Ser Thr Arg Arg Leu Lys Cys
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 3
<223> OTHER INFORMATION: Xaa = beta-beta'-di-phenyl-Ala

<400> SEQUENCE: 17

Cys Gln Xaa Asp Leu Ser Thr Arg Arg Leu Lys Cys
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 5
<223> OTHER INFORMATION: Xaa = beta-beta'-di-phenyl-Ala

<400> SEQUENCE: 18

Cys Gln Phe Asp Xaa Ser Thr Arg Arg Leu Lys Cys
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 9
<223> OTHER INFORMATION: Xaa = citrulline

<400> SEQUENCE: 19

Cys Gln Phe Asp Phe Ser Thr Arg Xaa Leu Lys Cys
 1               5                  10
```

```
<210> SEQ ID NO 20
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 20

Cys Gln Phe Asp Phe Ser Thr Arg Arg Leu Lys Cys
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 21

Cys Gln Phe Asp Glu Ser Thr Arg Arg Leu Lys Cys
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 22

Cys Gln Phe Asp Tyr Ser Thr Arg Arg Leu Lys Cys
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 23

Cys Gln Phe Asp Leu Ser Thr Arg Arg Gln Lys Cys
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 24

Cys Gln Phe Asp Leu Ser Thr Arg Gln Leu Lys Cys
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 25

Cys Gln Tyr Asn Leu Ser Thr Ala Arg Leu Lys Cys
 1               5                  10
```

```
<210> SEQ ID NO 26
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 26

Cys Gln Ala Asp Leu Ser Thr Arg Arg Leu Lys Cys
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 27

Cys Gln Phe Asp Ala Ser Thr Arg Arg Leu Lys Cys
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 28

Cys Gln Phe Asp Leu Ser Thr Ala Arg Leu Lys Cys
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 29

Cys Gln Phe Asp Leu Ser Thr Arg Arg Ala Lys Cys
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 30

Cys Gln Phe Asp Leu Ser Thr Arg Arg Glu Lys Cys
 1               5                  10

<210> SEQ ID NO 31
<211> LENGTH: 17
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 1
<223> OTHER INFORMATION: Xaa = N-acetylcysteine

<400> SEQUENCE: 31

Xaa Gln Phe Asp Leu Ser Thr Arg Arg Leu Arg Cys Gly Gly Gly Ser
```

-continued

```
1               5                   10                  15
Lys

<210> SEQ ID NO 32
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 32

Gly Gln Phe Asp Leu Ser Thr Arg Arg Leu Lys Gly
1               5                   10

<210> SEQ ID NO 33
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 33

Gly Gln His Asp Leu Ser Thr Arg Arg Leu Lys Gly
1               5                   10

<210> SEQ ID NO 34
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 34

Gly Gln Asn Asp Leu Ser Thr Arg Arg Leu Lys Gly
1               5                   10

<210> SEQ ID NO 35
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 35

Gly Gln Gln Asp Leu Ser Thr Arg Arg Leu Lys Gly
1               5                   10

<210> SEQ ID NO 36
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 3
<223> OTHER INFORMATION: Xaa = 2-bromo-L-phenylalanine

<400> SEQUENCE: 36

Gly Gln Xaa Asp Leu Ser Thr Arg Arg Leu Lys Gly
1               5                   10

<210> SEQ ID NO 37
<211> LENGTH: 12
<212> TYPE: PRT
<213> ORGANISM: Artificial Sequence
<220> FEATURE:
```

```
<223> OTHER INFORMATION: synthetically constructed peptide
<220> FEATURE:
<221> NAME/KEY: VARIANT
<222> LOCATION: 3
<223> OTHER INFORMATION: Xaa = 3-bromo-L-phenylalanine

<400> SEQUENCE: 37

Gly Gln Xaa Asp Leu Ser Thr Arg Arg Leu Lys Gly
 1               5                  10

<210> SEQ ID NO 38
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 3
<223> OTHER INFORMATION: Xaa = 4-bromo-L-phenylalanine

<400> SEQUENCE: 38

Gly Gln Xaa Asp Leu Ser Thr Arg Arg Leu Lys Gly
 1               5                  10

<210> SEQ ID NO 39
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 9
<223> OTHER INFORMATION: Xaa = citrulline

<400> SEQUENCE: 39

Gly Gln Phe Asp Leu Ser Thr Arg Xaa Leu Lys Gly
 1               5                  10

<210> SEQ ID NO 40
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 8, 9
<223> OTHER INFORMATION: Xaa = citrulline

<400> SEQUENCE: 40

Gly Gln Phe Asp Leu Ser Thr Xaa Xaa Leu Lys Gly
 1               5                  10

<210> SEQ ID NO 41
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 8
<223> OTHER INFORMATION: Xaa = citrulline

<400> SEQUENCE: 41

Gly Gln Phe Asp Leu Ser Thr Xaa Arg Leu Lys Gly
 1               5                  10
```

```
<210> SEQ ID NO 42
<211> LENGTH: 11
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 11
<223> OTHER INFORMATION: Xaa = 7-aminoheptanoic acid

<400> SEQUENCE: 42

Gln Phe Asp Leu Ser Thr Arg Arg Leu Lys Xaa
 1               5                  10

<210> SEQ ID NO 43
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 1, 12
<223> OTHER INFORMATION: Xaa = beta-alanine

<400> SEQUENCE: 43

Xaa Gln Phe Asp Leu Ser Thr Arg Arg Leu Lys Xaa
 1               5                  10

<210> SEQ ID NO 44
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 1
<223> OTHER INFORMATION: Xaa = diaminopropionic acid
<220> FEATURE:
<221> NAME/KEY: VARIANT
<222> LOCATION: 12
<223> OTHER INFORMATION: Xaa = iso-aspartic acid

<400> SEQUENCE: 44

Xaa Gln Phe Asp Leu Ser Thr Arg Arg Leu Lys Xaa
 1               5                  10

<210> SEQ ID NO 45
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 1
<223> OTHER INFORMATION: Xaa = beta-alanine
<220> FEATURE:
<221> NAME/KEY: VARIANT
<222> LOCATION: 12
<223> OTHER INFORMATION: Xaa = iso-aspartic acid

<400> SEQUENCE: 45

Xaa Gln Phe Asp Leu Ser Thr Arg Arg Leu Lys Xaa
 1               5                  10

<210> SEQ ID NO 46
<211> LENGTH: 12
```

```
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 1
<223> OTHER INFORMATION: Xaa = diaminoproprionic acid
<220> FEATURE:
<221> NAME/KEY: VARIANT
<222> LOCATION: 12
<223> OTHER INFORMATION: Xaa = beta-alanine

<400> SEQUENCE: 46

Xaa Gln Phe Asp Leu Ser Thr Arg Arg Leu Lys Xaa
 1               5                  10

<210> SEQ ID NO 47
<211> LENGTH: 9
<212> TYPE: PRT
<213> ORGANISM: Artificial Sequence
<220> FEATURE:
<223> OTHER INFORMATION: synthetically constructed peptide

<400> SEQUENCE: 47

Phe Asp Leu Ser Thr Arg Arg Leu Lys
 1               5

<210> SEQ ID NO 48
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 48

Cys Gln Phe Asp Leu Ser Thr Arg Arg Leu Lys Cys
 1               5                  10

<210> SEQ ID NO 49
<211> LENGTH: 11
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 11
<223> OTHER INFORMATION: Xaa = 7-aminoheptanoic acid

<400> SEQUENCE: 49

Gln Tyr Asp Leu Ser Thr Arg Arg Leu Lys Xaa
 1               5                  10

<210> SEQ ID NO 50
<211> LENGTH: 12
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 1
<223> OTHER INFORMATION: Xaa = beta-Azidoalanine
<220> FEATURE:
<221> NAME/KEY: VARIANT
<222> LOCATION: 12
<223> OTHER INFORMATION: Xaa = propargylglycine

<400> SEQUENCE: 50
```

```
Xaa Gln Phe Asp Leu Ser Thr Arg Arg Leu Lys Xaa
1               5                   10

<210> SEQ ID NO 51
<211> LENGTH: 11
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 2
<223> OTHER INFORMATION: Xaa = beta-beta'-di-phenyl-Ala
<220> FEATURE:
<221> NAME/KEY: VARIANT
<222> LOCATION: 11
<223> OTHER INFORMATION: Xaa = 7-aminoheptanoic acid

<400> SEQUENCE: 51

Gln Xaa Asp Leu Ser Thr Arg Arg Leu Lys Xaa
1               5                   10

<210> SEQ ID NO 52
<211> LENGTH: 11
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 1
<223> OTHER INFORMATION: Xaa = D-glutamine
<220> FEATURE:
<221> NAME/KEY: VARIANT
<222> LOCATION: 11
<223> OTHER INFORMATION: Xaa = 7-aminoheptanoic acid

<400> SEQUENCE: 52

Xaa Phe Asp Leu Ser Thr Arg Arg Leu Lys Xaa
1               5                   10

<210> SEQ ID NO 53
<211> LENGTH: 11
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 2, 4
<223> OTHER INFORMATION: Xaa = beta-beta'-di-phenyl-Ala
<220> FEATURE:
<221> NAME/KEY: VARIANT
<222> LOCATION: 11
<223> OTHER INFORMATION: Xaa = 7-aminoheptanoic acid

<400> SEQUENCE: 53

Gln Xaa Asp Xaa Ser Thr Arg Arg Leu Lys Xaa
1               5                   10

<210> SEQ ID NO 54
<211> LENGTH: 11
<212> TYPE: PRT
<213> ORGANISM: Artificial Sequence
<220> FEATURE:
<223> OTHER INFORMATION: synthetically constructed peptide
<220> FEATURE:
<221> NAME/KEY: VARIANT
<222> LOCATION: 7
<223> OTHER INFORMATION: Xaa = n-butyl-arginine
<220> FEATURE:
<221> NAME/KEY: VARIANT
```

<222> LOCATION: 11
<223> OTHER INFORMATION: Xaa = 7-aminoheptanoic acid

<400> SEQUENCE: 54

Gln Phe Asp Leu Ser Thr Xaa Arg Leu Lys Xaa
 1               5                  10

<210> SEQ ID NO 55
<211> LENGTH: 12
<212> TYPE: PRT
<213> ORGANISM: Artificial Sequence
<220> FEATURE:
<223> OTHER INFORMATION: synthetically constructed peptide

<400> SEQUENCE: 55

Ser Gln Phe Asp Leu Ser Thr Arg Arg Leu Lys Ser
 1               5                  10

<210> SEQ ID NO 56
<211> LENGTH: 594
<212> TYPE: DNA
<213> ORGANISM: Artificial Sequence
<220> FEATURE:
<223> OTHER INFORMATION: synthetically constructed SMT3-peptide-Protein
      L fusion

<400> SEQUENCE: 56
catcatcatc atcatcacag cagcggcctg gtgccgcgcg gcagccatat ggctagcatg     60
tcggactcag aagtcaatca agaagctaag ccagaggtca agccagaagt caagcctgag    120
actcacatca atttaaaggt gtccgatgga tcttcagaga tcttcttcaa gatcaaaaag    180
accactcctt taagaaggct gatggaagcg ttcgctaaaa gacagggtaa ggaaatggac    240
tccttaagat tcttgtacga cggtattaga attcaagctg atcagacccc tgaagatttg    300
gacatggagg ataacgatat tattgaggct cacagagaac agattggtgg atcctgccag    360
tttgatctga gcacccgccg tctgaaatgc ggtggcggtg atccgaagt taccatcaaa    420 gtcaacctga ttttcgcaga cggcaaaatc cagacggctg aatttaaagg cacgttcgaa    480
gaagctacgg cggaagcata tcgttacgcg gccctgctgg cgaaagtgaa cggcgaatac    540
acggcagacc tggaagacgg cggcaatcac atgaacatca aattcgctgg ctaa          594

<210> SEQ ID NO 57
<211> LENGTH: 197
<212> TYPE: PRT
<213> ORGANISM: Artificial Sequence
<220> FEATURE:
<223> OTHER INFORMATION: synthetically constructed
      His6-SMT3-peptide-Protein L fusion

<400> SEQUENCE: 57

His His His His His His Ser Ser Gly Leu Val Pro Arg Gly Ser His
 1               5                  10                  15

Met Ala Ser Met Ser Asp Ser Glu Val Asn Gln Glu Ala Lys Pro Glu
                20                  25                  30

Val Lys Pro Glu Val Lys Pro Glu Thr His Ile Asn Leu Lys Val Ser
            35                  40                  45

Asp Gly Ser Ser Glu Ile Phe Phe Lys Ile Lys Lys Thr Thr Pro Leu
        50                  55                  60

Arg Arg Leu Met Glu Ala Phe Ala Lys Arg Gln Gly Lys Glu Met Asp
65                  70                  75                  80

Ser Leu Arg Phe Leu Tyr Asp Gly Ile Arg Ile Gln Ala Asp Gln Thr

```
                    85                  90                  95
Pro Glu Asp Leu Asp Met Glu Asp Asn Asp Ile Ile Glu Ala His Arg
                100                 105                 110

Glu Gln Ile Gly Gly Ser Cys Gln Phe Asp Leu Ser Thr Arg Arg Leu
            115                 120                 125

Lys Cys Gly Gly Gly Ser Glu Val Thr Ile Lys Val Asn Leu Ile
130                 135                 140

Phe Ala Asp Gly Lys Ile Gln Thr Ala Glu Phe Lys Gly Thr Phe Glu
145                 150                 155                 160

Glu Ala Thr Ala Glu Ala Tyr Arg Tyr Ala Ala Leu Leu Ala Lys Val
                165                 170                 175

Asn Gly Glu Tyr Thr Ala Asp Leu Glu Asp Gly Gly Asn His Met Asn
            180                 185                 190

Ile Lys Phe Ala Gly
            195

<210> SEQ ID NO 58
<211> LENGTH: 80
<212> TYPE: PRT
<213> ORGANISM: Artificial Sequence
<220> FEATURE:
<223> OTHER INFORMATION: synthetically constructed peptide-Protein L
      fusion

<400> SEQUENCE: 58

Ser Cys Gln Phe Asp Leu Ser Thr Arg Arg Leu Lys Cys Gly Gly Gly
1               5                   10                  15

Gly Ser Glu Val Thr Ile Lys Val Asn Leu Ile Phe Ala Asp Gly Lys
            20                  25                  30

Ile Gln Thr Ala Glu Phe Lys Gly Thr Phe Glu Glu Ala Thr Ala Glu
        35                  40                  45

Ala Tyr Arg Tyr Ala Ala Leu Leu Ala Lys Val Asn Gly Glu Tyr Thr
    50                  55                  60

Ala Asp Leu Glu Asp Gly Gly Asn His Met Asn Ile Lys Phe Ala Gly
65                  70                  75                  80

<210> SEQ ID NO 59
<211> LENGTH: 80
<212> TYPE: PRT
<213> ORGANISM: Artificial Sequence
<220> FEATURE:
<223> OTHER INFORMATION: synthetically constructed peptide-Protein L
      fusion

<400> SEQUENCE: 59

Ser Cys Gln Phe Asp Leu Ser Thr Arg Arg Leu Arg Cys Gly Gly Gly
1               5                   10                  15

Gly Ser Glu Val Thr Ile Arg Val Asn Leu Ile Phe Ala Asp Gly Asn
            20                  25                  30

Ile Gln Thr Ala Glu Phe Arg Gly Thr Phe Glu Glu Ala Thr Ala Glu
        35                  40                  45

Ala Tyr Arg Tyr Ala Ala Leu Leu Ala Arg Val Asn Gly Glu Tyr Thr
    50                  55                  60

Ala Asp Leu Glu Asp Gly Gly Asn His Met Asn Ile Lys Phe Ala Gly
65                  70                  75                  80

<210> SEQ ID NO 60
<211> LENGTH: 726
<212> TYPE: DNA
```

<213> ORGANISM: Artificial Sequence
<220> FEATURE:
<223> OTHER INFORMATION: synthetic light chain

<400> SEQUENCE: 60

```
aagcttgccg ccaccatgga cacagacacg cttttgcttt gggtgttgtt gttgtgggtc      60
cccggttcga ccggtaccgg tgacatcttg ttgacgcagt cccccgtcat tctgagcgtg     120
tcccccggag agcgggtatc gttttcctgc cgagcctcgc aagatatcaa cactgcgatt     180
gcatggtatc aacagcgcac aaacgggtcg ccgagactgc tcatctactc agcctcgttc     240
ctttatagcg gtgtgccttc gaggttctcg ggatcacggt caggaacgga ttttacactc     300
agcatcaatt ccgtggaatc agaggacatt gcggactact attgtcagca gcactacacc     360
acaccaccga ccttcggcgc tgggacgaaa gtcgaaatca gcggaccgt agcagccccc      420
tcggtctttta tcttccctcc tagcgacgaa caattgaagt cagggaccgc ctcggtggta    480
tgcctgctta acaactttta cccacgggaa gccaaagtac agtggaaggt ggataatgcg     540
ctccagagcg gaaactccca agagagcgtg acagaacagg actcgaagga ttcgacgtac     600
tcactcagct caacgctgac cctgtcgaaa gcggactatg agaaacacaa ggtctacgcg     660
tgcgaggtga cccatcaggg cctgagctcc cccgtaacta agtcattcaa ccggggtgaa     720
tgctaa                                                                 726
```

<210> SEQ ID NO 61
<211> LENGTH: 241
<212> TYPE: PRT
<213> ORGANISM: Artificial Sequence
<220> FEATURE:
<223> OTHER INFORMATION: synthetic light chain

<400> SEQUENCE: 61

```
Lys Leu Ala Ala Thr Met Glu Thr Asp Thr Leu Leu Leu Trp Val Leu
  1               5                  10                  15

Leu Leu Trp Val Pro Gly Ser Thr Gly Thr Gly Asp Ile Leu Leu Thr
             20                  25                  30

Gln Ser Pro Val Ile Leu Ser Val Ser Pro Gly Glu Arg Val Ser Phe
         35                  40                  45

Ser Cys Arg Ala Ser Gln Asp Ile Asn Thr Ala Ile Ala Trp Tyr Gln
     50                  55                  60

Gln Arg Thr Asn Gly Ser Pro Arg Leu Leu Ile Tyr Ser Ala Ser Phe
 65                  70                  75                  80

Leu Tyr Ser Gly Val Pro Ser Arg Phe Ser Gly Ser Arg Ser Gly Thr
                 85                  90                  95

Asp Phe Thr Leu Ser Ile Asn Ser Val Glu Ser Glu Asp Ile Ala Asp
            100                 105                 110

Tyr Tyr Cys Gln Gln His Tyr Thr Thr Pro Thr Phe Gly Ala Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
```

195                 200                 205
Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 62
<211> LENGTH: 1425
<212> TYPE: DNA
<213> ORGANISM: Artificial Sequence
<220> FEATURE:
<223> OTHER INFORMATION: synthetic heavy chain

<400> SEQUENCE: 62
aagcttgccg ccaccatgaa atgctcgtgg gtgatctttt tccttatggc ggtagtaacc      60
ggagttaact cccaagtaca gcttaagcag tcgggtccgg ggctggtgca gccatcgcag     120
tcgttgtcaa tcacatgcac ggtgtcggga ttcaacatta agacaccta tatccactgg     180
gtccgacaat cccctggtaa agggctggag tggctcggtc ggatctaccc cacgaacgga     240
tacaccaggt ataacacgcc ctttacatcg agctttcaa ttaacgcgga taatagcaag     300
aatcaggtgt tcttcaagat gaatagcctc cagtcaaatg acactgcaat ctactactgt     360
gcccgctggg gaggggatgg ctttatgcg atggactatt ggggcagggg aacttttggtc     420
acagtaagct ccgctagcac aaagggacct agcgtgttc ccttggctcc ctcatcgaaa     480
tcaacgtccg gtgggacggc ggcattgggg tgtcttgtca aggactatt ccccgagccc     540
gtgacagtct cgtggaactc gggtgcccct acaagcggcg tacatacgtt cccgccgtg     600
ctccaatcat ccgactgta ttccctttca tccgtcgtga ctgtgccgtc ctcgtcactc     660
ggaacgcaaa cttacatttg caatgtcaac cacaaaccgt caaatacaaa ggtcgataag     720
aaggtcgagc caaagtcgtg tgataagacc cacacatgcc ctccctgtcc agcgccggag     780
ctgttgggag gccttcagt gttcctcttc ccgcccaaac ccaaggacac cctgatgatt     840
agccgcacac ccgaggtgac gtgtgtcgtc gtcgatgtct cacatgagga cccgaggta     900
aagttcaact ggtacgtgga tggagtcgaa gtgcacaacg caaaaacaaa acctcgggaa     960
gagcagtaca atagcacgta cagagtagtc agcgtgctca ccgtgctgca ccaggattgg    1020
ctcaatggaa aggagtacaa gtgtaaagtg tcgaataagg cgctgcctgc ccccatcgaa    1080
aagacaattt ccaaagctaa agggcaaccc cgcgagccgc aagtatacac cctcccaccc    1140
tcgcgcgatg aactgaccaa gaaccaggtg tcattgacgt gtctcgtcaa gggcttctat    1200
ccgagcgaca ttgcagtaga atgggaaagc aacggacagc cggaaaacaa ctacaagact    1260
acaccgcctg tccttgattc ggatggttcc ttctttcttt actcaaaact tacagtcgac    1320
aaatcgaggt ggcagcaggg aaatgtgttt tcgtgcagcg tgatgcacga ggccttgcat    1380
aatcactata cacagaagtc gttgtcactg tcgccgggaa agtaa                     1425

<210> SEQ ID NO 63
<211> LENGTH: 460
<212> TYPE: PRT
<213> ORGANISM: Artificial Sequence
<220> FEATURE:
<223> OTHER INFORMATION: synthetic heavy chain

<400> SEQUENCE: 63

Lys Leu Ala Ala Thr Met Lys Cys Ser Trp Val Ile Phe Phe Leu Met

```
  1               5                  10                 15
Ala Val Val Thr Gly Val Asn Ser Gln Val Gln Leu Lys Gln Ser Gly
                20                 25                 30
Pro Gly Leu Val Gln Pro Ser Gln Ser Leu Ser Ile Thr Cys Thr Val
                35                 40                 45
Ser Gly Phe Asn Ile Lys Asp Thr Tyr Ile His Trp Val Arg Gln Ser
            50                 55                 60
Pro Gly Lys Gly Leu Glu Trp Leu Gly Arg Ile Tyr Pro Thr Asn Gly
 65                 70                 75                 80
Tyr Thr Arg Tyr Asn Thr Pro Phe Thr Ser Arg Leu Ser Ile Asn Ala
                85                 90                 95
Asp Asn Ser Lys Asn Gln Val Phe Phe Lys Met Asn Ser Leu Gln Ser
               100                105                110
Asn Asp Thr Ala Ile Tyr Tyr Cys Ala Arg Trp Gly Gly Asp Gly Phe
               115                120                125
Tyr Ala Met Asp Tyr Trp Gly Gln Gly Thr Leu Val Thr Val Ser Ser
           130                135                140
Ala Ser Thr Lys Gly Pro Ser Val Phe Pro Leu Ala Pro Ser Ser Lys
145                150                155                160
Ser Thr Ser Gly Gly Thr Ala Ala Leu Gly Cys Leu Val Lys Asp Tyr
               165                170                175
Phe Pro Glu Pro Val Thr Val Ser Trp Asn Ser Gly Ala Leu Thr Ser
               180                185                190
Gly Val His Thr Phe Pro Ala Val Leu Gln Ser Ser Gly Leu Tyr Ser
               195                200                205
Leu Ser Ser Val Val Thr Val Pro Ser Ser Ser Leu Gly Thr Gln Thr
           210                215                220
Tyr Ile Cys Asn Val Asn His Lys Pro Ser Asn Thr Lys Val Asp Lys
225                230                235                240
Lys Val Glu Pro Lys Ser Cys Asp Lys Thr His Thr Cys Pro Pro Cys
               245                250                255
Pro Ala Pro Glu Leu Leu Gly Gly Pro Ser Val Phe Leu Phe Pro Pro
               260                265                270
Lys Pro Lys Asp Thr Leu Met Ile Ser Arg Thr Pro Glu Val Thr Cys
           275                280                285
Val Val Val Asp Val Ser His Glu Asp Pro Glu Val Lys Phe Asn Trp
           290                295                300
Tyr Val Asp Gly Val Glu Val His Asn Ala Lys Thr Lys Pro Arg Glu
305                310                315                320
Glu Gln Tyr Asn Ser Thr Tyr Arg Val Val Ser Val Leu Thr Val Leu
               325                330                335
His Gln Asp Trp Leu Asn Gly Lys Glu Tyr Lys Cys Lys Val Ser Asn
           340                345                350
Lys Ala Leu Pro Ala Pro Ile Glu Lys Thr Ile Ser Lys Ala Lys Gly
           355                360                365
Gln Pro Arg Glu Pro Gln Val Tyr Thr Leu Pro Pro Ser Arg Asp Glu
       370                375                380
Leu Thr Lys Asn Gln Val Ser Leu Thr Cys Leu Val Lys Gly Phe Tyr
385                390                395                400
Pro Ser Asp Ile Ala Val Glu Trp Glu Ser Asn Gly Gln Pro Glu Asn
               405                410                415
Asn Tyr Lys Thr Thr Pro Pro Val Leu Asp Ser Asp Gly Ser Phe Phe
           420                425                430
```

-continued

```
Leu Tyr Ser Lys Leu Thr Val Asp Lys Ser Arg Trp Gln Gln Gly Asn
            435                 440                 445
Val Phe Ser Cys Ser Val Met His Glu Ala Leu His
    450                 455                 460

<210> SEQ ID NO 64
<211> LENGTH: 98
<212> TYPE: PRT
<213> ORGANISM: Homo sapiens

<400> SEQUENCE: 64

Ala Ser Thr Lys Gly Pro Ser Val Phe Pro Leu Ala Pro Cys Ser Arg
  1               5                  10                  15
Ser Thr Ser Glu Ser Thr Ala Ala Leu Gly Cys Leu Val Lys Asp Tyr
             20                  25                  30
Phe Pro Glu Pro Val Thr Val Ser Trp Asn Ser Gly Ala Leu Thr Ser
         35                  40                  45
Gly Val His Thr Phe Pro Ala Val Leu Gln Ser Ser Gly Leu Tyr Ser
     50                  55                  60
Leu Ser Ser Val Val Thr Val Pro Ser Ser Asn Phe Gly Thr Gln Thr
 65                  70                  75                  80
Tyr Thr Cys Asn Val Asp His Lys Pro Ser Asn Thr Lys Val Asp Lys
                 85                  90                  95
Thr Val

<210> SEQ ID NO 65
<211> LENGTH: 98
<212> TYPE: PRT
<213> ORGANISM: Homo sapiens

<400> SEQUENCE: 65

Ala Ser Thr Lys Gly Pro Ser Val Phe Pro Leu Ala Pro Cys Ser Arg
  1               5                  10                  15
Ser Thr Ser Glu Ser Thr Ala Ala Leu Gly Cys Leu Val Lys Asp Tyr
             20                  25                  30
Phe Pro Glu Pro Val Thr Val Ser Trp Asn Ser Gly Ala Leu Thr Ser
         35                  40                  45
Gly Val His Thr Phe Pro Ala Val Leu Gln Ser Ser Gly Leu Tyr Ser
     50                  55                  60
Leu Ser Ser Val Val Thr Val Pro Ser Ser Ser Leu Gly Thr Lys Thr
 65                  70                  75                  80
Tyr Thr Cys Asn Val Asp His Lys Pro Ser Asn Thr Lys Val Asp Lys
                 85                  90                  95
Arg Val

<210> SEQ ID NO 66
<211> LENGTH: 98
<212> TYPE: PRT
<213> ORGANISM: Homo sapiens

<400> SEQUENCE: 66

Ala Ser Thr Lys Gly Pro Ser Val Phe Pro Leu Ala Pro Cys Ser Arg
  1               5                  10                  15
Ser Thr Ser Gly Gly Thr Ala Ala Leu Gly Cys Leu Val Lys Asp Tyr
             20                  25                  30
Phe Pro Glu Pro Val Thr Val Ser Trp Asn Ser Gly Ala Leu Thr Ser
         35                  40                  45
```

-continued

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                85                  90                  95

Arg Val

<210> SEQ ID NO 67
<211> LENGTH: 98
<212> TYPE: PRT
<213> ORGANISM: Homo sapiens

<400> SEQUENCE: 67

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val

<210> SEQ ID NO 68
<211> LENGTH: 238
<212> TYPE: PRT
<213> ORGANISM: Artificial Sequence
<220> FEATURE:
<223> OTHER INFORMATION: synthetic light chain

<400> SEQUENCE: 68

Met Glu Thr Asp Thr Leu Leu Leu Trp Val Leu Leu Leu Trp Val Pro
 1               5                  10                  15

Gly Ser Thr Gly Asp Ile Gln Leu Thr Gln Ser Pro Val Ile Leu Ser
                20                  25                  30

Ala Ser Val Gly Asp Arg Val Thr Ile Thr Cys Arg Ala Gly Glu Ser
            35                  40                  45

Val Asp Ile Phe Gly Val Gly Phe Leu His Trp Tyr Gln Gln Lys Thr
 50                  55                  60

Asn Gly Ser Pro Lys Leu Leu Ile Tyr Arg Ala Ser Asn Leu Glu Ser
 65                  70                  75                  80

Gly Val Pro Ser Arg Phe Ser Gly Ser Gly Ser Arg Thr Asp Phe Thr
                85                  90                  95

Leu Thr Ile Ser Ser Leu Gln Pro Glu Asp Ile Ala Asp Tyr Tyr Cys
            100                 105                 110

Gln Gln Thr Asn Glu Asp Pro Tyr Thr Phe Gly Gln Gly Thr Lys Val
            115                 120                 125

Glu Ile Lys Arg Thr Val Ala Ala Pro Ser Val Phe Ile Phe Pro Pro
            130                 135                 140

Ser Asp Glu Gln Leu Lys Ser Gly Ala Ala Ser Val Val Cys Leu Leu
145                 150                 155                 160

```
Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Thr Leu Thr Leu Ser Lys Ala
        195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 69
<211> LENGTH: 238
<212> TYPE: PRT
<213> ORGANISM: Artificial Sequence
<220> FEATURE:
<223> OTHER INFORMATION: synthetic light chain

<400> SEQUENCE: 69

Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Ser Leu Ser
            20                  25                  30

Ala Ser Val Gly Asp Arg Val Thr Ile Thr Cys Arg Ala Gly Glu Ser
        35                  40                  45

Val Asp Ile Phe Gly Val Gly Phe Leu His Trp Tyr Gln Gln Lys Pro
    50                  55                  60

Gly Lys Ala Pro Lys Leu Leu Ile Tyr Arg Ala Ser Asn Leu Glu Ser
65                  70                  75                  80

Gly Val Pro Ser Arg Phe Ser Gly Ser Gly Ser Arg Thr Asp Phe Thr
                85                  90                  95

Leu Thr Ile Ser Ser Leu Gln Pro Glu Asp Phe Ala Thr Tyr Tyr Cys
            100                 105                 110

Gln Gln Thr Asn Glu Asp Pro Tyr Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Ala Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Thr Leu Thr Leu Ser Lys Ala
        195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 70
<211> LENGTH: 451
<212> TYPE: PRT
<213> ORGANISM: Artificial Sequence
<220> FEATURE:
<223> OTHER INFORMATION: synthetic heavy chain
```

-continued

```
<400> SEQUENCE: 70

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Met His Trp Val Arg Gln Ala Pro Gly Lys Gly Leu Glu Trp Val
         35                  40                  45

Ala Arg Ile Asp Pro Ala Asn Gly Asn Ser Lys Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ala Pro Phe Gly Tyr Tyr Val Ser Asp Tyr Ala Met Ala Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 71
<211> LENGTH: 213
<212> TYPE: PRT
<213> ORGANISM: Artificial Sequence
<220> FEATURE:
<223> OTHER INFORMATION: synthetically constructed chimeric light chain

<400> SEQUENCE: 71

Asp Ile Leu Leu Thr Gln Ser Pro Val Ile Leu Ser Val Ser Pro Gly
  1               5                  10                  15

Glu Arg Val Ser Phe Ser Cys Arg Ala Ser Gln Ser Ile Gly Thr Asn
                 20                  25                  30

Ile His Trp Tyr Gln Gln Arg Thr Asn Gly Ser Pro Arg Leu Leu Ile
             35                  40                  45

Lys Tyr Ala Ser Glu Ser Ile Ser Gly Ile Pro Ser Arg Phe Ser Gly
         50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
    210

<210> SEQ ID NO 72
<211> LENGTH: 452
<212> TYPE: PRT
<213> ORGANISM: Artificial Sequence
<220> FEATURE:
<223> OTHER INFORMATION: synthetically constructed chimeric heavy chain

<400> SEQUENCE: 72

Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Asn Tyr
                 20                  25                  30

Gly Val His Trp Val Arg Gln Ser Pro Gly Lys Gly Leu Glu Trp Leu
```

```
            35                  40                  45
Gly Val Ile Trp Ser Gly Gly Asn Thr Asp Tyr Asn Thr Pro Phe Thr
 50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                     85                  90                  95

Arg Ala Leu Thr Tyr Tyr Asp Tyr Glu Phe Ala Tyr Trp Gly Gln Gly
                    100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                    180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                    245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
            450
```

```
<210> SEQ ID NO 73
<211> LENGTH: 120
<212> TYPE: PRT
<213> ORGANISM: Artificial Sequence
<220> FEATURE:
<223> OTHER INFORMATION: synthetic light chain

<400> SEQUENCE: 73

Asp Ile Gln Met Thr Gln Ser Pro Ile Leu Leu Ser Ala Ser Val Gly
 1               5                  10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro
        115                 120

<210> SEQ ID NO 74
<211> LENGTH: 120
<212> TYPE: PRT
<213> ORGANISM: Artificial Sequence
<220> FEATURE:
<223> OTHER INFORMATION: synthetically constructed peptide-enabled heavy
      chain

<400> SEQUENCE: 74

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ser Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 75
<211> LENGTH: 114
<212> TYPE: PRT
<213> ORGANISM: Artificial Sequence
<220> FEATURE:
<223> OTHER INFORMATION: synthetic light chain

<400> SEQUENCE: 75
```

```
Asp Ile Gln Leu Thr Gln Ser Pro Val Ile Leu Ser Ala Ser Val Gly
1               5                   10                  15

Asp Arg Val Thr Ile Thr Cys Arg Ala Gly Glu Ser Val Asp Ile Phe
            20                  25                  30

Gly Val Gly Phe Leu His Trp Tyr Gln Gln Lys Thr Asn Gly Ser Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Ile Ala Asp Tyr Tyr Cys Gln Gln Thr Asn
                85                  90                  95

Glu Asp Pro Tyr Thr Phe Gly Gln Gly Thr Lys Val Glu Ile Lys Arg
            100                 105                 110

Thr Val
```

```
<210> SEQ ID NO 76
<211> LENGTH: 110
<212> TYPE: PRT
<213> ORGANISM: Artificial Sequence
<220> FEATURE:
<223> OTHER INFORMATION: synthetically constructed CDR grafted light
      chain

<400> SEQUENCE: 76

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Asp Ile Asn Thr Ala
            20                  25                  30

Ile Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Ser Ile Asn Ser Val Glu Ser
65                  70                  75                  80

Glu Asp Ile Ala Asp Tyr Tyr Cys Gln Gln His Tyr Thr Thr Pro Pro
                85                  90                  95

Thr Phe Gly Ala Gly Thr Lys Leu Glu Ile Lys Arg Thr Val
            100                 105                 110
```

```
<210> SEQ ID NO 77
<211> LENGTH: 120
<212> TYPE: PRT
<213> ORGANISM: Artificial Sequence
<220> FEATURE:
<223> OTHER INFORMATION: synthetically constructed CDR grafted heavy
      chain

<400> SEQUENCE: 77

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Asn Ile Lys Asp Thr
            20                  25                  30

Tyr Ile His Trp Val Arg Gln Ser Pro Gly Lys Gly Leu Glu Trp Leu
        35                  40                  45

Gly Arg Ile Tyr Pro Thr Asn Gly Tyr Thr Arg Tyr Asn Thr Pro Phe
    50                  55                  60
```

```
Thr Ser Arg Leu Ser Ile Asn Ala Asp Asn Ser Lys Asn Gln Val Phe
 65                  70                  75                  80

Phe Lys Met Asn Ser Leu Gln Ser Asn Asp Thr Ala Ile Tyr Tyr Cys
             85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 78
<211> LENGTH: 443
<212> TYPE: PRT
<213> ORGANISM: Mus musculus
<220> FEATURE:
<221> NAME/KEY: VARIANT
<222> LOCATION: (1)...(443)
<223> OTHER INFORMATION: Xaa = any amino acid

<400> SEQUENCE: 78

Gln Val Gln Xaa Gln Ser Gly Ala Glu Xaa Ala Arg Pro Gly Ala
  1               5                  10                  15

Ser Val Lys Xaa Ser Cys Lys Ala Ser Gly Tyr Thr Phe Thr Asn Tyr
             20                  25                  30

Trp Met Gln Trp Val Lys Gln Arg Pro Gly Gln Gly Xaa Asp Trp Xaa
             35                  40                  45

Gly Ala Xaa Tyr Pro Gly Asp Gly Asn Thr Arg Tyr Thr Gln Lys Phe
         50                  55                  60

Lys Gly Lys Ala Thr Xaa Thr Ala Asp Lys Ser Ser Thr Ala Tyr
 65                  70                  75                  80

Met Gln Xaa Ser Ser Xaa Ala Ser Glu Asp Ser Ala Val Tyr Tyr Cys
             85                  90                  95

Ala Arg Gly Glu Gly Asn Tyr Ala Trp Phe Ala Tyr Trp Gly Gln Gly
            100                 105                 110

Thr Xaa Val Thr Val Ser Ala Ala Lys Thr Thr Pro Pro Ser Val Tyr
            115                 120                 125

Pro Xaa Ala Pro Gly Ser Ala Ala Gln Thr Asn Ser Met Val Thr Xaa
130                 135                 140

Gly Cys Xaa Val Lys Gly Tyr Phe Pro Glu Pro Val Thr Val Thr Trp
145                 150                 155                 160

Asn Ser Gly Ser Xaa Ser Ser Gly Val His Thr Phe Pro Ala Val Xaa
                165                 170                 175

Gln Ser Asp Xaa Tyr Thr Xaa Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Xaa Val Pro Arg Asp Cys Gly Cys Lys
        210                 215                 220

Pro Cys Xaa Cys Thr Val Pro Glu Val Ser Ser Val Phe Xaa Phe Pro
225                 230                 235                 240

Pro Lys Pro Lys Asp Val Xaa Thr Xaa Thr Xaa Thr Pro Lys Val Thr
                245                 250                 255

Cys Val Val Val Asp Xaa Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Xaa Pro Xaa
```

```
                    290                 295                 300
Met His Gln Asp Trp Xaa Asn Gly Lys Glu Phe Lys Cys Arg Val Asn
305                 310                 315                 320

Ser Ala Ala Phe Pro Ala Pro Xaa Glu Lys Thr Xaa Ser Lys Thr Lys
                325                 330                 335

Gly Arg Pro Lys Ala Pro Gln Val Tyr Thr Xaa Pro Pro Lys Glu
            340                 345                 350

Gln Met Ala Lys Asp Lys Val Ser Xaa Thr Cys Asn Xaa Thr Asp Phe
            355                 360                 365

Phe Pro Glu Asp Xaa Thr Val Glu Trp Gln Trp Asn Gly Gln Pro Ala
            370                 375                 380

Glu Asn Tyr Lys Asn Thr Gln Pro Xaa Met Asp Thr Asp Gly Ser Tyr
385                 390                 395                 400

Phe Val Tyr Ser Lys Xaa Asn Val Gln Lys Ser Asn Trp Glu Ala Gly
                405                 410                 415

Asn Thr Phe Thr Cys Ser Val Xaa His Glu Gly Xaa His Asn His His
                420                 425                 430

Thr Glu Lys Ser Xaa Ser His Ser Pro Gly Lys
            435                 440
```

<210> SEQ ID NO 79
<211> LENGTH: 450
<212> TYPE: PRT
<213> ORGANISM: Artificial Sequence
<220> FEATURE:
<223> OTHER INFORMATION: synthetically constructed chimeric antibody
      heavy chain

<400> SEQUENCE: 79

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Val His Trp Val Lys Gln Arg Pro Glu Gln Gly Leu Glu Trp Ile
        35                  40                  45

Gly Arg Ile Asp Pro Ala Asn Gly Tyr Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Pro Leu Tyr Asp Tyr Tyr Ala Met Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205
```

```
Ser Thr Lys Val Asp Lys Lys Ile Glu Pro Arg Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 80
<211> LENGTH: 450
<212> TYPE: PRT
<213> ORGANISM: Artificial Sequence
<220> FEATURE:
<223> OTHER INFORMATION: synthetically constructed chimeric antibody
      heavy chain

<400> SEQUENCE: 80

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Val His Trp Val Lys Gln Arg Pro Glu Gln Gly Leu Glu Trp Ile
        35                  40                  45

Gly Arg Ile Asp Pro Ala Asn Gly Tyr Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Pro Leu Tyr Asp Tyr Tyr Ala Met Asp Tyr Trp Gly Gln Gly
            100                 105                 110
```

```
Thr Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 81
<211> LENGTH: 451
<212> TYPE: PRT
<213> ORGANISM: Homo sapiens

<400> SEQUENCE: 81

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
```

-continued

```
                20                  25                  30
Ala Met His Trp Val Arg Gln Ala Pro Gly Lys Gly Leu Glu Trp Val
                35                  40                  45
Ser Ala Ile Thr Trp Asn Ser Gly His Ile Asp Tyr Ala Asp Ser Val
    50                  55                  60
Glu Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Val Ser Tyr Leu Ser Thr Ala Ser Ser Leu Asp Tyr Trp Gly
                100                 105                 110
Gln Gly Thr Leu Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
                130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
```

Pro Gly Lys
    450

<210> SEQ ID NO 82
<211> LENGTH: 451
<212> TYPE: PRT
<213> ORGANISM: Homo sapiens

<400> SEQUENCE: 82

Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser

```
                355                 360                 365
Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 83
<211> LENGTH: 442
<212> TYPE: PRT
<213> ORGANISM: Mus musculus

<400> SEQUENCE: 83

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Asn Trp Val Arg Gln Pro Pro Gly Lys Ala Leu Glu Trp Leu
        35                  40                  45

Gly Phe Ile Gly Asn Lys Ala Asn Gly Tyr Thr Thr Glu Tyr Ser Ala
    50                  55                  60

Ser Val Lys Gly Arg Phe Thr Ile Ser Arg Asp Lys Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Leu Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Pro Arg Pro Ser Glu Thr Val Thr Cys Asn Val Ala His Pro
        195                 200                 205

Ala Ser Ser Thr Lys Val Asp Lys Lys Ile Val Pro Arg Asp Cys Pro
    210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Asp Val Ser Glu Asp Asp Pro Asp Val
            260                 265                 270
```

Gln Ile Ser Trp Phe Val Asn Val Glu Val His Thr Ala Gln Thr
            275                 280                 285

Gln Thr His Arg Glu Asp Tyr Asn Ser Thr Leu Arg Val Val Ser Ala
        290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
            405                 410                 415

Val Glu Arg Asn Ser Tyr Ser Cys Ser Val Val His Glu Gly Leu His
        420                 425                 430

Asn His His Thr Thr Lys Ser Phe Ser Arg
            435                 440

<210> SEQ ID NO 84
<211> LENGTH: 442
<212> TYPE: PRT
<213> ORGANISM: Mus musculus

<400> SEQUENCE: 84

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
            20                  25                  30

Tyr Met Asn Trp Val Arg Gln Pro Pro Gly Lys Ala Leu Glu Trp Leu
        35                  40                  45

Gly Phe Ile Gly Asn Lys Ala Asn Gly Tyr Thr Thr Glu Tyr Ser Ala
    50                  55                  60

Ser Val Lys Gly Arg Phe Thr Ile Ser Arg Asp Lys Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Leu Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Pro Arg Pro Ser Glu Thr Val Thr Cys Asn Val Ala His Pro
        195                 200                 205

```
Ala Ser Ser Thr Lys Val Asp Lys Lys Ile Val Pro Arg Asp Cys Pro
    210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala
    290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
    370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg
        435                 440

<210> SEQ ID NO 85
<211> LENGTH: 453
<212> TYPE: PRT
<213> ORGANISM: Homo sapiens

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
```

```
                130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
                210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
                450

<210> SEQ ID NO 86
<211> LENGTH: 448
<212> TYPE: PRT
<213> ORGANISM: Homo sapiens

<400> SEQUENCE: 86

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
                20                  25                  30

Gly Met Asn Trp Val Arg Gln Ala Pro Gly Lys Gly Leu Glu Trp Val
                35                  40                  45
```

Ala Ile Ile Trp Tyr Asp Gly Asp Asn Gln Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Gly Leu Arg Ala Glu Asp Thr Ala Val Tyr Tyr Cys
                 85                  90                  95

Ala Arg Asp Leu Arg Thr Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 87
<211> LENGTH: 229
<212> TYPE: PRT

<213> ORGANISM: Homo sapiens

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225

<210> SEQ ID NO 88
<211> LENGTH: 449
<212> TYPE: PRT
<213> ORGANISM: Homo sapiens

<400> SEQUENCE: 88

Gln Val Gln Leu Gln Gln Ser Gly Ala Glu Val Lys Lys Phe Gly Ala
1               5                   10                  15

Ser Val Lys Val Ser Cys Glu Ala Ser Gly Tyr Thr Phe Pro Ser Tyr
            20                  25                  30

Val Leu His Trp Val Lys Gln Ala Pro Gly Gln Gly Leu Glu Trp Ile
        35                  40                  45

Gly Tyr Ile Asn Pro Tyr Asn Asp Gly Thr Gln Tyr Asn Lys Lys Phe
    50                  55                  60

Lys Gly Lys Ala Thr Leu Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Phe Gly Gly Ser Tyr Gly Phe Ala Tyr Trp Gly Gln Gly
            100                 105                 110

Thr Leu Val Ile Val Ser Ser Ala Ser Thr Lys Gly Pro Ser Val Phe

```
            115                 120                 125
Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Ser Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Glu Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Asn His Glu
            420                 425                 430

Ala Leu His Asn His Tyr Thr Gln Lys Ser Leu Ser Leu Ser Pro Gly
        435                 440                 445

Lys

<210> SEQ ID NO 89
<211> LENGTH: 446
<212> TYPE: PRT
<213> ORGANISM: Homo sapiens

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
```

```
                35                  40                  45
Gly Tyr Ile Asn Pro Ser Thr Gly Tyr Thr Glu Tyr Asn Gln Lys Phe
 50                  55                  60

Lys Asp Lys Ala Thr Ile Thr Ala Asp Glu Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Gly Val Phe Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                        165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 90
```

```
<211> LENGTH: 448
<212> TYPE: PRT
<213> ORGANISM: Homo sapiens

<400> SEQUENCE: 90

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Gly Ile Thr Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
```

-continued

```
                385                 390                 395                 400
Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Met His Glu Ala
                    420                 425                 430

Leu His Asn His Tyr Thr Gln Lys Ser Leu Ser Leu Ser Pro Gly Lys
                    435                 440                 445

<210> SEQ ID NO 91
<211> LENGTH: 448
<212> TYPE: PRT
<213> ORGANISM: Homo sapiens
<220> FEATURE:
<221> NAME/KEY: VARIANT
<222> LOCATION: 1
<223> OTHER INFORMATION: Xaa = any amino acid

<400> SEQUENCE: 91

Xaa Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Ser Asn Tyr
                20                  25                  30

Trp Ile Gln Trp Val Arg Gln Ala Pro Gly Gln Gly Leu Glu Trp Met
            35                  40                  45

Gly Glu Ile Leu Pro Gly Ser Gly Ser Thr Glu Tyr Thr Glu Asn Phe
        50                  55                  60

Lys Asp Arg Val Thr Met Thr Arg Asp Thr Ser Thr Ser Thr Val Tyr
 65                 70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 92
<211> LENGTH: 451
<212> TYPE: PRT
<213> ORGANISM: Artificial Sequence
<220> FEATURE:
<223> OTHER INFORMATION: synthetically constructed humanized heavy chain

<400> SEQUENCE: 92

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Phe Thr Gly His
                20                  25                  30

Trp Met Asn Trp Val Arg Gln Ala Pro Gly Lys Gly Leu Glu Trp Val
            35                  40                  45

Gly Met Ile His Pro Ser Asp Ser Glu Thr Arg Tyr Asn Gln Lys Phe
    50                  55                  60

Lys Asp Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Tyr Phe Tyr Gly Thr Thr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 93
<211> LENGTH: 447
<212> TYPE: PRT
<213> ORGANISM: Artificial Sequence
<220> FEATURE:
<223> OTHER INFORMATION: synthetically constructed chimeric heavy chain

<400> SEQUENCE: 93

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Ile Phe Thr Ser Ser
            20                  25                  30

Trp Ile Asn Trp Val Lys Gln Ala Pro Gly Gln Gly Leu Glu Trp Ile
        35                  40                  45

Gly Arg Ile Asp Pro Ser Asp Gly Glu Val His Tyr Asn Gln Asp Phe
    50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Phe Leu Pro Trp Phe Ala Asp Trp Gly Gln Gly Thr Leu
            100                 105                 110

Val Thr Val Ser Ser Ala Ser Thr Lys Gly Pro Ser Val Phe Pro Leu
        115                 120                 125
```

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 94
<211> LENGTH: 449
<212> TYPE: PRT
<213> ORGANISM: Mus musculus

<400> SEQUENCE: 94

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Asn Tyr
            20                  25                  30

Tyr Met Ser Trp Val Arg Gln Thr Pro Glu Lys Arg Leu Glu Leu Val
        35                  40                  45

Ala Ala Ile Asn Ser Asp Gly Gly Ile Thr Tyr Tyr Leu Asp Thr Val

```
            50                  55                  60
Lys Gly Arg Phe Thr Ile Ser Arg Asp Asn Ala Lys Asn Thr Leu Tyr
 65                      70                  75                  80

Leu Gln Met Ser Ser Leu Lys Ser Glu Asp Thr Ala Leu Phe Tyr Cys
                     85                  90                  95

Ala Arg His Arg Ser Gly Tyr Phe Ser Met Asp Tyr Trp Gly Gln Gly
                100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 95
<211> LENGTH: 443
```

<212> TYPE: PRT
<213> ORGANISM: Mus musculus

<400> SEQUENCE: 95

```
Gln Ala Tyr Leu Gln Gln Ser Gly Ala Glu Leu Val Arg Pro Gly Ala
 1               5                  10                  15

Ser Val Lys Met Ser Cys Lys Ala Ser Gly Tyr Thr Phe Thr Ser Tyr
             20                  25                  30

Asn Met His Trp Val Lys Gln Thr Pro Arg Gln Gly Leu Glu Trp Ile
         35                  40                  45

Gly Ala Ile Tyr Pro Gly Asn Gly Asp Thr Ser Tyr Asn Gln Lys Phe
     50                  55                  60

Lys Gly Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400
```

Asp Gly Ser Tyr Phe Met Tyr Ser Lys Leu Arg Val Glu Lys Lys Asn
            405                 410                 415

Trp Val Glu Arg Asn Ser Tyr Ser Cys Ser Val Val His Glu Gly Leu
            420                 425                 430

His Asn His His Thr Thr Lys Ser Phe Ser Arg
            435                 440

<210> SEQ ID NO 96
<211> LENGTH: 443
<212> TYPE: PRT
<213> ORGANISM: Mus musculus

<400> SEQUENCE: 96

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile

```
                       325                 330                 335
Ser Lys Pro Lys Gly Ser Val Arg Ala Pro Gln Val Tyr Val Leu Pro
                   340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg
                435                 440

<210> SEQ ID NO 97
<211> LENGTH: 448
<212> TYPE: PRT
<213> ORGANISM: Homo sapiens

<400> SEQUENCE: 97

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 98
<211> LENGTH: 399
<212> TYPE: PRT
<213> ORGANISM: Artificial Sequence
<220> FEATURE:
<223> OTHER INFORMATION: synthetically constructed humanized heavy chain

<400> SEQUENCE: 98

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Ser Tyr
            20                  25                  30

Ser Val His Trp Val Arg Gln Pro Pro Gly Lys Gly Leu Glu Trp Leu
            35                  40                  45

Gly Val Ile Trp Ala Ser Gly Gly Thr Asp Tyr Asn Ser Ala Leu Met
            50                  55                  60

Ser Arg Leu Ser Ile Ser Lys Asp Thr Ser Arg Asn Gln Val Val Leu
65                  70                  75                  80

Thr Met Thr Asn Met Asp Pro Val Asp Thr Ala Thr Tyr Tyr Cys Ala
            85                  90                  95

Arg Asp Pro Pro Ser Ser Leu Leu Arg Leu Asp Tyr Trp Gly Arg Gly
            100                 105                 110

Thr Pro Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

-continued

Gln Ser Ser Gly Leu Tyr Ser Leu Ser Ser Val Val Thr Val Pro Ser
                180                 185                 190

Ser Ser Leu Gly Thr Gln Thr Tyr Asp Thr Leu Met Ile Ser Arg Thr
            195                 200                 205

Pro Glu Val Thr Cys Val Val Val Asp Val Ser His Glu Asp Pro Glu
210                 215                 220

Val Lys Phe Asn Trp Tyr Val Asp Gly Val Glu Val His Asn Ala Lys
225                 230                 235                 240

Thr Lys Pro Arg Glu Glu Gln Tyr Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Lys Val Ser Asn Lys Ala Leu Pro Ala Pro Ile Glu Lys Thr Ile
        275                 280                 285

Ser Lys Ala Lys Gly Gln Pro Arg Glu Pro Gln Val Tyr Thr Leu Pro
    290                 295                 300

Pro Ser Arg Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Lys Leu Thr Val Asp Lys Ser Arg
        355                 360                 365

Trp Gln Gln Gly Asn Val Phe Ser Cys Ser Val Met His Glu Ala Leu
370                 375                 380

His Asn His Tyr Thr Gln Lys Ser Leu Ser Leu Ser Pro Gly Lys
385                 390                 395

<210> SEQ ID NO 99
<211> LENGTH: 450
<212> TYPE: PRT
<213> ORGANISM: Mus musculus

<400> SEQUENCE: 99

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Gly Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

```
Asn Ser Gly Ser Leu Ser Ser Gly Val His Thr Phe Pro Ala Val Leu
            165                 170                 175

Gln Ser Asp Leu Tyr Thr Leu Ser Ser Ser Val Thr Val Thr Ser Ser
        180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 100
<211> LENGTH: 450
<212> TYPE: PRT
<213> ORGANISM: Mus musculus

<400> SEQUENCE: 100

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
```

```
                65                  70                  75                  80
            Met Gln Leu Ser Ser Leu Thr Ser Glu Asp Ser Ala Val Tyr Tyr Cys
                            85                  90                  95

Ala Arg Tyr Tyr Asp Asp His Tyr Cys Leu Asp Tyr Trp Gly Gln Gly
                        100                 105                 110

Thr Thr Leu Thr Val Ser Ser Ala Lys Thr Thr Ala Pro Ser Val Tyr
                        115                 120                 125

Pro Leu Ala Pro Val Cys Gly Gly Thr Thr Gly Ser Ser Val Thr Leu
                    130                 135                 140

Gly Cys Leu Val Lys Gly Tyr Phe Pro Glu Pro Val Thr Leu Thr Trp
            145                 150                 155                 160

Asn Ser Gly Ser Leu Ser Ser Gly Val His Thr Phe Pro Ala Val Leu
                            165                 170                 175

Gln Ser Asp Leu Tyr Thr Leu Ser Ser Val Thr Val Thr Ser Ser
                        180                 185                 190

Thr Trp Pro Ser Gln Ser Ile Thr Cys Asn Val Ala His Pro Ala Ser
                        195                 200                 205

Ser Thr Lys Val Asp Lys Lys Ile Glu Pro Arg Pro Lys Ser Cys Asp
                    210                 215                 220

Lys Thr His Thr Cys Pro Pro Cys Pro Ala Pro Glu Leu Leu Gly Gly
            225                 230                 235                 240

Pro Ser Val Phe Leu Phe Pro Pro Lys Pro Lys Asp Thr Leu Met Ile
                            245                 250                 255

Ser Arg Thr Pro Glu Val Thr Cys Val Val Val Asp Val Ser His Glu
                        260                 265                 270

Asp Pro Glu Val Lys Phe Asn Trp Tyr Val Asp Gly Val Glu Val His
                        275                 280                 285

Asn Ala Lys Thr Lys Pro Arg Glu Glu Gln Tyr Asn Ser Thr Tyr Arg
                    290                 295                 300

Val Val Ser Val Leu Thr Val Leu His Gln Asp Trp Leu Asn Gly Lys
            305                 310                 315                 320

Glu Tyr Lys Cys Lys Val Ser Asn Lys Ala Leu Pro Ala Pro Ile Glu
                            325                 330                 335

Lys Thr Ile Ser Lys Ala Lys Gly Gln Pro Arg Glu Pro Gln Val Tyr
                        340                 345                 350

Thr Leu Pro Pro Ser Arg Asp Glu Leu Thr Lys Asn Gln Val Ser Leu
                        355                 360                 365

Thr Cys Leu Val Lys Gly Phe Tyr Pro Ser Asp Ile Ala Val Glu Trp
                    370                 375                 380

Glu Ser Asn Gly Gln Pro Glu Asn Asn Tyr Lys Thr Thr Pro Pro Val
            385                 390                 395                 400

Leu Asp Ser Asp Gly Ser Phe Phe Leu Tyr Ser Lys Leu Thr Val Asp
                            405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                        435                 440                 445

Gly Lys
                450

<210> SEQ ID NO 101
<211> LENGTH: 450
<212> TYPE: PRT
<213> ORGANISM: Artificial Sequence
```

<220> FEATURE:
<223> OTHER INFORMATION: synthetically constructed humanized heavy chain

<400> SEQUENCE: 101

```
Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Arg Leu Glu Trp Met
        35                  40                  45

Gly Arg Ile Asp Pro Ala Asn Gly Tyr Thr Lys Tyr Asp Pro Lys Phe
50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Asn Tyr Gly Val Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400
```

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 102
<211> LENGTH: 452
<212> TYPE: PRT
<213> ORGANISM: Artificial Sequence
<220> FEATURE:
<223> OTHER INFORMATION: synthetically constructed humanized heavy chain

<400> SEQUENCE: 102

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 103
<211> LENGTH: 451
<212> TYPE: PRT
<213> ORGANISM: Artificial Sequence
<220> FEATURE:
<223> OTHER INFORMATION: synthetically constructed humanized heavy chain

<400> SEQUENCE: 103

Glu Val Gln Leu Val Glu Ser Gly Gly Gly Leu Val Gln Pro Gly Gly
 1               5                  10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

```
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 104
<211> LENGTH: 120
<212> TYPE: PRT
<213> ORGANISM: Artificial Sequence
<220> FEATURE:
<223> OTHER INFORMATION: synthetically constructed humanized heavy chain

<400> SEQUENCE: 104

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110
```

Gly Thr Thr Val Thr Val Ser Ser
        115                 120

<210> SEQ ID NO 105
<211> LENGTH: 435
<212> TYPE: PRT
<213> ORGANISM: Artificial Sequence
<220> FEATURE:
<223> OTHER INFORMATION: synthetically constructed humanized heavy chain

<400> SEQUENCE: 105

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
 50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Glu Arg Lys Cys Cys Val Glu Cys Pro Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Gln Phe Asn Trp Tyr Val Asp Gly Val Glu Val
            260                 265                 270

His Asn Ala Lys Thr Lys Pro Arg Glu Glu Gln Phe Asn Ser Thr Phe
        275                 280                 285

Arg Val Val Ser Val Leu Thr Val His Gln Asp Trp Leu Asn Gly
    290                 295                 300

Lys Glu Tyr Lys Cys Lys Val Ser Asn Lys Gly Leu Pro Ala Pro Ile
305                 310                 315                 320

Glu Lys Thr Ile Ser Lys Thr Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

```
Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
    370                 375                 380

Met Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
            405                 410                 415

His Glu Ala Leu His Asn His Tyr Thr Gln Lys Ser Leu Ser Leu Ser
        420                 425                 430

Pro Gly Lys
    435

<210> SEQ ID NO 106
<211> LENGTH: 231
<212> TYPE: PRT
<213> ORGANISM: Artificial Sequence
<220> FEATURE:
<223> OTHER INFORMATION: synthetically constructed humanized heavy chain

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Val Glu Pro Lys
210                 215                 220

Ser Cys Asp Lys Thr His Leu
225                 230

<210> SEQ ID NO 107
<211> LENGTH: 451
<212> TYPE: PRT
<213> ORGANISM: Artificial Sequence
```

<220> FEATURE:
<223> OTHER INFORMATION: synthetically constructed chimeric heavy chain

<400> SEQUENCE: 107

```
Gln Val Gln Leu Gln Gln Pro Gly Ala Glu Leu Val Lys Pro Gly Ala
 1               5                  10                  15
Ser Val Lys Met Ser Cys Lys Ala Ser Gly Tyr Thr Phe Thr Ser Tyr
            20                  25                  30
Asn Met His Trp Val Lys Gln Thr Pro Gly Arg Gly Leu Glu Trp Ile
        35                  40                  45
Gly Ala Ile Tyr Pro Gly Asn Gly Asp Thr Ser Tyr Asn Gln Lys Phe
    50                  55                  60
Lys Gly Lys Ala Thr Leu Thr Ala Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Ser Thr Tyr Tyr Gly Gly Asp Trp Tyr Phe Asn Val Trp Gly
            100                 105                 110
Ala Gly Thr Thr Val Thr Val Ser Ala Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
```

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 108
<211> LENGTH: 432
<212> TYPE: PRT
<213> ORGANISM: Mus musculus

<400> SEQUENCE: 108

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Ala Lys Gln Lys Pro Glu Gln Gly Leu Glu Trp Ile
        35                  40                  45

Gly Tyr Ile Ser Pro Gly Asn Asp Asp Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Tyr Tyr Gly His Trp Gly Gln Gly Thr Thr Leu Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Cys Pro Pro Cys Lys Cys Pro Ala Pro Asn Leu Leu
    210                 215                 220

Gly Gly Pro Ser Val Phe Ile Phe Pro Pro Lys Ile Lys Asp Val Leu
225                 230                 235                 240

Met Ile Ser Leu Ser Pro Ile Val Thr Cys Val Val Val Asp Val Ser
                245                 250                 255

Glu Asp Asp Pro Asp Val Gln Ile Ser Trp Phe Val Asn Asn Val Glu
            260                 265                 270

Val His Thr Ala Gln Thr Gln Thr His Arg Glu Asp Tyr Asn Ser Thr
        275                 280                 285

Leu Arg Val Val Ser Ala Leu Pro Ile Gln His Gln Asp Trp Met Ser
    290                 295                 300

Gly Lys Glu Phe Lys Cys Lys Val Asn Asn Lys Asp Leu Pro Ala Pro

```
                305                 310                 315                 320
Ile Glu Arg Thr Ile Ser Lys Pro Lys Gly Ser Val Arg Ala Pro Gln
                    325                 330                 335

Val Tyr Val Leu Pro Pro Glu Glu Met Thr Lys Lys Gln Val
                340                 345                 350

Thr Leu Thr Cys Met Val Thr Asp Phe Met Pro Glu Asp Ile Tyr Val
                355                 360                 365

Glu Trp Thr Asn Asn Gly Lys Thr Glu Leu Asn Tyr Lys Asn Thr Glu
            370                 375                 380

Pro Val Leu Asp Ser Asp Gly Ser Tyr Phe Met Tyr Ser Lys Leu Arg
385                 390                 395                 400

Val Glu Lys Lys Asn Trp Val Glu Arg Asn Ser Tyr Ser Cys Ser Val
                405                 410                 415

Val His Glu Gly Leu His Asn His His Thr Thr Lys Ser Phe Ser Arg
                420                 425                 430

<210> SEQ ID NO 109
<211> LENGTH: 432
<212> TYPE: PRT
<213> ORGANISM: Mus musculus

<400> SEQUENCE: 109

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Ala Lys Gln Lys Pro Glu Gln Gly Leu Glu Trp Ile
            35                  40                  45

Gly Tyr Ile Ser Pro Gly Asn Asp Asp Ile Lys Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Tyr Tyr Gly His Trp Gly Gln Gly Thr Thr Leu Thr Val
                100                 105                 110

Ser Ser Ala Ser Thr Lys Gly Pro Ser Val Phe Pro Leu Ala Pro Cys
            115                 120                 125

Ser Arg Ser Thr Ser Glu Ser Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Lys Thr Tyr Thr Cys Asn Val Asp His Lys Pro Ser Asn Thr Lys Val
            195                 200                 205

Asp Lys Arg Val Cys Pro Pro Cys Lys Cys Pro Ala Pro Asn Leu Leu
        210                 215                 220

Gly Gly Pro Ser Val Phe Ile Phe Pro Pro Lys Ile Lys Asp Val Leu
225                 230                 235                 240

Met Ile Ser Leu Ser Pro Ile Val Thr Cys Val Val Val Asp Val Ser
                245                 250                 255
```

```
Glu Asp Asp Pro Asp Val Gln Ile Ser Trp Phe Val Asn Asn Val Glu
                260                 265                 270

Val His Thr Ala Gln Thr Gln Thr His Arg Glu Asp Tyr Asn Ser Thr
            275                 280                 285

Leu Arg Val Val Ser Ala Leu Pro Ile Gln His Gln Asp Trp Met Ser
        290                 295                 300

Gly Lys Glu Phe Lys Cys Lys Val Asn Asn Lys Asp Leu Pro Ala Pro
305                 310                 315                 320

Ile Glu Arg Thr Ile Ser Lys Pro Lys Gly Ser Val Arg Ala Pro Gln
                325                 330                 335

Val Tyr Val Leu Pro Pro Glu Glu Glu Met Thr Lys Lys Gln Val
            340                 345                 350

Thr Leu Thr Cys Met Val Thr Asp Phe Met Pro Glu Asp Ile Tyr Val
            355                 360                 365

Glu Trp Thr Asn Asn Gly Lys Thr Glu Leu Asn Tyr Lys Asn Thr Glu
        370                 375                 380

Pro Val Leu Asp Ser Asp Gly Ser Tyr Phe Met Tyr Ser Lys Leu Arg
385                 390                 395                 400

Val Glu Lys Lys Asn Trp Val Glu Arg Asn Ser Tyr Ser Cys Ser Val
                405                 410                 415

Val His Glu Gly Leu His Asn His His Thr Thr Lys Ser Phe Ser Arg
            420                 425                 430

<210> SEQ ID NO 110
<211> LENGTH: 448
<212> TYPE: PRT
<213> ORGANISM: Artificial Sequence
<220> FEATURE:
<223> OTHER INFORMATION: synthetically constructed humanized heavy chain
<220> FEATURE:
<221> NAME/KEY: VARIANT
<222> LOCATION: 1
<223> OTHER INFORMATION: Xaa = any amino acid

<400> SEQUENCE: 110

Xaa Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
              180                 185                 190

Ser Ser Leu Gly Thr Gln Thr Tyr Ile Cys Asn Val Asn His Lys Pro
          195                 200                 205

Ser Asn Thr Lys Val Asp Lys Lys Val Glu Pro Lys Ser Cys Asp Lys
      210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
              260                 265                 270

Pro Glu Val Lys Phe Asn Trp Tyr Val Asp Gly Val Glu Val His Asn
          275                 280                 285

Ala Lys Thr Lys Pro Arg Glu Glu Gln Tyr Asn Ser Thr Tyr Arg Val
      290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
              340                 345                 350

Leu Pro Pro Ser Arg Asp Glu Leu Thr Lys Asn Gln Val Ser Leu Thr
          355                 360                 365

Cys Leu Val Lys Gly Phe Tyr Pro Ser Asp Ile Ala Val Glu Trp Glu
      370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
              420                 425                 430

Ala Leu His Asn His Tyr Thr Gln Lys Ser Leu Ser Leu Ser Pro Gly
          435                 440                 445

<210> SEQ ID NO 111
<211> LENGTH: 447
<212> TYPE: PRT
<213> ORGANISM: Mus musculus

<400> SEQUENCE: 111

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp

```
            100                 105                 110
Gly Thr Gly Thr Thr Val Thr Val Ser Gly Pro Ser Val Phe Pro Leu
            115                 120                 125

Ala Pro Ser Ser Lys Ser Thr Ser Gly Gly Thr Ala Ala Leu Gly Cys
            130                 135             140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Ala Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 112
<211> LENGTH: 447
<212> TYPE: PRT
<213> ORGANISM: Mus musculus

<400> SEQUENCE: 112

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30
```

-continued

```
Asn Met His Trp Val Lys Gln Thr Pro Arg Gln Gly Leu Glu Trp Ile
         35                  40                  45

Gly Ala Ile Tyr Pro Gly Asn Gly Asp Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Val Val Tyr Tyr Ser Asn Ser Tyr Trp Tyr Phe Asp Val Trp
             100                 105                 110

Gly Thr Gly Thr Thr Val Thr Val Ser Gly Pro Ser Val Phe Pro Leu
         115                 120                 125

Ala Pro Ser Ser Lys Ser Thr Ser Gly Gly Thr Ala Ala Leu Gly Cys
     130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                 165                 170                 175

Ser Gly Leu Tyr Ser Leu Ser Ser Val Val Thr Val Pro Ser Ser Ser
             180                 185                 190

Leu Gly Thr Gln Thr Tyr Ile Cys Asn Val Asn His Lys Pro Ser Asn
         195                 200                 205

Thr Lys Val Asp Lys Lys Ala Glu Pro Lys Ser Cys Asp Lys Thr His
     210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Asp Val Ser His Glu Asp Pro Glu
             260                 265                 270

Val Lys Phe Asn Trp Tyr Val Asp Gly Val Glu Val His Asn Ala Lys
         275                 280                 285

Thr Lys Pro Arg Glu Glu Gln Tyr Asn Ser Thr Tyr Arg Val Val Ser
     290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                 325                 330                 335

Ser Lys Ala Lys Gly Gln Pro Arg Glu Pro Gln Val Tyr Thr Leu Pro
             340                 345                 350

Pro Ser Arg Asp Glu Leu Thr Lys Asn Gln Val Ser Leu Thr Cys Leu
         355                 360                 365

Val Lys Gly Phe Tyr Pro Ser Asp Ile Ala Val Glu Trp Glu Ser Asn
     370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                 405                 410                 415

Trp Gln Gln Gly Asn Val Phe Ser Cys Ser Val Met His Glu Ala Leu
             420                 425                 430

His Asn His Tyr Thr Gln Lys Ser Leu Ser Leu Ser Pro Gly Lys
         435                 440                 445
```

<210> SEQ ID NO 113
<211> LENGTH: 451
<212> TYPE: PRT
<213> ORGANISM: Artificial Sequence
<220> FEATURE:
<223> OTHER INFORMATION: synthetically constructed humanized heavy chain

<400> SEQUENCE: 113

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
```

```
                    370                 375                 380
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 114
<211> LENGTH: 451
<212> TYPE: PRT
<213> ORGANISM: Artificial Sequence
<220> FEATURE:
<223> OTHER INFORMATION: synthetically constructed humanized heavy chain

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
```

```
                275                 280                 285
His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 115
<211> LENGTH: 449
<212> TYPE: PRT
<213> ORGANISM: Homo sapiens

<400> SEQUENCE: 115

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
            100                 105                 110

Thr Leu Val Thr Val Ser Ser Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
    435                 440                 445

Lys

<210> SEQ ID NO 116
<211> LENGTH: 455
<212> TYPE: PRT
<213> ORGANISM: Homo sapiens

<400> SEQUENCE: 116

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110
```

```
Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 117
<211> LENGTH: 448
<212> TYPE: PRT
<213> ORGANISM: Artificial Sequence
<220> FEATURE:
<223> OTHER INFORMATION: synthetically constructed humanized heavy chain

<400> SEQUENCE: 117

Glu Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Phe Thr Phe Ile Ser Tyr
        20                  25                  30

Ala Met Ser Trp Val Arg Gln Ala Pro Gly Lys Gly Leu Glu Trp Val
    35                  40                  45

Ala Ser Ile Ser Ser Gly Gly Asn Thr Tyr Tyr Pro Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
            85                  90                  95

Arg Leu Asp Gly Tyr Tyr Phe Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Leu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys

-continued

```
          435                 440                 445
```

<210> SEQ ID NO 118
<211> LENGTH: 448
<212> TYPE: PRT
<213> ORGANISM: Artificial Sequence
<220> FEATURE:
<223> OTHER INFORMATION: synthetically constructed humanized heavy chain

<400> SEQUENCE: 118

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
```

```
                    355                 360                 365
Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

<210> SEQ ID NO 119
<211> LENGTH: 447
<212> TYPE: PRT
<213> ORGANISM: Artificial Sequence
<220> FEATURE:
<223> OTHER INFORMATION: synthetically constructed humanized heavy chain

<400> SEQUENCE: 119

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Gly Gly
            20                  25                  30

Tyr Leu Trp Asn Trp Ile Arg Gln Pro Pro Gly Lys Gly Leu Glu Trp
        35                  40                  45

Ile Gly Tyr Ile Ser Tyr Asp Gly Thr Asn Asn Tyr Lys Pro Ser Leu
50                  55                  60

Lys Asp Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Gly Arg Val Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
```

```
                275                 280                 285
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 120
<211> LENGTH: 119
<212> TYPE: PRT
<213> ORGANISM: Artificial Sequence
<220> FEATURE:
<223> OTHER INFORMATION: synthetically constructed humanized heavy chain

<400> SEQUENCE: 120

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Ser Tyr Asn Gly Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser
        115

<210> SEQ ID NO 121
<211> LENGTH: 447
<212> TYPE: PRT
<213> ORGANISM: Homo sapiens

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30
```

Ser Ile His Trp Val Arg Gln Ala Pro Gly Lys Gly Leu Glu Trp Met
        35                  40                  45
Gly Gly Phe Asp Pro Glu Glu Asn Glu Ile Val Tyr Ala Gln Arg Phe
    50                  55                  60
Gln Gly Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Ile Val Gly Ser Phe Ser Pro Leu Thr Leu Gly Leu Trp Gly Gln
            100                 105                 110
Gly Thr Met Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Ser Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445

<210> SEQ ID NO 122
<211> LENGTH: 451
<212> TYPE: PRT
<213> ORGANISM: Homo sapiens

<400> SEQUENCE: 122

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

```
Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 123
<211> LENGTH: 448
<212> TYPE: PRT
<213> ORGANISM: Homo sapiens

<400> SEQUENCE: 123

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
```

```
                290                 295                 300
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 124
<211> LENGTH: 451
<212> TYPE: PRT
<213> ORGANISM: Homo sapiens

<400> SEQUENCE: 124

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asp Tyr Asn Pro Ser
50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
            100                 105                 110

Gln Gly Thr Leu Val Thr Val Ser Ala Ser Thr Lys Gly Pro Ser
        115                 120                 125

Val Leu Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220
```

Asp Lys Thr His Thr Cys Pro Pro Cys Pro Ala Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 125
<211> LENGTH: 214
<212> TYPE: PRT
<213> ORGANISM: Mus musculus
<220> FEATURE:
<221> NAME/KEY: VARIANT
<222> LOCATION: (1)...(214)
<223> OTHER INFORMATION: Xaa = Isoleucine or Leucine

<400> SEQUENCE: 125

Asp Ile Gln Met Thr Gln Ser Pro Ala Ser Leu Ser Ala Ser Val Gly
1               5                   10                  15

Glu Thr Val Thr Xaa Thr Cys Arg Ala Ser Glu Asn Xaa Tyr Ser Tyr
            20                  25                  30

Xaa Ala Trp His Gln Gln Lys Gln Gly Lys Ser Pro Gln Xaa Xaa Val
        35                  40                  45

Tyr Asn Ala Lys Thr Xaa Ala Gly Gly Val Ser Ser Arg Phe Ser Gly
    50                  55                  60

Ser Gly Ser Gly Thr His Phe Ser Xaa Lys Xaa Lys Ser Xaa Gln Pro
65                  70                  75                  80

Glu Asp Phe Gly Xaa Tyr Tyr Cys Gln His His Tyr Gly Xaa Phe Pro
                85                  90                  95

Thr Phe Gly Gly Gly Thr Lys Xaa Glu Xaa Lys Arg Ala Asp Ala Ala
            100                 105                 110

Pro Thr Val Ser Xaa Phe Pro Pro Ser Ser Glu Gln Xaa Thr Ser Gly

```
                    115                 120                 125
Gly Ala Ser Val Val Cys Phe Xaa Asn Asn Phe Tyr Pro Lys Asp Xaa
            130                 135                 140

Asn Val Lys Trp Lys Xaa Asp Gly Ser Glu Arg Gln Asn Gly Val Xaa
145                 150                 155                 160

Asn Ser Trp Thr Asp Gln Asp Ser Lys Asp Ser Thr Tyr Ser Met Ser
                165                 170                 175

Ser Thr Xaa Thr Xaa Thr Lys Asp Glu Tyr Glu Arg His Asn Ser Tyr
            180                 185                 190

Thr Cys Glu Ala Thr His Lys Thr Ser Thr Ser Pro Xaa Val Lys Ser
                195                 200                 205

Phe Asn Arg Asn Glu Cys
    210

<210> SEQ ID NO 126
<211> LENGTH: 214
<212> TYPE: PRT
<213> ORGANISM: Artificial Sequence
<220> FEATURE:
<223> OTHER INFORMATION: synthetically constructed chimeric light chain

<400> SEQUENCE: 126

Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Met Gly Leu Ile
        35                  40                  45

Tyr Tyr Gly Thr Asn Leu Val Asp Gly Val Pro Ser Arg Phe Ser Gly
    50                  55                  60

Ser Gly Ser Gly Ala Asp Tyr Ser Leu Thr Ile Ser Ser Leu Asp Ser
65                  70                  75                  80

Glu Asp Phe Ala Asp Tyr Tyr Cys Val Gln Tyr Ala Gln Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
                195                 200                 205

Phe Asn Arg Asn Glu Cys
    210

<210> SEQ ID NO 127
<211> LENGTH: 214
<212> TYPE: PRT
<213> ORGANISM: Artificial Sequence
<220> FEATURE:
<223> OTHER INFORMATION: synthetically constructed chimeric light chain
```

<400> SEQUENCE: 127

```
Asp Ile Leu Met Thr Gln Ser Pro Ser Ser Met Ser Val Ser Leu Gly
  1               5                  10                  15

Asp Thr Val Ser Ile Thr Cys His Ala Ser Gln Gly Ile Ser Ser Asn
             20                  25                  30

Ile Gly Trp Leu Gln Gln Lys Pro Gly Lys Ser Phe Met Gly Leu Ile
         35                  40                  45

Tyr Tyr Gly Thr Asn Leu Val Asp Gly Val Pro Ser Arg Phe Ser Gly
     50                  55                  60

Ser Gly Ser Gly Ala Asp Tyr Ser Leu Thr Ile Ser Ser Leu Asp Ser
 65                  70                  75                  80

Glu Asp Phe Ala Asp Tyr Tyr Cys Val Gln Tyr Ala Gln Leu Pro Tyr
                 85                  90                  95

Thr Phe Gly Gly Gly Thr Lys Leu Glu Ile Lys Arg Ala Asp Ala Ala
                100                 105                 110

Pro Thr Val Ser Ile Phe Pro Pro Ser Glu Gln Leu Thr Ser Gly
                115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
        210
```

<210> SEQ ID NO 128
<211> LENGTH: 214
<212> TYPE: PRT
<213> ORGANISM: Homo sapiens

<400> SEQUENCE: 128

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 129
<211> LENGTH: 214
<212> TYPE: PRT
<213> ORGANISM: Artificial Sequence
<220> FEATURE:
<223> OTHER INFORMATION: synthetically constructed humanized light chain

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
                20                  25                  30

Leu Asn Trp Tyr Gln Gln Lys Pro Gly Lys Ala Pro Lys Leu Leu Ile
            35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 130
<211> LENGTH: 213
<212> TYPE: PRT
<213> ORGANISM: Mus musculus

<400> SEQUENCE: 130

Gln Thr Val Leu Ser Gln Ser Pro Ala Ile Leu Ser Ala Ser Pro Gly
1               5                   10                  15
```

Glu Lys Val Thr Met Thr Cys Arg Ala Ser Ser Ser Val Thr Tyr Ile
            20                  25                  30

His Trp Tyr Gln Gln Lys Pro Gly Ser Ser Pro Lys Ser Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln His Trp Ser Ser Lys Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 131
<211> LENGTH: 213
<212> TYPE: PRT
<213> ORGANISM: Mus musculus

<400> SEQUENCE: 131

Gln Thr Val Leu Ser Gln Ser Pro Ala Ile Leu Ser Ala Ser Pro Gly
1               5                   10                  15

Glu Lys Val Thr Met Thr Cys Arg Ala Ser Ser Ser Val Thr Tyr Ile
            20                  25                  30

His Trp Tyr Gln Gln Lys Pro Gly Ser Ser Pro Lys Ser Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln His Trp Ser Ser Lys Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

```
Thr Leu Thr Leu Thr Lys Asp Glu Tyr Glu Arg His Asn Ser Tyr Thr
            180                 185                 190
Cys Glu Ala Thr His Lys Thr Ser Thr Ser Pro Ile Val Lys Ser Phe
            195                 200                 205
Asn Arg Asn Glu Cys
            210

<210> SEQ ID NO 132
<211> LENGTH: 214
<212> TYPE: PRT
<213> ORGANISM: Artificial Sequence
<220> FEATURE:
<223> OTHER INFORMATION: synthetically constructed humanized light chain

<400> SEQUENCE: 132

Asp Ile Gln Met Thr Gln Ser Pro Ser Ser Leu Ser Ala Ser Val Gly
  1               5                  10                  15
Asp Arg Val Thr Ile Thr Cys Ser Ala Ser Gln Asp Ile Ser Asn Tyr
             20                  25                  30
Leu Asn Trp Tyr Gln Gln Lys Pro Gly Lys Ala Pro Lys Val Leu Ile
         35                  40                  45
Tyr Phe Thr Ser Ser Leu His Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Ser Thr Val Pro Trp
                 85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 133
<211> LENGTH: 394
<212> TYPE: PRT
<213> ORGANISM: Homo sapiens

<400> SEQUENCE: 133

Gln Val Gln Leu Val Glu Ser Gly Gly Gly Val Val Gln Pro Gly Arg
  1               5                  10                  15
Ser Leu Arg Leu Ser Cys Ala Ala Ser Gly Phe Thr Phe Ser Val Tyr
             20                  25                  30
Gly Met Asn Trp Val Arg Gln Ala Pro Gly Lys Gly Leu Glu Trp Val
         35                  40                  45
```

```
Ala Ile Ile Trp Tyr Asp Gly Asp Asn Gln Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Gly Leu Arg Ala Glu Asp Thr Ala Val Tyr Tyr Cys
                 85                  90                  95

Ala Arg Asp Leu Arg Thr Gly Pro Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Glu Ile Val Leu Thr Gln Ser Pro Asp Phe Gln Ser
            180                 185                 190

Val Thr Pro Lys Glu Lys Val Thr Ile Thr Cys Arg Ala Ser Gln Ser
        195                 200                 205

Ile Gly Ser Ser Leu His Trp Tyr Gln Gln Lys Pro Asp Gln Ser Pro
210                 215                 220

Lys Leu Leu Ile Lys Tyr Ala Ser Gln Ser Phe Ser Gly Val Pro Ser
225                 230                 235                 240

Arg Phe Ser Gly Ser Gly Ser Gly Thr Asp Phe Thr Leu Thr Ile Asn
                245                 250                 255

Ser Leu Glu Ala Glu Asp Ala Ala Ala Tyr Tyr Cys His Gln Ser Ser
            260                 265                 270

Ser Leu Pro Phe Thr Phe Gly Pro Gly Thr Lys Val Asp Ile Lys Arg
        275                 280                 285

Thr Val Ala Ala Pro Ser Val Phe Ile Phe Pro Pro Ser Asp Glu Gln
    290                 295                 300

Leu Lys Ser Gly Thr Ala Ser Val Val Cys Leu Leu Asn Asn Phe Tyr
305                 310                 315                 320

Pro Arg Glu Ala Lys Val Gln Trp Lys Val Asp Asn Ala Leu Gln Ser
                325                 330                 335

Gly Asn Ser Gln Glu Ser Val Thr Glu Gln Asp Ser Lys Asp Ser Thr
            340                 345                 350

Tyr Ser Leu Ser Ser Thr Leu Thr Leu Ser Lys Ala Asp Tyr Glu Lys
        355                 360                 365

His Lys Val Tyr Ala Cys Glu Val Thr His Gln Gly Leu Ser Ser Pro
370                 375                 380

Val Thr Lys Ser Phe Asn Arg Gly Glu Cys
385                 390

<210> SEQ ID NO 134
<211> LENGTH: 214
<212> TYPE: PRT
<213> ORGANISM: Homo sapiens

<400> SEQUENCE: 134

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asn Val Gly Thr Asn
                 20                  25                  30
```

```
Val Ala Trp Tyr Gln Gln Lys Pro Gly Lys Ala Pro Lys Ala Leu Ile
     35                  40                  45

Tyr Ser Ala Ser Phe Leu Tyr Ser Gly Val Pro Tyr Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ile Tyr Pro Leu
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 135
<211> LENGTH: 213
<212> TYPE: PRT
<213> ORGANISM: Artificial Sequence
<220> FEATURE:
<223> OTHER INFORMATION: synthetically constructed chimeric light chain

<400> SEQUENCE: 135

Asp Ile Leu Leu Thr Gln Ser Pro Val Ile Leu Ser Val Ser Pro Gly
 1               5                  10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
         35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
    210

<210> SEQ ID NO 136
<211> LENGTH: 215
<212> TYPE: PRT
<213> ORGANISM: Artificial Sequence
<220> FEATURE:
<223> OTHER INFORMATION: synthetically constructed humanized light chain

<400> SEQUENCE: 136

Asp Ile Gln Leu Thr Gln Ser Pro Ser Ser Leu Ser Ala Ser Val Gly
 1               5                  10                  15

Asp Arg Val Thr Met Thr Cys Ser Ala Ser Ser Val Ser Ser Ser
            20                  25                  30

Tyr Leu Tyr Trp Tyr Gln Gln Lys Pro Gly Lys Ala Pro Lys Leu Trp
        35                  40                  45

Ile Tyr Ser Thr Ser Asn Leu Ala Ser Gly Val Pro Ala Arg Phe Ser
50                  55                  60

Gly Ser Gly Ser Gly Thr Asp Phe Thr Leu Thr Ile Ser Ser Leu Gln
65                  70                  75                  80

Pro Glu Asp Ser Ala Ser Tyr Phe Cys His Gln Trp Asn Arg Tyr Pro
                85                  90                  95

Tyr Thr Phe Gly Gly Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Pro Arg Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 137
<211> LENGTH: 213
<212> TYPE: PRT
<213> ORGANISM: Artificial Sequence
<220> FEATURE:
<223> OTHER INFORMATION: synthetically constructed humanized light chain

<400> SEQUENCE: 137

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
```

```
                35                  40                  45
Thr Thr Ser Asn Leu Ala Ser Gly Val Pro Ala Arg Phe Ser Gly Ser
     50                  55                  60
Gly Ser Gly Thr Glu Phe Thr Leu Thr Ile Ser Ser Leu Gln Pro Asp
 65                  70                  75                  80
Asp Phe Ala Thr Tyr Tyr Cys His Gln Arg Ser Thr Tyr Pro Leu Thr
                 85                  90                  95
Phe Gly Gln Gly Thr Lys Val Glu Val Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 138
<211> LENGTH: 215
<212> TYPE: PRT
<213> ORGANISM: Homo sapiens

<400> SEQUENCE: 138

Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Arg Gly Arg
             20                  25                  30
Tyr Leu Ala Trp Tyr Gln Gln Lys Pro Gly Gln Ala Pro Arg Leu Leu
         35                  40                  45
Ile Tyr Gly Ala Ser Ser Arg Ala Thr Gly Ile Pro Asp Arg Phe Ser
     50                  55                  60
Gly Ser Gly Ser Gly Thr Asp Phe Thr Leu Thr Ile Ser Arg Leu Glu
 65                  70                  75                  80
Pro Glu Asp Phe Ala Val Phe Tyr Cys Gln Gln Tyr Gly Ser Ser Pro
                 85                  90                  95
Arg Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
```

```
Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 139
<211> LENGTH: 214
<212> TYPE: PRT
<213> ORGANISM: Artificial Sequence
<220> FEATURE:
<223> OTHER INFORMATION: synthetically constructed humanized light chain

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 140
<211> LENGTH: 214
<212> TYPE: PRT
<213> ORGANISM: Artificial Sequence
<220> FEATURE:
<223> OTHER INFORMATION: synthetically constructed humanized light chain

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Thr Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 141
<211> LENGTH: 214
<212> TYPE: PRT
<213> ORGANISM: Homo sapiens

<400> SEQUENCE: 141

Asp Ile Gln Met Thr Gln Ser Pro Ser Thr Leu Ser Ala Ser Val Gly
1               5                   10                  15

Asp Arg Val Thr Ile Thr Cys Lys Ala Ser Glu Asn Val Asp Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gly Gln Ser Tyr Asn Tyr Pro Phe
                85                  90                  95

Thr Phe Gly Gln Gly Thr Lys Val Glu Val Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys

<210> SEQ ID NO 142
<211> LENGTH: 214
<212> TYPE: PRT
<213> ORGANISM: Artificial Sequence
<220> FEATURE:
<223> OTHER INFORMATION: synthetically constructed chimeric light chain

<400> SEQUENCE: 142

Asp Ile Val Met Thr Gln Ser Gln Arg Phe Met Ser Thr Thr Val Gly
1               5                   10                  15

Asp Arg Val Ser Ile Thr Cys Lys Ala Ser Gln Asn Val Val Ser Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Phe Phe Cys Gln Gln Tyr Ser Asn Tyr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 143
<211> LENGTH: 209
<212> TYPE: PRT
<213> ORGANISM: Mus musculus

<400> SEQUENCE: 143

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

```
Phe Gly Ala Gly Thr Lys Leu Glu Leu Lys Arg Ala Asp Ala Ala Pro
                100                 105                 110

Thr Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn

<210> SEQ ID NO 144
<211> LENGTH: 209
<212> TYPE: PRT
<213> ORGANISM: Mus musculus

<400> SEQUENCE: 144

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
            35                  40                  45

Ala Pro Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Ala Asp Ala Ala Pro
                100                 105                 110

Thr Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn

<210> SEQ ID NO 145
<211> LENGTH: 215
<212> TYPE: PRT
<213> ORGANISM: Homo sapiens
```

-continued

```
<400> SEQUENCE: 145

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Gly Ser Ser
            20                  25                  30

Tyr Leu Ala Trp Tyr Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 146
<211> LENGTH: 220
<212> TYPE: PRT
<213> ORGANISM: Artificial Sequence
<220> FEATURE:
<223> OTHER INFORMATION: synthetically constructed humanized light chain

<400> SEQUENCE: 146

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
```

```
                130                 135                 140
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 147
<211> LENGTH: 213
<212> TYPE: PRT
<213> ORGANISM: Mus musculus

<400> SEQUENCE: 147

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 148
<211> LENGTH: 213
<212> TYPE: PRT
<213> ORGANISM: Artificial Sequence
<220> FEATURE:
<223> OTHER INFORMATION: synthetically constructed humanized light chain

<400> SEQUENCE: 148

Asp Ile Gln Met Thr Gln Ser Pro Ser Ser Leu Ser Ala Ser Val Gly
1               5                   10                  15
```

```
Asp Arg Val Thr Ile Thr Cys Lys Thr Ser Gln Asp Ile Asn Lys Tyr
            20                  25                  30

Met Ala Trp Tyr Gln Gln Thr Pro Gly Lys Ala Pro Arg Leu Leu Ile
        35                  40                  45

His Tyr Thr Ser Ala Leu Gln Pro Gly Ile Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 149
<211> LENGTH: 214
<212> TYPE: PRT
<213> ORGANISM: Homo sapiens

<400> SEQUENCE: 149

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 150
<211> LENGTH: 218
<212> TYPE: PRT
<213> ORGANISM: Artificial Sequence
<220> FEATURE:
<223> OTHER INFORMATION: synthetically constructed humanized light chain

<400> SEQUENCE: 150

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 151
<211> LENGTH: 214
<212> TYPE: PRT
<213> ORGANISM: Homo sapiens

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

Tyr Asp Ala Ser Asn Leu Glu Thr Gly Val Pro Ser Arg Phe Ser Gly
            50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln His Phe Asp His Leu Pro Leu
                 85                  90                  95

Ala Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 152
<211> LENGTH: 214
<212> TYPE: PRT
<213> ORGANISM: Artificial Sequence
<220> FEATURE:
<223> OTHER INFORMATION: synthetically constructed humanized light chain

<400> SEQUENCE: 152

Asp Ile Gln Leu Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 153
<211> LENGTH: 213
<212> TYPE: PRT
<213> ORGANISM: Artificial Sequence
<220> FEATURE:
<223> OTHER INFORMATION: synthetically constructed chimeric light chain

<400> SEQUENCE: 153

Gln Ile Val Leu Ser Gln Ser Pro Ala Ile Leu Ser Ala Ser Pro Gly
  1               5                  10                  15

Glu Lys Val Thr Met Thr Cys Arg Ala Ser Ser Ser Val Ser Tyr Ile
             20                  25                  30

His Trp Phe Gln Gln Lys Pro Gly Ser Ser Pro Lys Pro Trp Ile Tyr
         35                  40                  45

Ala Thr Ser Asn Leu Ala Ser Gly Val Pro Val Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 154
<211> LENGTH: 210
<212> TYPE: PRT
<213> ORGANISM: Mus musculus

<400> SEQUENCE: 154

Asp Ile Gln Met Thr Gln Ser Pro Ala Ser Leu Ser Val Ser Val Gly
  1               5                  10                  15

Glu Thr Val Thr Ile Thr Cys Arg Ala Ser Glu Asn Ile Tyr Ser Asn
             20                  25                  30

Leu Ala Trp Tyr Gln Gln Lys Gln Gly Lys Ser Pro Gln Leu Leu Val
         35                  40                  45

Tyr Ala Ala Thr Asn Leu Ala Asp Gly Val Pro Ser Arg Phe Ser Gly
     50                  55                  60
```

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
            85                  90                  95

Thr Phe Gly Gly Gly Thr Arg Leu Glu Ile Lys Arg Ala Asp Ala Ala
            100                 105                 110

Pro Thr Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn
    210

<210> SEQ ID NO 155
<211> LENGTH: 210
<212> TYPE: PRT
<213> ORGANISM: Mus musculus

<400> SEQUENCE: 155

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
            85                  90                  95

Thr Phe Gly Gly Gly Thr Arg Leu Glu Ile Lys Arg Ala Asp Ala Ala
            100                 105                 110

Pro Thr Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn
    210

<210> SEQ ID NO 156
<211> LENGTH: 214
<212> TYPE: PRT
<213> ORGANISM: Artificial Sequence
<220> FEATURE:
<223> OTHER INFORMATION: synthetically constructed humanized light chain

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 157
<211> LENGTH: 210
<212> TYPE: PRT
<213> ORGANISM: Mus musculus

<400> SEQUENCE: 157

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

```
Phe Gly Ala Gly Thr Lys Leu Glu Leu Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210

<210> SEQ ID NO 158
<211> LENGTH: 210
<212> TYPE: PRT
<213> ORGANISM: Mus musculus

<400> SEQUENCE: 158

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
            35                  40                  45

Ala Pro Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210

<210> SEQ ID NO 159
<211> LENGTH: 214
<212> TYPE: PRT
<213> ORGANISM: Artificial Sequence
```

<220> FEATURE:
<223> OTHER INFORMATION: synthetically constructed humanized light chain

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 160
<211> LENGTH: 214
<212> TYPE: PRT
<213> ORGANISM: Artificial Sequence
<220> FEATURE:
<223> OTHER INFORMATION: synthetically constructed humanized light chain

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly

```
                    115                 120                 125
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 161
<211> LENGTH: 214
<212> TYPE: PRT
<213> ORGANISM: Homo sapiens

<400> SEQUENCE: 161

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 162
<211> LENGTH: 214
<212> TYPE: PRT
<213> ORGANISM: Homo sapiens

<400> SEQUENCE: 162

Ala Ile Gln Leu Thr Gln Ser Pro Ser Ser Leu Ser Ala Ser Val Gly
```

```
              1               5                  10                 15
Asp Arg Val Thr Ile Thr Cys Arg Ala Ser Gln Asp Ile Ser Ser Ala
                20                  25                 30

Leu Val Trp Tyr Gln Gln Lys Pro Gly Lys Ala Pro Lys Leu Leu Ile
                35                  40                 45

Tyr Asp Ala Ser Ser Leu Glu Ser Gly Val Pro Ser Arg Phe Ser Gly
            50                  55                 60

Ser Glu Ser Gly Thr Asp Phe Thr Leu Thr Ile Ser Ser Leu Gln Pro
65                  70                  75                 80

Glu Asp Phe Ala Thr Tyr Tyr Cys Gln Gln Phe Asn Ser Tyr Pro Leu
                85                  90                 95

Thr Phe Gly Gly Gly Thr Lys Val Glu Ile Lys Arg Thr Val Ala Ala
                100                 105                110

Pro Ser Val Phe Ile Phe Pro Pro Ser Asp Glu Gln Leu Lys Ser Gly
                115                 120                125

Thr Ala Ser Val Val Cys Leu Leu Asn Asn Phe Tyr Pro Arg Glu Ala
            130                 135                140

Lys Val Gln Trp Lys Val Asp Asn Ala Leu Gln Ser Gly Asn Ser Gln
145                 150                 155                160

Glu Ser Val Thr Glu Gln Asp Ser Lys Asp Ser Thr Tyr Ser Leu Ser
                165                 170                175

Ser Thr Leu Thr Leu Ser Lys Ala Asp Tyr Glu Lys His Lys Val Tyr
            180                 185                190

Ala Cys Glu Val Thr His Gln Gly Leu Ser Ser Pro Val Thr Lys Ser
                195                 200                205

Phe Asn Arg Gly Glu Cys
        210

<210> SEQ ID NO 163
<211> LENGTH: 218
<212> TYPE: PRT
<213> ORGANISM: Artificial Sequence
<220> FEATURE:
<223> OTHER INFORMATION: synthetically constructed humanized light chain

<400> SEQUENCE: 163

Asp Ile Gln Met Thr Gln Ser Pro Ser Ser Leu Ser Ala Ser Val Gly
1               5                   10                 15

Asp Arg Val Thr Ile Thr Cys Lys Ala Ser Glu Ser Val Asp Asn Tyr
                20                  25                 30

Gly Lys Ser Leu Met His Trp Tyr Gln Gln Lys Pro Gly Lys Ala Pro
            35                  40                 45

Lys Leu Leu Ile Tyr Arg Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                 80

Ser Leu Gln Pro Glu Asp Phe Ala Thr Tyr Tyr Cys Gln Gln Ser Asn
                85                  90                 95

Glu Asp Pro Trp Thr Phe Gly Gly Gly Thr Lys Val Glu Ile Lys Arg
                100                 105                110

Thr Val Ala Ala Pro Ser Val Phe Ile Phe Pro Pro Ser Asp Glu Gln
                115                 120                125

Leu Lys Ser Gly Thr Ala Ser Val Val Cys Leu Leu Asn Asn Phe Tyr
            130                 135                140

Pro Arg Glu Ala Lys Val Gln Trp Lys Val Asp Asn Ala Leu Gln Ser
```

```
                145                 150                 155                 160
        Gly Asn Ser Gln Glu Ser Val Thr Glu Gln Asp Ser Lys Asp Ser Thr
                        165                 170                 175

Tyr Ser Leu Ser Ser Thr Leu Thr Leu Ser Lys Ala Asp Tyr Glu Lys
                        180                 185                 190

His Lys Val Tyr Ala Cys Glu Val Thr His Gln Gly Leu Ser Ser Pro
                        195                 200                 205

Val Thr Lys Ser Phe Asn Arg Gly Glu Cys
                        210                 215

<210> SEQ ID NO 164
<211> LENGTH: 219
<212> TYPE: PRT
<213> ORGANISM: Artificial Sequence
<220> FEATURE:
<223> OTHER INFORMATION: synthetically constructed humanized light chain

<400> SEQUENCE: 164

Asp Val Val Met Thr Gln Ser Pro Leu Ser Leu Pro Val Thr Pro Gly
        1               5                   10                  15

Glu Pro Ala Ser Ile Ser Cys Lys Ser Ser Gln Ser Leu Leu Asp Ser
                        20                  25                  30

Asp Gly Lys Thr Tyr Leu Asn Trp Leu Leu Gln Lys Pro Gly Gln Ser
                        35                  40                  45

Pro Gln Arg Leu Ile Tyr Leu Val Ser Lys Leu Asp Ser Gly Val Pro
                50                  55                  60

Asp Arg Phe Ser Gly Ser Gly Ser Gly Thr Asp Phe Thr Leu Lys Ile
        65                  70                  75                  80

Ser Arg Val Glu Ala Glu Asp Val Gly Val Tyr Tyr Cys Trp Gln Gly
                        85                  90                  95

Thr His Phe Pro Arg Thr Phe Gly Gln Gly Thr Lys Val Glu Ile Lys
                        100                 105                 110

Arg Thr Val Ala Ala Pro Ser Val Phe Ile Phe Pro Pro Ser Asp Glu
                        115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
        145                 150                 155                 160

Ser Gly Asn Ser Gln Glu Ser Val Thr Glu Gln Asp Ser Lys Asp Ser
                        165                 170                 175

Thr Tyr Ser Leu Ser Ser Thr Leu Thr Leu Ser Lys Ala Asp Tyr Glu
                        180                 185                 190

Lys His Lys Val Tyr Ala Cys Glu Val Thr His Gln Gly Leu Ser Ser
                        195                 200                 205

Pro Val Thr Lys Ser Phe Asn Arg Gly Glu Cys
                        210                 215

<210> SEQ ID NO 165
<211> LENGTH: 219
<212> TYPE: PRT
<213> ORGANISM: Artificial Sequence
<220> FEATURE:
<223> OTHER INFORMATION: synthetically constructed humanized light chain

<400> SEQUENCE: 165

Asp Ile Val Met Thr Gln Ser Pro Leu Ser Leu Pro Val Thr Pro Gly
        1               5                   10                  15
```

Glu Pro Ala Ser Ile Ser Cys Arg Ser Ser Gln Ser Ile Val His Ser
                20                  25                  30

Asn Gly Asn Thr Tyr Leu Gln Trp Tyr Leu Gln Lys Pro Gly Gln Ser
            35                  40                  45

Pro Gln Leu Leu Ile Tyr Lys Val Ser Asn Arg Leu Tyr Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 166
<211> LENGTH: 111
<212> TYPE: PRT
<213> ORGANISM: Artificial Sequence
<220> FEATURE:
<223> OTHER INFORMATION: synthetically constructed humanized light chain

<400> SEQUENCE: 166

Asp Ile Val Met Thr Gln Ser Pro Asp Ser Leu Ala Val Ser Leu Gly
1               5                   10                  15

Glu Arg Ala Thr Ile Ser Cys Arg Ala Ser Glu Ser Val Asp Asn Tyr
                20                  25                  30

Gly Ile Ser Phe Met Lys Trp Phe Gln Gln Lys Pro Gly Gln Pro Pro
            35                  40                  45

Lys Leu Leu Ile Tyr Ala Ala Ser Asn Gln Gly Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Trp Thr Phe Gly Gly Gly Thr Lys Val Glu Ile Lys
            100                 105                 110

<210> SEQ ID NO 167
<211> LENGTH: 217
<212> TYPE: PRT
<213> ORGANISM: Homo sapiens

<400> SEQUENCE: 167

Gln Ser Val Leu Thr Gln Pro Pro Ser Val Ser Gly Ala Pro Gly Gln

```
               1               5                  10                 15
            Arg Val Thr Ile Ser Cys Thr Gly Ser Gly Ser Asn Ile Gly Ala Pro
                            20                  25                 30

Tyr Asp Val Ser Trp Tyr Gln Gln Leu Pro Gly Thr Ala Pro Lys Leu
                            35                  40                 45

Leu Ile Tyr His Asn Asn Lys Arg Pro Ser Gly Val Pro Asp Arg Phe
                            50                  55                 60

Ser Gly Ser Lys Ser Gly Thr Ser Ala Ser Leu Ala Ile Thr Gly Leu
             65                  70                  75                 80

Gln Ala Glu Asp Glu Ala Asp Tyr Tyr Cys Ala Thr Val Glu Ala Gly
                            85                  90                 95

Leu Ser Gly Ser Val Phe Gly Gly Gly Thr Lys Leu Thr Val Leu Gly
                           100                 105                110

Gln Pro Lys Ala Ala Pro Ser Val Thr Leu Phe Pro Pro Ser Ser Glu
                           115                 120                125

Glu Leu Gln Ala Asn Lys Ala Thr Leu Val Cys Leu Ile Ser Asp Phe
                           130                 135                140

Tyr Pro Gly Ala Val Thr Val Ala Trp Lys Ala Asp Ser Ser Pro Val
            145                 150                 155                160

Lys Ala Gly Val Glu Thr Thr Thr Pro Ser Lys Gln Ser Asn Asn Lys
                           165                 170                175

Tyr Ala Ala Ser Ser Tyr Leu Ser Leu Thr Pro Glu Gln Trp Lys Ser
                           180                 185                190

His Arg Ser Tyr Ser Cys Gln Val Thr His Glu Gly Ser Thr Val Glu
                           195                 200                205

Lys Thr Val Ala Pro Thr Glu Cys Ser
                           210                 215
```

<210> SEQ ID NO 168
<211> LENGTH: 214
<212> TYPE: PRT
<213> ORGANISM: Homo sapiens

<400> SEQUENCE: 168

```
            Asp Ile Gln Met Thr Gln Ser Pro Ser Ser Leu Ser Ala Ser Val Gly
             1               5                  10                 15

Asp Arg Val Thr Ile Thr Cys Arg Ala Ser Gln Ser Ile Asn Ser Tyr
                            20                  25                 30

Leu Asp Trp Tyr Gln Gln Lys Pro Gly Lys Ala Pro Lys Leu Leu Ile
                            35                  40                 45

Tyr Ala Ala Ser Ser Leu Gln Ser Gly Val Pro Ser Arg Phe Ser Gly
             50                  55                  60

Ser Gly Ser Gly Thr Asp Phe Thr Leu Thr Ile Ser Ser Leu Gln Pro
             65                  70                  75                 80

Glu Asp Phe Ala Thr Tyr Tyr Cys Gln Gln Tyr Tyr Ser Thr Pro Phe
                            85                  90                 95

Thr Phe Gly Pro Gly Thr Lys Val Glu Ile Lys Arg Thr Val Ala Ala
                           100                 105                110

Pro Ser Val Phe Ile Phe Pro Pro Ser Asp Glu Gln Leu Lys Ser Gly
                           115                 120                125

Thr Ala Ser Val Val Cys Leu Leu Asn Asn Phe Tyr Pro Arg Glu Ala
                           130                 135                140

Lys Val Gln Trp Lys Val Asp Asn Ala Leu Gln Ser Gly Asn Ser Gln
            145                 150                 155                160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 169
<211> LENGTH: 216
<212> TYPE: PRT
<213> ORGANISM: Homo sapiens

<400> SEQUENCE: 169

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 170
<211> LENGTH: 214
<212> TYPE: PRT
<213> ORGANISM: Homo sapiens

<400> SEQUENCE: 170

Glu Ile Val Met Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45
```

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys His Gln Tyr Gly Ser Thr Pro Leu
                 85                  90                  95

Thr Phe Gly Gly Gly Thr Lys Ala Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 171
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: light chain segment

<400> SEQUENCE: 171

Gln Arg Thr Asn Gly Ser
 1               5

<210> SEQ ID NO 172
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: light chain segment

<400> SEQUENCE: 172

Ile Ala Asp Tyr Tyr
 1               5

<210> SEQ ID NO 173
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: light chain segment

```
<400> SEQUENCE: 173

Ala Gly Thr Lys Leu Glu
1               5

<210> SEQ ID NO 174
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: light chain segment

<400> SEQUENCE: 174

Gln Lys Pro Gly Gln Ser
1               5

<210> SEQ ID NO 175
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(5)
<223> OTHER INFORMATION: light chain segment

<400> SEQUENCE: 175

Leu Gly Val Tyr Phe
1               5

<210> SEQ ID NO 176
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: light chain segment

<400> SEQUENCE: 176

Gln Lys Pro Gly Lys Ala
1               5

<210> SEQ ID NO 177
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(5)
<223> OTHER INFORMATION: light chain segment

<400> SEQUENCE: 177

Phe Ala Thr Tyr Tyr
1               5

<210> SEQ ID NO 178
<211> LENGTH: 6
<212> TYPE: PRT
<213> ORGANISM: Artificial Sequence
<220> FEATURE:
```

```
<223> OTHER INFORMATION: synthetic construct
<220> FEATURE:
<221> NAME/KEY: CHAIN
<222> LOCATION: (1)...(6)
<223> OTHER INFORMATION: light chain segment

<400> SEQUENCE: 178

Gln Gly Thr Lys Val Glu
 1               5

<210> SEQ ID NO 179
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: heavy chain segment

<400> SEQUENCE: 179

Gln Ser Pro Gly Lys Gly
 1               5

<210> SEQ ID NO 180
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(4)
<223> OTHER INFORMATION: heavy chain segment

<400> SEQUENCE: 180

Gln Gly Thr Leu
 1

<210> SEQ ID NO 181
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: heavy chain segment

<400> SEQUENCE: 181

Gln Asn Ile Gly Lys Ser
 1               5

<210> SEQ ID NO 182
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(4)
<223> OTHER INFORMATION: heavy chain segment

<400> SEQUENCE: 182

Gln Gly Thr Ser
 1
```

```
<210> SEQ ID NO 183
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(6)
<223> OTHER INFORMATION: heavy chain segment

<400> SEQUENCE: 183

Gln Ala Pro Gly Lys Gly
 1               5

<210> SEQ ID NO 184
<211> LENGTH: 12
<212> TYPE: PRT
<213> ORGANISM: Artificial Sequence
<220> FEATURE:
<223> OTHER INFORMATION: synthetically constructed linker sequence

<400> SEQUENCE: 184

Gly Gly Gly Ser Gly Gly Gly Ser Gly Gly Gly Ser
 1               5                  10

<210> SEQ ID NO 185
<211> LENGTH: 16
<212> TYPE: PRT
<213> ORGANISM: Artificial Sequence
<220> FEATURE:
<223> OTHER INFORMATION: synthetically constructed linker sequence

<400> SEQUENCE: 185

Gly Gly Gly Ser Gly Gly Gly Ser Gly Gly Gly Ser Gly Gly Gly Ser
 1               5                  10                  15

<210> SEQ ID NO 186
<211> LENGTH: 20
<212> TYPE: PRT
<213> ORGANISM: Artificial Sequence
<220> FEATURE:
<223> OTHER INFORMATION: synthetically constructed linker sequence

<400> SEQUENCE: 186

Gly Gly Gly Ser Gly Gly Gly Ser Gly Gly Gly Ser Gly Gly Gly Ser
 1               5                  10                  15

Gly Gly Gly Ser
             20

<210> SEQ ID NO 187
<211> LENGTH: 17
<212> TYPE: PRT
<213> ORGANISM: Artificial Sequence
<220> FEATURE:
<223> OTHER INFORMATION: synthetically constructed meditope

<400> SEQUENCE: 187

Cys Gln Phe Asp Leu Ser Thr Arg Arg Leu Arg Cys Gly Gly Gly Ser
 1               5                  10                  15

Lys

<210> SEQ ID NO 188
<211> LENGTH: 221
<212> TYPE: PRT
<213> ORGANISM: Homo sapiens
```

-continued

```
<220> FEATURE:
<221> NAME/KEY: DOMAIN
<222> LOCATION: (1)...(221)
<223> OTHER INFORMATION: IgG Fab domain

<400> SEQUENCE: 188
```

Gln Val Gln Leu Lys Gln Ser Gly Pro Gly Leu Val Gln Pro Ser Gln
 1               5                   10                  15

Ser Leu Ser Ile Thr Cys Thr Val Ser Gly Phe Ser Leu Thr Asn Tyr
             20                  25                  30

Gly Val His Trp Val Arg Gln Ser Pro Gly Lys Gly Leu Glu Trp Leu
         35                  40                  45

Gly Val Ile Trp Ser Gly Gly Asn Thr Asp Tyr Asn Thr Pro Phe Thr
     50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
             100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser
    210                 215                 220

```
<210> SEQ ID NO 189
<211> LENGTH: 221
<212> TYPE: PRT
<213> ORGANISM: Homo sapiens
<220> FEATURE:
<221> NAME/KEY: DOMAIN
<222> LOCATION: (1)...(221)
<223> OTHER INFORMATION: IgE Fab domain

<400> SEQUENCE: 189
```

Gln Val Ser Leu Arg Glu Ser Gly Gly Gly Leu Val Gln Pro Gly Arg
 1               5                   10                  15

Ser Leu Arg Leu Ser Cys Thr Ala Ser Gly Phe Thr Phe Arg His His
             20                  25                  30

Gly Met Thr Trp Val Arg Gln Ala Pro Gly Lys Gly Leu Glu Trp Val
         35                  40                  45

Ala Ser Leu Ser Gly Ser Gly Thr Lys Thr His Phe Ala Asp Ser Val
     50                  55                  60

Lys Gly Arg Phe Thr Ile Ser Arg Asp Asn Ser Asn Asn Thr Leu Tyr
 65                  70                  75                  80

Leu Gln Met Asp Asn Val Arg Asp Glu Asp Thr Ala Ile Tyr Tyr Cys
                 85                  90                  95

-continued

```
Ala Lys Ala Lys Arg Val Gly Ala Thr Gly Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro
        210                 215                 220
```

MEDITOPES AND MEDITOPE-BINDING ANTIBODIES AND USES THEREOF

PRIORITY CLAIM

This application is a divisional of U.S. application Ser. No. 13/443,804, filed Apr. 10, 2012, now U.S. Pat. No. 8,962,804, which claims the benefit of International Application Number PCT/US2011/055656 filed Oct. 10, 2011, and U.S. Provisional Patent Application Ser. No. 61/597,708, filed Feb. 10, 2012, and is a continuation-in-part of U.S. application Ser. No. 13/270,207, filed Oct. 10, 2011, now U.S. Pat. No. 8,658,774, which claims the benefit of U.S. Provisional Patent Application Ser. No. 61/391,558, filed Oct. 8, 2010, the contents of each of which are incorporated herein by reference in their entirety.

This invention was made with Government support of NCI Comprehensive Cancer Center Grant number CA0335752-28. The government has certain rights in this invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 706122000110SeqList.txt, date recorded: Aug. 5, 2014, size: 331,783 KB).

BACKGROUND

Monoclonal antibodies (mAbs) are used in a number of therapeutic, diagnostic, and research applications. Therapeutic and diagnostic areas include cancer, antiviral treatment, autoimmune and inflammatory disease, allergy, cardiovascular disease, osteoporosis, and rheumatology.

Protein engineering and other efforts have generated mAbs with improved efficacy and targeting (e.g., bispecific mAbs), improved localization, tissue penetration, and blood clearance (e.g., single chain Fab variable fragments (scFvs), diabodies, minibodies, and other fragments), and altered immunostimulatory, safety, toxicity, and/or pharmacokinetic/pharmacodynamics properties, such as those containing modified Fc regions (e.g., through mutation or glycosylation). mAbs have been reengineered to permit site-specific conjugation of small molecules for improved delivery (e.g., ThioMABs) or to irreversibly bind to their antigen (e.g., infinite affinity mAbs). mAbs have also been developed to improve the circulation and presentation of bioactive peptides and other biologics (e.g., CovX-bodies). Conjugation to various agents has allowed targeted immunotherapy and diagnostic methods. Hetero-multimeric scFvs and scFvs or mAbs fused to avidin have been developed for pre-targeted therapy and to improve the detection limits for tumor imaging.

Although mAbs can be effective and have advantages over small molecule approaches, existing antibodies and methods have various limitations. These can include adverse side effects resulting from off-target interactions, and/or collateral damage due to, among other things, long circulation times of antibody-drug conjugates). There is a need for improved antibodies and associated compounds, including those providing improved efficacy, synergy, specificity, and safety, and methods and uses of the same. Provided are antibodies, compounds and compositions including peptides and other molecules, and related methods that address such needs.

SUMMARY

Among the provided embodiments are antibodies, compounds and compositions, including peptides and other molecules for use with the antibodies, as well as methods and uses thereof and for producing the same, as well as compounds, compositions, complexes, mixtures, and systems, e.g., kits, containing the same. In some aspects, the provided embodiments afford improved efficacy, synergy, specificity, and/or safety, compared with available antibodies and associated compounds, compositions, methods and uses.

Provided are antibodies, including meditope-enabled antibodies (including fragments thereof), which bind to (i.e., are capable of binding to) one or more meditope. In some aspects, the antibodies bind to a meditope that is a cyclic peptide derived from a peptide having an amino acid sequence of SEQ ID NO: 1.

In some aspects, the antibodies bind to a meditope that is a cyclic peptide derived from a peptide having an amino acid sequence of SEQ ID NO: 2. In some aspects, the antibodies bind to a meditope that is a peptide having an amino acid sequence selected from the group consisting of the sequences set forth in SEQ ID NO: 1, 2, 16-18, 23, 29, 31, 32, 36, 39, 42, 43, 45, 46, 51, 52, 54, and 55, or a cyclic peptide derived therefrom, or the sequences set forth in SEQ ID NOs: 1, 2, and 15-55, or a cyclic peptide derived therefrom, or to any of the meditopes described herein. In some cases, the meditope is a cyclic peptide derived from a peptide of the amino acid sequence set forth in SEQ ID NO: 1 or 2.

In some aspects, the antibody or fragment binds to the meditope with a particular affinity, such as an affinity that is equal to or substantially equal to one of the exemplary antibodies described herein, such as cetuximab, meditope-enabled trastuzumab, meditope-enabled M5A, or other exemplified antibody. In some examples, the antibodies bind to the meditope or meditopes with a dissociation constant of less than at or about 10 µM, less than at or about 5 µM, or less than at or about 2 µM, less than at or about 1 µM, less than at or about 500, 400, 300, 200, 100 nM, or less, such as at or about 200 picomolar or less, for example, with such a dissociation constant, as measured by a particular technique, such as surface plasmon resonance (SPR), Isothermal Titration calorimetry (ITC), fluorescence, fluorescence polarization, NMR, IR, calorimetry titrations; Kinetic exclusion; Circular dichroism, differential scanning calorimetry, or other known method, e.g., by SPR.

In some aspects, the antibodies include a heavy chain variable (VH) region and/or a light chain variable (VL) region. In some aspects, the VL region has an amino acid sequence comprising a threonine, serine, or aspartate at position 40, a residue other than glycine at position 41, and/or an aspartate or asparagine at position 85, according to Kabat numbering, and/or comprises an isoleucine or leucine at position 10 and isoleucine at position 83, according to Kabat numbering, and/or comprises a valine or isoleucine at position 9 and a residue other than glutamine at position 100, according to Kabat numbering. In some examples, the amino acid sequence of the VL region has a threonine at position 40, an asparagine at position 41, and an aspartate at position 85, according to Kabat numbering.

In some aspects, the VH region has an amino acid sequence comprising a serine or proline at position 40 and an isoleucine, tyrosine, methionine, phenylalanine, or tryptophan at position 89, according to Kabat numbering. In some examples, the amino acid sequence of the VH region has a serine at position 40 and an isoleucine at position 89, according to Kabat numbering.

In some examples, the amino acid sequence of the VL region has a valine or isoleucine at position 9, an isoleucine or leucine at position 10, an arginine at position 39, a threonine at position 40, an asparagine at position 41, a glycine at position 42, a serine at position 43, an isoleucine at position 83, an aspartate at position 85, and an alanine at position 100, according to Kabat numbering; and/or the amino acid sequence of the VH region has a serine at position 40 and an isoleucine at position 89, according to Kabat numbering.

In some aspects of the provided antibodies, the VL region does not contain a proline at position 40, a glycine at position 41, and/or a threonine at position 85, according to Kabat numbering, and/or the VH region does not contain an asparagine or alanine at position 40 and/or a valine at position 89, according to Kabat numbering.

In some aspects, the VL region does not contain an serine at position 10, a proline at position 40, a glycine at position 41, an phenylalanine at position 83, and/or a threonine at position 85, according to Kabat numbering, and/or the VH region does not contain an asparagine or alanine at position 40 and/or a valine at position 89, according to Kabat numbering.

In some aspects, the antibodies (including fragments) further include one or more constant regions, typically human constant region(s), such as a CL and/or CH1, e.g., human CL and/or CH1.

In some aspects, the provided antibody or fragment has a VL region with an amino acid sequence comprising a light chain framework region (FR) 1 (FR-L1), an FR-L2, an FR-L3, and/or an FR-L4 of the light chain sequence set forth in SEQ ID NO: 71 or SEQ ID NO: 61 (or an FR-L1, FR-L2, FR-L3, and/or FR-L4 that is at least at or about 75, 80, 85, 90, 91, 92, 93, 94, 95, 96, 97, 98, or 99% identical to the FR-L1, FR-L2, FR-L3, and/or FR-L4 of the light chain of SEQ ID NO: 71 or 61), and in some aspects at least one complementarity determining region (CDR) that is distinct from the CDRs of the light chain sequence set forth in SEQ ID NO: 71; and/or a VH region with an amino acid sequence having a heavy chain FR1 (FR-H1), an FR-H2, an FR-H3, and/or an FR-H4, of the heavy chain sequence set forth in SEQ ID NO: 72 or SEQ ID NO: 63 (or an FR-H1, FR-H2, FR-H3, and/or FR-H4 that is at least at or about 75, 80, 85, 90, 91, 92, 93, 94, 95, 96, 97, 98, or 99% identical to the FR-H1, FR-H2, FR-H3, and/or FR-H4 of the heavy chain of SEQ ID NO: 72 or 63), and in some aspects at least one CDR that is distinct from the CDRs of the heavy chain sequence set forth in SEQ ID NO: 72.

In some aspects, the provided antibody or fragment has a CDR of the light chain sequence set forth in SEQ ID NO: 61, a CDR of the heavy chain sequence set forth in SEQ ID NO: 63.

In some aspects, the VL comprises the amino acid sequence of SEQ ID NO: 76 and the VH comprises the amino acid sequence of SEQ ID NO: 77.

In some aspects, the antibody has a VL region with an amino acid sequence comprising a light chain framework region (FR) 1 (FR-L1), an FR-L2, an FR-L3, and/or an FR-L4 of the light chain sequence set forth in SEQ ID NO: 9 (or an FR-L1, FR-L2, FR-L3, and/or FR-L4 that is at least at or about 75, 80, 85, 90, 91, 92, 93, 94, 95, 96, 97, 98, or 99% identical to the FR-L1, FR-L2, FR-L3, and/or FR-L4 of SEQ ID NO: 9); and/or a VH region with an amino acid sequence having a heavy chain FR1 (FR-H1), an FR-H2, an FR-H3, and/or an FR-H4 of the heavy chain sequence set forth in SEQ ID NO: 6 (or an FR-H1, FR-H2, FR-H3, and/or FR-H4 that is at least at or about 75, 80, 85, 90, 91, 92, 93, 94, 95, 96, 97, 98, or 99% identical to the FR-H1, FR-H2, FR-H3, and/or FR-H4 of SEQ ID NO: 9). In some examples, the VL region comprises at least one complementarity determining region (CDR) that is distinct from the CDRs of the VL sequence set forth in SEQ ID NO: 9; and/or the VH region comprises at least one CDR that is distinct from the CDRs of the VH sequence set forth in SEQ ID NO: 6.

In some examples, the VL region comprises the amino acid sequence of SEQ ID NO: 73. In some examples, the VH region comprises the amino acid sequence of SEQ ID NO: 74.

In some aspects, the antibody or fragment has a VL region with an amino acid sequence comprising a light chain framework region (FR) 1 (FR-L1), an FR-L2, an FR-L3, and/or an FR-L4 of the light chain sequence set forth in SEQ ID NO: 68 (or an FR-L1, FR-L2, FR-L3, and/or FR-L4 that is at least at or about 75, 80, 85, 90, 91, 92, 93, 94, 95, 96, 97, 98, or 99% identical to the FR-L1, FR-L2, FR-L3, and/or FR-L4 of the light chain of SEQ ID NO: 68). In some examples, the VL region comprises at least one complementarity determining region (CDR) that is distinct from the CDRs of the light chain sequence set forth in SEQ ID NO: 69; and/or the VH region comprises at least one CDR that is distinct from the CDRs of the heavy chain sequence set forth in SEQ ID NO: 70.

In some examples, the VL region comprises the amino acid sequence of SEQ ID NO: 75.

In some aspects, the antibody does not specifically bind to the epitope of an EGFR that is specifically bound by cetuximab, does not contain the CDRs of cetuximab, and/or does not compete for antigen binding with cetuximab. In other aspects, the antibody is cetuximab.

In some aspects, the antibodies or fragments compete for antigen binding with, specifically bind to the same antigen or epitope as, and/or contain one, more, or all CDRs (or CDRs comprising at least at or about 75, 80, 85, 90, 91, 92, 93, 94, 95, 96, 97, 98, or 99% identity to the CDRs), e.g., including a heavy chain CDR 1, 2, and/or 3 and/or a light chain CDR1, 2, and/or 3, of one or more known antibodies, including any commercially available antibody, such as abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benraliзumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, Fbta05, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, Trbs07, ustekinumab, visilizumab, votumumab, zalutumumab, and/or brodalumab; and/or anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, the antibody produced by the hybridoma 10B5 (see Edelson & Unanue, *Curr Opin Immunol*, 2000 August; 12(4):425-31), B6H12.2 (abcam) or other anti-CD47 antibody (see Chao et al., *Cell*, 142, 699-713, Sep. 3, 2010); and/or an antibody or fragment thereof having a sequence set forth in any of SEQ ID NOs: 78-124, and/or 125-170.

In some aspects, the antibody or fragment specifically binds to an antigen selected from the group consisting of: CA-125, glycoprotein (GP) IIb/IIIa receptor, TNF-alpha, CD52, TAG-72, Carcinoembryonic antigen (CEA), interleukin-6 receptor (IL-6R), IL-2, interleukin-2 receptor a-chain (CD25), CD22, B-cell activating factor, interleukin-5 receptor (CD125), VEGF, VEGF-A, CD30, IL-1beta, prostate specific membrane antigen (PSMA), CD3, EpCAM, EGF receptor (EGFR), MUC1, human interleukin-2 receptor, Tac, RANK ligand, a complement protein, e.g., C5, EpCAM, CD11a, e.g., human CD11a, an integrin, e.g., alpha-v beta-3 integrin, vitronectin receptor alpha v beta 3 integrin, HER2, neu, CD3, CD15, CD20 (small and/or large loops), Interferon gamma, CD33, CA-IX, TNF alpha, CTLA-4, carcinoembryonic antigen, IL-5, CD3 epsilon, CAM, Alpha-4-integrin, IgE, e.g., IgE Fc region, an RSV antigen, e.g., F protein of respiratory syncytial virus (RSV), TAG-72, NCA-90 (granulocyte cell antigen), IL-6, GD2, GD3, IL-12, IL-23, IL-17, CTAA16.88, IL13, interleukin-1 beta, beta-amyloid, IGF-1 receptor (IGF-1R), delta-like ligand 4 (DLL4), alpha subunit of granulocyte macrophage colony stimulating factor receptor, hepatocyte growth factor, IFN-alpha, nerve growth factor, IL-13, CD326, Programmed cell death 1 ligand 1 (PD-L1, a.k.a. CD274, B7-H1), CD47, and CD137.

In some aspects, the antibody or fragment has a light chain having P8, V9 or I9, I10 or L10, Q38, R39, T40, N41 G42, S43, P44, R45, D82, I83, A84, D85, Y86, Y87, G99, A100, G101, T102, K103, L104, E105, R142, S162, V163, T164, E165, Q166, D167, S168, and/or Y173, according to Kabat numbering, and/or has a heavy chain having Q6, P9, R38, Q39, S40, P41, G42, K43, G44, L45, S84, D86, T87, A88, I89, Y90, Y91, W103, G104, Q105, G106, T107, L108, V111, T110, Y147, E150, P151, V152, T173, F174, P175, A176, V177, Y185, S186, and/or L187, according to Kabat numbering.

Also provided are complexes containing an antibody or antibodies (e.g., meditope-enabled antibodies) bound to one or more meditope. The antibody or antibody can be any of the meditope-enabled antibodies described herein, such as any of the aforementioned antibodies (including fragments thereof). The one or more meditope can include any one or more of the meditopes described herein, such as those described in this section, including monovalent and multivalent meditopes, and labeled meditopes, as well as meditope fusion proteins.

Also provided are meditopes, e.g., isolated meditopes. Among the provided meditopes are those described above. Among the provided meditopes are those comprising a peptide that binds to a meditope binding site of a meditope-enabled antibody, wherein the peptide is not a peptide of SEQ ID NO: 1 or 2 or cyclic peptide derived therefrom. In other aspects, the meditope is a peptide of SEQ ID NO: 1 or 2, or a cyclic peptide derived therefrom.

In some aspects, the meditope (e.g., the peptide) binds to the meditope binding site with a dissociation constant of less than at or about 10 μM, less than at or about 5 μM, less than at or about 2 μM, less than at or about 1 μM, less than at or about 500, 400, 300, 200, 100 nM, or less, such as at or about 200 picomolar or less, for example, with such a dissociation constant, as measured by a particular technique, such as surface plasmon resonance (SPR), Isothermal Titration calorimetry (ITC), fluorescence, fluorescence polarization, NMR, IR, calorimetry titrations; Kinetic exclusion; Circular dichroism, differential scanning calorimetry, or other known method, e.g., by SPR.

In some aspects, the meditope binding site includes residues 40, 41, 83, and/or 85 of the light chain of the meditope-enabled antibody, according to Kabat numbering, and/or residues 39, 89, 105, and/or 108 of the heavy chain of the meditope-enabled antibody, according to Kabat numbering.

In some aspects, the meditope binds to a meditope-enabled antibody having: a light chain comprising an amino acid sequence set forth in SEQ ID NO: 71 and a heavy chain comprising an amino acid sequence set forth in SEQ ID NO: 72; to a meditope-enabled antibody having a light chain having an amino acid sequence set forth in SEQ ID NO: 9 and a heavy chain comprising an amino acid sequence set forth in SEQ ID NO: 6; and/or to a meditope-enabled antibody having a light chain having an amino acid sequence set forth in SEQ ID NO: 68 and/or a heavy chain having an amino acid sequence set forth in SEQ ID NO: 70.

In some aspects, the peptide is between 5 and 16 amino acids in length.

In some aspects, the peptide has the formula:

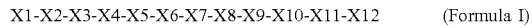

$$X1\text{-}X2\text{-}X3\text{-}X4\text{-}X5\text{-}X6\text{-}X7\text{-}X8\text{-}X9\text{-}X10\text{-}X11\text{-}X12 \qquad \text{(Formula I)}$$

wherein:
X1=Cys, Gly, β-alanine, 2,3-diaminopropionic acid, β-azidoalanine, or null;
X2=Gln or null;
X3=Phe, Tyr, β-β'-diphenyl-Ala, His, Asp, 2-bromo-L-phenylalanine, 3-bromo-L-phenylalanine, or 4-bromo-L-phenylalanine, Asn, Gln, a modified Phe, a hydratable carbonyl-containing residue; or a boronic acid-containing residue;
X4=Asp or Asn;
X5=Leu; β-β'-diphenyl-Ala; Phe; a non-natural analog of phenylalanine, tryptophan, or tyrosine; a hydratable carbonyl-containing residue; or a boronic acid-containing residue;
X6=Ser or Cys;
X7=Thr or Ser or Cys;
X8=Arg, a modified Arg, or a hydratable carbonyl or boronic acid-containing residue;
X9=Arg, Ala;
X10=Leu, Gln, Glu, β-β'-diphenyl-Ala; Phe; a non-natural analog of phenylalanine, tryptophan, or tyrosine; a hydratable carbonyl-containing residue; or a boronic acid-containing residue;
X11=Lys; and
X12=Cys, Gly, 7-aminoheptanoic acid, β-alanine, diaminopropionic acid, propargylglycine, isoaspartic acid, or null, wherein:
the modified Arg has a structure of the formula shown in FIG. 34,
the modified Phe is a Phe with one or more halogen incorporated into the phenyl ring, and
formula I is not SEQ ID NO: 1 or SEQ ID NO: 2 or a cyclic peptide derived therefrom.

In some aspects, the peptide is a cyclic peptide, such as one in which the cyclization is by disulfide bridge, a thioether bridge, a lactam linkage, cycloaddition. In certain aspects, where the peptide is one of Formula I, the cyclization is via a linkage between X1 and X12, X1 and X11, X3 and X11, X4 and X11, or X2 and X12. In some aspects, where the peptide is one of Formula I, the non-natural amino acid is β-β'-diphenyl-Ala, a branched alkyl, or an extended aromatic. In some aspects, where the peptide is one of Formula I, each of the one or more halogen is an ortho-, meta-, or para-bromo phenyl substituent.

Among the provided meditopes are peptides having an amino acid selected from the group consisting of the sequences set forth in SEQ ID NOs: 1, 2, and 15-55, e.g., 1, 2, 16-18, 23, 29, 31, 32, 36, 39, 42, 43, 45, 46, 51, 52, 54, and 55, e.g., 16-18, 23, 29, 31, 32, 36, 39, 42, 43, 45, 46, 51, 52, 54, and 55, or a cyclic peptide derived therefrom.

In some embodiments, the meditope comprises a compound of Formula (X):

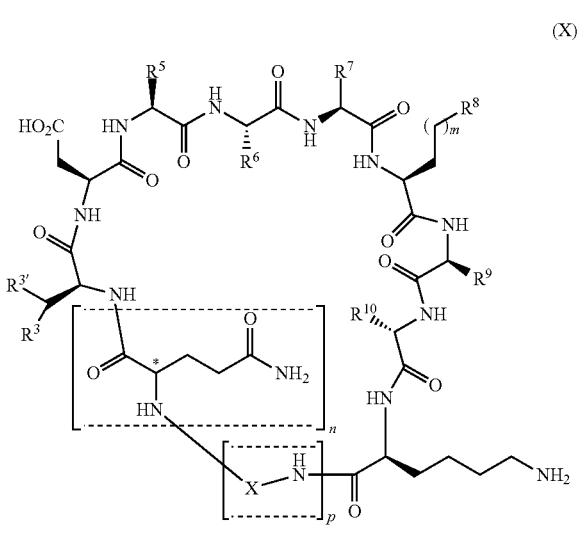

wherein:
the center marked with "*" is in the "R" or "S" configuration;
$R^3$ and $R^{3'}$ are each, independently, H or phenyl, optionally substituted with one, two, or three substituents independently selected from $C_{1-4}$alkyl, —OH, fluoro, chloro, bromo, and iodo;
$R^5$ is:
(A) $C_{1-8}$alkyl, optionally substituted with one or more substituents selected from the group consisting of oxo, acetal, ketal, —B(OH)$_2$, boronic ester, phosphonate ester, ortho ester, —CO$_2$C$_{1-4}$alkyl, —CH=CH—CHO, —CH=CH—C(O)C$_{1-4}$alkyl, —CH=CH—CO$_2$ C$_{1-4}$alkyl, —CO$_2$H, and —CONH$_2$ group; or
(B) a $C_{1-4}$alkyl group substituted with:
a) one or two phenyl groups, wherein each phenyl is optionally substituted with one, two, or three substituents independently selected from —OH, fluoro, chloro, bromo, and iodo; or
b) a naphthyl, imidazole, or indole group;
$R^6$ is —C$_{1-4}$alkyl-OH or —C$_{1-4}$alkyl-SH;
$R^7$ is —C$_{1-4}$alkyl-OH or —C$_{1-4}$alkyl-SH;
m is 0, 1, 2, 3, 4, or 5;
$R^8$ is:
(a) —OH, —NR$^a$R$^b$, —N(R$^c$)C(O)R$^c$, or —N(R$^c$)C(=NR$^d$)R$^e$;
wherein:
$R^a$ is H;
$R^b$ is H or $C_{1-8}$alkyl optionally substituted with one or more substituents selected from the group consisting of oxo, acetal, and ketal, —B(OH)$_2$, —SH, boronic ester, phosphonate ester, ortho ester, —CH=CH—CHO, —CH=CH—C(O)C$_{1-4}$alkyl, —CH=CH—CO$_2$C$_{1-4}$alkyl, —CO$_2$H, or —CO$_2$C$_{1-4}$alkyl group;

$R^c$ is H, $C_{1-8}$alkyl, $C_{3-8}$cycloalkyl, branched alkyl, or aryl;
$R^d$ is H or a $C_{1-8}$alkyl, $C_{2-8}$alkenyl, $C_{2-8}$alkynyl, $C_{3-8}$cycloalkyl, branched alkyl, or aryl group, each optionally substituted with one or more substituents selected from the group consisting of —N$_3$, —NH$_2$, —OH, —SH, halogen, oxo, acetal, ketal, —B(OH)$_2$, boronic ester, phosphonate ester, ortho ester, —CH=CH—CHO, —CH=CH—C(O)C$_{1-4}$alkyl, —CH=CH—CO$_2$C$_{1-4}$alkyl, —CO$_2$H, and —CO$_2$C$_{1-4}$alkyl group; and
$R^e$ is H; —NHR$^d$; or a $C_{1-4}$alkyl, $C_{3-8}$cycloalkyl, $C_{2-12}$alkenyl, $C_{2-8}$alkynyl, or aryl group, each optionally substituted with one or more substituents selected from the group consisting of —N$_3$, —NH$_2$, —OH, —SH, oxo, $C_{2-4}$acetal, $C_{2-4}$ketal, —B(OH)$_2$, boronic ester, phosphonate ester, ortho ester, —CH=CH—CHO, —CH=CH—C(O)C$_{1-4}$alkyl, —CH=CH—CO$_2$C$_{1-4}$alkyl, and —CO$_2$C$_{1-4}$alkyl group; or
(b) a $C_{1-12}$ alkyl substituted with an oxo, acetal, ketal, —B(OH)$_2$, boronic ester, —SH, —OH, phosphonate ester, ortho ester, —CH=CH—CHO, —CH=CH—C(O)C$_{1-4}$alkyl, —CH=CH—CO$_2$C$_{1-4}$alkyl, or —CO$_2$C$_{1-4}$alkyl group;
$R^9$ is $C_{1-8}$alkyl or —C$_{1-2}$alkylene-R$^x$;
wherein $R^x$ is —CO$_2$H, —CONH$_2$, —CH$_2$NHC(O)NH$_2$, or —CH$_2$NHC(=NH)NH$_2$;
$R^{10}$ is:
(1) a $C_{1-8}$alkyl optionally substituted with one or more substituents selected from the group consisting of oxo, acetal, ketal, —B(OH)$_2$, boronic ester, phosphonate ester, ortho ester, —CH=CH—CHO, —CH=CH—C(O)C$_{1-4}$alkyl, —CH=CH—CO$_2$C$_{1-4}$alkyl, —CO$_2$C$_{1-4}$alkyl, —CO$_2$H, and —CONH$_2$ group; or
(2) a $C_{1-4}$alkyl group substituted with one or two phenyl groups, or one naphthyl, imidazole, or indole group, wherein each phenyl is optionally substituted with one, two, or three substituents independently selected from —OH, fluoro, chloro, bromo, and iodo;
n is 0 or 1;
p is 0 or 1;
X is $C_{1-8}$alkylene or $C_{2-8}$alkenylene, each carbon thereof optionally substituted with —CO$_2$H, —NH$_2$, or —NHC(O)R$^y$;
wherein one carbon of said alkylene is optionally replaced with —C(O)NH—, a 5-membered heteroaryl ring, or —S—S—; and
$R^y$ is —C$_{1-4}$alkyl or —CH(R$^z$)CO$_2$H;
wherein $R^z$ is —H or —C$_{1-4}$alkyl optionally substituted with —OH, —SH, or —NH$_2$;
or a pharmaceutically acceptable salt thereof.

In one embodiment, a meditope contains a cysteine that covalently binds to a cysteine in a meditope binding site. Such a meditope may be conjugated to any substance, molecule or compound, which may be a therapeutic molecule, such as a small molecule diagnostic molecule, such as a marker. In some aspects, the "Cys meditope" directs the conjugate to the Ig and binds via a covalent linkage.

Also among the provided meditopes are labeled meditopes, such as those comprising a meditope (such as any of those described above) and a therapeutic or diagnostic agent. In some aspects, the therapeutic or diagnostic agent is selected from the group consisting of: a metal chelator bound to a metal ion, a small molecule, a chemotherapeutic agent, a therapeutic antibody or functional fragment, a toxin, a radioisotope, an enzyme, a nuclease, a hormone, an immunomodulator, an oligonucleotide, an organic or inorganic nanoparticle, an RNAi molecule, an siRNA, a chelator, a boron compound, a photoactive agent, a dye, fluorescent or luminescent substance, an enzyme, an enhancing agent, a radioactive substance, and a chelator.

Also among the provided meditopes are multivalent meditopes, such as those comprising two or more meditopes and one or more linker, e.g., where each of the two or more meditopes is a peptide that binds to a meditope binding site of a meditope-enabled antibody. Such multivalent meditopes may comprise any of the meditopes described herein, e.g., above. In one aspect, the two or more meditopes comprise at least three meditopes, or at least four meditopes. In one aspect, the one or more linker includes a peptide, a small chemical scaffold, a biotin-streptavidin, an organic or inorganic nanoparticle, a polynucleotide sequence, peptide nucleic acid, an organic polymer, or an immunoglobulin Fc domain.

Also among the provided embodiments are meditope-enabled antibody-meditope complexes, including those containing any of the meditope-enabled antibodies and any of the meditopes described herein, e.g., described above. In some cases, the peptide binds to the meditope binding site with a dissociation constant of less than 10 µM, as measured by surface plasmon resonance (SPR), or another affinity as described above.

Also provided are methods using the meditopes and/or antibodies, such as any of the above meditopes and/or antibodies. For example, provided are methods for purifying a meditope-enabled antibody or fragment thereof, or a cell expressing the meditope-enabled antibody or fragment thereof. In one aspect, such methods include a step of contacting a composition containing the meditope-enabled antibody, fragment, or cell with a meditope, under conditions whereby the meditope-enabled antibody or fragment binds to the peptide. In some aspect, they further include then isolating the antibody or fragment or cell. Such methods in some aspects thereby purify the antibody, fragment, or cell.

In some aspects, the meditope is coupled to a solid support. In some aspects, the isolation or purification is effected by a change in pH.

Also provided are compositions, e.g., pharmaceutical compositions, comprising the meditopes (including multivalent and labeled meditopes), meditope-enabled antibodies, and complexes, and/or other compounds described herein, e.g., above. In one example, the composition includes the complex, meditope, and/or meditope-enabled antibody, and a pharmaceutically acceptable carrier.

Also provided are methods of treatment, such as those carried out by administering to a subject such pharmaceutical compositions, or any of the meditope-enabled antibodies, meditopes, complexes, and/or other compound described herein, e.g., above. In one example, the methods include administering to the subject an antibody or fragment as described above.

In one example, the method of treatment includes administering to a subject one or more meditope-enabled antibody or fragment, e.g., any of those described above. In one example, the method includes administering to the subject one or more meditope-enabled antibody or fragment as described above, and a meditope, e.g., any of those described above, including multivalent meditopes and meditopes coupled to a therapeutic or diagnostic agent. In one aspect, the meditope-enabled antibody or fragment and one or more meditope are administered sequentially. In another aspect, they are administered simultaneously. Generally, the one or more meditope comprises a peptide that binds to a meditope binding site of the meditope-enabled antibody or fragment. In one aspect, the meditope-enabled antibody or fragment is bound to the one or more meditope, such that administration of the meditope-enabled antibody and the one or more meditope comprises administering a complex of the meditope-enabled antibody and the meditope. In another aspect, the meditope-enabled antibody is administered prior to administration of the one or more meditope.

In some aspects, the one or more meditope is coupled to a therapeutic agent, such as a therapeutic agent selected from the group consisting of: drugs, chemotherapeutic agents, therapeutic antibodies, toxins, radioisotopes, enzymes, chelators, boron compounds, photoactive agents, dyes, metals, metal alloys, and nanoparticles.

Also provided are diagnostic methods, such as those carried out by administering to a subject such pharmaceutical compositions, or any of the meditope-enabled antibodies, meditopes, complexes, and/or other compound described herein, e.g., above, and detecting binding of the administered composition, antibody, meditope, complex, and/or compound to a substance in the subject, e.g., to an antigen. In some aspects, the diagnostic method includes administering to a subject one or more meditope-enabled antibody or fragment thereof, e.g., any of those described above. In some aspects, it further includes detecting binding of the antibody or fragment to an antigen in the subject. In some aspects, the meditope-enabled antibody or fragment and one or more meditope are administered sequentially; in other aspects, they are administered simultaneously. In one example, the meditope-enabled antibody or fragment is bound to the one or more meditope, such that administration of the meditope-enabled antibody and the one or more meditope comprises administering a complex of the meditope-enabled antibody and the meditope. In another example, the meditope-enabled antibody is administered prior to administration of the one or more meditope. In some aspects, the meditope or meditopes is a multivalent meditope. In some aspects, the meditope is coupled to a diagnostic agent, such as an imaging agent, such as an imaging agent selected from the group consisting of: fluorescent substances, luminescent substances, dyes, indicators, and radioactive substances. In some cases, the imaging agent is DOTA.

Also provided are methods for generating meditope-enabled antibodies or fragments thereof, e.g., based on template antibodies. In some aspects, such methods include effecting one or more amino acid substitutions in a template antibody or fragment thereof. In one example, the substitutions include a substitution at position 40, 41, or 85 of the VL region, and/or position 40 or position 89 of the VH region, according to Kabat numbering.

In some aspects, the methods generate a meditope-enabled antibody or fragment thereof which binds to a meditope that is a peptide having an amino acid sequence selected from the group consisting of the sequences set forth in SEQ ID NO: 1, 2, 16-18, 23, 29, 31, 32, 36, 39, 42, 43, 45, 46, 51, 52, 54, and 55, or a cyclic peptide derived therefrom.

In some aspects, the template antibody or fragment is selected from the group consisting of abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, Fbta05, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, Trbs07, ustekinumab, visilizumab, votumumab, zalutumumab, and brodalumab, or is the antibody produced by the hybridoma 10B5, or is B6H12.2.

In some aspects, the meditope-enabled antibody binds to one or more meditopes (e.g., one of SEQ ID NO: 1, 2, or cyclic peptide derived therefrom), e.g., those described above, with a particular affinity, such as with a dissociation constant of less than 10, 5, or 2 (or other number specified above) μM, as measured by SPR, or other method described above.

In some aspects, each of the one or more amino acid substitutions is at a position selected from the group consisting of: position 8, 9, 10, 38, 39, 40, 41 42, 43, 44, 45, 82, 83, 84, 85, 86, 87, 99, 100, 101, 102, 103, 104, 105, 142, 162, 163, 164, 165, 166, 167, 168, and 173 of the light chain, and/or 6, 9, 38, 39, 40, 41, 42, 43, 44, 45, 84, 86, 87, 88, 89, 90, 91, 103, 104, 105, 106, 107, 108, 109, 110, 147, 150, 151, 152, 173, 174, 175, 176, 177, 185, 186, and 187 of the heavy chain, according to Kabat numbering. In some aspects, the meditope-enabled antibody contains a light chain having P8, V9 or I9, I10 or L10, Q38, R39, T40, N41 G42, S43, P44, R45, D82, I83, A84, D85, Y86, Y87, G99, A100, G101, T102, K103, L104, E105, R142, S162, V163, T164, E165, Q166, D167, S168, and Y173, according to Kabat numbering and a heavy chain having Q6, P9, R38, Q39, S40, P41, G42, K43, G44, L45, S84, D86, T87, A88, I89, Y90, Y91, W103, G104, Q105, G106, T107, L108, V111, T110, Y147, E150, P151, V152, T173, F174, P175, A176, V177, Y185, S186, and L187, according to Kabat numbering.

Also provided are polynucleotides comprising a nucleotide sequence encoding the meditope-enabled antibodies and meditopes, as well as vectors including the same, and libraries comprising the vectors.

Also provided are screening methods, such as those including the steps of expressing antibodies or fragments thereof from the libraries, and selecting an antibody or fragment thereof from among the expressed antibodies or fragments. In some cases, the selection is based on a binding affinity, pH tolerance, pH dependence, toxicity, PK, or PD of the selected antibody or fragment thereof, and/or is effected by contacting the antibodies or fragments thereof with a meditope and detecting binding to one or more of the antibodies or fragments thereto.

Also provided are methods for selecting a meditope analog or meditope variant, including those comprising: (a) combining a meditope and a meditope-enabled antibody or fragment thereof, whereby the meditope non-covalently binds to the antibody or fragment thereof; and (b) adding a candidate meditope variant or analog; and (c) measuring displacement of the meditope by the candidate meditope variant or analog, wherein displacement of the meditope by the candidate variant or analog identifies it as the meditope variant or analog.

Also provided are methods for modifying meditopes and meditope-enabled antibodies, including a method for modifying a meditope, comprising effecting one or more amino acid substitutions, insertions, or deletions, to a peptide having the sequence set forth in any of SEQ ID NOs: 1, 2, 16-18, 23, 29, 31, 32, 36, 39, 42, 43, 45, 46, 51, 52, 54, and 55, or cyclic peptide derived therefrom, thereby altering the pH-dependence of the binding affinity of the peptide for a meditope-enabled antibody or fragment thereof, such as any of those described above. In some aspects, the method decreases the binding affinity of the peptide for the antibody or fragment at a lysosomal pH level. In other aspects, the method increases the binding affinity in a hypoxic environment.

Also provided are methods for modifying a meditope-enabled antibody, such as those comprising: effecting one or more modifications at position 8, 9, 10, 38, 39, 40, 41 42, 43, 44, 45, 82, 83, 84, 85, 86, 87, 99, 100, 101, 102, 103, 104, 105, 142, 162, 163, 164, 165, 166, 167, 168, and/or 173 of the light chain, or 6, 9, 38, 39, 40, 41, 42, 43, 44, 45, 84, 86, 87, 88, 89, 90, 91, 103, 104, 105, 106, 107, 108, 109, 110, 147, 150, 151, 152, 173, 174, 175, 176, 177, 185, 186, and/or 187 of the heavy chain, of the meditope-enabled antibody, according to Kabat numbering. In some aspects, the modification methods are provided in tandem, to produce modified meditopes and modified meditope-enabled antibodies that bind to one another, such as by making modifications in the antibody based on modifications in a modified meditope, or vice versa.

Also provided are meditope analogs, including those that bind to any of the meditope-enabled antibodies described above, and/or with binding properties comparable to any of the meditopes described above.

BRIEF DESCRIPTION OF THE DRAWINGS

FIG. 1 shows meditope peptides binding to framework loops of cetuximab. FIG. 1A: The complex of cetuximab Fab (light chain is denoted by $V_L$ and $C_L$; heavy chain is denoted by $V_H$ and $C_H$) and cyclic CQFDLSTRRLKC (depicted within the shaded area and labeled with the word "meditope") (SEQ ID NO: 1) indicates that the meditope binds to an interface of the Fab framework, which is distinct from the CDR loops of cetuximab. FIG. 1B (top) shows the stick representation of the cQFD meditope and (bottom) the stick representation of the cQYN meditope. The N- and C-terminal cysteines are solvent exposed and display high thermal factors.

FIG. 2A shows residues of ch14.18, and the humanized trastuzumab, which correspond to those residues of Cetuximab that make contact with the meditope. Sequences shown include QRTNGS (SEQ ID NO:171); IADYY (SEQ ID NO:172); AGTKLE (SEQ ID NO:173); QKPGQS (SEQ ID NO:174); LGVYF (SEQ ID NO:175); QKPGKA (SEQ ID NO:176); FATYY (SEQ ID NO:177); QGTKVE (SEQ ID NO:178); QSPGKG (SEQ ID NO:179); QGTL (SEQ ID NO:180); QNIGKS (SEQ ID NO:181); QGTS (SEQ ID NO:182); QAPGKG (SEQ ID NO:183). FIG. 2B shows a stereoview of Arg9 of the cQFD meditope that occupies a distinct pocket encoded by the murine sequence of Cetuximab (foreground). There is a salt bridge from Asp85 to the guanidinium group of the meditope Arg9 and the backbone amide of Leu10.

FIG. 4 illustrates that the cQFD and cQYN meditopes do not bind to the CDRs of cetuximab, as was previously hypothesized. FIG. 4A shows an overlay of two crystal structures, one of a cetuximab Fab and its antigen, EGFR domain III, the other showing the cQFD meditope and cetuximab Fab, in which the cQFD meditope binds to the central cavity of the cetuximab Fab. The antigen, EGFR domain III, binds at the complementarity determining regions at a significant distance from the meditope binding site. FIG. 4B shows SDS-PAGE results on the left-hand side and the corresponding size exclusion chromatography results on the right-hand side. Size exclusion experiments of the individual components, Fab, EGFR domain III, and SMT-cQFD meditope, as well as an admixture of all three, indicate the formation of a hetero-trimeric complex that coeluted. The non-reducing SDS-PAGE gel shows the fraction that eluted first, indicating the presence of all three components within the new peak (the left-most peak for "complex," shaded light gray) observed from the admixture. FIG. 4C shows the results of a FACS analysis, indicating that the cQFD meditope bound to EGFR positive MD-MBA-468 cells only in the presence of cetuximab (arrows). The meditope alone or the meditope in the presence of M425, a murine EGFR antibody, did not bind.

FIG. 15 shows the nucleic acid sequence (SEQ ID NO:3) and the corresponding amino acid sequence (SEQ ID NO:4) for a meditope-Fc fusion protein according to some embodiments.

FIG. 22 Illustrates that a meditope-enabled trastuzumab binds to a meditope-Fc fusion protein. The meditope binding site was created on trastuzumab, a humanized mAb that binds to the tumor antigen, HER2. FACS analysis in the top panel shows that meditope-enabled trastuzumab binds to SKBR3 cells that overexpress HER2 (top two traces). In the bottom graph, the meditope-Fc binds to meditope-enabled trastuzumab (top two traces—peak shifted right), but not to wild-type trastuzumab (second from bottom) or to the negative control (bottom trace).

FIG. 23A shows the nucleic acid (SEQ ID NO:5) sequence of a meditope-enabled trastuzumab heavy chain sequence. Signal peptide sequence is shaded in grey. FIG. 23B shows the amino acid (SEQ ID NO:6) sequence of a meditope-enabled trastuzumab heavy chain sequence as compared to the wild-type (SEQ ID NO:7). Differences are highlighted in grey. After the amino acids shown in FIG. 23B, there are no differences remaining in the human sequence of the heavy chain shown. FIG. 23C shows the nucleic acid (SEQ ID NO:8) sequence of a meditope-enabled trastuzumab light chain sequence. Signal peptide sequence is shaded in grey. FIG. 23D shows the amino acid (SEQ ID NO:9) sequence of a meditope-enabled trastuzumab light chain sequence as compared to the wild-type (SEQ ID NO:10). Differences are highlighted in grey.

In FIG. 24A, FACS analysis shows that HER2-CDR grafted meditope-enabled mAb binds to SKBR3 cells, which overexpresses HER2 (top three traces at different concentrations). FIG. 24B shows that while the meditope-Fc bound to the HER2-CDR grafted, meditope-enabled mAb (top three traces—peak shifted right in concentration dependent manner), it did not bind to wild-type trastuzumab (second from bottom) or to the negative control (bottom trace).

FIG. 25A shows nucleic acid (SEQ ID NO: 11) and amino acid (SEQ ID NO: 12) sequences for the heavy chain of a trastuzumab with secretion sequence and engineered restriction sites (underlined). FIG. 25B shows nucleic acid (SEQ ID NO: 13) and amino acid (SEQ ID NO: 14) sequences for a light chain of trastuzumab with secretion sequence and engineered restriction sites (underlined). Shaded areas indicate exemplary residues that in some aspects could be altered to enhance or alter the specificity of the meditope, or could participate in binding interactions with a modified epitope.

FIG. 26 illustrates examples of sequence and structural alignment of the IgG and IgE Fab domains (SEQ ID NOs: 188-189, respectively), with shaded areas indicating certain residues corresponding to residues near a meditope binding site.

FIG. 28A shows results of a study in which a meditope-Fc, but not a monomeric meditope, inhibited cell growth when combined with cetuximab. FIG. 28B shows that the meditope-Fc enhances the cell-killing capacity of cetuximab, similar to the combination of M425 and cetuximab.

FIG. 30A shows a SPR sensogram of an unmodified meditope cQFD (SEQ ID NO:1) and a QYN meditope (SEQ ID NO:2) using a cetuximab Fab chip. FIG. 30B shows a representative binding isotherm of the meditope (SEQ ID NO: 1) and cetuximab Fab (top) and integration (bottom). FIG. 30C shows superposition of both meditopes. Oval 1 indicates the Phe/Tyr position. The arrow indicates a shift of the backbone that leads to a favorable hydrogen bond network and may account for a favorable change in the enthalpy. The hydrophobic groups, F/Y3 L5, and L10 are nearly identically positioned, but the hydroxyl group of Y5 in the cQYN meditope prevents R8 from interacting with the Q105 backbone, as observed in the cQFD meditope ("steric clash"). This rearrangement also results in a concomitant change in the backbone residues of the β-turn ("backbone rotation"). FIG. 30D shows individual thermodynamic parameters determined by ITC of different meditope variants. The Phe3Tyr variant (meditope 2, SEQ ID NO: 2) shows a significant change in ΔH though lower affinity. Based on the structure, Gln2 in the meditope of SEQ ID NO:

1 was replaced with the D-stereomer. ITC analysis of this meditope, (SEQ ID NO:15), revealed a significant increase in entropy and loss in enthalpy.

Figure 31:
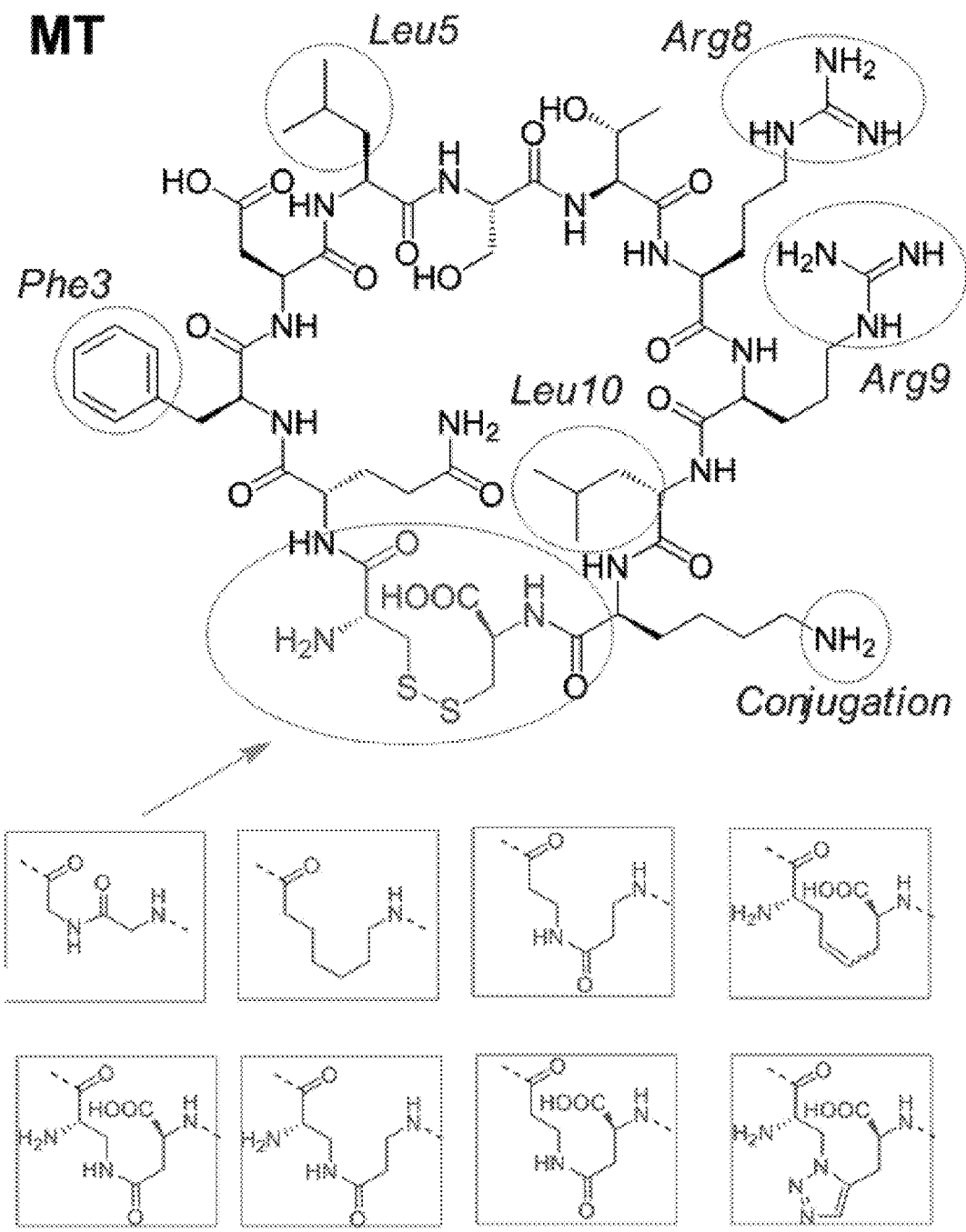

FIG. 31 shows the chemical structure of a meditope according to some embodiments. The circles indicate positions that can be modified, e.g., to improve meditope affinity for the Fab. The boxes indicate cyclization strategies. 'Click' chemistry and olefin metathesis, top and bottom far right boxes, respectively, are additional routes to cyclize the meditope.

Figure 32:
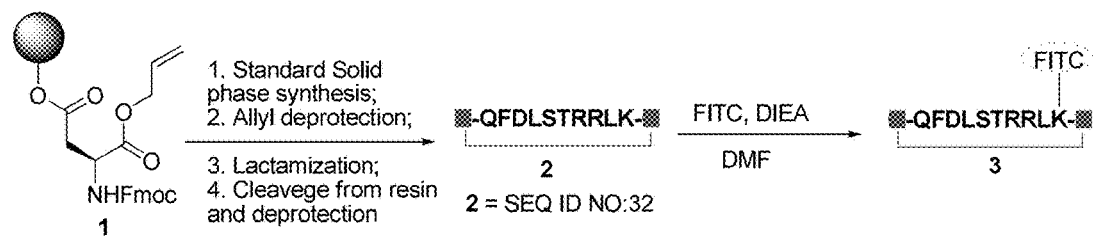

FIG. 32 illustrates the synthesis of a meditope containing a lactam linkage (2, SEQ ID NO: 32) and a fluorescein-labeled meditope containing a lactam linkage (SEQ ID NO: 32) (3).

Figure 33:
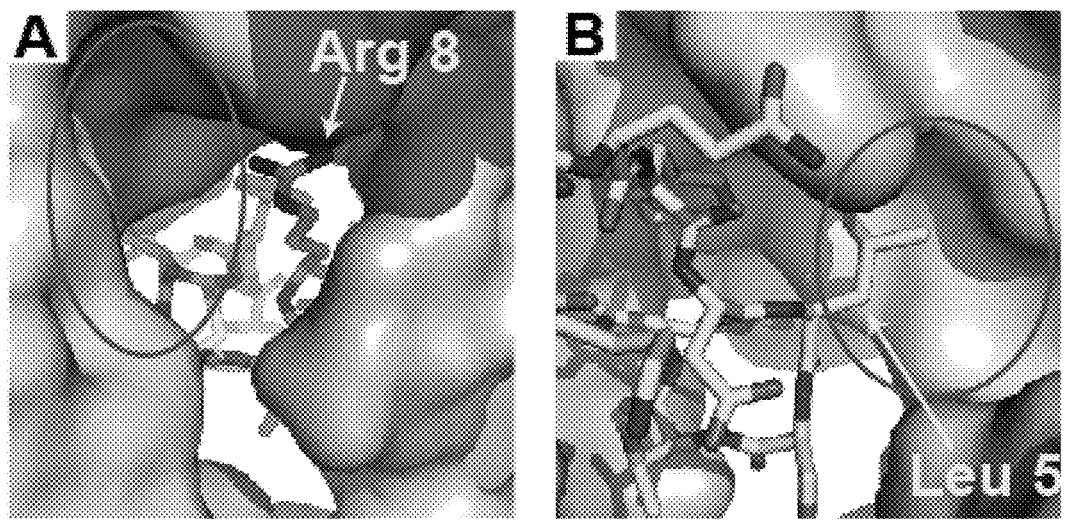

FIG. 33, in panels (A) and (B), shows the sites of optimization according to some embodiments. Ovals indicate cavities in the Fab region of the mAb that may be exploited to optimize the affinity of a meditope.

Figure 34:
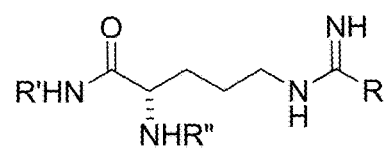

FIG. 34 shows a modified Arg8 residue that may be used to optimize meditope binding parameters, and may be used in accordance with the embodiments described herein (R=alkyl, substituted alkyl, aromatic or NHR''', where R'''=alkyl, substituted alkyl, or aromatic).

Figure 35:
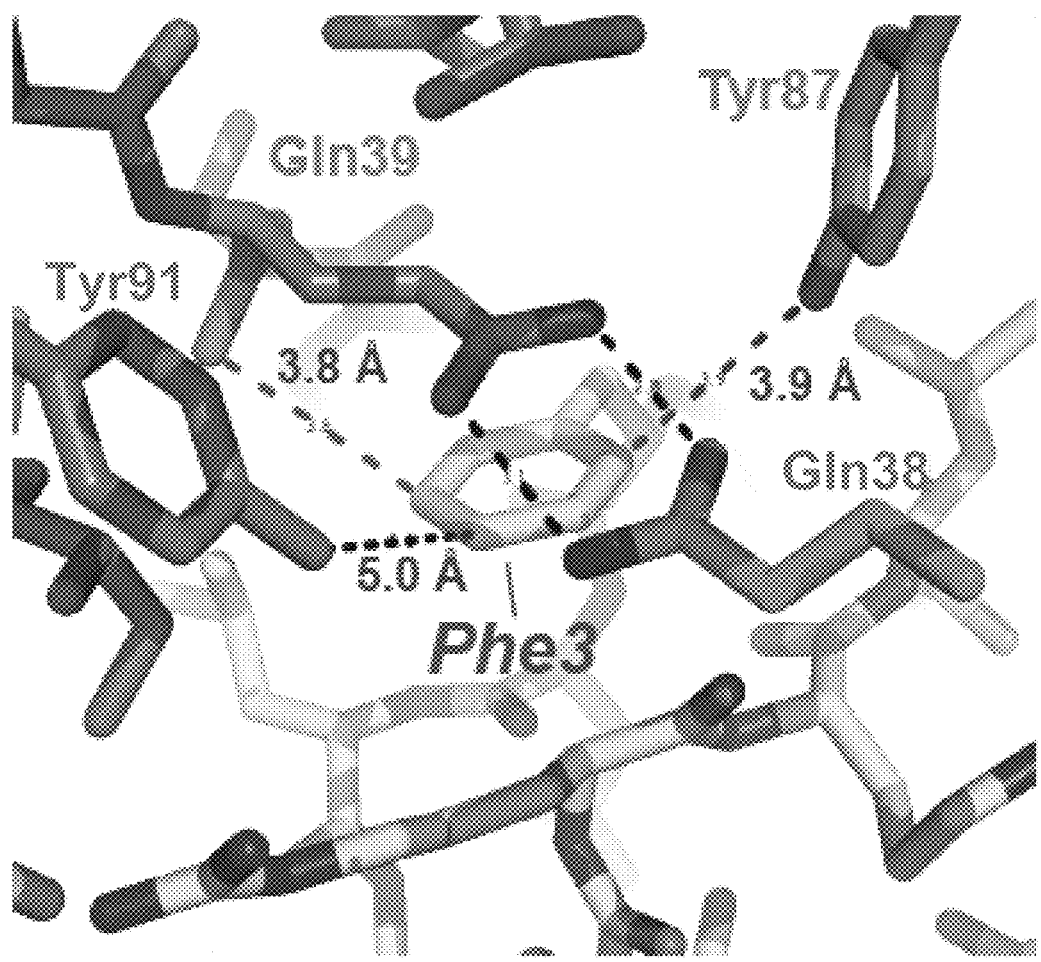

FIG. 35 shows the hydrophilic interface in the vicinity of Phe3 of a meditope. Halogens incorporated in the phenyl ring may form strong noncovalent bonds to the hydroxyl group of cetuximab Tyr87 or Tyr91, as well as to backbone carbonyls.

Figure 36:
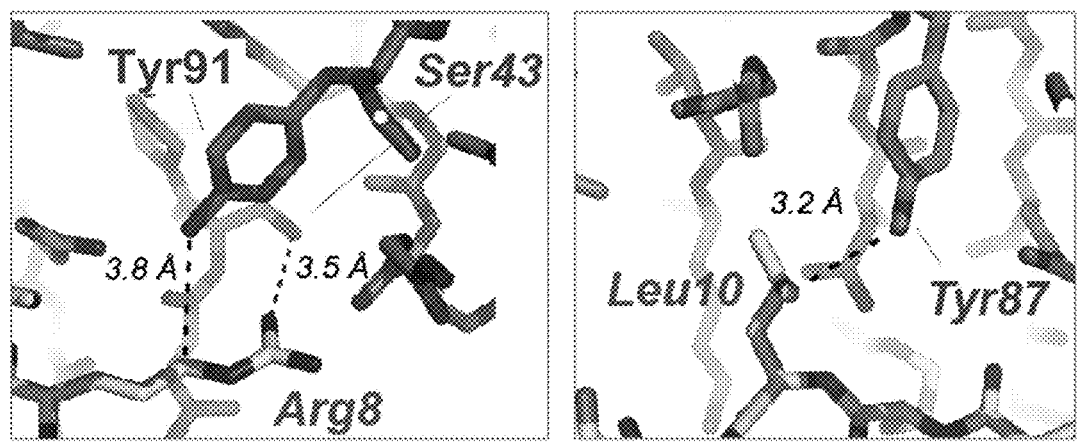

FIG. 36 illustrates covalent interactions between a meditope and the backbone of cetuximab. A hydratable side chain may be incorporated at Arg8 (left) or Leu10 (right) to form a covalent bond to the hydroxyl groups of Ser or Tyr of the Fab.

Figure 37:
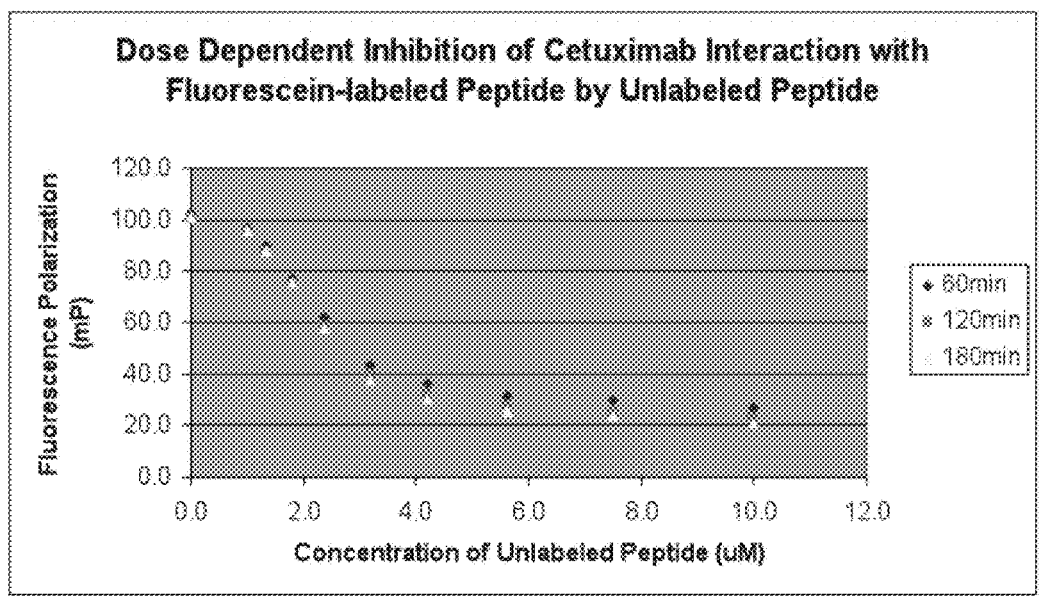

FIG. 37 illustrates a fluorescence polarization assay of dose-dependent inhibition of the interaction between cetuximab and a fluorescein-labeled peptide by unlabeled peptide. The assay identified small molecule compounds that could compete with the meditope for mAb binding and thus can be developed to function in a similar manner as a meditope. As a control, it was demonstrated that a non-labeled meditope could displace the fluorescently-labeled meditope. Equilibration of the displacement at three times points indicates that the assay is robust and amendable to high throughput screening.

FIG. 38 shows five lead compounds identified from the fluorescence polarization screen.

Figure 39:
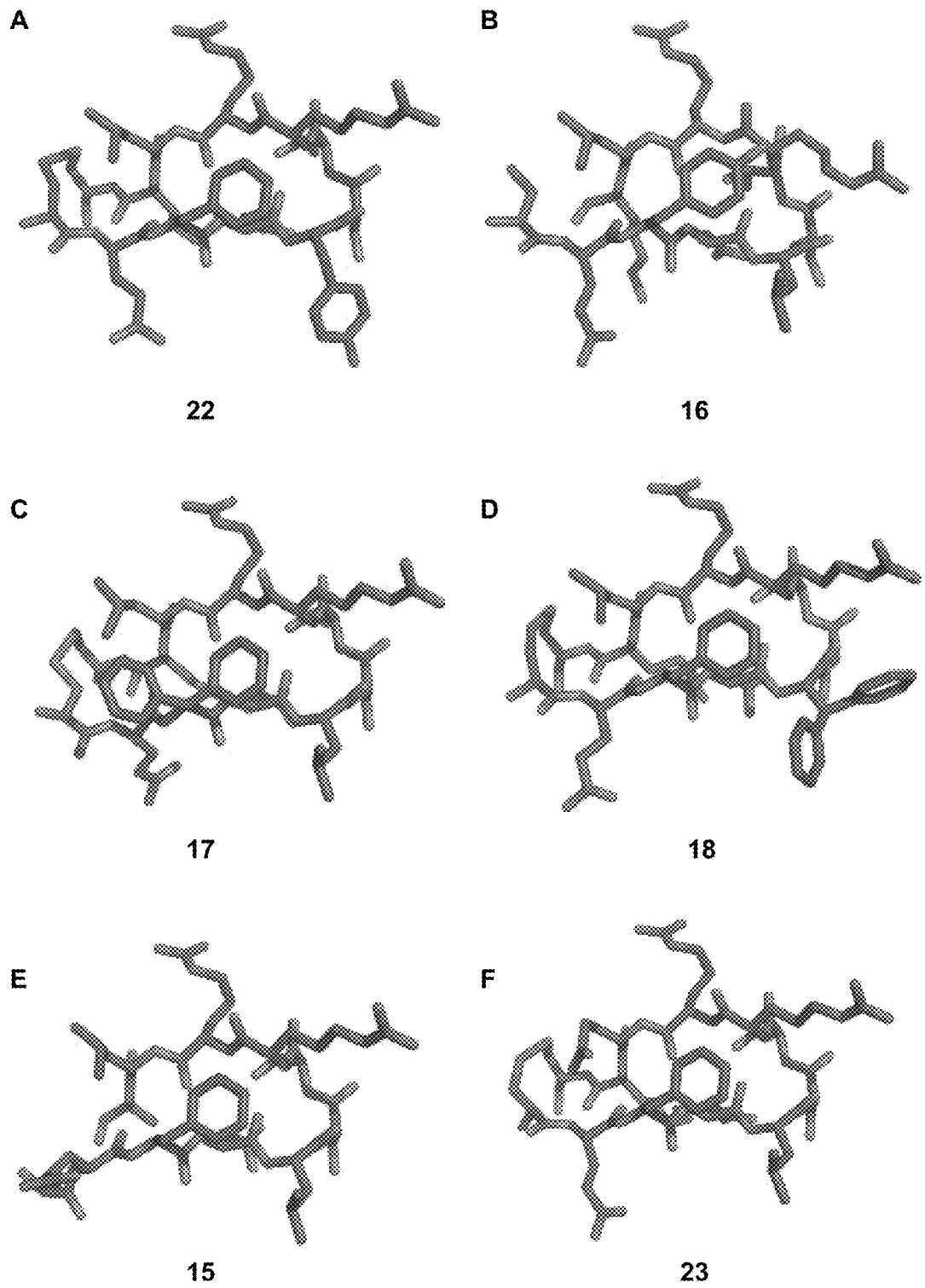
Figure 39:
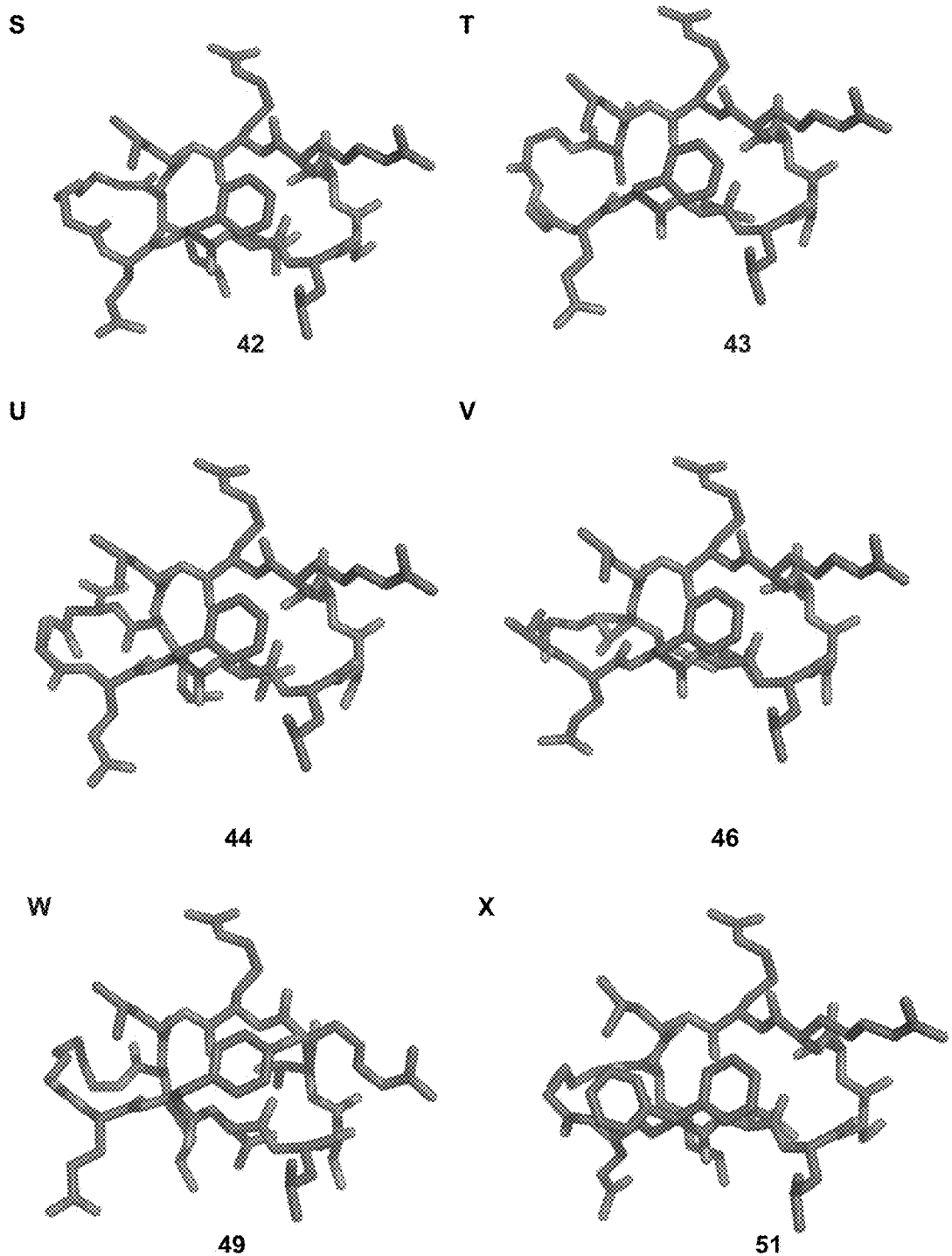
Figure 39:
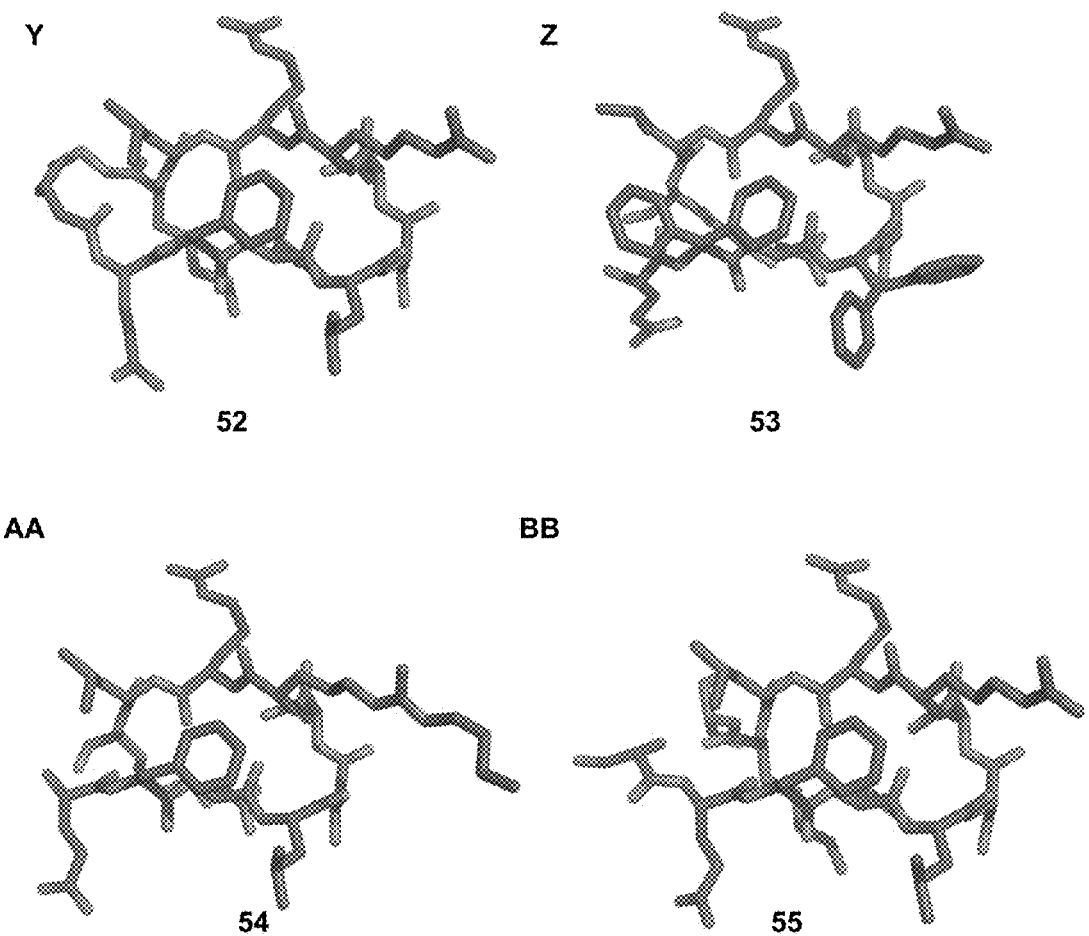

FIG. 39 shows stick structures for eighteen modified meditopes, corresponding to SEQ ID NO:22 (A), SEQ ID NO:16 (B), SEQ ID NO:17 (C), SEQ ID NO:18 (D), SEQ ID NO:15 (E), SEQ ID NO:23 (F), SEQ ID NO:24 (G), SEQ ID NO:25 (H), SEQ ID NO:32 (I), SEQ ID NO:33 (J), SEQ ID NO:34 (K), SEQ ID NO:35 (L), SEQ ID NO:36 (M), SEQ ID NO:37 (N), SEQ ID NO:38 (O), SEQ ID NO:39 (P), SEQ ID NO:40 (Q) and SEQ ID NO:41 (R), SEQ ID NO:42 (S), SEQ ID NO:43 (T), SEQ ID NO:44 (U), SEQ ID NO:46 (V) SEQ ID NO:49 (W), SEQ ID NO:51 (X), SEQ ID NO:52 (Y), SEQ ID NO:53 (Z), SEQ ID NO:54 (AA), and SEQ ID NO:55 (BB). The sequence of these structures is shown in Tables 3 and 4.

FIG. 40 is a table showing the X-ray diffraction data for the structures shown in FIG. 39 and additional meditopes in Tables 3 and 4.

FIG. 41 shows representative surface plasmon resonance studies of meditope variants. Based on the structural information of the Phe3His mutation in the cQFD meditope, a variant meditope was synthesized with β,β'-diphenylalanine at position 3 (top trace). A significant improvement in the binding affinity for cetuximab of ~4 fold, was observed by surface plasmon resonance Aminohexanoic acid was used to replace the disulfide bridge of the original meditope (bottom trace). While the binding affinity was decreased, these data indicate that modifications can be made to meditopes to address potential issues with pharmacokinetics, pharmacodynamics and toxicity in animal and human studies. It is noted that this combination can be combined with unnatural amino acids at other positions within a meditope.

Figure 42:
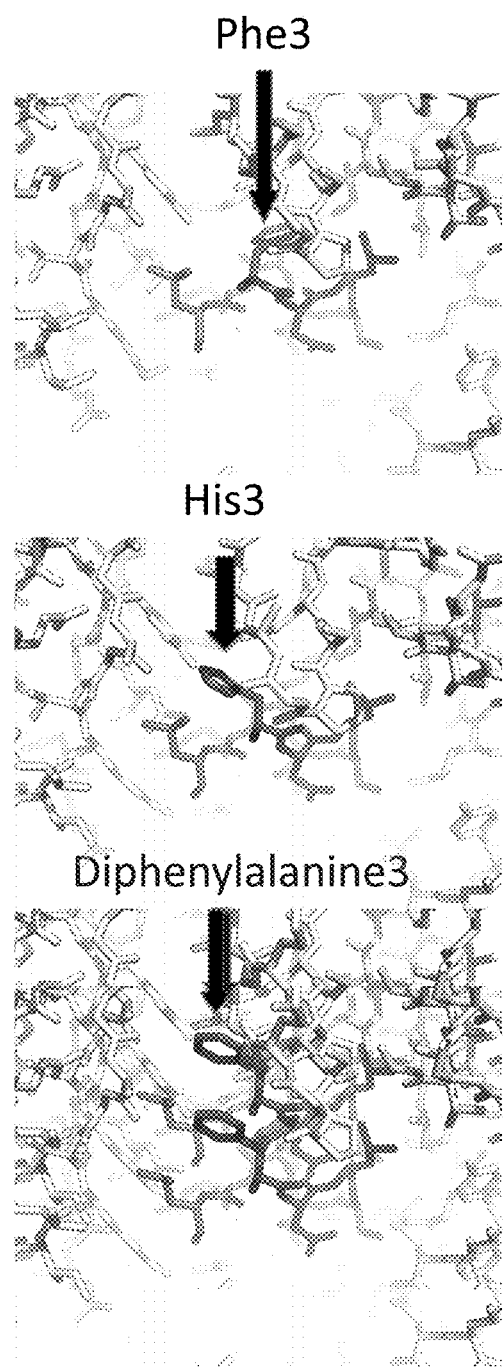

FIG. 42 illustrates structural information that can be useful, e.g., to improve meditope affinity. The top panel shows a crystal structure of a meditope bound cetuximab, showing Phe3 bound within the Fab cavity of cetuximab. Substitution of this position with histidine and subsequent structural analysis indicates the side chain (imidazole) takes on a new conformation (middle panel). Based on this observation, β,β'-diphenylalanine which could place one phenyl side chain at the original position and one phenyl side chain at the imidazole ring was substituted at position 3. The crystal structure indicates that this substitution mimics both side chain conformations. Surface plasmon resonance studies shows that this substitute binds with higher affinity (FIG. 41, top panel).

Figure 43:
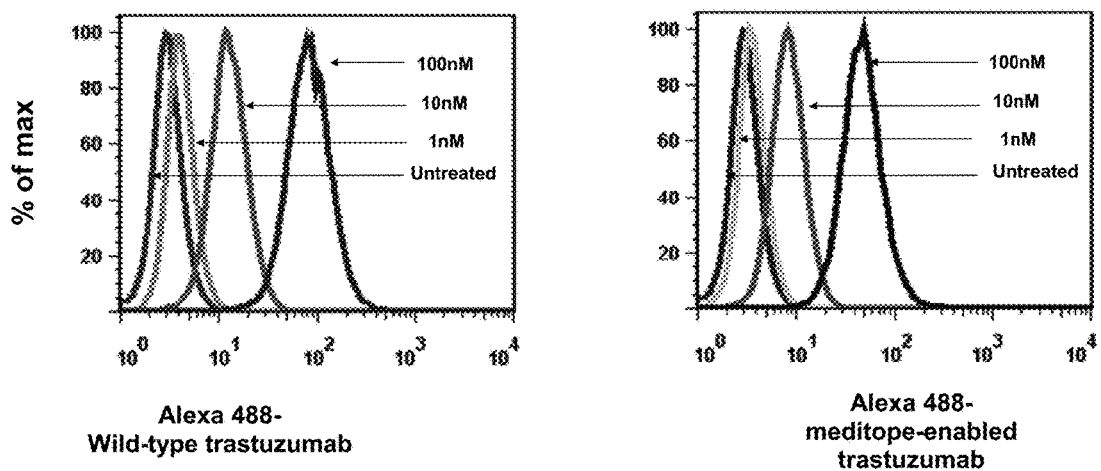

FIG. 43 shows results of a study demonstrating that a meditope-enabled trastuzumab provided herein has a similar binding affinity for antigen as wild-type trastuzumab, as described in Example 4.

Figure 44:
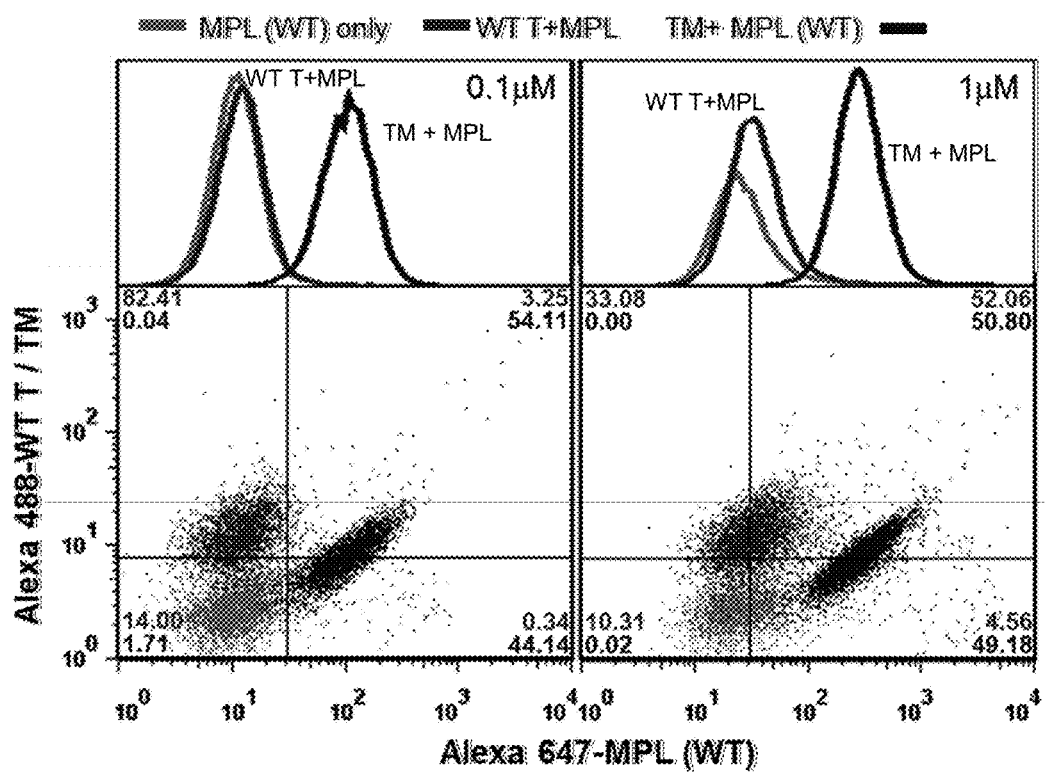

FIG. 44 shows results of a study described in Example 4, demonstrating that HER2-expressing cells pre-bound with meditope-enabled trastuzumab (TM), but not those pre-bound with wild-type trastuzumab (WT T), bound to a cQFD (SEQ ID NO: 1) meditope-Protein L fusion (MPL). Control cells, without pre-bound antibody (MPL (WT) only) also did not bind to MPL.

Figure 45:
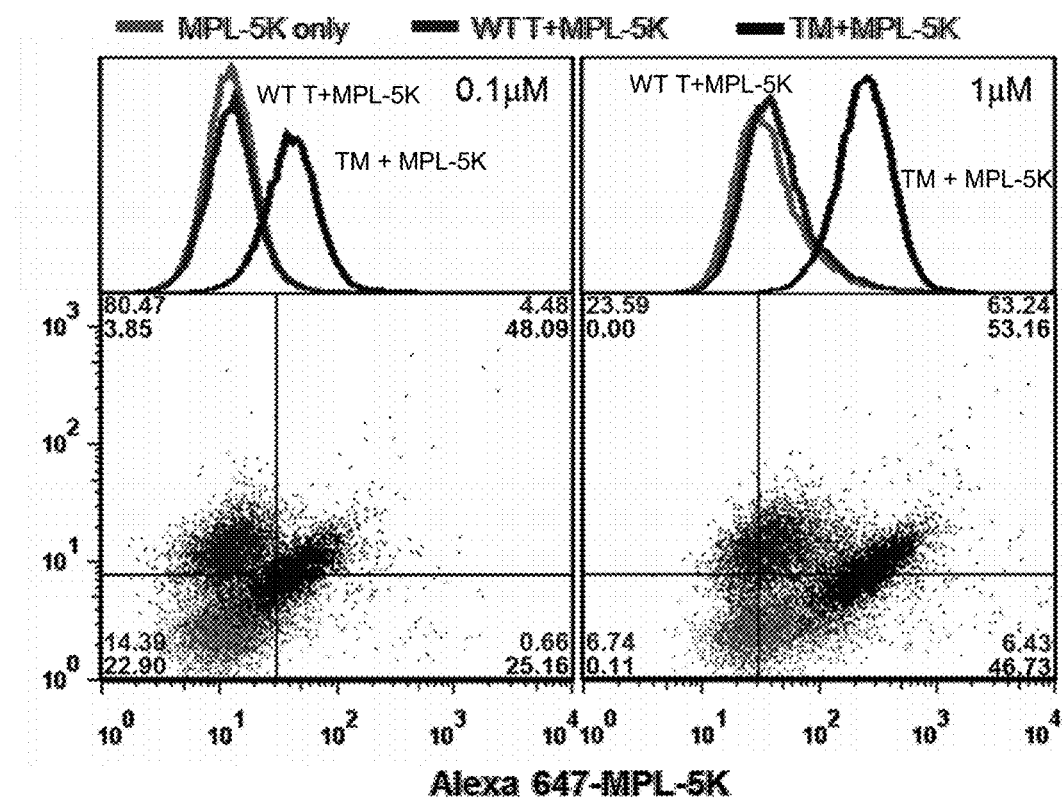

FIG. 45 shows results of a study described in Example 4, demonstrating that HER2-expressing cells (SKBR3) pre-bound with meditope-enabled trastuzumab (TM), but not those pre-bound with wild-type trastuzumab (WT T), bound to a cQFD (SEQ ID NO: 1) meditope-Protein L fusion in which all but one lysine of Protein L were mutated to arginine and asparagine (MPL-5K). Control cells, not pre-bound with any antibody (MPL-5K only) also did not bind to MPL-5K.

Figure 46:
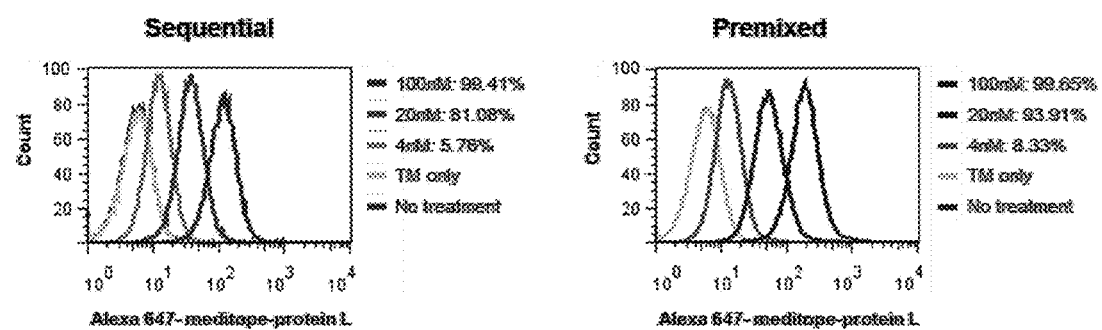

FIG. 46 shows results of a study described in Example 4, demonstrating that meditope binds to meditope-enabled trastuzumab to a similar degree whether the antibody is pre-bound to cells expressing antigen prior to incubation with the meditope (left panel), or meditope—Protein L—and antibody are pre-mixed and then incubated with cells expressing antigen (right panel). TM=meditope-enabled trastuzumab. The percentage of MPL-positive cells relative to no-treatment control is shown in the legend.

FIG. 47A shows light chain nucleic acid (SEQ ID NO: 61) and light chain amino acid (SEQ ID NO: 61) sequences of a CDR-grafted meditope-enabled trastuzumab (with trastuzumab-like CDRs grafted onto a cetuximab-like framework), with the signal sequence and other residues shaded. FIG. 47B shows heavy chain nucleic acid (SEQ ID NO: 62) and heavy chain amino acid (SEQ ID NO: 63) of this antibody.

Figure 48:
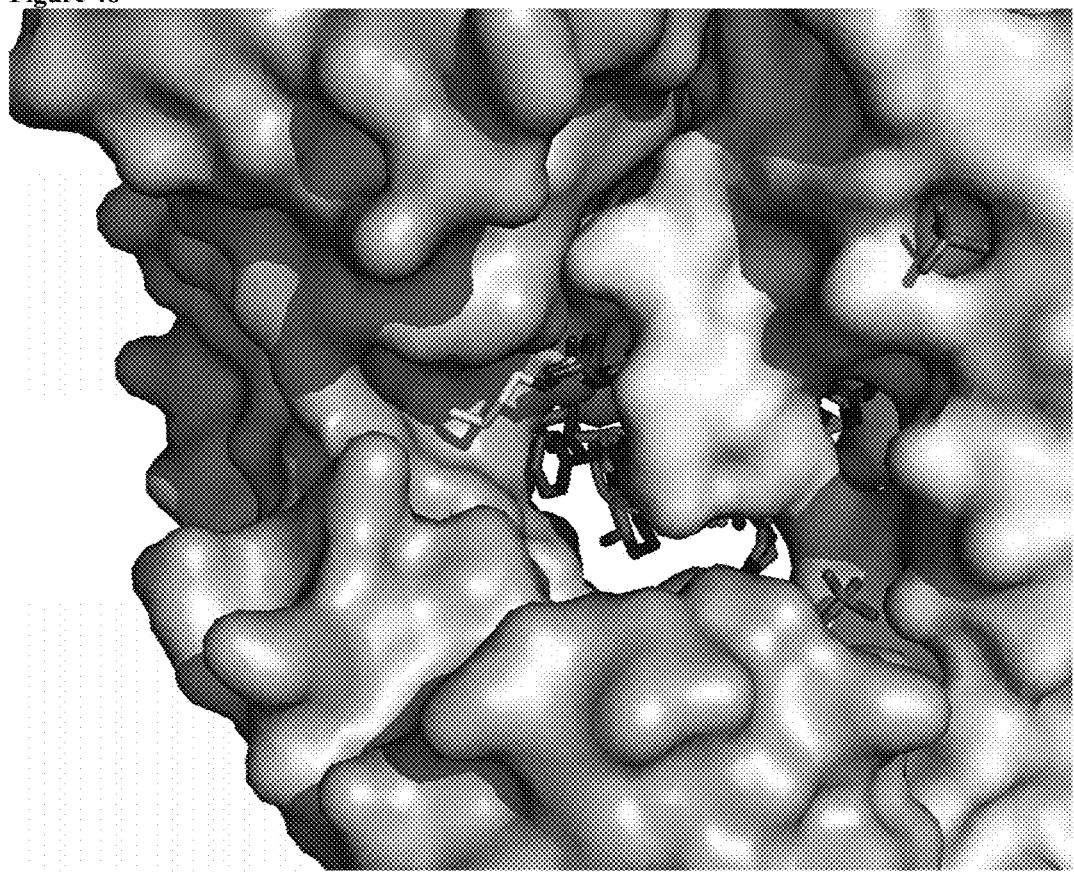

FIG. 48 shows the structure of meditope 54 (see Table 4) bound to a cetuximab Fab fragment (backside view), with structures of the 5-position β,β'-diphenylalanine meditope (SEQ ID NO: 18, meditope 18) and cQFD (meditope 1, SEQ ID NO: 1) superimposed.

Figure 49:
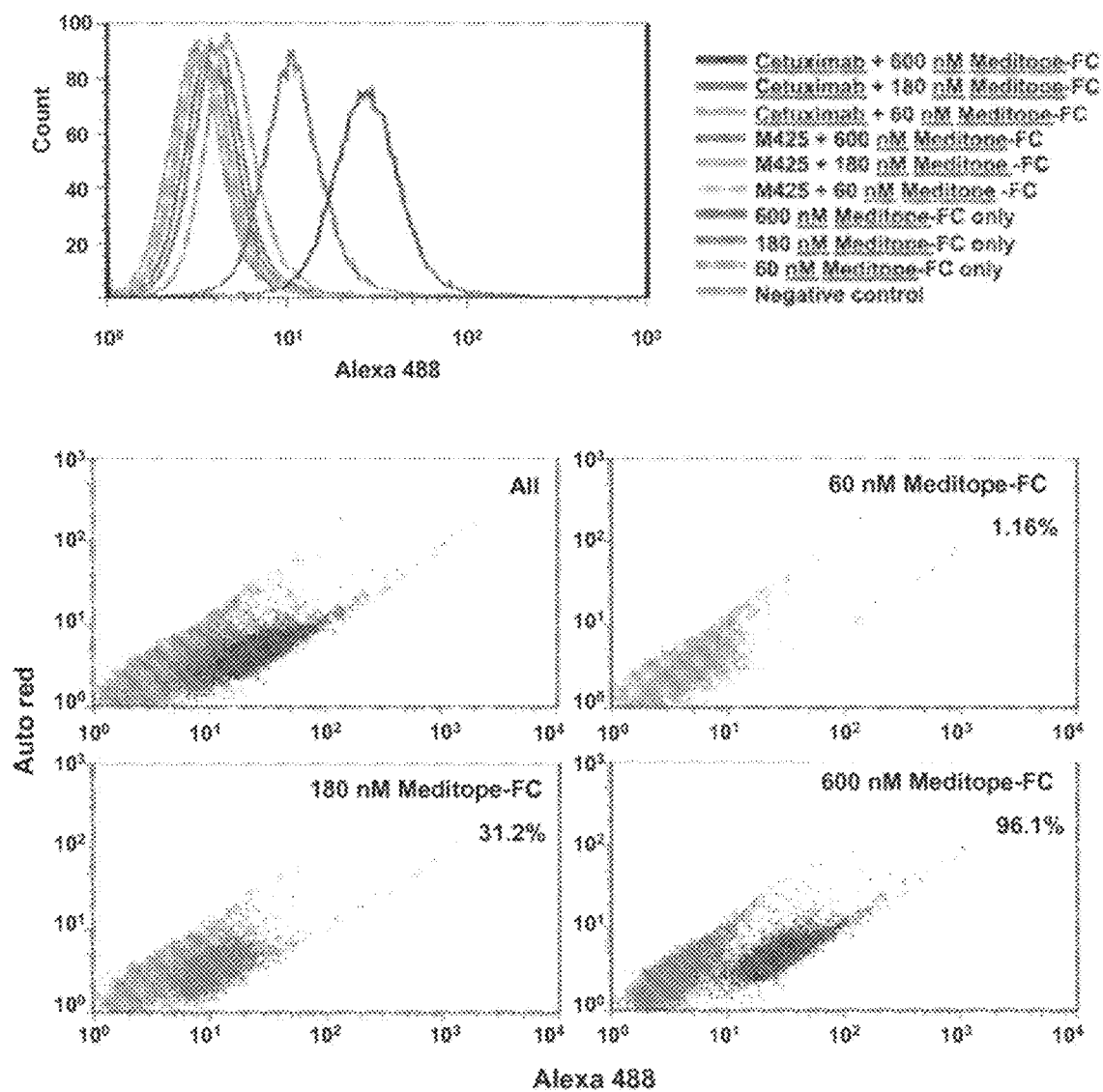

FIG. 49 shows the results of a study in which an Alexa488-labeled meditope-Fc fusion protein (600 nM, 180 nM, or 60 nM) was incubated with MDA-MB-468 cells, pre-labeled with cetuximab or M425 (a mouse anti-EGFR antibody) for 30 minutes, and antibody binding and meditope binding analyzed by FACS analysis.

Figure 50:
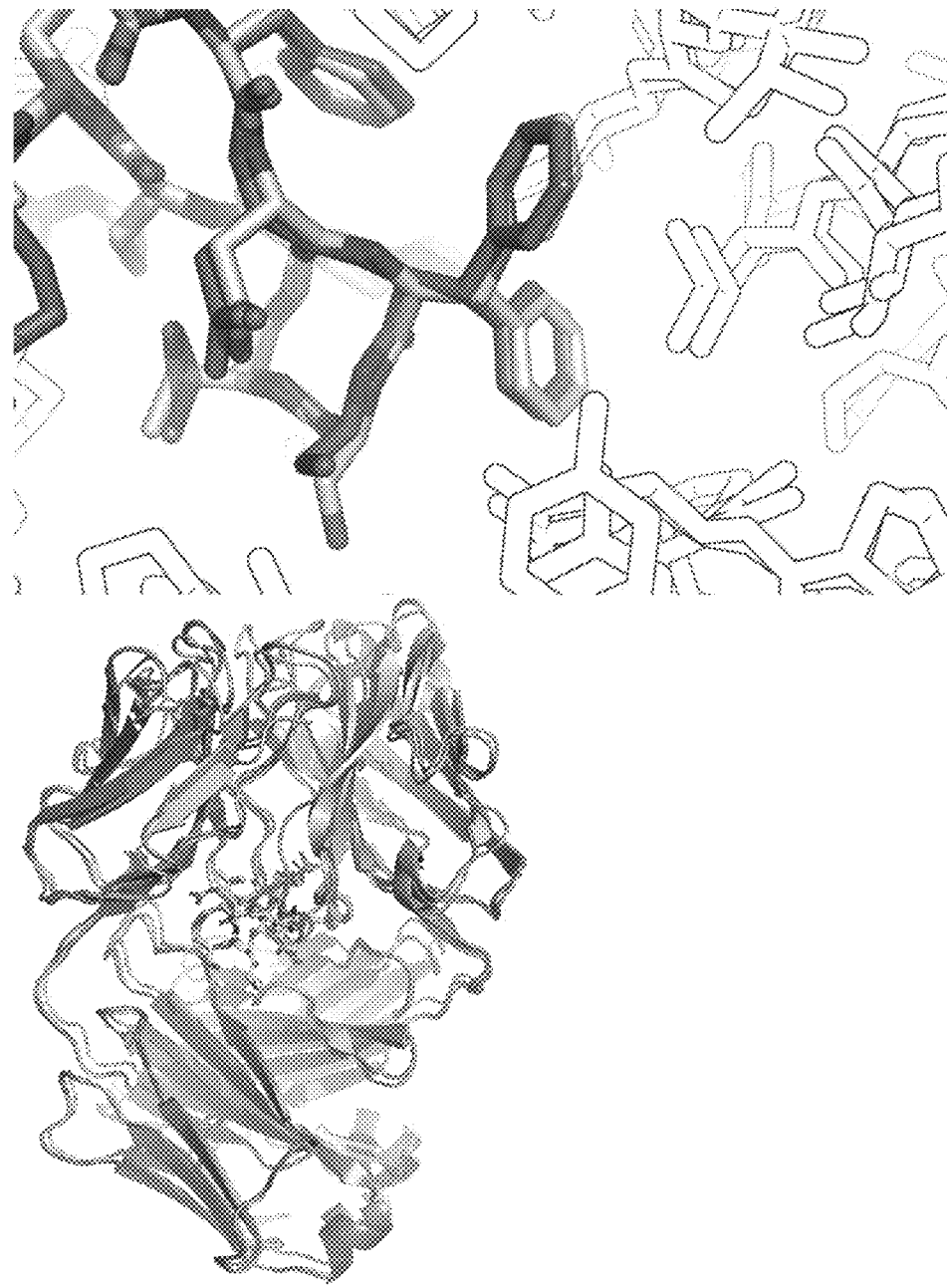

FIG. 50 (top panel) shows stick representations of the structures of meditope 18 (SEQ ID NO: 18, shown in Table 3, with a β,β'-diphenylalanine at position 5) bound to cetuximab (dark grey sticks), the same meditope (18) bound to meditope-enabled trastuzumab (white sticks), and wild-type trastuzumab (outline), superimposed. The bottom panel shows a ribbon cartoon comparing wild-type and meditope-enabled trastuzumab.

Figure 51:
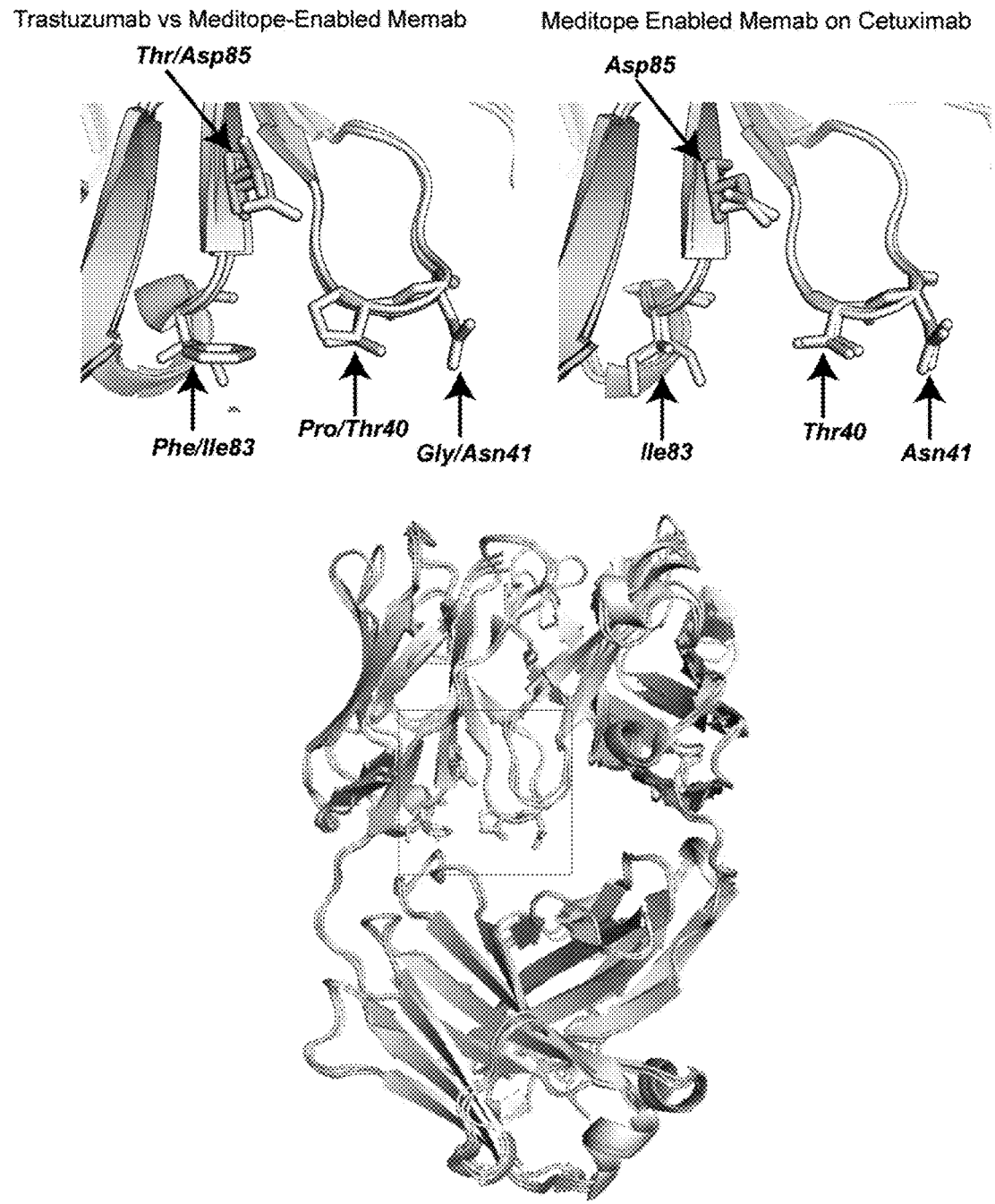

FIG. 51, in the upper-left panel, shows a superposition of the structures of trastuzumab and trastuzumab memab (in this figure, the trastuzumab memab is labeled as "Meditope-enabled Memab") with certain residues involved in meditope-binding in the meditope-enabled antibody illustrated by sticks. The top right panel shows a superposition of the structures of meditope-enabled trastuzumab (memab) and cetuximab, with the same residues labeled. The bottom panel shows a "cartoon/ribbon diagram" of all three of these structures superimposed.

Figure 52:
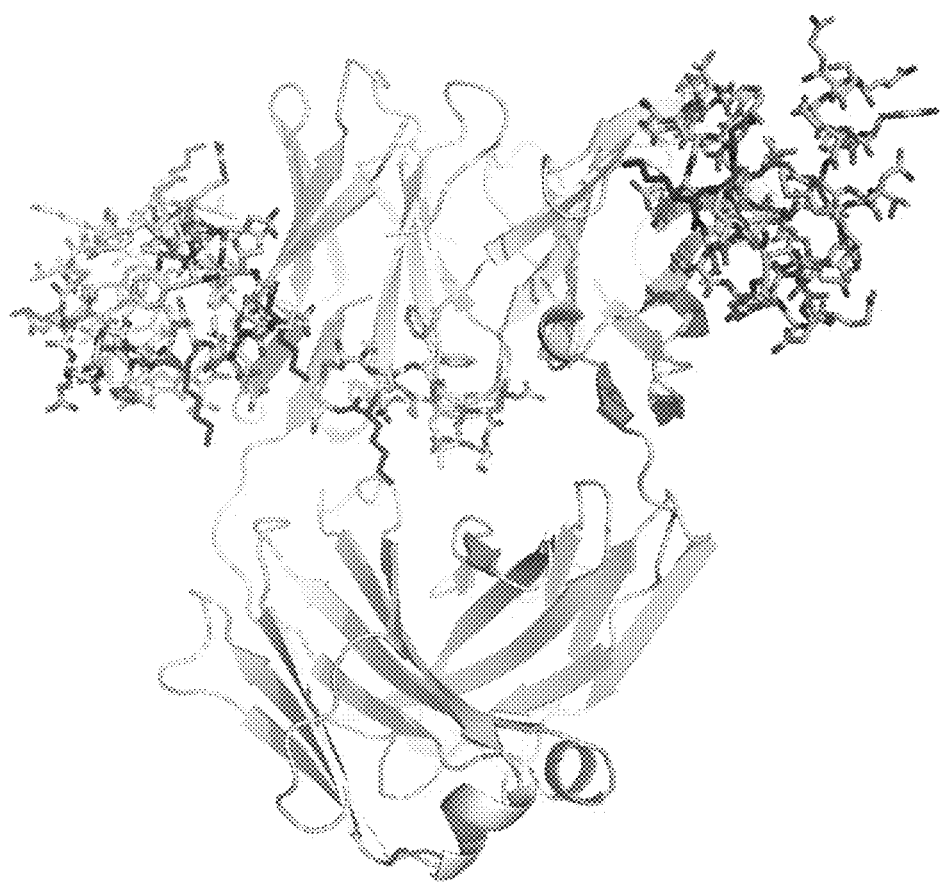

FIG. 52 shows the structure of meditope (position 3β,β' diphenyl), Protein L (left), Protein A (right) and Fab (grey cartoon). Lysines in Protein L and the meditope that were mutated in MPLs described herein are shown in black.

Figure 53:
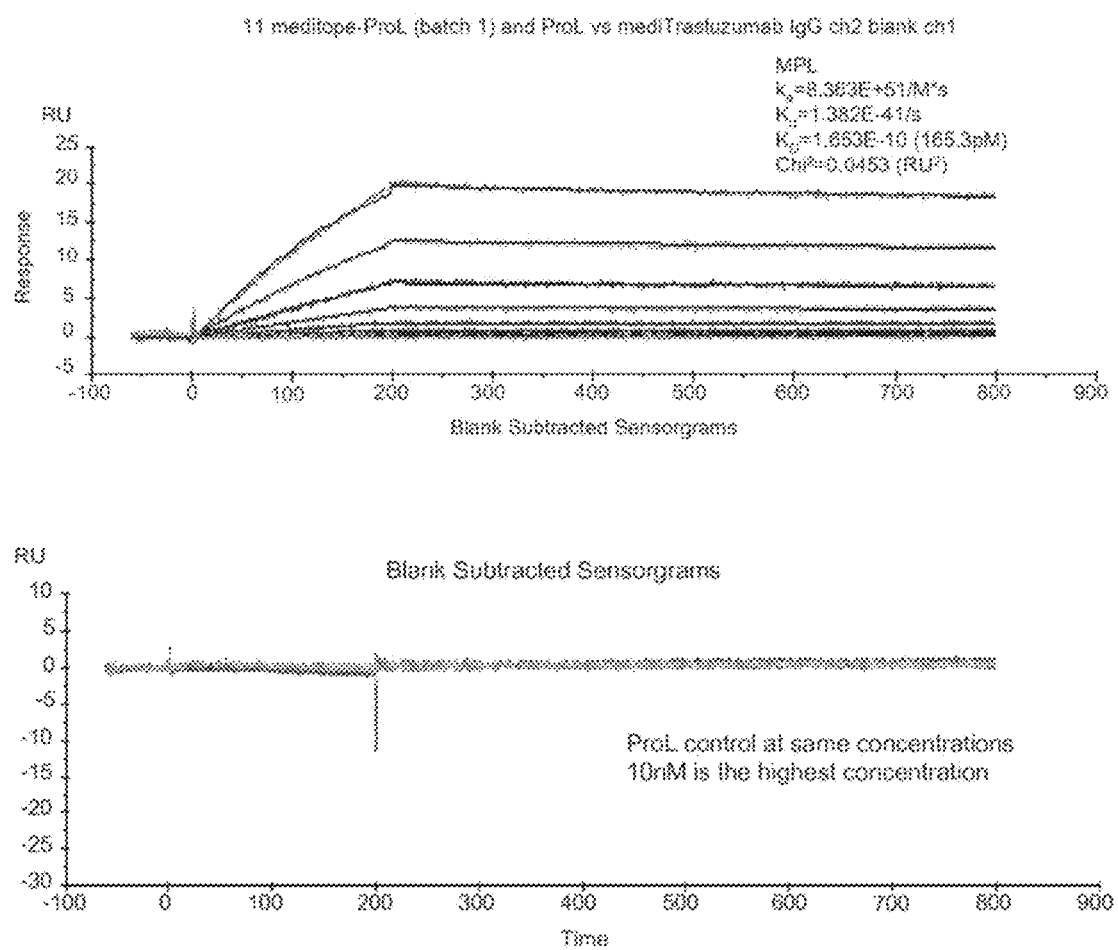

FIG. 53 shows surface plasmon resonance (SPR) data for a meditope-Protein L fusion (MPL): Top panel shows the traces of MPL being added to the meditope-enabled trastuzumab at concentrations up to 10 nM. The fit data indicates a binding affinity of 165 pM. The bottom panel shows the traces of Protein L (only) added at the same concentrations to the meditope-enabled trastuzumab, showing that there is not binding at this concentration.

Figure 54:
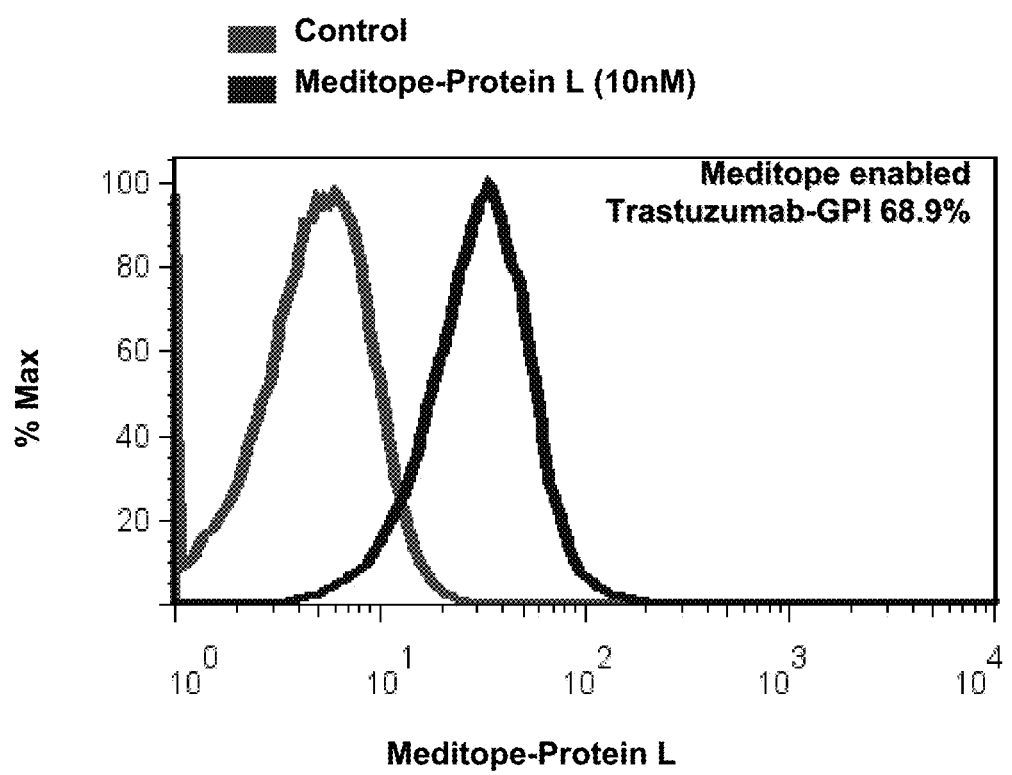

FIG. 54 shows that a GPI-linked meditope-enabled trastuzumab binds to a meditope-Protein L (MPL) fusion protein. $1 \times 10^6$ cells/sample were used. Cells were removed from plates by gentle pipetting and were washed once with 0.1% BSA (w/v) in PBS. AF647-labeled-MPL was diluted to 10 nM in wash buffer and incubated with cells for 30 min at RT. Cells were washed twice and then analyzed by FACS.

FIG. 55A shows a sequence comparison between the CH1 domain of a human IgG2, IgG4, IgG3, and IgG1 (SEQ ID NOs: 64-67). FIG. 55B shows the differences between these sequences mapped onto the co-crystal structure of cetuximab and meditope 1 (SEQ ID NO:1, cQFD).

FIG. 56 shows the amino acid sequence of the light chain of a meditope-enabled ("medi") anti-CEA antibody (meditope-enabled M5A) (SEQ ID NO: 68) compared to the wild-type M5A light chain sequence (SEQ ID NO: 69). Shaded residues represent eight point mutations that were introduced in the light chain of the M5A antibody, allowing it to bind to meditopes (for reference the heavy chain M5A sequence is set forth in SEQ ID NO: 70).

Figure 57:
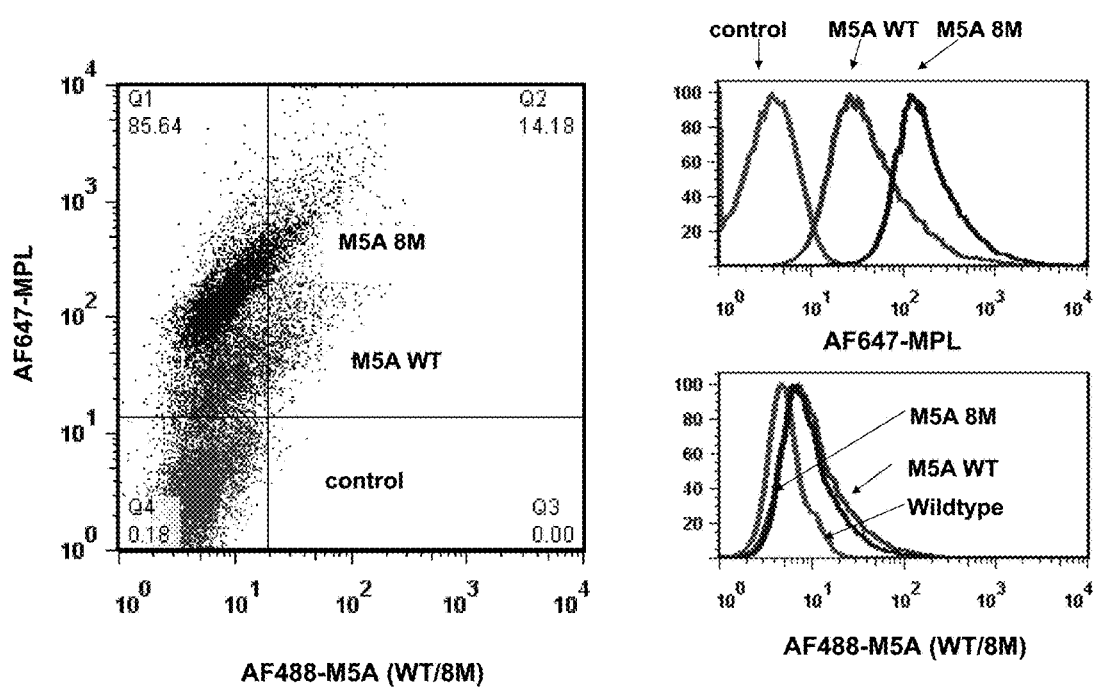

FIG. 57 shows results of FACS analysis, demonstrating binding of the meditope-enabled M5A antibody (M5A 8M) to the M5A antigen (CEA) on LS174T cells.

Figure 58:
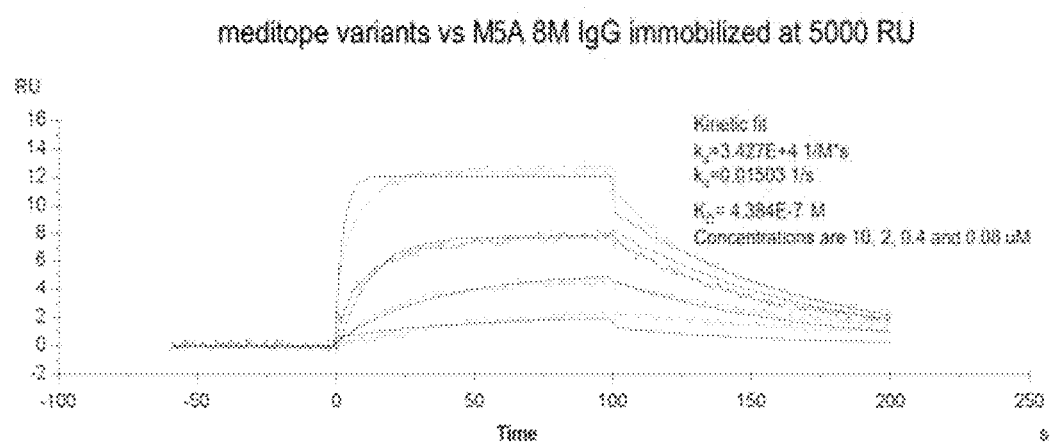

FIG. 58 shows surface plasmon resonance (SPR) data for a 5-diphenyl meditope bound (CQFDA(diphenyl) STRRLKC) (SEQ ID NO:18) to an M5A 8M meditope enabled antibody.

FIG. 59 illustrates the characterization of meditope 54, with an HPLC trace and its mass spectrum.

Figure 60:
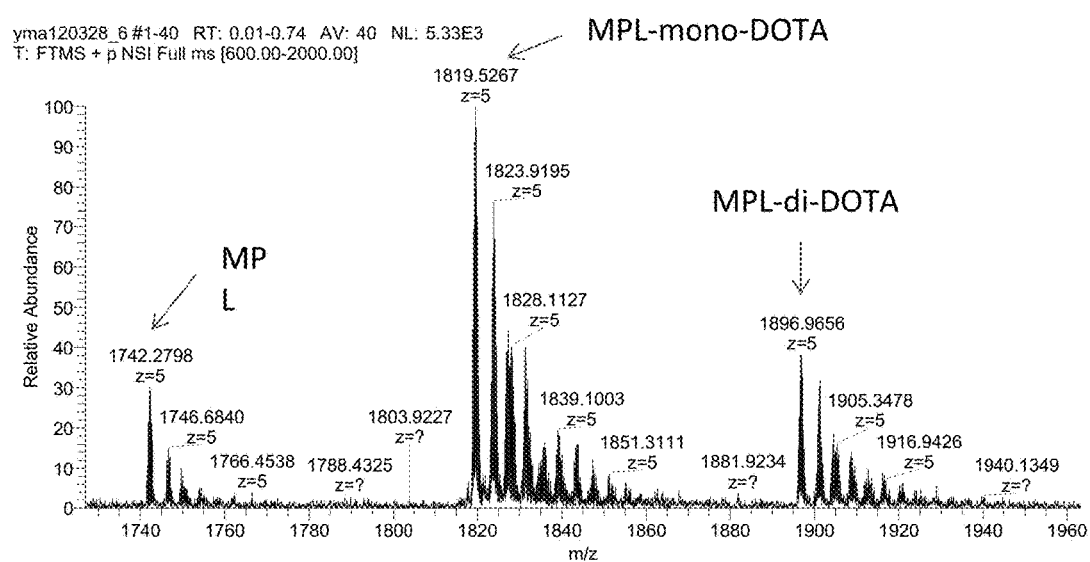

FIG. 60 illustrates the mass spectrum of DOTA-NHS-MPL conjugates formed from a starting material ratio of 120:1 (DOTA-NHS:MPL).

Figure 61:
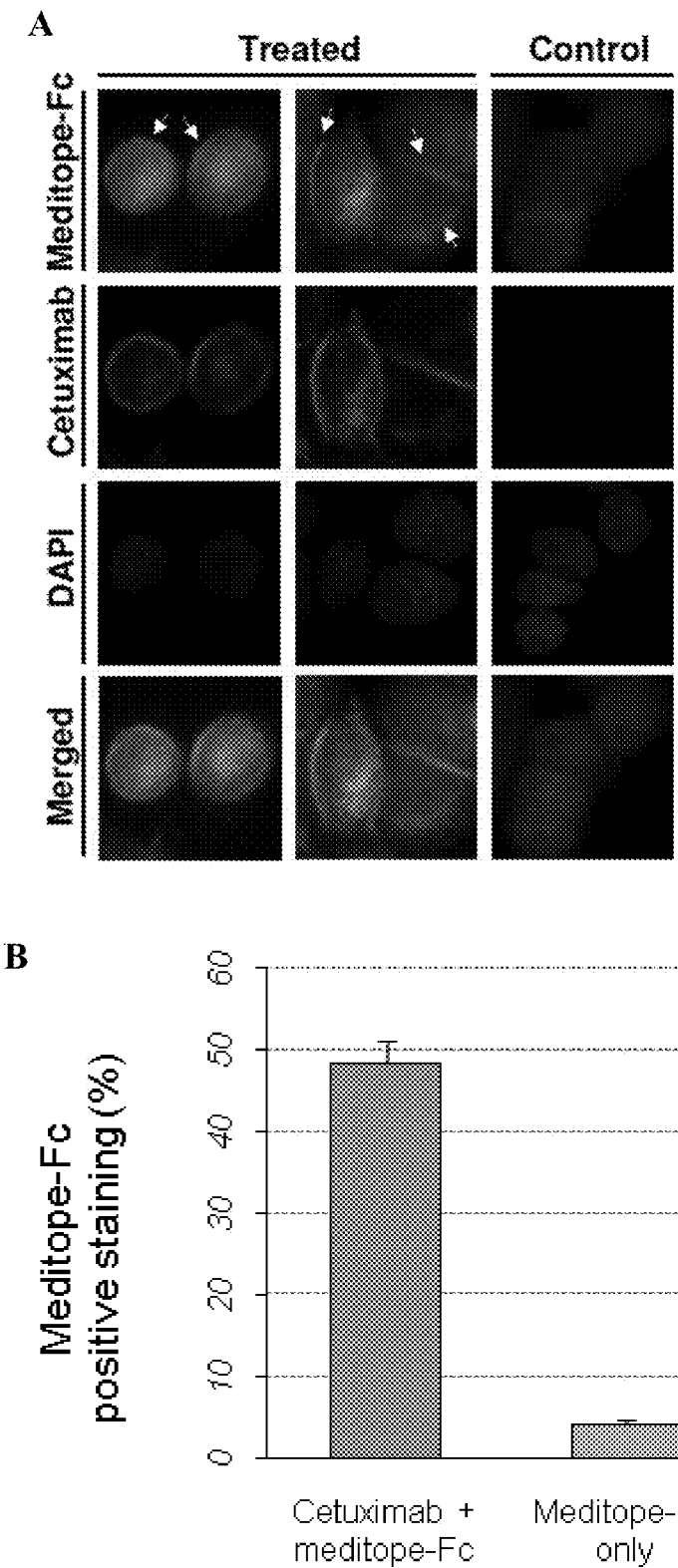

FIG. 61A shows MDA-MB-468 cells that were pre-incubated with Alexa 555-cetuximab and then incubated with Alexa 488-meditope-Fc. DAPI was used as counter stain. Images were taken with an Olympus AX70 Automatic Upright Microscope. White arrows indicate positive meditope-Fc staining. FIG. 61B shows quantification of meditope-Fc-positive cells. Bar graph showed shows percentage of meditope-Fc-positive cells of total cells from cetuximab pre-treated or untreated samples counted from two fields.

DETAILED DESCRIPTION

A. Definitions

An "antibody," as used herein, refers to an immunoglobulin molecule that specifically binds to, or is immunologically reactive with an antigen or epitope, and includes both polyclonal and monoclonal antibodies, as well as functional antibody fragments, including but not limited to fragment antigen binding (Fab) fragments, F(ab')$_2$ fragments, Fab' fragments, Fv fragments, recombinant IgG (rIgG) fragments, single chain variable fragments (scFv) and single domain antibodies (e.g., sdAb, sdFv, nanobody) fragments. The term "antibody" includes genetically engineered or otherwise modified forms of immunoglobulins, such as intrabodies, peptibodies, chimeric antibodies, fully human antibodies, humanized antibodies, meditope-enabled antibodies and heteroconjugate antibodies (e.g., bispecific antibodies, diabodies, triabodies, tetrabodies, tandem di-scFv, tandem tri-scFv). Unless otherwise stated, the term "antibody" should be understood to encompass functional antibody fragments thereof.

The terms "complementarity determining region," and "CDR," are known in the art to refer to non-contiguous sequences of amino acids within antibody variable regions, which confer antigen specificity and binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each heavy chain variable region (FR-H1, FR-H2, FR-H3, and FR-H4), and four FRs in each light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745." (Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Plückthun A, "Yet another numbering scheme for immunoglobulin variable domains: an automatic modeling and analysis tool," J Mol Biol, 2001 Jun. 8; 309(3):657-70, (AHo numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table 1, below, lists the positions of CDR-L1, CDR-L2, CDR-L3 and CDR-H1, CDR-H2, CDR-H3 as identified by the Kabat, Chothia, and Contact schemes, respectively. For CDR-H1, residue numbering is given listed using both the Kabat and Chothia numbering schemes. It is noted that because the Kabat numbering scheme places insertions at H35A and H35B, the end of the Chothia CDR-H1 loop when numbered using the Kabat numbering convention varies between H32 and H34, depending on the length of the loop.

TABLE 1

| CDR | Kabat | Chothia | Contact |
| --- | --- | --- | --- |
| CDR-L1 | L24--L34 | L24--L34 | L30--L36 |
| CDR-L2 | L50--L56 | L50--L56 | L46--L55 |
| CDR-L3 | L89--L97 | L89--L97 | L89--L96 |
| CDR-H1 (Kabat Numbering[1]) | H31--H35B | H26--H32 . . . 34 | H30--H35B |
| CDR-H1 (Chothia Numbering[2]) | H31--H35 | H26--H32 | H30--H35 |
| CDR-H2 | H50--H65 | H52--H56 | H47--H58 |
| CDR-H3 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., "CDR-H1, CDR-H2), of a given antibody or region thereof, such as a variable region thereof, should be understood to encompass a (or the specific) complementary determining region as defined by any of the known schemes. Likewise, unless otherwise specified, a "FR" or "framework region," or individual specified FRs (e.g., "FR-H1, FR-H2), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, or Contact method. In other cases, the particular amino acid sequence of a CDR or FR is given.

The term "meditope-enabled" antibody and "meMAb" refer to an antibody or functional fragment thereof that is able to bind to a meditope, via a meditope binding site. Examples of meditope-enabled antibodies include, but are not limited to, cetuximab and others described herein. A "meditope binding site" is a region of the meditope-enabled antibody containing the amino acid residues that interact with a bound meditope, which residues include framework region (FR) residues of the heavy and light chains. With reference to a Fab fragment or a Fab portion of an antibody, the meditope binding site is located within the central cavity of the Fab fragment or portion.

The "central cavity," with respect to the three-dimensional structure of a Fab, refers to the internal cavity of the Fab, lined by portions of the heavy and light chain variable and constant regions. The central cavity thus is lined by residues of the VH, VL, CH1, and CL regions and does not include the antigen binding site.

In some embodiments, the meditope binding site includes residues 40, 41, 83, and 85 of the light chain of a meditope-enabled antibody, according to Kabat numbering, and/or residues 39, 89, 105, and 108 of the heavy chain of the meditope-enabled antibody, according to Kabat numbering.

In some embodiments, the meditope binding site is located within a cavity formed by residues 8, 9, 10, 38, 39, 40, 41 42, 43, 44, 45, 82, 83, 84, 85, 86, 87, 99, 100, 101, 102, 103, 104, 105, 142, 162, 163, 164, 165, 166, 167, 168, and 173 of the light chain and 6, 9, 38, 39, 40, 41, 42, 43, 44, 45, 84, 86, 87, 88, 89, 90, 91, 103, 104, 105, 106, 107, 108, 111, 110, 147, 150, 151, 152, 173, 174, 175, 176, 177, 185, 186, and 187 of the heavy chain of the antibody, according to Kabat numbering.

With respect to a Fab portion of a meditope-enabled antibody, the meditope binding site includes residues within the central cavity. The meditope-binding site typically further includes constant region residues.

The terms "meditope", as used herein, refers to a peptide or peptides that binds to a meditope-binding site of a meditope-enabled antibody, which antibody has a threonine at position 40, an asparagine at position 41, and an aspartate at position 85 of its light chain, according to Kabat numbering, or contains a meditope binding site containing residues that correspond to those within the meditope-binding site of cetuximab, meditope-enabled trastuzumab, or meditope-enabled M5A, disclosed herein. Exemplary meditopes include, but are not limited to, the cQFD and cQYN peptides and variants thereof ("meditope variants" or "variant meditopes"), as well as multivalent and labeled meditopes. Other molecules may also bind to meditope binding sites of meditope-enabled antibodies, with functional characteristics similar to those of a meditope. Such molecules, meditope analogs, may include, but are not limited to, small molecules, aptamers, nucleic acid molecules, peptibodies and any other substance able to bind to the same meditope binding site as a meditope.

A "therapeutic agent," as used herein, is an atom, molecule, or compound that is useful in treatment of a disease or condition.

A "therapeutically effective amount," "therapeutically effective concentration" or "therapeutically effective dose" is the amount of a compound that produces a desired therapeutic effect in a subject, such as preventing or treating a target condition, alleviating symptoms associated with the condition, producing a desired physiological effect, or allowing imaging or diagnosis of a condition that leads to treatment of the disease or condition. The precise therapeutically effective amount is the amount of the composition that will yield the most effective results in terms of efficacy of treatment in a given subject. This amount will vary depending upon a variety of factors, including, but not limited to, the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that outweighs its therapeutic benefits.

A "route of administration" may refer to any administration pathway known in the art, including but not limited to aerosol, enteral, nasal, ophthalmic, oral, parenteral, rectal, transdermal, or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

"In combination" or "in combination with," when used herein in the context of multiple agents, therapeutics, or treatments, means in the course of treating the same disease or condition in a subject administering two or more agents, drugs, treatment regimens, treatment modalities or a combination thereof (e.g., an antibody in combination with a meditope or a multivalent tethering agent), in any order. This includes simultaneous administration (or "coadministration"), administration of a first agent prior to or after administration of a second agent, as well as in a temporally spaced order of up to several days apart. Such combination treatment may also include more than a single administration of any one or more of the agents, drugs, treatment regimens or treatment modalities. Further, the administration of the two or more agents, drugs, treatment regimens, treatment modalities or a combination thereof may be by the same or different routes of administration.

A "therapeutic antibody" may refer to any antibody or functional fragment thereof that is used to treat cancer, autoimmune diseases, transplant rejection, cardiovascular disease or other diseases or conditions such as those described herein. Examples of therapeutic antibodies that may be used according to the embodiments described herein include, but are not limited to murine antibodies, murinized or humanized chimera antibodies or human antibodies including, but not limited to, Erbitux (cetuximab), ReoPro (abciximab), Simulect (basiliximab), Remicade (infliximab); Orthoclone OKT3 (muromonab-CD3); Rituxan (rituximab), Bexxar (tositumomab) Humira (adalimumab), Campath (alemtuzumab), Simulect (basiliximab), Avastin (bevacizumab), Cimzia (certolizumab pegol), Zenapax (daclizumab), Soliris (eculizumab), Raptiva (efalizumab), Mylotarg (gemtuzumab), Zevalin (ibritumomab tiuxetan), Tysabri (natalizumab), Xolair (omalizumab), Synagis (palivizumab), Vectibix (panitumumab), Lucentis (ranibizumab), and Herceptin (trastuzumab).

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

As used herein, the terms "including," "containing," and "comprising" are used in their open, non-limiting sense.

As used herein, the singular forms "a," "an," and "the" include plural referents unless the context clearly dictates otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

As used herein, "alkyl" refers to a saturated, straight- or branched-chain hydrocarbon group having from 1 to 12 carbon atoms. Representative alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl, and the like, and longer alkyl groups, such as heptyl, octyl, and the like. The term "$C_{x-y}$alkyl," where x and y are integers, refers to an alkyl with x-y carbon atoms.

As used herein, an "alkenyl" refers to a straight- or branched-chain hydrocarbon group having one or more double bonds therein and having from 2 to 12 carbon atoms. Illustrative alkenyl groups include, but are not limited to, ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, and the like. The term "$C_{x-y}$alkenyl," where x and y are integers, refers to an alkenyl with x-y carbon atoms.

The term "alkylenyl" or "alkylene" refers to a divalent alkyl group. The term "alkenylene" or "alkenylene" refers to a divalent alkenyl group.

As used herein, "alkynyl" refers to a straight- or branched-chain hydrocarbon group having one or more triple bonds therein and having from 2 to 10 carbon atoms. Exemplary alkynyl groups include, but are not limited to, ethynyl, propynyl, butynyl, pentynyl, hexynyl, methylpropynyl, 4-methyl-1-butynyl, 4-propyl-2-pentynyl, 4-butyl-2-hexynyl, and the like.

"Aryl" means a mono-, bi-, or tricyclic aromatic group, wherein all rings of the group are aromatic. For bi- or tricyclic systems, the individual aromatic rings are fused to one another. Exemplary aryl groups include, but are not limited to, phenyl, naphthalene, and anthracene.

The term "boronic ester" refers to a substituent —B(OR)$_2$, wherein each R group is independently a $C_{1-4}$alkyl, or the two R groups taken together form a $C_{2-6}$alkylene.

The term "acetal" refers to a —CH(OR)$_2$ group, wherein each R group is independently a $C_{1-4}$alkyl, or the two R groups taken together form a $C_{2-6}$alkylene. Exemplary acetal groups include dimethylacetal or diethylacetal, or a cyclic acetal. The term "ketal" refers to a —C(OR)$_2$— group, wherein each R group is independently a $C_{1-4}$alkyl, or the two R groups taken together form a $C_{2-6}$alkylene. Exemplary ketals include dimethylketal or diethylketal, or a cyclic ketal.

The term "halo" represents chloro, fluoro, bromo, or iodo. In some embodiments, halo is chloro, fluoro, or bromo. The term "halogen" as used herein refers to fluorine, chlorine, bromine, or iodine.

The term "ortho ester" refers to a —$C(OR)_3$ group, wherein each R group is independently a $C_{1-4}$alkyl, or two of the R groups taken together form a $C_{2-6}$alkylene.

The term "oxo" means an =O group and may be attached to a carbon atom or a sulfur atom.

The term "phosphonate ester" refers to a —$P(O)(OR)_2$ group, wherein each R group is independently a $C_{1-4}$alkyl, or the two R groups taken together form a $C_{2-6}$alkylene.

As used herein, the term "cycloalkyl" refers to a saturated or partially saturated, monocyclic, fused polycyclic, bridged polycyclic, or spiro polycyclic carbocycle having from 3 to 15 ring carbon atoms. A non limiting category of cycloalkyl groups are saturated or partially saturated, monocyclic carbocycles having from 3 to 6 carbon atoms. Illustrative examples of cycloalkyl groups include, but are not limited to, the following moieties:

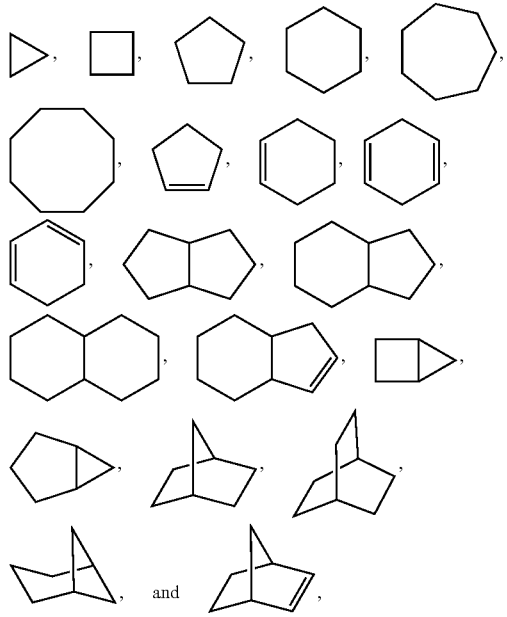

As used herein, the term "5-membered heteroaryl" refers to a monocyclic, aromatic heterocycle having five ring atoms that are selected from carbon, oxygen, nitrogen, and sulfur. Examples of 5-membered heteroaryl groups include, but are not limited to, imidazolyl, pyrazolyl, triazolyl, tetrazolyl, furanyl, thienyl, isoxazolyl, thiazolyl, oxazolyl, isothiazolyl, pyrrolyl, and thiadiazolyl. Particular examples of 5-membered heteroaryls include those that may be formed by 1,3-cycloaddition reactions such as a Huisgen reaction between an azide and a propargyl group.

As used herein, the term "substituted" means that the specified group or moiety bears one or more suitable substituents. As used herein, the term "unsubstituted" means that the specified group bears no substituents. As used herein, the term "optionally substituted" means that the specified group is unsubstituted or substituted by the specified number of substituents. Where the term "substituted" is used to describe a structural system, the substitution is meant to occur at any valency-allowed position on the system.

As used herein, the expression "one or more substituents" denotes one to maximum possible number of substitution(s) that can occur at any valency-allowed position on the system. In a certain embodiment, "one or more substituents" means 1, 2, 3, 4, or 5 substituents. In another embodiment, one or more substituent means 1, 2, or 3 substituents.

Any atom that is represented herein with an unsatisfied valence is assumed to have the sufficient number of hydrogen atoms to satisfy the atom's valence.

When any variable, such as alkyl, $R^3$, or $R^5$, appears in more than one place in any formula or description provided herein, the definition of that variable on each occurrence is independent of its definition at every other occurrence.

Numerical ranges, as used herein, are intended to include sequential whole numbers. For example, a range expressed as "from 0 to 4" or "0-4" includes 0, 1, 2, 3 and 4.

When a multifunctional moiety is shown, the point of attachment to the core is indicated by a line or hyphen. For example, —OH refers to a moiety in which an oxygen atom is the point of attachment of the hydroxyl group to the remainder of the molecule.

Any formula given herein is intended to represent compounds having structures depicted by the structural formula as well as certain variations or forms. For example, compounds of any formula given herein may have asymmetric or chiral centers and therefore exist in different stereoisomeric forms. All stereoisomers, including optical isomers, enantiomers, and diastereomers, of the compounds of the general formula, and mixtures thereof, are considered to fall within the scope of the formula. Furthermore, certain structures may exist as geometric isomers (i.e., cis and trans isomers), as tautomers, or as atropisomers. All such isomeric forms, and mixtures thereof, are contemplated herein as part of the present invention. Thus, any formula given herein is intended to represent a racemate, one or more enantiomeric forms, one or more diastereomeric forms, one or more tautomeric or atropisomeric forms, and mixtures thereof.

Diastereomeric mixtures may be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride, or formation of a mixture of diastereomeric salts), separating the diastereomers and converting (e.g., hydrolyzing or de-salting) the individual diastereomers to the corresponding pure enantiomers. Enantiomers may also be separated by use of chiral HPLC column. The chiral centers of compounds of the present invention may be designated as "R" or "S" as defined by the IUPAC 1974 Recommendations, or by "D" or "L" designations consistent with the peptide literature.

As used herein, a box around a portion of a structure, drawn with a subscript, indicates that the structural fragment that appears within the box is repeated according to the subscript. For example, the substructure:

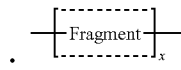

where x is 0, 1, or 2, indicates the fragment is absent from the structure, or is —Fragment—, or is —Fragment—Fragment—. For example, within formula (X), the following substructure:

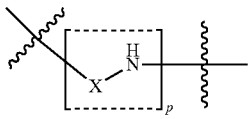

where p is 0 or 1, means that the —X—NH— group within the box is absent from the structure (p is 0), or is present once (p is 1).

The compounds of the invention can form pharmaceutically acceptable salts, which are also within the scope of this invention. A "pharmaceutically acceptable salt" refers to a salt of a free acid or base of a compound described herein that is non-toxic, is physiologically tolerable, is compatible with the pharmaceutical composition in which it is formulated, and is otherwise suitable for formulation and/or administration to a subject. Reference to a compound herein is understood to include reference to a pharmaceutically acceptable salt of said compound unless otherwise indicated.

Compound salts include acidic salts formed with inorganic and/or organic acids, as well as basic salts formed with inorganic and/or organic bases. In addition, where a given compound contains both a basic moiety, such as, but not limited to, a pyridine or imidazole, and an acidic moiety, such as, but not limited to, a carboxylic acid, one of skill in the art will recognize that the compound may exist as a zwitterion ("inner salt"); such salts are included within the term "salt" as used herein. Salts of the compounds of the invention may be prepared, for example, by reacting a compound with an amount of a suitable acid or base, such as an equivalent amount, in a medium such as one in which the salt precipitates or in an aqueous medium followed by lyophilization.

Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate ("mesylate"), ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counter ion.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

Additionally, acids and bases which are generally considered suitable for the formation of pharmaceutically useful salts from pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, MD, available from FDA). These disclosures are incorporated herein by reference thereto.

Additionally, any compound described herein is intended to refer also to any unsolvated form, or a hydrate, solvate, or polymorph of such a compound, and mixtures thereof, even if such forms are not listed explicitly. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of a crystalline solid. "Solvate" encompasses both solution-phase and isolatable solvates. Suitable solvates include those formed with pharmaceutically acceptable solvents such as water, ethanol, and the like. In some embodiments, the solvent is water and the solvates are hydrates.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (for example with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly suitable for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

B. Antibodies and Antibody-Binding Substances

Provided herein are antibodies, including monoclonal antibodies (mAbs), and fragments, e.g., functional fragments, thereof, and compounds and compositions, including peptides, such as meditopes, and meditope analogs, that bind to the antibodies. The substances, e.g., meditopes, generally bind to regions/binding sites of the antibodies and fragments other than (e.g., separate from) the complementarity determining regions (CDRs), typically to residues within the framework regions (FRs) and/or constant regions of the antibodies and fragments. Also provided are complexes, compounds, and compositions containing the antibodies and substances, e.g., meditopes, as well as methods and uses of the same, including therapeutic, diagnostic, research, and other uses of the antibodies and substances, and methods for producing the same.

Figure 4D:
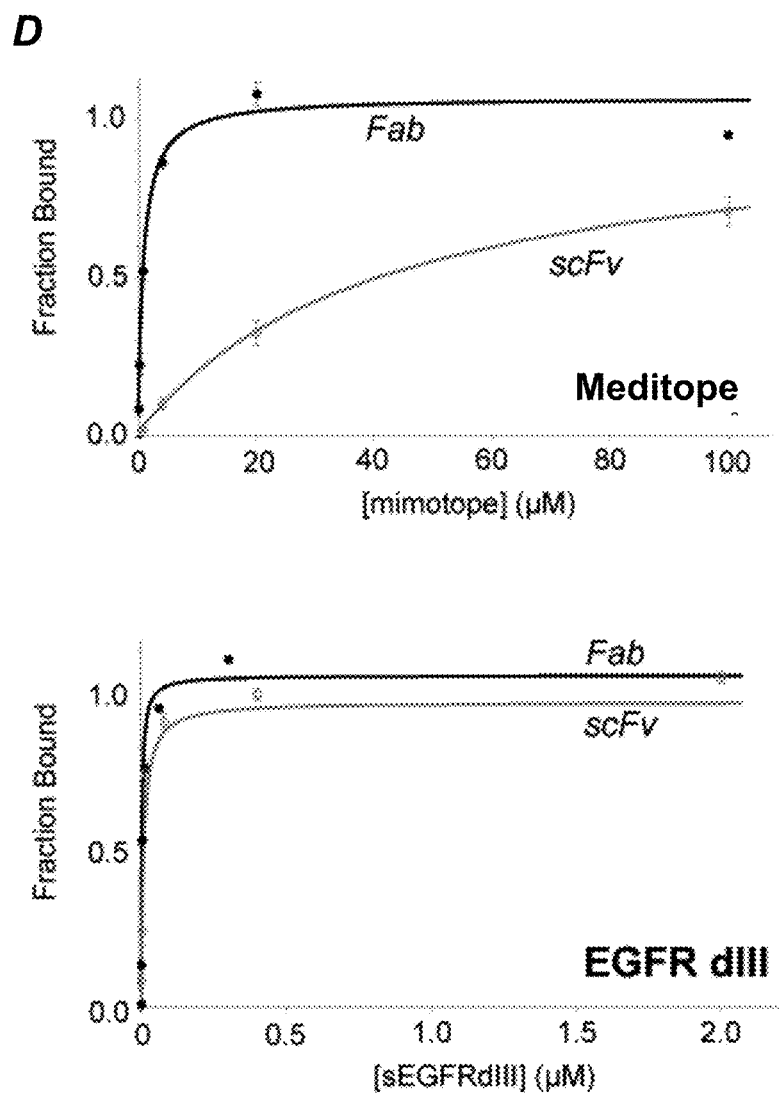
FIG. 4D shows results of surface plasmon resonance experiments using a sensor chip coupled with a cetuximab scFv or Fab. The experiments indicate that saturation of the scFv could not be achieved at concentrations as high as 100 µM of the cQFD meditope. The same experiments using the cetuximab Fab coupled sensor chip indicate full saturation. The dissociation constant from this experiment is 660 nM. Control SPR experiments (bottom panel) show that the cetuximab scFv readily binds to the soluble EGFR domain III fragment, indicating that the CDR loops were functional.
Figure 5:
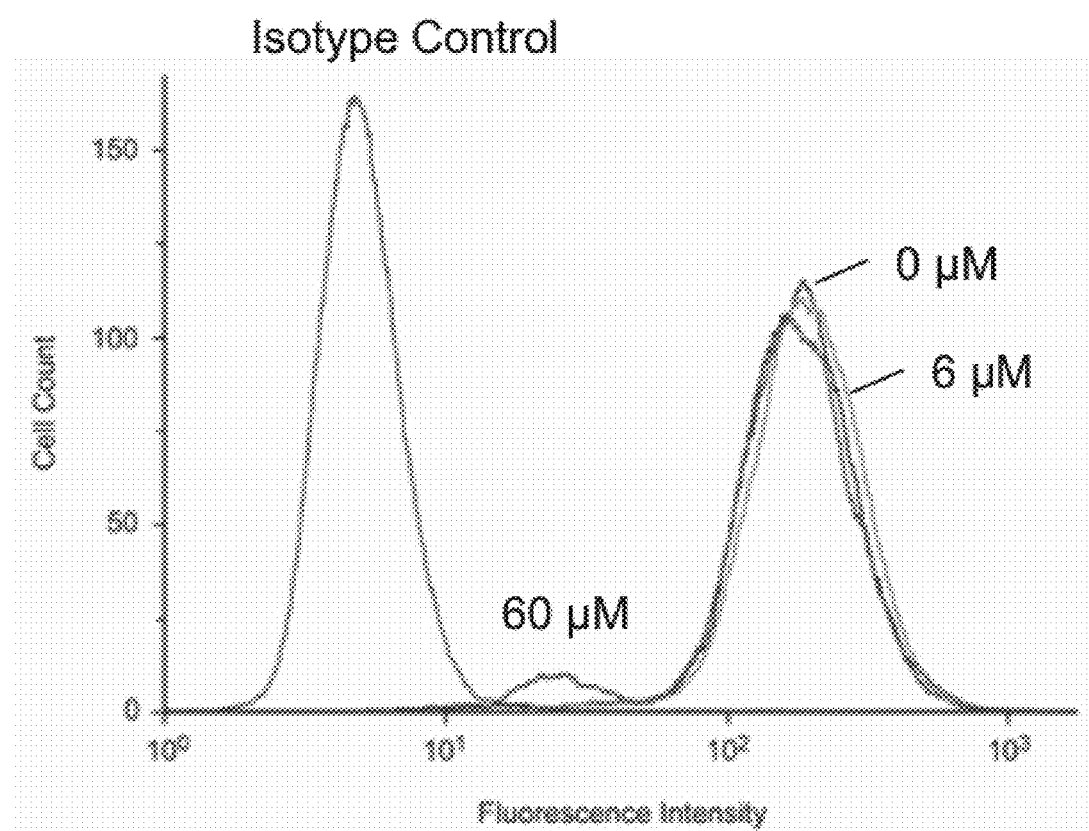
FIG. 5 is a graph of fluorescence intensity compared to cell count and shows fluorescently-labeled cetuximab binding to MDA-MB-468 cells in the presence of cQFD. Cetuximab binds to MDA-MB-468 cells without meditope, and in the presence of 6 µM and 60 µM meditope. As expected, the Figure shows that there was no binding of the isotype IgG control to EGFR on MDA-MB468 cells.
Figure 7:
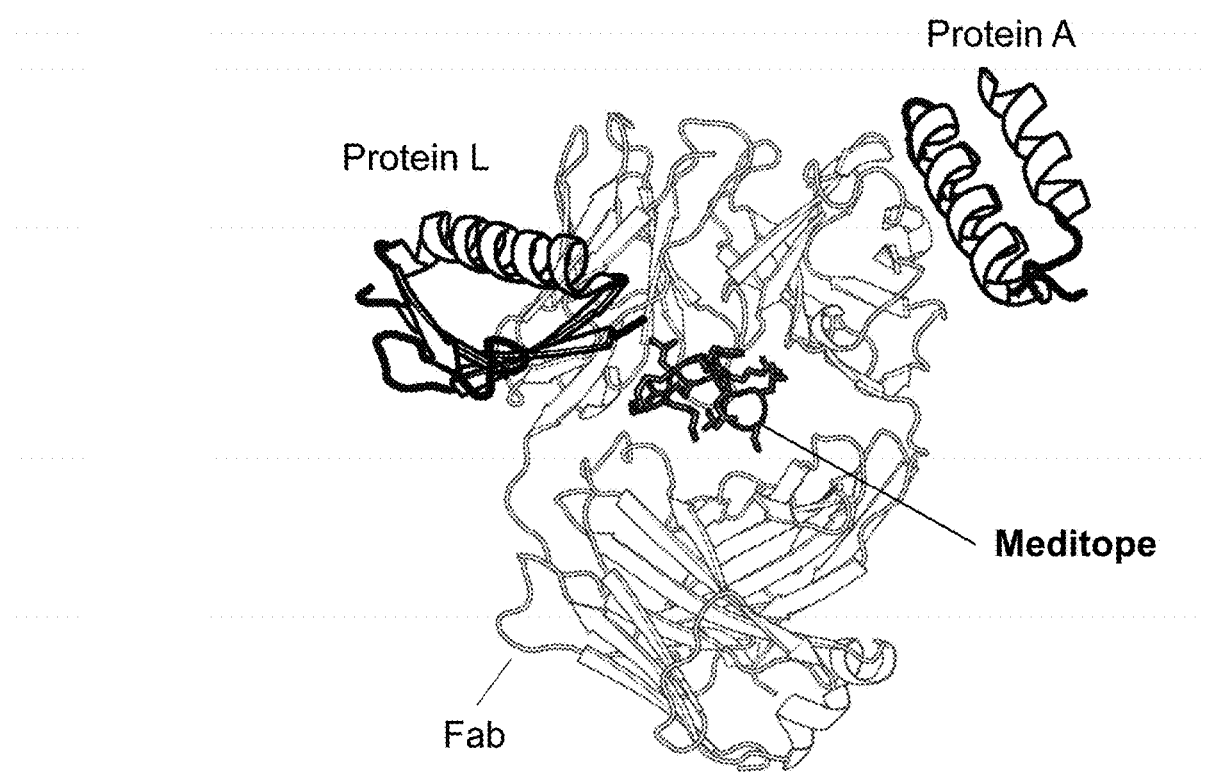
FIG. 7 shows Fab framework binders. Superposition of Fabs bound to meditope, Protein A, and Protein L indicate that each binds to a unique site on the cetuximab Fab.

In certain aspects, the provided embodiments are based on the discovery described herein that certain peptides, C-QFDLSTRRLK-C (cQFD; SEQ ID NO: 1) and C-QYN-LSSRALK-C (cQYN; SEQ ID NO: 2), non-covalently bind to a murine-human chimeric antibody, cetuximab, by interacting with residues outside the complementarity determining regions (CDRs), including residues in the framework and constant region. Also as described herein, the ability to bind to these peptides was based on certain aspects specific to cetuximab and in the studies herein binding was not observed, for example, to fully human antibodies, murine antibodies, or other chimeric antibodies). As demonstrated herein, these meditopes are capable of binding the chimeric antibody simultaneously with its antigen. See FIG. 4. As demonstrated herein, the binding site for these meditopes on cetuximab also are distinct from the binding sites of other framework-binding antigens such as the superantigens Staphylococcal Protein A (SpA) and *Peptostreptococcus magnus* Protein L (PpL) (FIG. 7). In certain aspects, the provided embodiments build upon this discovery, for example, by modifying other mAbs to allow their binding to these and other meditopes (i.e., "meditope-enabling") and generating variant meditopes and/or altered meditope-enabled antibodies, for example, those having altered properties, including improved binding affinity, toxicity, PK/PD, and/or pH dependence.

C. Meditope-Enabled Antibodies and Complexes

Provided are meditope-enabled antibodies that are capable of binding to one or more meditopes via meditope-binding sites. In some cases, the meditope-enabled antibody binds to a cyclic peptide of SEQ ID NO: 1 or 2 (meditope 1 or 2) and/or to one or more variants thereof, such as meditopes 1, 2, 16-18, 23, 29, 31, 32, 36, 39, 42, 43, 45, 46, 51, 52, 54, or 55 (meditopes based on peptides having the sequences set forth in SEQ ID NOs: 1, 2, 16-18, 23, 29, 31, 32, 36, 39, 42, 43, 45, 46, 51, 52, 54, or 55), or in some cases, any of meditopes 1, 2, or 15-55. Among the provided meditope-enabled antibodies are those that bind to a meditope or meditopes with an affinity similar to that of cetuximab. For example, in certain aspects, the antibodies bind to the meditope(s) with a dissociation constant of less than at or about 10 µM, less than at or about 5 µM, or less than at or about 2 µM, less than at or about 1 µM, less than at or about 500, 400, 300, 200, 100 nM, or less, such as at or about 200 picomolar or less. In some cases, the dissociation constant, such as any of those listed herein, is that measured using a particular technique, such as surface plasmon resonance (SPR), isothermal titration calorimetry (ITC), fluorescence, fluorescence polarization, NMR, IR, calorimetry titrations; kinetic exclusion; circular dichroism, differential scanning calorimetry, or other known method. For example, in some cases, the analog or meditope exhibits a binding constant of less than at or about 10 µM, less than at or about 5 µM, or less than at or about 2 µM, less than at or about 1 µM, less than at or about 500, 400, 300, 200, 100 nm, or less, as measured by SPR or as measured by ITC or as measured by any of these methods.

In some examples, the meditope-binding site is a structural feature of the monoclonal antibody, cetuximab, a human-murine chimeric antibody used for the treatment of EGFR-expressing metastatic colorectal cancer and head and neck cancers. Thus, in some cases, the meditope-binding site contains residues corresponding to those within the meditope binding site of cetuximab. In a study reported herein, x-ray crystallographic analysis has revealed that the peptides of SEQ ID NO: 1 binds to a meditope-binding site within the central cavity of the cetuximab Fab fragment, defined by various residues of the heavy and light chains (see FIGS. 1 and 4A), with a binding constant of ~700 nM (see FIGS. 30A-30B).

Figure 29:
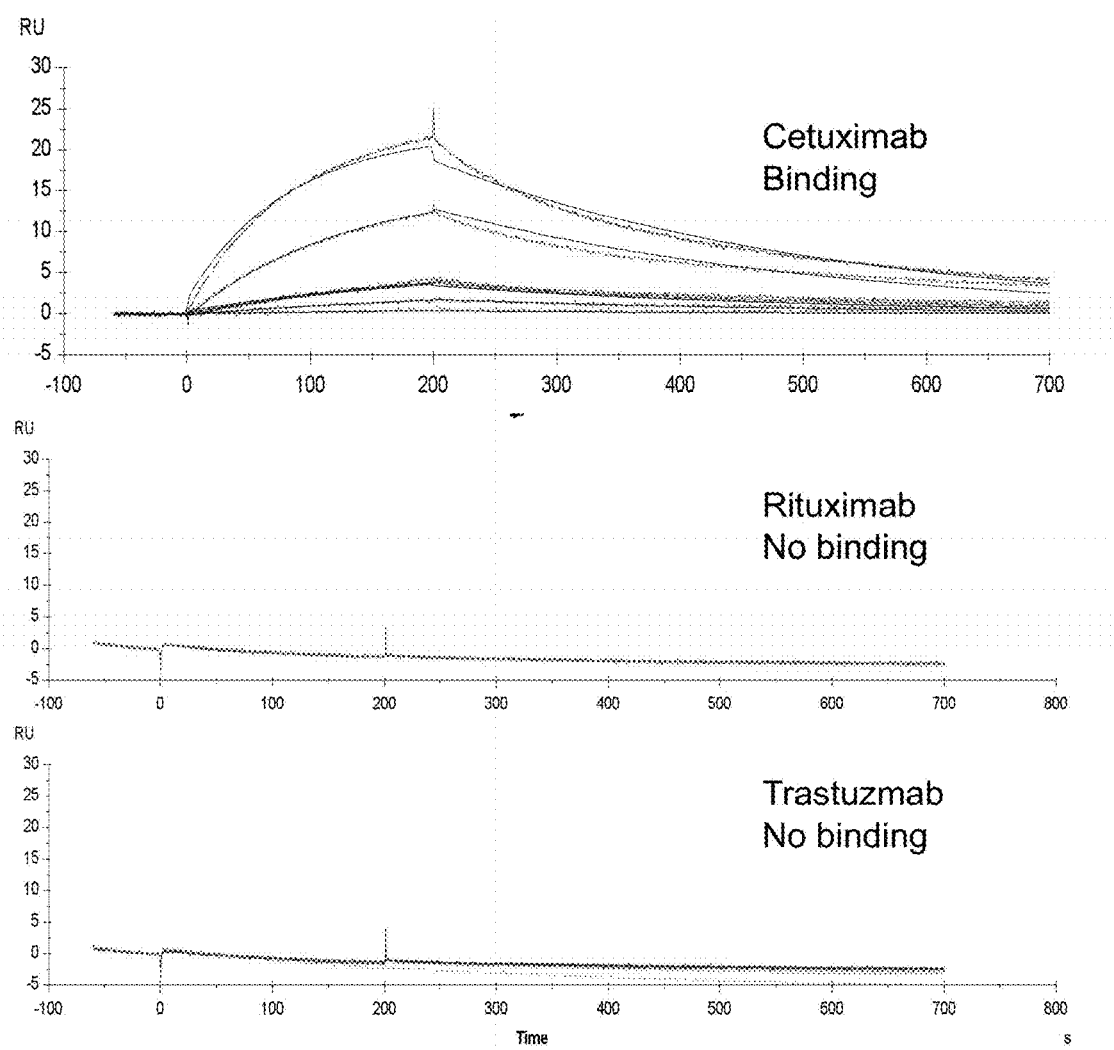
FIG. 29 illustrates binding of a meditope to a cetuximab meditope binding site ("Cetuximab Binding" as shown in Figure), but not to a fully humanized framework ("Trastuzumab No binding" as shown in Figure) or another murine-chimera framework ("Rituximab No binding" as shown in Figure). The cQFD meditope (meditope 1, SEQ ID NO: 1) was conjugated to a CM5 chip for surface plasmon resonance studies and cetuximab (meditope binding Fab), trastuzumab (fully humanized framework), and rituximab (murine-human chimeric framework) were tested at concentrations of 0.01, 0.05, 0.1, 0.5 and 1 µM. Only cetuximab bound to the meditope-conjugated chip.

Several interactions between cetuximab's meditope binding site and the cQFD (SEQ ID NO: 1, meditope 1) and cQYN (SEQ ID NO: 2, meditope 2) meditopes are based on particular structural features of cetuximab, particularly within the framework and constant regions of the central cavity of the Fab fragment. The regions of cetuximab that constitute the meditope binding site are unique and appear to be the result of the chimeric nature of this antibody. Specifically, the Fab variable regions (Fvs) are murine and the Fab constant regions (CH1 and CL) are human. The engineering of this Fab produced a combination of residues not found in a sequence alignment of murine and human chimeric antibodies. For example, data herein show that the meditopes did not bind to fully human IgG framework (e.g., trastuzumab), to other chimeric antibodies such as rituximab (FIG. 29), or to mouse antibodies, confirming that the cetuximab meditope-binding site is highly specific. In addition to these results, superposition of the molecular structure of trastuzumab (1N8Z; Cho et al., *Nature*, "Structure of the extracellular region of HER2 alone and in complex with the Herceptin Fab," 2003 Feb. 13; 421(6924):756-60) and rituxumab (2OSL; Du et al., *J Biol Chem*, 2007 May 18;282(20):15073-80. Epub 2007 Mar. 29) Fabs on to the meditope bound cetuximab Fab structure further highlighted the uniqueness of the framework. Superposition of multiple human and murine Fabs onto the cetuximab-cyclic peptide (meditope 1) structure indicated that the key interactions between this peptide and murine-human chimeric Fab are absent in both human-only and murine-only IgG structures compared in this study. Point mutations of key residues within the cQFD cyclic peptide (meditope 1) reduced its binding affinity for the cetuximab Fab, further confirming the high specificity and structural model. Thus, the interaction appears to be specific to the central cavity of this specific murine-human chimera Fab and the selected meditope.

In certain embodiments, the unique interactions between the meditopes and the cetuximab binding site are exploited to generate additional meditope-enabled antibodies. Meditope-enabled antibodies are useful, for example, to improve antibody and cell purification methods, improving the therapeutic efficacy of mAbs, enhancing targeted delivery of imaging or therapeutic agents, including in pre-targeted delivery and imaging, and improving mAb-based imaging methods, and in some aspects are broadly applicable to any monoclonal antibody.

In some embodiments, the meditope-enabled antibodies are generated by modifying an antibody other than cetuximab (sometimes referred to as the template antibody), such as an antibody having one or more CDRs distinct from those of cetuximab, to confer the ability to bind to one or more of the provided meditopes, such as a meditope of SEQ ID NO: 1 or 2, or variant thereof. The template antibody can be a human or humanized antibody or a mouse antibody. In one aspect, the modifications include substituting residues within the central cavity of the Fab fragment, typically within the framework regions (FRs) of the heavy and light chain variable regions and/or the constant regions to render the template antibody meditope-enabled. For example, where the template antibody is a human or humanized antibody, the modifications generally include substitutions at residues within the heavy and light chain variable region FRs. In some embodiments, such residues are replaced with the corresponding residue present in cetuximab, or comparable amino acid. Thus, in certain embodiments, residues within the FRs of a human or humanized antibody are replaced with corresponding murine residues; in certain embodiments, they are replaced by other residues, such as those having similar functional groups or moieties for interacting with the meditopes. Typically, the residues replaced by corresponding murine (or other) residues are found within the central Fab cavity, and thus are not exposed to the immune system. As such, in some embodiments, introducing these amino acid substitutions in a human or humanized antibody do not increase or do not substantially increase the antigenicity of the modified template antibody, in the context of delivery to a human subject. In addition, antigenicity prediction algorithms may be further used to indicate that the human sequence with the point mutations should not be antigenic.

In some embodiments, the one or more residues that are replaced, are selected from light chain framework residues 10, 39-43, 83, 85, 100 and 104, according to Kabat numbering (see Kabat E. A., et al. (1991) Sequences of Proteins of Immunological Interest, Fifth Edition. NIH Publication No. 91-3242, incorporated herein by reference in its entirety), and/or heavy chain framework residue numbers 40, 89 and 105, according to Kabat numbering (see FIG. 2). In general, unless otherwise specified, amino acid positions in the heavy or light chain of an antibody refer to Kabat numbering. Also encompassed within the present disclosure are residues in other antibodies corresponding to the residues of cetuximab described herein, such as those within the cetuximab meditope-binding site. In some embodiments, residues in the template antibody corresponding to light chain residues 9, 10, 39, 40, 41, 42, 43, 83, 85, 100, and/or 104, and/or heavy chain residues 40, 89, and/or 105, are replaced, for example, with amino acids present at those positions within cetuximab.

In one embodiment, the one or more residues replaced are light chain framework residues including, but not limited to, 40, 41, 83 and 85, according to Kabat numbering. In one embodiment, light chain residue 40 is replaced with threonine; light chain residue 41 is replaced with asparagine, light chain residue 83 is replaced with isoleucine or valine, and/or light chain residue 85 is replaced with aspartate. In a particular example, light chain framework Pro40 is replaced with Thr (P40T) or Ser (P40S), light chain framework Gly41 is replaced with Asn (G41N), light chain framework residue Phe83 is replaced with Ile (F83I) or Val (F83V) and light chain framework residue Thr85 is replaced with Asp (T85D) or Asn (T85N).

Thus, among the provided meditope-enabled antibodies are antibodies having one or more modifications, typically amino acid substitutions, at residues that correspond to positions within the meditope binding site of cetuximab or other meditope-enabled antibody, such as those described herein, including meditope-enabled trastuzumab and meditope-enabled M5A. Among the antibodies are those having a VL region with a threonine, serine, or aspartate at position 40, a residue other than glycine at position 41, and an aspartate or asparagine at position 85, according to Kabat numbering, for example, an antibody with a VL region having a threonine at position 40, an asparagine at position 41, and an aspartate at position 85. In some embodiments, the antibody has a VH region with a serine at position 40 and an isoleucine at position 89 and/or a VH region with a serine or proline at position 40 and an isoleucine, tyrosine, methionine, phenylalanine, or tryptophan at position 89, according to Kabat numbering. In some embodiments, the VL region has an isoleucine or leucine at position 10, and/or an isoleucine at position 83. In some embodiments, the VL region has a valine or isoleucine at position 9 and/or a residue other than glutamine at position 100.

In some examples, the VL region has a valine or isoleucine at position 9, an isoleucine or leucine at position 10, an arginine at position 39, a threonine at position 40, an asparagine at position 41, a glycine at position 42, a serine at position 43, an isoleucine at position 83, an aspartate at position 85, and an alanine at position 100; and the VH region has a serine at position 40 and an isoleucine at position 89, according to Kabat numbering.

In some examples, the VL region does not contain a proline at position 40, a glycine at position 41, or a threonine at position 85, according to Kabat numbering, and/or the VH region does not contain an asparagine or alanine at position 40 or a valine at position 89, according to Kabat numbering. In some examples, the VL region does not contain an serine at position 10, a proline at position 40, a glycine at position 41, an phenylalanine at position 83, or a threonine at position 85, according to Kabat numbering, and/or the VH region does not contain an asparagine or alanine at position 40 or a valine at position 89, according to Kabat numbering.

In some aspects, the antibody has a light chain having P8, V9 or 19, I10 or L10, Q38, R39, T40, N41 G42, S43, P44, R45, D82, I83, A84, D85, Y86, Y87, G99, A100, G101, T102, K103, L104, E105, R142, S162, V163, T164, E165, Q166, D167, S168, and Y173, according to Kabat numbering, and/or a heavy chain having Q6, P9, R38, Q39, S40, P41, G42, K43, G44, L45, S84, D86, T87, A88, I89, Y90, Y91, W103, G104, Q105, G106, T107, L108, V109, T110, V111, Y147, E150, P151, V152, T173, F174, P175, A176, V177, Y185, S186, and L187, according to Kabat numbering.

In other embodiments, the meditope-enabled antibodies are generated via CDR grafting, typically by modifying one or more complementarity determining region (CDR) (e.g., one or more of CDRs 1-3) of the heavy and/or light chain of a meditope-enabled antibody, such as any of the meditope-enabled antibodies described herein, to replace them with other CDRs, such as CDRs of existing or new antibodies. CDR grafting is standard practice for producing humanized monoclonal antibodies, e.g., by grafting CDRs of an antibody generated in a non-human species, such as mouse, onto a human antibody framework. See U.S. Pat. Nos. 5,558,864 and 8,133,982; Kettleborough et al., "Humanization of a mouse monoclonal antibody by CDR-grafting: the importance of framework residues on loop conformation," *Protein Eng.*, 4:773-783 (1991). Thus, in certain embodiments, the antigen specificity of a meditope-enabled antibody is altered by grafting the CDRs of preexisting or newly-generated antibodies of interest. Also among the provided meditope-enabled antibodies are such CDR-grafted meditope-enabled antibodies.

In some embodiments, the meditope-enabled antibodies are generated, using one of the antibodies disclosed herein (e.g., cetuximab, meditope-enabled trastuzumab, or meditope-enabled M5A (anti-CEA) antibody) as a template sequence, and carrying out one or more known antibody engineering methods to alter it, for example, to alter its antigen-binding characteristics, producing a meditope-enabled antibody with distinct characteristics. Known antibody engineering methods typically employed to alter antigen binding and other properties include various in vitro randomization, affinity maturation, and selection methods, including error-prone PCR, spiked PCR, site-directed mutagenesis, phage display and other selection methods. Also provided are constructs, libraries, and expression systems, including GPI-linked expression systems, for carrying out such methods.

Thus, in certain embodiments, the provided meditope-enabled antibody has a light chain and/or heavy chain variable region with the framework region or regions (FRs) of a meditope-enabled antibody, such as cetuximab, a meditope-enabled trastuzumab, or a meditope-enabled M5A (or FR(s) with at least at or about 75, 80, 85, 90, 91, 92, 93, 94, 95, 96, 97, 98, or 99% identity to the FR(s) of such an antibody). In some aspects, such an antibody has one or more CDRs that are distinct from the CDRs of that meditope-enabled antibody.

For example, in some embodiments, the VL region has an amino acid sequence comprising a light chain framework region (FR) 1 (FR-L1), an FR-L2, an FR-L3, and/or an FR-L4 of the light chain sequence set forth in SEQ ID NO: 71 (or an FR-L1, FR-L2, FR-L3, and/or FR-L4 that is at least at or about 75, 80, 85, 90, 91, 92, 93, 94, 95, 96, 97, 98, or 99% identical to the FR-L1, FR-L2, FR-L3, and/or FR-L4 of SEQ ID NO: 71), and in some aspects at least one CDR that is distinct from the CDRs of the light chain sequence set forth in SEQ ID NO: 71; and/or a VH region with an amino acid sequence having a heavy chain FR1 (FR-HD, an FR-H2, an FR-H3, and/or an FR-H4, of the heavy chain sequence set forth in SEQ ID NO: 72 (or an FR-H1, FR-H2, FR-H3, and/or FR-H4 that is at least at or about 75, 80, 85, 90, 91, 92, 93, 94, 95, 96, 97, 98, or 99% identical to the FR-H1, FR-H2, FR-H3, and/or FR-H4 of SEQ ID NO: 72), and in some aspects at least one CDR that is distinct from the CDRs of the heavy chain sequence set forth in SEQ ID NO: 72.

In some embodiments, the VL region has an amino acid sequence comprising a light chain framework region (FR) 1 (FR-L1), an FR-L2, an FR-L3, and/or an FR-L4 of the light chain sequence set forth in SEQ ID NO: 9 (or an FR-L1, FR-L2, FR-L3, and/or FR-L4 that is at least at or about 75, 80, 85, 90, 91, 92, 93, 94, 95, 96, 97, 98, or 99% identical to the FR-L1, FR-L2, FR-L3, and/or FR-L4 of SEQ ID NO: 9), and in some aspects at least one CDR that is distinct from the CDRs of the light chain sequence set forth in SEQ ID NO: 9; and/or a VH region with an amino acid sequence having a heavy chain FR1 (FR-H1), an FR-H2, an FR-H3, and/or an FR-H4, of the heavy chain sequence set forth in SEQ ID NO: 6 (or an FR-H1, FR-H2, FR-H3, and/or FR-H4 that is at least at or about 75, 80, 85, 90, 91, 92, 93, 94, 95, 96, 97, 98, or 99% identical to the FR-H1, FR-H2, FR-H3, and/or FR-H4 of SEQ ID NO: 6), and in some aspects at least one CDR that is distinct from the CDRs of the heavy chain sequence set forth in SEQ ID NO: 6.

In some embodiments, the VL region has an amino acid sequence comprising a light chain framework region (FR) 1 (FR-L1), an FR-L2, an FR-L3, and/or an FR-L4 of the light chain sequence set forth in SEQ ID NO: 68 (or an FR-L1, FR-L2, FR-L3, and/or FR-L4 that is at least at or about 75, 80, 85, 90, 91, 92, 93, 94, 95, 96, 97, 98, or 99% identical to the FR-L1, FR-L2, FR-L3, and/or FR-L4 of SEQ ID NO: 68), and in some aspects at least one CDR that is distinct from the CDRs of the light chain sequence set forth in SEQ ID NO: 68; and/or a VH region with an amino acid sequence having a heavy chain FR1 (FR-H1), an FR-H2, an FR-H3, and/or an FR-H4, of the heavy chain sequence set forth in SEQ ID NO: 70 (or an FR-H1, FR-H2, FR-H3, and/or FR-H4 that is at least at or about 75, 80, 85, 90, 91, 92, 93, 94, 95, 96, 97, 98, or 99% identical to the FR-H1, FR-H2, FR-H3, and/or FR-H4 of SEQ ID NO: 70), and in some aspects at least one CDR that is distinct from the CDRs of the heavy chain sequence set forth in SEQ ID NO: 70.

In some embodiments, the VL region has an amino acid sequence comprising a light chain framework region (FR) 1 (FR-L1), an FR-L2, an FR-L3, and/or an FR-L4 of the light chain sequence set forth in SEQ ID NO: 61 (or an FR-L1, FR-L2, FR-L3, and/or FR-L4 that is at least at or about 75, 80, 85, 90, 91, 92, 93, 94, 95, 96, 97, 98, or 99% identical to the FR-L1, FR-L2, FR-L3, and/or FR-L4 of SEQ ID NO: 61), and in some aspects at least one CDR that is distinct from the CDRs of the light chain sequence set forth in SEQ ID NO: 61; and/or a VH region with an amino acid sequence having a heavy chain FR1 (FR-H1), an FR-H2, an FR-H3, and/or an FR-H4, of the heavy chain sequence set forth in SEQ ID NO: 63 (or an FR-H1, FR-H2, FR-H3, and/or FR-H4 that is at least at or about 75, 80, 85, 90, 91, 92, 93, 94, 95, 96, 97, 98, or 99% identical to the FR-H1, FR-H2, FR-H3, and/or FR-H4 of SEQ ID NO: 63), and in some aspects at least one CDR that is distinct from the CDRs of the heavy chain sequence set forth in SEQ ID NO: 63.

In some embodiments, the meditope-enabled antibody has one or more CDRs distinct from the CDRs set forth in SEQ ID NO: 6, 7, 9, 10, 12, 14, 61, 63, 68, 69, 70, 71, and/or 72.

In some embodiments, the meditope is an antibody other than cetuximab, does not specifically bind to an EGFR, binds to an antigen other than EGFR, and/or does not specifically bind to the epitope on EGFR that is specifically bound by cetuximab.

In some examples, the meditope-enabled antibody is generated based on a template antibody that is selected from among abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, Fbta05, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, Trbs07, ustekinumab, visilizumab, votumumab, zalutumumab, brodalumab, anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, the antibody produced by the hybridoma 10B5, B6H12.2, and urelumab, fragments thereof, antibodies having the CDRs and/or antigen-binding regions thereof, and/or antibodies that compete for binding with such antibodies; and/or antibodies having a sequence set forth in any of SEQ ID NOs: 78-124, and/or 125-170, fragments thereof antibodies having the CDRs and/or antigen-binding regions thereof, and/or antibodies that compete for binding with such antibodies.

Table 2 lists CAS® Registry Numbers for certain antibodies.

TABLE 2

| Antibody | CAS Registry number |
|---|---|
| abagovomab | 792921-10-9 |
| abciximab | 143653-53-6 |
| adalimumab | 331731-18-1 |
| adecatumumab | 503605-66-1 |
| alemtuzumab | 216503-57-0 |
| indium (111In) altumomab pentetate | 156586-92-4 |
| arcitumomab | 154361-48-5 |
| arcitumumab | 154361-48-5 |
| atlizumab | 375823-41-9 |
| basiliximab | 152923-56-3 |
| bectumomab | 158318-63-9 |
| belimumab | 356547-88-1 |
| benralizumab | 1044511-01-4 |
| bevacizumab | 216974-75-3 |
| brentuximab | 914088-09-8 |
| canakinumab | 914613-48-2 |
| capromab pendetide | 145464-28-4 |
| capromab | 151763-64-3 |
| catumaxomab | 509077-98-9 |
| certolizumab | 428863-50-7 |
| certolizumab | 428863-50-7 |
| cetuximab | 205923-56-4 |
| clivatuzumab tetraxetan | 943976-23-6 |
| daclizumab | 152923-56-3 |
| denosumab | 615258-40-7 |
| eculizumab | 219685-50-4 |
| edrecolomab | 156586-89-9 |
| efalizumab | 214745-43-4 |
| etaracizumab | 892553-42-3 |
| etrumaxomab | 509077-99-0 |
| fanolesomab | 225239-31-6 |
| FBTA05 | Lymphomun/FBTA05 |
| fontolizumab | 326859-36-3 |
| gemtuzumab | 220578-59-6 |
| girentuximab | 916138-87-9 |
| golimumab | 476181-74-5 |
| ibritumomab | 174722-31-7 |
| igovomab | 171656-50-1 |
| Infliximab | 170277-31-3 |
| ipilimumab | 477202-00-9 |
| labetuzumab | 219649-07-7 |
| mepolizumab | 196078-29-2 |
| muromonab-CD3 | 140608-64-6 |
| natalizumab | 189261-10-7 |
| nimotuzumab | 828933-61-3 |
| ofatumumab | 679818-59-8 |
| omalizumab | 242138-07-4 |
| oregovomab | 213327-37-8 |
| palivizumab | 188039-54-5 |
| panitumumab | 339177-26-3 |
| ranibizumab | 347396-82-1 |
| rituximab | 174722-31-7 |
| satumomab | 138955-26-7 |
| sulesomab | 167747-19-5 |
| tiuxetan (ibritumomab) | 174722-31-7 |
| tocilizumab | 375823-41-9 |
| tositumomab | 192391-48-3 |
| trastuzumab | 180288-69-1 |
| ustekinumab | 815610-63-0 |
| votumumab | 148189-70-2 |
| zalutumumab | 667901-13-5 |

TABLE 2-continued

| Antibody | CAS Registry number |
|---|---|
| brodalumab | 1174395-19-7 |
| anrukinzumab | 910649-32-0 |
| bapineuzumab | 648895-38-9 |
| dalotuzumab | 1005389-60-5 |
| demcizumab (OMP-21M18) | 1292853-12-3 |
| ganitumab | 905703-97-1 |
| inotuzumab | 635715-01-4 |
| mavrilimumab | 1085337-57-0 |
| moxetumomab | 1020748-57-5 |
| moxetumomab pasudotox | 1020748-57-5 |
| rilotumumab | 872514-65-3 |
| sifalimumab | 1143503-67-6 |
| tanezumab | 880266-57-9 |
| tralokinumab | 1044515-88-9 |
| tremelimumab | 745013-59-6 |
| urelumab | 934823-49-1 |
| necitumumab | 906805-06-9 |

In other examples, the template antibody is selected from among: abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, Fbta05, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, Trbs07, ustekinumab, visilizumab, votumumab, zalutumumab, the antibody produced by the hybridoma 10B5, and brodalumab, or tiuzetan. In some such examples, the one or more CDRs are CDRs present in these template antibodies, and/or the antibodies specifically bind to the same antigen or epitope as such antibodies, and/or compete for binding with such antibodies to their antigens.

Thus, in some cases, the meditope-enabled antibodies (including fragments thereof) specifically binds to an antigen selected from the group consisting of: CA-125, glycoprotein (GP) IIb/IIIa receptor, TNF-alpha, CD52, TAG-72, Carcinoembryonic antigen (CEA), interleukin-6 receptor (IL-6R), IL-2, interleukin-2 receptor a-chain (CD25), CD22, B-cell activating factor, interleukin-5 receptor (CD125), VEGF, VEGF-A, CD30, IL-1beta, prostate specific membrane antigen (PSMA), CD3, EpCAM, EGF receptor (EGFR), MUC1, human interleukin-2 receptor, Tac, RANK ligand, a complement protein, e.g., C5, EpCAM, CD11a, e.g., human CD11a, an integrin, e.g., alpha-v beta-3 integrin, vitronectin receptor alpha v beta 3 integrin, HER2, neu, CD3, CD15, CD20 (small and/or large loops), Interferon gamma, CD33, CA-IX, TNF alpha, CTLA-4, carcinoembryonic antigen, IL-5, CD3 epsilon, CAM, Alpha-4-integrin, IgE, e.g., IgE Fc region, an RSV antigen, e.g., fusion protein of respiratory syncytial virus (RSV), TAG-72, NCA-90 (granulocyte cell antigen), IL-6, GD2, GD3, IL-12, IL-23, IL-17, CTAA16.88, IL13, interleukin-1 beta, beta-amyloid, IGF-1 receptor (IGF-1R), delta-like ligand 4 (DLL4), alpha subunit of granulocyte macrophage colony stimulating factor receptor, hepatocyte growth factor, IFN-alpha, nerve growth factor, IL-13, PD-L1, CD326, CD47, and CD137. In some examples, the meditope-enabled antigen binds to another antigen identified as a target in a disease or condition of interest, such as cancer or other disease.

The meditope-enabled antibodies generally further include a constant region, typically a heavy and light chain constant region, which generally are human or partially human constant regions. In some aspects, the heavy chain constant region includes a CH1, or a portion thereof. In some aspects, the light chain constant region includes a CL, or a portion thereof. In some embodiments, the portion of the constant region is sufficient to render the antibody capable of binding to the meditope, e.g., with the requisite binding affinity. In some aspects, the constant regions are the constant regions of cetuximab or trastuzumab. Thus, in some aspects, the heavy chain constant regions are one or more human IgG1 constant regions; in some aspects, the light chain constant regions are kappa constant chain regions. In other examples, the constant regions can include those of other isotypes, including human (or other organism, e.g., murine or chicken) IgG1, IgG2, IgG3, IgG4, IgEs, IgA1, IgA2, IgD, or IgM, and can include kappa or lambda constant regions. Thus, among the provided meditope-enabled antibodies are those generated by mutation of residues in other IgGs, such as human, murine, or chicken, or other immunoglobulins. In other words, the meditope-enabling methods provided herein may be used for any antibody, including IgA, IgE, IgD, and IgM and from any organism that produces antibodies including but not limited to chicken, murine, rat, bovine, rabbit, primates, and goat.

For example, the sequences of the first constant region (CH1) of a human IgG1, IgG2, IgG3, and IgG4, are compared in FIG. 55A. FIG. 55B shows the sequence differences in the IgG2-4 CH1, compared to the IgG1 CH1, mapped onto the co-crystal structure of cetuximab and the cQFD meditope (meditope 1, SEQ ID NO: 1). As shown in the Figure, the residues that are different among these isotypes are not within the meditope-binding region of cetuximab, confirming that the meditope-enabling technology is applicable to isotypes other than the IgG1 of cetuximab. As another example, the sequence and structural alignment of an IgG1 and an IgE Fab domain indicates residues on the IgE near the meditope binding site (FIG. 26).

The provided methods for meditope-site grafting of the Fab cavity within monoclonal antibodies can be used to create a unique handle for meditope binding and used with the technology previously disclosed and for newly-generated antibodies. In certain embodiments, the meditope binding site can be created on pre-existing and all future monoclonal antibodies.

As described below in section F, also provided are methods for modifying the meditope-enabled antibodies, for example, to alter various properties of the meditope-enabled antibodies, including aspects of the interaction with the meditopes, including affinity, avidity, pH-dependence, as well as other aspects, including pharmacokinetics (PK) and pharmacodynamics (PD) of the antibodies. Thus, also among the provided meditope-enabled antibodies are those modified antibodies generated according to those methods, e.g., by generating a pharmacophore binding model, including antibodies having any one or more of the modifications described in section F, below.

Also among the antibodies used as template antibodies to generate the meditope-enabled antibodies are modified antibodies and portions thereof, such as a CovX-Body™. Thus, among the provided meditope-enabled antibodies are CovX-bodies, modified to allow their binding to one or more of the provided meditopes, e.g., with an affinity as described herein.

Also provided are complexes containing one or more meditope bound to a meditope-enabled antibody, such as any of the antibodies described herein.

Also provided are nucleic acids, such as cDNA and RNA molecules, encoding the meditope-enabled antibodies, and vectors and libraries containing the same, as well as methods for their use, including selection and expression methods and methods for generating transgenic animals using such constructs.

D. Meditopes

Also provided are meditopes, including variant, modified, and multivalent meditopes, that bind to meditope-enabled antibodies, and complexes and compositions containing the same, and methods and uses thereof. In certain embodiments, the meditopes include meditopes 1 and 2 (cQFD (SEQ ID NO: 1) and cQYN (SEQ ID NO: 2)), which were originally identified as candidate peptides for binding to the CDR region of cetuximab, as described by Riemer, et al. (2004); *J Immunol* 173, 394-401; Riemer, et al. (2005); *J Natl Cancer Inst* 97, 1663-1670. As demonstrated herein, the cQFD and cQYN meditopes bind to sites within cetuximab distinct from the cetuximab CDRs, and thus were not likely candidates for specific cetuximab-like antibody immunogens for use as a vaccine.

Nucleic acids encoding the meditopes, including meditope variants and multivalent meditopes, as well as vectors, cells, libraries, and other systems containing the same, also are provided.

I. Variant Meditopes

Among the provided meditopes are meditope variants (also called variant meditopes), having one or more modifications, e.g., structural modifications, as compared to meditope 1 or 2 (meditope of SEQ ID NO: 1 or 2), and methods for producing the same. In some embodiments, cQFD and cQYN meditopes are used as starting points in the design of meditope variants. In some aspects, the meditope variants are designed to have altered properties, such as increased or altered affinity, altered pH dependence, or different affinities under different physiological conditions for one or more of the provided meditope-enabled antibodies, including cetuximab and other antibodies described herein, e.g., as compared to the unmodified meditopes, cQFD and cQYN. Meditope variants are designed and produced using various chemical and biophysical methods.

Meditope variants include, but are not limited to, variants incorporating modifications to meditopes, e.g., cQFD and cQYN and others described herein. Suitable modifications include, but are not limited to, any peptide modification known in the art, such as, but not limited to, modifications to the manner and/or position of peptide cyclization, modifications to one or more amino acid components of the cyclic peptide, or adding or deleting one or more amino acid from the cyclic peptide. In a particular example, cQFD may be altered with one or more of the following modifications: a modification of Arg8, a modification of Phe3, a modification of Leu5, a modification of Leu10, change to the mode of peptide cyclization, and/or an incorporation of hydratable carbonyl functionality at one or more positions, and one or more amino acid deletions or additions. In the case of cQYN, suitable modifications may include one or more of the following: a modification of Arg8, a modification of Leu5, a modification of Leu10, change to the mode of peptide cyclization, and/or an incorporation of hydratable carbonyl functionality at one or more positions, and one or more deletions or additions. Certain amino acid positions within the meditope may be deleted or replaced with a different natural amino acid or an unnatural amino acid, or the meditope may be chemically conjugated with a fragment. It is shown herein that a meditope in which Arg9 of SEQ ID NO: 1 has been mutated to citrulline binds to cetuximab. In addition, the amino and carboxy termini can be extended with further amino acids beyond (i.e., in addition to) the cyclic portion of the meditope variant in order to make additional contact to the Fab. For example, Protein L has been added to the C-terminus of the cQFD meditope and preliminary data shows that this binds with much higher affinity. Such modifications are discussed further in Examples 6 and 7.

In some embodiments, the meditopes include those listed in Tables 3 and 4, as well as such meditopes with additional amino acids, such as those up to 16 amino acids in length. For example, in some aspects, the meditope is one of meditopes 1, 2, or 15-55, further including a serine before the first residues, i.e., at position zero. The meditopes listed in Table 3 employ a disulfide linkage to connect the C and N termini (except that meditope 31 contained an additional tail, meaning that the disulfide linkage is not between the two terminal residues); for the peptides in Table 4, a lactam bridge, a linkage other than disulfide (such as [3+2] cycloaddition), or no linkage is used (e.g., an acyclic or linear variant). Additional meditopes that may be used according to the embodiments described herein include any meditope as defined herein peptide that binds to an antibody framework binding interface (i.e., between the Fab light and heavy chains) of cetuximab or any other therapeutic antibody. For example, in addition to the cyclic peptides cQFD and cQYN, some embodiments include one or more variants of cQFD and cQYN.

TABLE 3

| SEQ ID NO | Meditope Number | Sequence | Modification (red) | Linkage method |
|---|---|---|---|---|
| 1 | 1 | C-QFDLSTRRLK-C | original | Disulfide 1-Cys:12-Cys |
| 2 | 2 | C-QYNLSSRALK-C | original | Disulfide 1-Cys:12-Cys |
| 15 | 15 | C-qFDLSTRRLK-C | q = D-glutamine | Disulfide 1-Cys:12-Cys |
| 16 | 16 | C-QYDLSTRRLK-C | Y = tyrosine | Disulfide 1-Cys:12-Cys |
| 17 | 17 | C-QXDLSTRRLK-C | X = β-β'-di-phenyl-Ala | Disulfide 1-Cys:12-Cys |
| 18 | 18 | C-QFDXSTRRLK-C | X = β-β'-di-phenyl-Ala | Disulfide 1-Cys:12-Cys |
| 19 | 19 | C-QFDFSTRXLK-C | F = phenylalanine, X = citrulline | Disulfide 1-Cys:12-Cys |
| 20 | 20 | C-QFDFSTRRLK-C | F = phenylalanine | Disulfide 1-Cys:12-Cys |
| 21 | 21 | C-QFDESTRRLK-C | E = glutamic acid | Disulfide 1-Cys:12-Cys |
| 22 | 22 | C-QFDYSTRRLK-C | Y = tyrosine | Disulfide 1-Cys:12-Cys |
| 23 | 23 | C-QFDLSTRRQK-C | Q = glutamine | Disulfide 1-Cys:12-Cys |
| 24 | 24 | C-QFDLSTRQLK-C | Q = glutamine | Disulfide 1-Cys:12-Cys |
| 25 | 25 | C-QYNLSTARLK-C | Y = tyrosine; N = asparagine; A = alanine | Disulfide 1-Cys:12-Cys |
| 26 | 26 | C-QADLSTRRLK-C | A = alanine | Disulfide 1-Cys:12-Cys |
| 27 | 27 | C-QFDASTRRLK-C | A = alanine | Disulfide 1-Cys:12-Cys |
| 28 | 28 | C-QFDLSTARLK-C | A = alanine | Disulfide 1-Cys:12-Cys |
| 29 | 29 | C-QFDLSTRRAK-C | A = alanine | Disulfide 1-Cys:12-Cys |
| 30 | 30 | C-QFDLSTRREK-C | E = glutamic acid | Disulfide 1-Cys:12-Cys |
| 31 | 31 | AcC-QFDLSTRRLR-CGGGSK | AcC-N-acetylcysteine R = arginine | Disulfide 1-AcCys:12-Cys |

TABLE 4

| SEQ ID NO | | Sequence | Modification (red) | Linkage method |
|---|---|---|---|---|
| 32 | 32 | G-QFDLSTRRLK-G | G = glycine | Lactam 1-Gly:12-Gly |
| 33 | 33 | G-QHDLSTRRLK-G | H = histidine | Lactam 1-Gly:12-Gly |
| 34 | 34 | G-QNDLSTRRLK-G | N = asparagine | Lactam 1-Gly:12-Gly |
| 35 | 35 | G-QQDLSTRRLK-G | Q = glutamine | Lactam 1-Gly:12-Gly |

TABLE 4-continued

| SEQ ID NO | | Sequence | Modification (red) | Linkage method |
|---|---|---|---|---|
| 36 | 36 | G-QXDLSTRRLK-G | X = 2-bromo-L-phenylalanine | Lactam 1-Gly:12-Gly |
| 37 | 37 | G-QXDLSTRRLK-G | X = 3-bromo-L-phenylalanine | Lactam 1-Gly:12-Gly |
| 38 | 38 | G-QXDLSTRRLK-G | X = 4-bromo-L-phenylalanine | Lactam 1-Gly:12-Gly |
| 39 | 39 | G-QFDLSTRXLK-G | X = citrulline | Lactam 1-Gly:12-Gly |
| 40 | 40 | G-QFDLSTXXLK-G | X = citrulline | Lactam 1-Gly:12-Gly |
| 41 | 41 | G-QFDLSTXRLK-G | X = citrulline | Lactam 1-Gly:12-Gly |
| 42 | 42 | Q-FDLSTRRLK-X | X = 7-aminoheptanoic acid | Lactam 1-Gln:11-X |
| 43 | 43 | X-QFDLSTRRLK-X | X = β-alanine | Lactam 1-X:12-X |
| 44 | 44 | X-QFDLSTRRLK-X' | X = diaminopropionic acid; X' = iso-aspartic acid | Lactam 1-X:12-X' |
| 45 | 45 | X-QFDLSTRRLK-X' | X = β-alanine; X' = iso-aspartic acid | Lactam 1-X:12-X' |
| 46 | 46 | X-QFDLSTRRLK-X' | X = diaminopropionic acid; X' = β-alanine | Lactam 1-X:12-X' |
| 47 | 47 | F-DLSTRRL-K |  | Lactam 1-Phe:9-Lys |
| 48 | 48 | C-QFDLSTRRLK-C |  | Disulfide 1-Cys:12-Cys; Lactam 4-Asp to 11-Lys |
| 49 | 49 | Q-YDLSTRRLK-X | Y = tyrosine, X = 7-aminoheptanoic acid | Lactam 1-Gln:11-X |
| 50 | 50 | X-QFDLSTRRLK-X' | X = β-azidoalanine, X' = propargylglycine | [3 + 2] cycloaddition Azide-1-X:alkyne-12-X' |
| 51 | 51 | Q-XDLSTRRLK-X' | X = β-β'-di-phenyl-Ala, X'= 7-aminoheptanoic acid | Lactam 1-Gln:11-X' |
| 52 | 52 | qFDLSTRRLK-X | q = D-glutamine, X = 7-aminoheptanoic acid | Lactam 1-Gln:11-X |
| 53 | 53 | Q-XDXSTRRLK-X' | X = β-β'-di-phenyl-Ala, X'= 7-aminoheptanoic acid | Lactam 1-Gln:11-X' |
| 54 | 54 | Q-FDLSTXRLK-X' | X = n-butyl-arginine, X' = 7-aminoheptanoic acid | Lactam 1-Gln:11-X' |
| 55 | 55 | SQFDLSTRRLKS |  | No linkage |

The meditope variants typically have an amino acid sequence length of between 5 and 16 amino acids, e.g., 5, 6, 7, 8, 9, 10, 11, 12, 13, 14, 15, or 16 amino acids in length, such as between 8 and 13 amino acids in length, e.g., between 9 and 12 amino acids in length. The meditope can additionally be conjugated to or associated with (e.g., as part of a fusion protein or peptide) with another molecule, such as another peptide, including a linker or agent. Thus, in this case, the compound containing the meditope may contain additional amino acid residues beyond the lengths described in this paragraph, where the meditope portion contains between 5 and 16 amino acids and the complex or compound contains additional amino acids. Examples are described herein, e.g., SEQ ID NO: 31 above.

In some embodiments, the variant meditopes are cyclic peptides. In other embodiments, they are linear or acyclic peptides.

The meditopes can include peptides, or cyclic peptides derived from such peptides, for example, where the peptides have the formula:

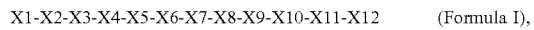

for example, where:
X1=Cys, Gly, β-alanine, diaminopropionic acid, β-azidoalanine, or null;
X2=Gln or null;
X3=Phe, Tyr, β-β'-diphenyl-Ala, His, Asp, 2-bromo-L-phenylalanine, 3-bromo-L-phenylalanine, or 4-bromo-L-phenylalanine, Asn, Gln, a modified Phe, a hydratable carbonyl-containing residue; or a boronic acid-containing residue;
X4=Asp or Asn;
X5=Leu; β-β'-diphenyl-Ala; Phe; a non-natural analog of phenylalanine, tryptophan, or tyrosine; a hydratable carbonyl-containing residue; or a boronic acid-containing residue;

X6=Ser;
X7=Thr or Ser;
X8=Arg, a modified Arg, or a hydratable carbonyl or boronic acid-containing residue;
X9=Arg, Ala;
X10=Leu, Gln, Glu, β-β'-diphenyl-Ala; Phe; a non-natural analog of phenylalanine, tryptophan, or tyrosine; a hydratable carbonyl-containing residue; or a boronic acid-containing residue;
X11=Lys; and
X12=Cys, Gly, 7-aminoheptanoic acid, β-alanine, diaminopropionic acid, propargylglycine, isoaspartic acid, or null.

In some aspects, the modified Arg has a structure of the formula shown in FIG. 34. In some aspects, the modified Phe is a Phe with one or more halogen incorporated into the phenyl ring. In some aspects, formula I is not SEQ ID NO: 1 or SEQ ID NO: 2.

In some embodiments, the meditopes are peptides having the structure of Formula (X):

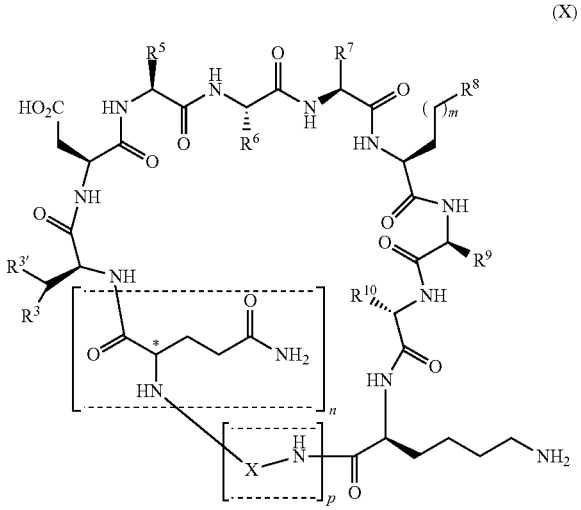

(X)

wherein:
the center marked with "*" is in the "R" or "S" configuration;
$R^3$ and $R^{3'}$ are each, independently, H or phenyl, optionally substituted with one, two, or three substituents independently selected from $C_{1-4}$alkyl, —OH, fluoro, chloro, bromo, and iodo;
$R^5$ is:
(A) $C_{1-8}$alkyl, optionally substituted with one or more substituents selected from the group consisting of oxo, acetal, ketal, —B(OH)$_2$, boronic ester, phosphonate ester, ortho ester, —CO$_2$C$_{1-4}$alkyl, —CH=CH—CHO, —CH=CH—C(O)C$_{1-4}$alkyl, —CH=CH—CO$_2$C$_{1-4}$alkyl, —CO$_2$H, and —CONH$_2$ group; or
(B) a $C_{1-4}$alkyl group substituted with:
  a) one or two phenyl groups, wherein each phenyl is optionally substituted with one, two, or three substituents independently selected from —OH, fluoro, chloro, bromo, and iodo; or
  b) a naphthyl, imidazole, or indole group;
$R^6$ is —C$_{1-4}$alkyl-OH or —C$_{1-4}$alkyl-SH;
$R^7$ is —C$_{1-4}$alkyl-OH or —C$_{1-4}$alkyl-SH;
m is 0, 1, 2, 3, 4, or 5;
$R^8$ is:
(a) —OH, —NR$^a$R$^b$, —N(R$^c$)C(O)R$^e$, or —N(R$^c$)C(=NR$^d$)R$^e$;
wherein:
  $R^a$ is H;
  $R^b$ is H or $C_{1-8}$alkyl optionally substituted with one or more substituents selected from the group consisting of oxo, acetal, and ketal, —B(OH)$_2$, —SH, boronic ester, phosphonate ester, ortho ester, —CH=CH—CHO, —CH=CH—C(O)C$_{1-4}$alkyl, —CH=CH—CO$_2$C$_{1-4}$alkyl, —CO$_2$H, or —CO$_2$C$_{1-4}$alkyl group;
  $R^c$ is H, $C_{1-8}$alkyl, $C_{3-8}$cycloalkyl, branched alkyl, or aryl;
  $R^d$ is H or a $C_{1-8}$alkyl, $C_{2-8}$alkenyl, $C_{2-8}$alkynyl, $C_{3-8}$cycloalkyl, branched alkyl, or aryl group, each optionally substituted with one or more substituents selected from the group consisting of —N$_3$, —NH$_2$, —OH, —SH, halogen, oxo, acetal, ketal, —B(OH)$_2$, boronic ester, phosphonate ester, ortho ester, —CH=CH—CHO, —CH=CH—C(O)C$_{1-4}$alkyl, —CH=CH—CO$_2$C$_{1-4}$alkyl, —CO$_2$H, and —CO$_2$C$_{1-4}$alkyl group; and
  $R^e$ is H; —NHR$^d$; or a $C_{1-4}$alkyl, $C_{3-8}$cycloalkyl, $C_{2-12}$alkenyl, $C_{2-8}$alkynyl, or aryl group, each optionally substituted with one or more substituents selected from the group consisting of —N$_3$, —NH$_2$, —OH, —SH, oxo, $C_{2-4}$acetal, $C_{2-4}$ketal, —B(OH)$_2$, boronic ester, phosphonate ester, ortho ester, —CH=CH—CHO, —CH=CH—C(O)C$_{1-4}$alkyl, —CH=CH—CO$_2$C$_{1-4}$alkyl, and —CO$_2$C$_{1-4}$alkyl group; or
(b) a $C_{1-12}$ alkyl substituted with an oxo, acetal, ketal, —B(OH)$_2$, boronic ester, —SH, —OH, phosphonate ester, ortho ester, —CH=CH—CHO, —CH=CH—C(O)C$_{1-4}$alkyl, —CH=CH—CO$_2$C$_{1-4}$alkyl, or —CO$_2$C$_{1-4}$alkyl group;
$R^9$ is $C_{1-4}$alkyl or —C$_{1-2}$alkylene-R$^x$;
wherein $R^x$ is —CO$_2$H, —CONH$_2$, —CH$_2$NHC(O)NH$_2$, or —CH$_2$NHC(=NH)NH$_2$;
$R^{10}$ is:
(1) a $C_{1-8}$alkyl optionally substituted with one or more substituents selected from the group consisting of oxo, acetal, ketal, —B(OH)$_2$, boronic ester, phosphonate ester, ortho ester, —CH=CH—CHO, —CH=CH—C(O)C$_{1-4}$alkyl, —CH=CH—CO$_2$C$_{1-4}$alkyl, —CO$_2$C$_{1-4}$alkyl, —CO$_2$H, and —CONH$_2$ group; or
(2) a $C_{1-4}$alkyl group substituted with one or two phenyl groups, or one naphthyl, imidazole, or indole group, wherein each phenyl is optionally substituted with one, two, or three substituents independently selected from —OH, fluoro, chloro, bromo, and iodo;
n is 0 or 1;
p is 0 or 1;
X is $C_{1-8}$alkylene or $C_{2-8}$alkenylene, each carbon thereof optionally substituted with —CO$_2$H, —NH$_2$, or —NHC(O)R$^y$;
wherein one carbon of said alkylene is optionally replaced with —C(O)NH—, a 5-membered heteroaryl ring, or —S—S—; and
$R^y$ is —C$_{1-4}$alkyl or —CH(R$^z$)CO$_2$H;
wherein $R^z$ is —H or —C$_{1-4}$alkyl optionally substituted with —OH, —SH, or —NH$_2$; or a pharmaceutically acceptable salt thereof.

In some cases, such meditopes are not SEQ ID NO: 1 or 2, or are not cyclic peptides derived from such sequences, and/or are not meditope 1 or 2.

In some embodiments of the meditope of Formula (X), m is 0, 1, or 2. In other embodiments, $R^3$ is H or phenyl and $R^{3'}$ is phenyl, 2-bromophenyl, 3-bromophenyl, or 4-bromophenyl. In further embodiments, $R^5$ is methyl, ethyl, propyl, isopropyl, butyl, isobutyl, sec-butyl, or tert-butyl, each optionally substituted with an oxo, —B(OH)$_2$, —CO$_2$H, or —CONH$_2$ group, or with one or two phenyl groups each optionally substituted with a bromo or chloro substituent. In further embodiments, $R^8$ is —OH, —NH$_2$, —N($R^c$)C(O)$R^e$, or —N($R^c$)C(=N$R^d$)$R^e$. In still further embodiments, $R^c$ is H or methyl, $R^d$ is H or C$_{1-4}$alkyl, and $R^e$ is C$_{1-4}$alkyl, or —NH(C$_{1-4}$alkyl). In other embodiments, $R^9$ is methyl or ethyl, optionally substituted with —CO$_2$H, —CONH$_2$, —CH$_2$NHC(O)NH$_2$, or —CH$_2$NHC(=NH)NH$_2$. In still other embodiments, $R^{10}$ is methyl, ethyl, propyl, isopropyl, butyl, isobutyl, sec-butyl, or tert-butyl, each optionally substituted with an oxo, —B(OH)$_2$, —CO$_2$H, or —CONH$_2$ group. In still other embodiments, —X—NH— is -Cys-Cys-, -Gly-Gly-, —C(O)(CH$_2$)$_6$—NH—, -β-Ala-β-Ala-, —C(O)CH(NH$_2$)CH$_2$CH=CHCH$_2$CH(CO$_2$H)—NH—, —C(O)CH(NH$_2$)CH$_2$NHC(O)CH$_2$CH(CO$_2$H)—NH—, -β-Ala-C(O)CH$_2$CH(CO$_2$H)—NH—, or —C(O)CH(NH$_2$)CH$_2$-triazinyl-CH$_2$—CH(CO$_2$H)—NH—.

Modifications

Based on the structural and thermodynamic data, multiple positions within the meditopes 1 and 2 described herein have been identified as target sites for modification, e.g., with different natural or non-natural amino acids, to enhance the overall binding affinity and/or to alter another property as described herein. Such modifications include, but are not limited to, modification of cQFD or cQYN to generate a head-to-tail cyclic lactam peptide, modification of Arg8, modification of position 3 (e.g., Phe3 of cQFD or variant thereof), modification of Leu5, modification of Leu10, and/or incorporation of hydratable carbonyl functionality (see FIG. 31). As demonstrated herein, mutation of each of Phe3, Leu5, and Arg8 to alanine in the original meditope of cQFD reduced the affinity of the resulting compounds for the meditope-enabled antibody binding interface by 10-140-fold. In some aspects, the variant meditopes include those having modifications at one or more of position 1, 3, 5, 8, 10, and 12 of the meditope of SEQ ID NO: 1 or 2, or other meditope listed in Table 3 or 4.

Position 8

In some embodiments, the meditope variants contain a modification in the position corresponding to position 8 (Arg8) of meditope 1 or 2. In the unmodified meditope (cQFD; SEQ ID NO: 1), Arg8 is extended, making a hydrogen bond with the heavy chain carbonyl of Q105 of the meditope-enabled antibody heavy chain. The immediate area about this residue is hydrophobic yet solvent exposed (FIG. 33A). In some aspects, the meditopes contain a modified residue at this position (e.g., modified Arg8). In some examples, the modified residue maintains the iminium functionality of the Arg8 residue useful for meditope-enabled antibody H-bonding, and introduces a substituted or unsubstituted hydrophobic arm to fill the cavity. Such modifications result in significant gains in binding, due to entropic increases, as supported by ligand docking calculations. Such modifications may be incorporated by using an N-alkyl guanidinium group, or an alkyl-amidine functionality. In either case, the substituted group of the terminal N-atom can be alkyl or aryl, wherein each position of the alkyl or aryl group may be optionally substituted with additional functionalities within the group including the terminal position. In one example, a modified Arginine (modified Arg8), having a structure as shown in FIG. 34, is substituted for Arg8 of the meditope, e.g., of SEQ ID NO: 1 or 2 with the butyl group on the NH$_2$ (shown in FIG. 34 as NHR). In some aspects, the variant meditope contains an n-butyl-arginine or butylamidine modification at position 8.

Position 3

In some embodiments, the meditope variants contain a modification in the position corresponding to position 3, such as Phe3 of meditope 1. As shown herein with structural data, the hydroxyl group of the meditope variant Phe3Tyr cQYN (SEQ ID NO: 2) has an alteration in the extended conformation of the Arg8 side chain as compared to cQFD (SEQ ID NO: 1) (see FIGS. 30C and 35). Data herein suggest the formation of a favorable hydrogen bond network, with water bound to the Fab. Enthalpy-driven optimization has proven successful in many small-molecule approaches in drug design and there are opportunities in the provided meditopes for engineering increases in entropy. In some embodiments, approaches resulting in enthalpic and/or entropic gains in meditope designs are used to generate the variant meditopes, e.g., to optimize binding.

For example, when bound to a meditope-enabled antibody, the hydrophobic phenyl ring of Phe3 is surrounded by a fairly polar array of side chain residues of the meditope-enabled antibody Fab (FIG. 35). In some embodiments, one or more halogens is introduced on the phenyl ring of this residue, to allow for a halogen bonding interaction with the polar side chain residues. A halogen bond is a relatively strong non-covalent bond, similar to a hydrogen bond but involving the interaction of a halogen such as bromine or chlorine (or other halogen), with an oxygen atom. In some aspects, the residue at this position is modified to incorporate a halogen substituent. In some aspects, Phe3 is replaced with 2-bromo-, 3-bromo-, or 4-bromophenylalanine, in order to place a bromine atom in a position suitable for halogen bonding with a meditope-enabled antibody, e.g., at positions Tyr87 (light chain), Gln38, and/or Tyr91 (heavy chain) of a meditope-enabled antibody, respectively. Such phenylalanine derivatives are commercially available and in some aspects are incorporated into the cyclic peptide meditope variant by solid phase peptide synthesis (SPPS). Exemplary variant meditopes include those containing 2-bromo-L-phenylalanine, 3-bromo-L-phenylalanine, or 4-bromo-L-phenylalanine in the position corresponding to Phe3 of meditope 1.

In another example, the meditope incorporates an additional phenyl group at this position, for example, by replacing Phe3 with β,β'-diphenylalanine.

Positions 5 and 10 (e.g., Leu5, Leu10 of Meditopes 1 or 2)

In some embodiments, the meditope variants contain a modification in the position corresponding to position 5 or 10 (Leu5 or Leu10) of meditopes 1 or 2. As shown herein, the side chains of Leu5 and Leu10 of meditope 1 make hydrophobic contacts to the meditope-enabled Fab, cetuximab (see FIG. 36, right panel; Leu10). In certain embodiments, one or more properties of the meditopes, e.g., affinity, are altered by incorporating a different natural amino acid, or a non-natural amino acid at one or both of these positions, e.g., thereby changing the amount of surface area that can be extended. In one embodiment, natural amino acids (Phe/Tyr/Trp) and non-natural analogs (e.g., β,β'-diphenyl-L-alanine, or amino acids incorporating side chains that include branched alkyl, extended aromatics such as napthyl, or other hydrophobic groups) are systematically introduced via SPPS at one or both positions.

"Hydratable" Functionality

In certain embodiments, one or more Fab hydroxyl-bearing side chains surrounding the meditope-binding site of a meditope-enabled antibody is/are exploited through selective trapping, by formation of a covalent bond with a meditope that incorporates a hydratable functionality. Thus, in some embodiments, the meditope contains one or more residues with hydratable substituents, e.g., in order to create a highly selective but irreversible interaction with a meditope-enabled antibody or other substance. For example, Arg8 of the meditope 1 extends in proximity to Ser43 of the light chain (3.5 Å) and Tyr91 (3.8 Å) of the meditope-enabled antibody heavy chain, according to Kabat numbering (FIG. 36, left panel). Incorporation of a hydratable functionality at the end of Arg8 or Leu10 of the meditope would allow for selective formation of a serine or tyrosine hemi-acetal. Such a covalent adduct would essentially afford irreversible binding. In addition, residues containing boronic acid may also be integrated into the meditope as a hydratable group. Boronic acid plays an important role in the structural activity of bortezamib (Velcade®), which is used to treat multiple myeloma. Further representative examples of hydratable residues are also shown in FIG. 34, where R=—$CH_2CHO$ or —$CH_2B(OH)_2$. In some examples, such variants are prepared by incorporating residues containing such groups using SPPS.

Such hydratable strategies can be applied to engineering new amino acid residues within the antibody Fab-meditope binding site and introducing the requisite complementary "hydratable" functionalities within different positions of the meditope. A similar strategy can be applied by introducing cysteine residues into the Fab region and use this functionality for nucleophilic attack on a "hydratable" functionality such as an electrophilic carbonyl group or derivative thereof contained within the meditope or for making selective disulfide bonds (—S—S—) between the Fab region and the meditope containing the requisite thiol or thiol equivalent functionalities. Other embodiments of this idea would include introducing Michael acceptors contained in the meditope such as α,β-unsaturated carbonyl functionalities. These functionalities are well-known to selectively react with thiols to form stable covalent carbon-sulfur bonds.

Alternative Cyclization Strategies and Replacement of Disulfide Bridge

In certain embodiments, the variant meditopes include a disulfide bridge, as in cQFD and cQYN. Disulfide bridges may be formed by the reaction of the side chains of two cysteine residues. In certain embodiments, the disulfide bridge in a meditope, e.g., meditope 1 or 2, is replaced with an alternative linkage or is removed. Thus, among the variant meditopes are those having alternative linkages or lacking the disulfide bridge of the original meditopes.

In some aspects, the linkage is made between one or more unnatural amino acids within the amino acid chain. Examples of linkages that may be made with unnatural amino acids include linkages comprising (i) stable hydrazone or oxime-based linkages made by reaction of a residue comprising an aldehyde or ketone with a residue comprising an amine group, where the amine nitrogen is substituted with —NH2 or alkyloxy group (e.g., reaction of a p-acetylphenylalanine, m-acetylphenylalanine, or p-(3-oxobutanoyl)-L-phenylalanine residue with a p-(2-amino-3-hydroxyethyl)-phenylalanine residue), (ii) thiol reactive by incorporating phenylselenidylalanine, (iii) a UV crosslinker containing benzophenone by incorporating p-benzoyl-L-phenylalanine, (iv) amine reactive by incorporating p-isopropylthiocarbonyl-phenylalanine or p-ethylthiocarbonyl-phenylalanine, (v) heterocyclic linkages, such as a triazine, thiazole, thiazolidine, or oxazole linkage, made, for example, by reaction of a residue containing an azide group with a residue containing an alkyne group via Huisgen cycloaddition (e.g., reaction of a p-propargyloxyphenylalanine residue with a p-azidophenylalanine residue); (v) an amide bond made by reaction of an acid group in one residue with an amine group in another residue; (vi) an ester bond made by reaction of an acid group in one residue with an alcohol in another residue, such as a serine; (vii) a double bond, made by reaction of two residues each containing a terminal olefin, e.g., by olefin metathesis (e.g., reaction of two allylglycine residues or two N-allyl substituted amino acids), or (viii) by reaction of any other pair of suitable residues known in the art. For a review, see, for example, Davies, J. S., "The Cyclization of Peptides and Depsipeptides," *J. Peptide Sci.* 2003, 9, 471-501. In one embodiment, the meditope may direct a reactive group to an unnatural amino acid incorporated into the Fab, such as p-acetylphenylalanine.

Various methods for cyclization of a meditope may be used, e.g., to address in vivo stability and to enable chemoselective control for subsequent conjugation chemistry. In some embodiments, the cyclization strategy is a lactam cyclization strategy, including head-to-tail (head-tail) lactam cyclization (between the terminal residues of the acyclic peptide) and/or lactam linkage between other residues. Lactam formation may also be effected by incorporating residues such as glycine, β-Ala, 7-aminoheptanoic acid, and the like, into the acyclic meditope cyclization precursors to produce different lactam ring sizes and modes of connectivity. Additional cyclization strategies such as "click" chemistry and olefin metathesis also can be used (see FIG. 31, right boxes). Such methods of peptide and peptidomimetic cyclization are well known in the art.

In some embodiments, the meditopes containing lactam linkages are more stable, in vivo, e.g., have a linkage that is more stable in vivo compared to meditopes with other linkages.

In some embodiments, the terminal residues of an acyclic peptide are reacted to form a cyclic meditope, e.g., cyclic meditope variant. In other embodiments, other positions are amenable to cyclization, including between residues 3 and 11 and 4 and 11. Thus, in some aspects, the meditopes contain a linkage formed between residues other than the N-terminal and C-terminal residues, such as between residues 3 and 11 and/or 4 and 11, e.g., of a 12-amino acid peptide.

Figure 13:
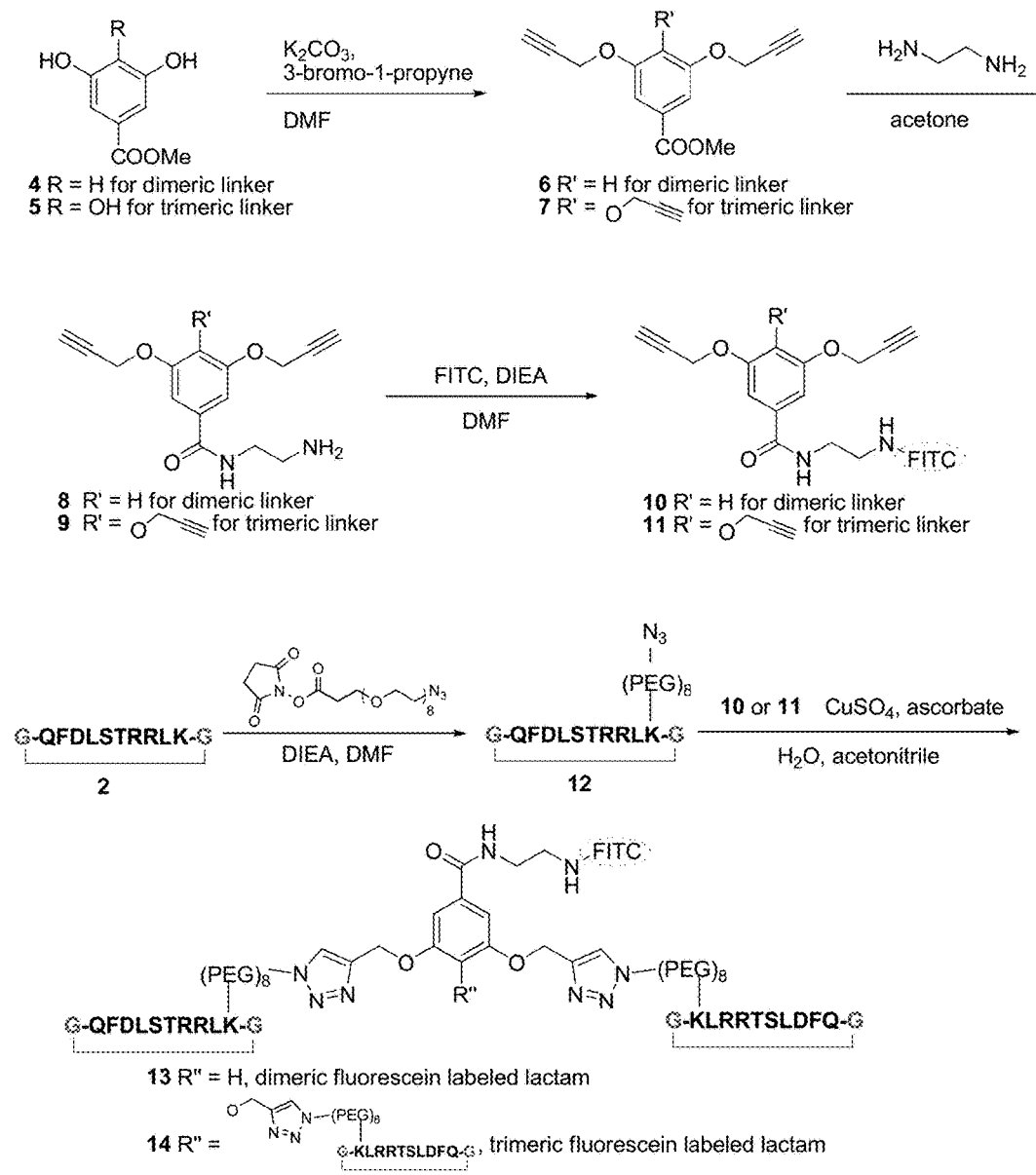
FIG. 13 illustrates the synthesis of dimeric and trimeric meditopes (G-QFDLSTRRLK-G, SEQ ID NO: 32, in either orientation) according to some embodiments, for meditopes containing lactam linkages.

In some embodiments, the meditopes, e.g., variant meditopes, contain a reactive amine functionality (e.g., Lys11), which can be used for subsequent conjugation of the meditope variant, e.g., to a scaffold or linker or to an agent, such as a diagnostic, e.g., imaging, agent or therapeutic agent as described herein. For example, FIG. 13 shows a procedure for conjugation of a meditope variant with fluorescein for FACS analysis; this strategy can be applied to other imaging and other agents, including DOTA for in vivo PET imaging.

In some embodiments, thiol functionalities can be introduced in any suitable position on the meditope and can be selectively modified using a number of external reagents containing imagining agents, other proteins and peptides, metal chelators, siRNAs, nanoparticles, and cytotoxic drugs.

Characterization of Meditopes

In some embodiments, the meditopes, such as variant meditopes, are characterized, for example, by ITC, SPR and/or diffraction and/or other methods, such as those described herein in the Examples. In one example, the synthesis of meditopes and characterization thereof is carried out in an iterative fashion, e.g., such that the meditope variant with the most desirable property, e.g., highest affinity for one or more meditope-enabled antibodies or other desired property, such as pH dependence, is subsequently modified to improve the desired property.

In one example, for characterization of binding of meditopes to meditope-enabled antibodies, the meditope is purified to >95% homogeneity and structurally characterized by mass spectrometry. Peptides are dialyzed in water, their concentrations measured by UV-Vis and calibrated with elemental analysis, and diluted (>100×) into the appropriate buffer. Binding to a meditope-enabled antibody is rigorously characterized by ITC, SPR, X-ray diffraction, or a combination thereof. ITC measurements may be performed on a TA Instruments nanoITC, with only 1-2 mg of peptide per measurement. In one example, for SPR measurements, low density and high density chips are conjugated with a meditope-enabled antibody, e.g., a Fab or a full IgG. In some cases, the chips are first characterized using an antigen, such as a soluble fragment of the entire extracellular domain of EGFR (residues 1-621) in the case of cetuximab. In a study reported herein, the cQFD meditope bound with similar enthalpy and entropy to the cetuximab Fab fragment as compared to the fully intact cetuximab IgG, e.g., as measured by SPR and ITC. Accordingly, binding measurements may be carried out using the full IgG or Fab fragment of cetuximab or other meditope-enabled antibody. In one example, for diffraction, the co-crystallization conditions of the cetuximab Fab fragment and the meditope of SEQ ID NO: 1 are well-established and diffraction quality crystals are typically obtained in 1 to 3 days, typically 1 day. Full data sets are collected in 8 to 12 hours with an in-house source (Rigaku 007-HF and an R-Axis IV++) and in 10 min at the Stanford Synchrotron Radiation Lightsource, which allows for rapid characterization of the interactions of the meditope variants with meditope-enabled antibodies.

In some aspects, ITC, SPR and X-ray diffraction data, e.g., collectively, provide atomic detail to guide subsequent chemical modifications and ultimately improve the affinity of the meditopes and/or make other alterations to the meditopes. A calculation based on $\Delta G=-RT \ln Ka$ shows that the difference between micromolar and nanomolar affinity of a meditope for cetuximab results from a change in free energy at 300 K of ~4 kCal/mol, which is on the order of a strong hydrogen bond. Thus, the loss of an ordered water molecule from a protein binding pocket or the reorientation of an amino acid residue-chain may be sufficient to alter binding by orders of magnitude.

In some examples, other approaches are used to alter properties of the meditopes, e.g., to improve the affinity of the meditope-Fab interaction. In one example, structural data, such as those obtained in the studies described above, may be used to replace residues in the Fab, by mutagenesis, for example, to add additional hydrogen bonds, substitute amino acids for unnatural amino acids or alter the hydrophobic interface, for example, in ways that might better complement meditope binding. In some examples, fluorescence polarization assays are used to identify meditope variants that can displace a given meditope, such as SEQ ID NO: 1. In other examples, the same technique is used to identify small molecules that can displace the meditope and then use these small molecules as templates to further improve the binding affinity of the meditopes.

Figure 27:
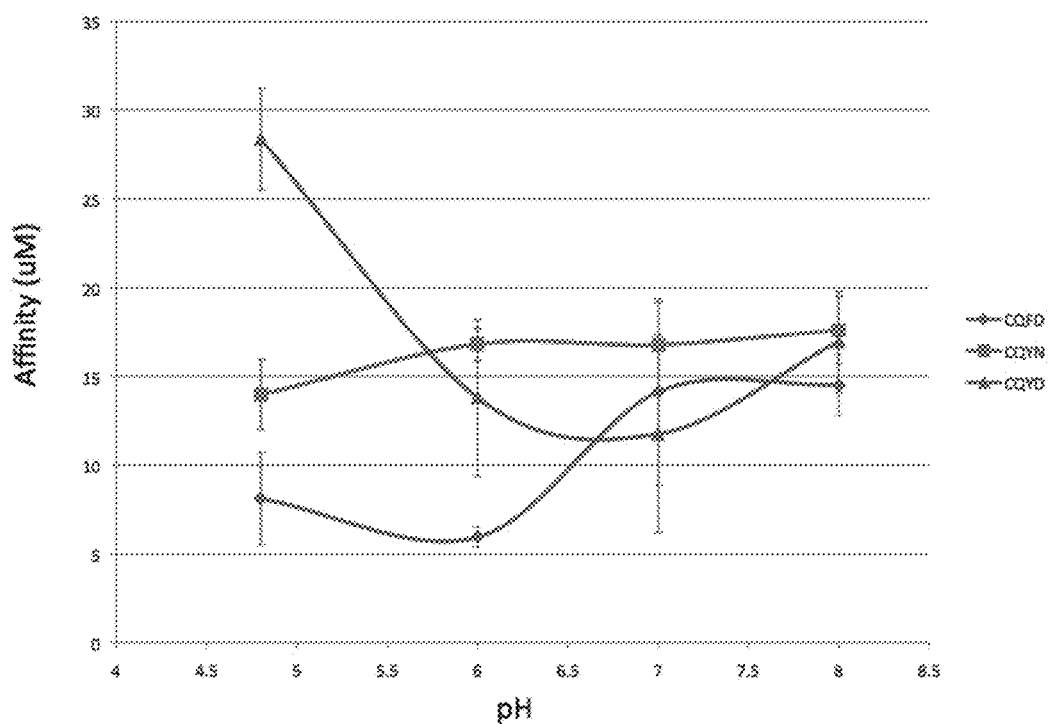
FIG. 27 is a graph showing surface plasmon resonance (SPR) studies. The binding affinity of different meditopes to cetuximab [cQFD (meditope 1, SEQ ID NO: 1), cQYN (meditope 2, SEQ ID NO: 2), and cQYD (meditope 16, SEQ ID NO: 16)] was determined from pH=4.0 to pH=8.0.

In some examples, the meditope variants are designed based on pH dependence, e.g., to have differing affinities at different pH conditions. Thus, in certain embodiments, the meMAb-meditope interaction is tailored with respect to pH. Examples of such meditopes are described herein. In some aspects, the binding affinities of the meditope variants are measured as a function of buffer pH. For example, variant meditopes include meditopes with a binding affinity for one or more meditope-enabled antibody or fragment that is decreased at a lysosomal pH level or is increased in a hypoxic environment. For example, provided are variant meditopes that exhibit higher binding affinity for a meditope-enabled antibody at a neutral pH (e.g., pH 7-8, e.g., pH 7.3-7.5) and exhibit a relatively lower binding affinity for the antibody at a more acidic pH, such as a pH between at or about 4 and 6.5, e.g., at an endosomal pH (e.g., between at or about 5 and at or about 6.5) or at a lysosomal pH (e.g., between at or about 4.5 and at or about 5). See FIG. 27, showing several examples. In another example, the meditopes have increased binding affinity for the antibody in a hypoxic environment, such as a tumor environment, for example, as compared to the affinity observed under other physiological conditions, such as in the blood. In some embodiments, modification of meditope variants or meditope "analogs" for the specific release at low pHs (e.g., in lysosomes for drug delivery) is provided; and modification of meditopes so that they bind with higher affinity in a hypoxic environment (e.g., tumor stroma pH is often lower than normal tissues). Also provided are methods for generating such meditope variants.

According to some embodiments, the meditope binding site may be exploited or optimized to enhance binding of, purification of, and/or imaging or other method using the meditope-enabled antibodies and functional fragments thereof. In a separate embodiment, a meditope may contain one or more cysteine residue that binds to one or more engineered cysteine in the Fab at the meditope binding site (e.g., ThioMAbs). The meditope is thereby conjugated to any diagnostic and/or therapeutic substance, molecule or compound. For example, the substance may be a small molecule diagnostic molecule, such as a marker. The "Cys meditope" directs the conjugate to the antibody and binds via a covalent linkage. Alternatively, the meditope may be conjugated to the Fab to one or more unnatural amino acids that are incorporated into the meditope binding site.

II. Multivalent Meditopes

Also among the provided meditopes are multivalent meditopes. In certain aspects, conjugation of a meditope, to a linker or scaffold (e.g., to form a multivalent tethering entity), significantly improves overall affinity for and targeting to a meditope-enabled mAb bound to an antigen, e.g., a tumor-associated antigen.

Full-length monoclonal antibodies (mAbs) and F(Ab)'$_2$ fragments include two Fab domains (in the case of full-length mAbs, coupled to a dimeric Fc). Such bivalent antibodies (e.g., IgGs) preferentially bind to cells expressing antigen at high densities. Combinations of monoclonal antibodies (mAbs) that recognize unique epitopes on the same antigen can produce synergistic effects, including enhancement of various antibody effector functions (e.g., ADCC, complement-dependent lysis, signaling inhibition), enhancement of cell death, and in the case of cancer-targeting antibodies, enhancement of tumor growth inhibition. See, for example, Dechant M et al., "Complement-dependent tumor cell lysis triggered by combinations of epidermal growth factor receptor antibodies," *Cancer Res*, 2008 Jul. 1; 68(13):4998-5003; Scheuer W et al., "Strongly enhanced antitumor activity of trastuzumab and pertuzumab combination treatment on HER2-positive human xenograft tumor models," *Cancer Res*, 2009 Dec. 15; 69(24):9330-6; Cardarelli P M et al., "Binding to CD20 by anti-B1 antibody or F(ab')(2) is sufficient for induction of apoptosis in B-cell lines," *Cancer Immunol Immunother,* 2002 March; 51(1): 15-24. Epub 2001 Dec. 18. While the precise mechanism of this enhanced cell death remains debated, studies indicate that both mAbs should be multivalent (e.g., full antibodies or F(ab)'$_2$) to achieve enhanced effects, suggesting that the second bivalent mAb (which binds to a unique epitope on the same antigen) can cluster cell surface antigens and act more efficiently, e.g., more efficiently kill tumor cells. See FIGS. 8 and 16.

In some embodiments herein, such clustering is recapitulated using multivalent meditopes. In some aspects, the multivalent meditope used instead of a second antibody, in some aspects to achieve synergy in combination with a meditope-enabled antibody. In some aspects, the multivalent meditopes provide advantages compared to use of a second antibody recognizing a separate epitope. For example, production of the multivalent meditopes can be more efficient, and cost-effective when compared to a second antibody. For example, although a number of preclinical/clinical trials are investigating the co-administration of two monoclonal antibodies, the costs of producing and marketing such a therapeutic is likely to be prohibitive. In some aspects, the multivalent meditopes also are comparatively more easily targeted to disease sites, such as tumors. Given the nature of the meditope binding site (within the meditope binding site, separate from the antibody CDRs), and the broadly applicable methods provided herein for meditope-enabling any antibody of choice, the multivalent meditopes also have the advantage of being readily applicable to a large range of therapeutic antibodies, without the need to identify a second antibody or epitope with therapeutically acceptable characteristics. Thus, in some aspects, use of a multivalent meditope avoids the need to identify a second mAb with acceptable characteristics, and the associated and significant cost of its development thereof.

Specificity and affinity are often achieved through multivalency. For a bivalent ligand with a linker, this can be expressed as $\Delta G_{Total} = \Delta G1 + \Delta G2 - \Delta G_{linker}$. In other words, $K_{Total} = K_1 * K_2 / K_{linker}$. In the case where the linker makes no contribution to the free energy ($K_{linker} \sim 1$), the apparent affinity of the bivalent ligand for the bivalent target is the product of the monomeric binding constants. Thus, significant gains in affinity can be achieved through multivalency in general (e.g., for a meditope with $K_D = 1$ µM, the affinity of a 'theoretical' bivalent meditope is 1 pM). While such large gains are rarely seen in general (primarily due to the geometry of bivalent/trivalent/multivalent receptors), synergy is observed. The geometry of a cell surface-expressed antigen can place strict constraints on the linker of a multivalent meditope, but can also ensure specificity, which can be an important goal in some contexts, such as for targeted delivery, e.g., by minimizing the risk of off-target effects.

In one example, the multivalent meditope contains an Fc region of an antibody or portion thereof, such as substantially all of the Fc region. The use of the Fc region to 'dimerize' ligands is established and described, for example, by Jazayeri J A & Carroll G J., "Fc-based cytokines: prospects for engineering superior therapeutics," *BioDrugs,* 22(1):11-26 (2008) In some examples, to generate a bivalent meditope, the meditope is fused to an Fc region (e.g., to the N-terminus of the Fc region of an IgG) through a linker, typically a peptide linker, e.g., a flexible peptide linker. In one example, the length of the linker is chosen to roughly match the distance between the Fabs of an IgG, such as of 17 amino acids in length. In some aspects, the linker contains glycines, serines, and/or a combination thereof. Exemplary "meditope-Fc" fusions are shown in FIG. 15 (SEQ ID NO: 3 and 4, respectively). See also FIG. 16.

Figure 18:
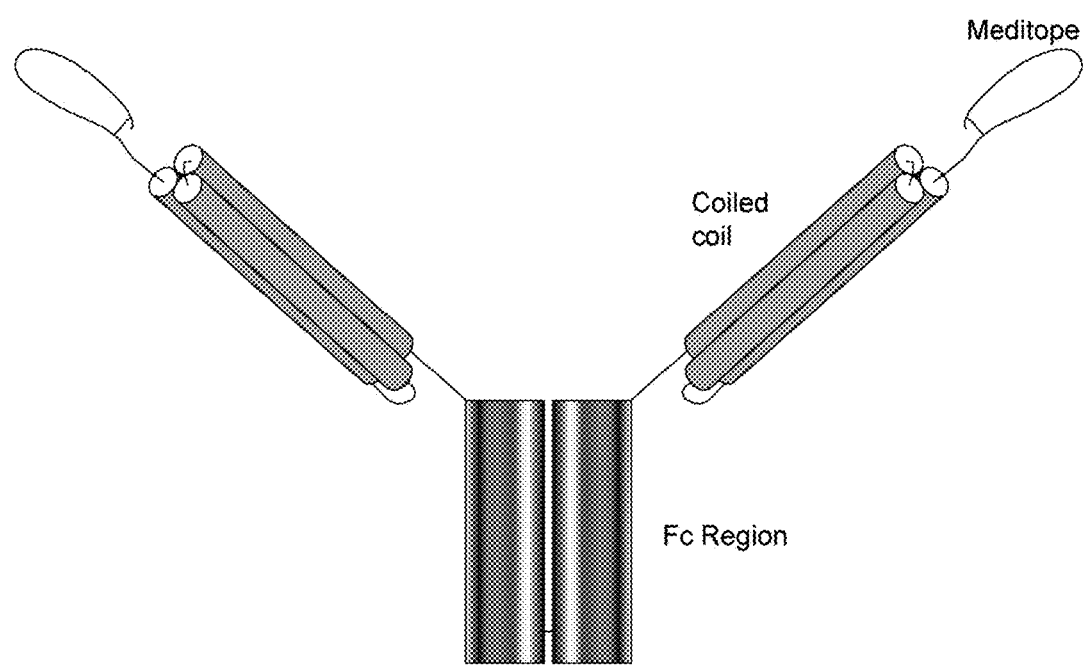
FIG. 18 is a depiction of an alternative meditope-Fc linker, a coiled coil, which may be used in accordance with certain embodiments.

In some embodiments, the composition of the linker and/or the distance between the Fc and the meditope is systematically altered, e.g., to optimize affinity and specificity. In one embodiment, each natural or unnatural residue can be substituted at any position within the linker for optimization. In some aspects, the linker is between at or about 2 and 100 residues in length, e.g., at or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 125, 150, 175, or 200 residues (amino acids) in length, or more. In one example, such linkers are generated using current and future DNA synthesizers, and inserted between the meditope and the Fc regions. The linker may also be 'rigidified' to limit the radius of gyration and to enhance the affinity and specificity of the Fc-meditope. For example, a coiled coil domain may be placed between the meditope and the Fc (FIG. 18). In other examples, inert protein domains (e.g., immunoglobulin folds) are substituted for the linker. Multiple immunoglobulin folds can be placed between the meditope and the Fc domain. In certain embodiments, the composition of the linker is of human origin to mitigate potential antigenicity.

In some examples, the provided meditopes are tethered to a scaffold to create a multivalent meditope, e.g., for enhanced selectivity and binding affinity. In some embodiments, multivalent meditope scaffolds are used to scaffold or "daisy-chain" meditope-enabled mAbs bound to tumor associated antigen to enhance ligand antagonism, alter receptor endocytosis, and/or improve an immune response through ADCC/CDC (see FIG. 8). Thus, in some embodiments, the meditopes are used to tether two or more antibodies or functional fragments thereof. Such meditopes may be part of a multivalent tethering agent, for example, to enhance cancer or tumor therapy and imaging. A multivalent tethering agent may include two or more meditopes coupled through linker(s), such as through a long linker and biotin to streptavidin, to create a multivalent meditope tethering entity.

Figure 12:
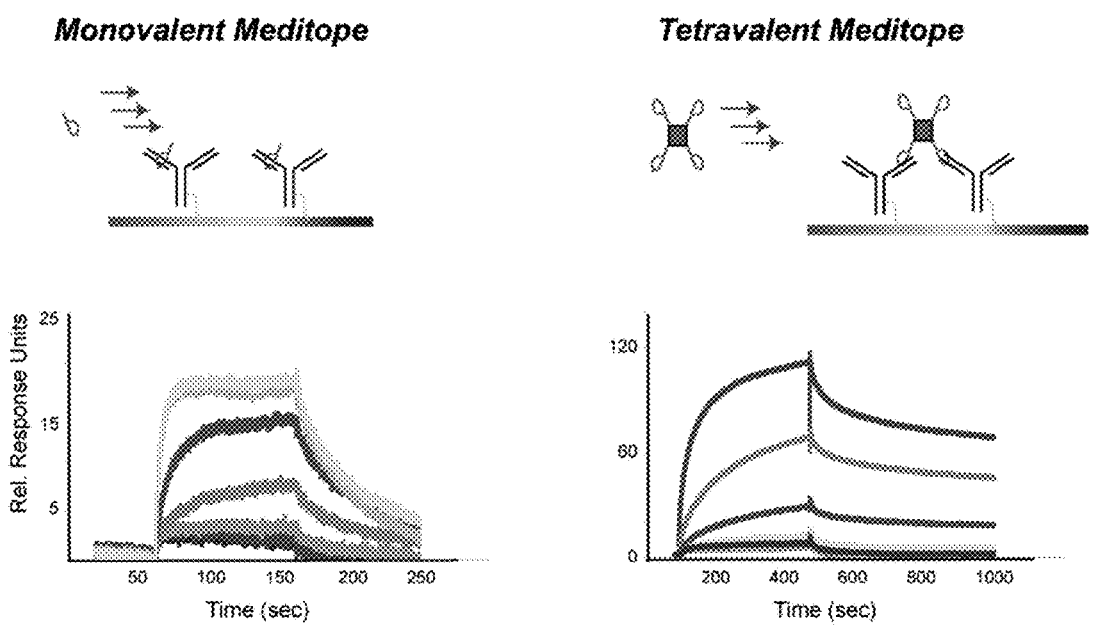
FIG. 12 shows SPR-determined binding kinetics for monovalent (left panel) and tetravalent (right panel) meditopes to cetuximab. The panel above the surface plasmon resonance traces depicts a cartoon of the monovalent meditopes being passed over the bivalent IgG. As shown in the right panel, avidin was saturated with biotinylated meditope and passed over the same immobilized cetuximab IgG. The off-rate of the multivalent meditope was reduced by at least 36 fold. (Note the time scales between the two experiments are different.)

In one embodiment, the multivalent meditope tethering entity is a tetravalent meditope tethering agent. In one aspect, the tetrameric tethering entity is shown by surface plasmon resonance to have enhanced binding to an antibody as compared to the monovalent peptide, which is consistent with a multivalent interaction. In one example, use of such multivalent meditopes (e.g., tetravalent meditope) produces enhanced binding affinity of the meditope-enabled antibody to the antigen (e.g., in the case of cetuximab, binding affinity for EGFR positive cells), compared to use of the antibody alone or monovalent meditope alone. Such binding affinities can be determined using well-known methods, e.g., by FACS analysis. See FIG. 12.

In some embodiments, to address the receptor constraints on the linker, unmodified or modified, e.g., variant, e.g., optimized, meditopes, such as those obtained as described in Example 6, are coupled to a multivalent scaffold, such as by optimizing the linker. In some aspects, the multivalent meditope is able to "latch-on" to adjacent antibodies, e.g., IgGs, to form a "daisy-chain"-like array (see FIG. 8), which can be used, for example, in antibodies targeting tumor antigens, given the high antigen density of tumor cells. While an intramolecular association of a bivalent meditope and antibody is possible, the C2 symmetry of the antibody, e.g., IgG, can place severe geometrical constraints on the linker for such an interaction. Thus, in some aspects, the meditope is based on a trivalent or higher valency scaffold, ensuring that more than one antibody would be "daisy chained". By including a third meditope arm, the lifetime of the initial encounter of a trivalent meditope to antigen-bound antibody can increase. This, in turn, can increase the probability that an additional arm will bind to a neighboring antigen-bound antibody, thus stabilizing the overall complex. In other embodiments, a multifunctional meditope may be constructed to simultaneously bind a memab and other targets, such as other B and T-cell surface proteins, such as T cell receptor and costimulatory molecules. In some embodiments, multiple meditope-enabled antibodies (for example, including one or more modified meditope-enabled antibodies) having specificities for different meditopes are used together with such different meditopes in such multivalent embodiments.

Various linkers and scaffolds are known in the art and may be used in connection with these embodiments. An exemplary scaffold synthesis scheme is shown in FIG. 13 and discussed in the Examples herein. In some aspects, the use of templates 4 and 5 shown in FIG. 13 allows for the formation of both bi- and trivalent meditopes, respectively. In some embodiments, different length polyethylene glycol (PEG) and/or other linkers are used, for example, to improve or alter binding or other properties. In some aspects, the PEG length is between at or about 10 A and at or about 1000 A. The synthetic approach is also amenable to DOTA incorporation for radionuclide imaging. For example, a 30 Å PEG bifunctional arm has been incorporated in the synthesis of a FITC-labeled divalent meditope, namely compound 13 (FIG. 13). The distance between the CDR regions within an IgG is ~130 Å. The length of the PEG linker may be systematically varied to ensure this approach is optimal. End-to-end distances of commercially available PEGs extend to 90 Å (Pierce), which would exceed the IgG distance.

In other embodiments, other scaffolds and/or linkers are used, e.g., to generate high affinity multivalent meditopes and/or to create synergy. For example, DNA may be used as a scaffold for the meditopes to create a more rigid scaffold. For example, different scaffolds of biological and chemical origin may also be used to achieve multivalency. This includes, but is not limited to, constructing a bivalent or trivalent scaffold, using streptavidin or (see European Application, Publication No.: EP 2065402 A1), streptavidin as a tetravalent scaffold, unique scaffolds (see Hutchins et al., *J. Molecular. Biology*, 2011, 406(4), 595-603), Origami DNA (see Gu et al., *Nature Nanotechnology* 4, 245-248 (2009)) and the like. A chemical scaffold may also be created using molecules including, but not limited to, DNA (single strand, duplex, Holliday junctions, aptamers and the like), RNA (single strand, hairpin, stem loop, aptamers and the like), PNA (peptide nucleic acids), DNA/PNA duplexes and triplexes for rigidity, organic and or inorganic nanoparticles (directly coupled or coupled through organic polymers such as PEG), organic polymers that can form duplexes with themselves and/or with DNA or PNA.

Characterization of Multivalent Meditopes

Binding properties of the multivalent meditopes to meditope-enabled antibodies can be characterized by any of a number of known methods, including SPR and ITC, for example, to ensure that conjugation to the multivalent scaffold does not affect the meditope-Ig interaction. In some cases, such measurements can be limited in their ability to determine mutlivalency and synergistic effects, given that these approaches generally do not involve antigen present on a cell surface (such as on the surface of a tumor cell). Thus, in some aspects, FACS analysis and/or cell viability assays are used to quantify the effect of the multivalent meditope directly on cells expressing antigen recognized by the meditope-enabled antibody (e.g., cells that overexpress EGFR in the context of cetuximab). Exemplary protocols are described in Example 7. In general, a cell line expressing (e.g., overexpressing) the antigen recognized by the meditope-enabled antibody is incubated with the meditope-enabled antibody under conditions whereby the antibody binds to the antigen expressed on the cells. In some cases, varying concentrations of the antibody are used. Either simultaneously or subsequently, the cells are incubated with the multivalent meditope, in some cases in varying concentrations. Appropriate incubation times and washes are carried out. A second antibody and monovalent meditopes may be used as positive and negative controls, respectively. The antibodies and meditopes may be labeled with agents detectable by flow cytometry or microscopy, which are well known. In some examples, a shift (in the case of FACS) or increased signal in the presence of multivalent meditope, compared to monovalent meditope, indicates a synergistic or additive effect. In another example, to further confirm the additive effects of the multivalent meditope, the non-labeled, monovalent meditope is used in a competition assay, to determine whether it can compete with the labeled multivalent meditope for the antigen-bound meditope-enabled antibody.

In other examples, cell viability assays are used to determine the ability of a multivalent meditope to enhance cell-killing effects of a meditope-enabled antibody. For example, a cell expressing the antigen of interest may be incubated with varying concentrations of the meditope-enabled antibody and/or multivalent meditope. Monovalent meditopes and second antibodies again are useful as controls. In some examples, MTT (3-(4,5-Dimethylthiazol-2-yl)-2,5-diphenyltetrazolium bromide), is used to quantify the number or percentage of viable cells. Other approaches for measuring cell viability, proliferation, and/or death are known in the art and may be used.

In another example, for multivalent meditopes that demonstrate activity in such assays, Western blot analysis or other biochemical or signaling approach is performed to investigate inhibition of signaling associated with a particular antigen, such as a cell surface receptor (e.g., in the case of cetuximab, to follow the phosphorylation status of EGFR, AKT, MAP which are part of the EGFR signaling pathway). Data from such studies may be compared with data from cells treated only with meditope-enabled antibody (i.e., without meditope), with monovalent meditopes, and/or with tyrosine kinase or other known inhibitors (AG1478, etc.). In some examples, an increase in cell death as a function of multivalent meditope concentration is observed, demonstrating synergistic cell killing effects of the multivalent meditopes.

III. Fusion Proteins

Also provided are fusion proteins containing one or more meditopes. As demonstrated herein by diffraction on the meditope-enabled Fab fragment bound to a cQFD meditope (meditope 1), the N- and C-termini of that antibody-bound meditope were shown to be juxtaposed to the location of bound Protein L, a bacterial protein that binds to human antibodies, including IgMs, IgDs, IgGs, IgEs, and IgAs. In some embodiments, provided are meditope-Protein L fusion proteins (MPLs). In some aspects, the Protein L-meditope fusions exhibit binding to meditope-enabled antibodies with greater affinity as compared to meditopes alone and/or Protein alone, e.g., via energy additivity. The MPLs also can be advantageous compared to Protein L alone and other multivalent conjugates of Protein L, Protein A, and/or similar antibody-binding proteins, in that they provide specificity for meditope-enabled antibodies and will not target endogenous immunoglobulin molecules when administered therapeutically.

Originally isolated from bacterium *Peptostreptococcus magnus*, Protein L is a protein that binds to the kappa light chain of human and other antibodies. Exemplary meditope-Protein L (MPL) fusion proteins include those in which a provided meditope is coupled to a Protein L, which can be wild-type Protein L or a variant thereof, such as one of several variants known in the art, or a variant modified to improve one or more property, such as to reduce antigenicity. Methods for modifying similar proteins, such as to reduce antigenicity or immunogenicity, or to improve "immune tolerance," are known in the art and described, for example, by Ahlgren et al., *J Nucl Med,* 2010; 51:1131-1138; Feldwisch J et al., *J Mol Biol,* 2010 Apr. 30;398(2):232-47. Epub 2010 Mar. 10. For example, amino acid substitutions can be made, e.g., in an iterative process, randomly or based on structural modeling, following by analysis of the desired property, e.g., antigenicity. In another example, mutations are introduced to improve specificity. In other embodiments, the meditopes are fused with other antibody-binding substances, such as other antibody-binding proteins, for example, Protein A or Protein G.

The MPLs generally include a linker, linking the meditope portion to the Protein L portion. The linker typically includes at least 2, more typically at least 3, e.g., 3, 4, 5, 6, 7, 8, 9, or 10 amino acid residues (e.g., four glycines). In some aspects, such residues link the C-terminus of the meditope and the N-terminus of Protein L. In one example, the meditope-Protein L fusion protein has the sequence set forth in SEQ ID NO: 58 (S C Q F D L S T R R L K C G G G G G S E V T I K V N L I F A D G K I Q T A E F K G T F E E A T A E A Y R Y A A L L A K V N G E Y T A D L E D G G N H M N I K F A G).

In some embodiments, the MPLs are used in connection with meditope-enabled antibodies, in the methods and uses described herein, including those involving the conjugation of the meditopes to agents, such as therapeutic or diagnostic agents, such as cytotoxins, radionuclides, DOTA, proteins or other biological molecules, e.g., to target disease and/or image disease sites. In some aspects, to facilitate such conjugation, one or more lysines in the Protein L fusion are mutated, for example, to arginine or asparagine, to generate a Protein L fusion protein that can be specifically conjugated to other molecules, for example, by leaving the N-terminal amine and the epsilon amine available for conjugation, the latter being solvent exposed and more reactive. An exemplary fusion protein has the sequence set forth in SEQ ID NO: 59(S C Q F D L S T R R L R C G G G G S E V T I R V N L I F A D G N I Q T A E F R G T F E E A T A E A Y R Y A A L L A R V N G E Y T A D L E D G G N H M N I K F A G), in which all lysines but one have been removed.

The coding sequence of an exemplary meditope-Protein L fusion protein is set forth in SEQ ID NO: 56. The sequence of exemplary meditope-Protein L fusion proteins are set forth in SEQ ID NO: 57 (His6-Smt3-meditope-ProteinL) and SEQ ID NO: 58 (containing two cysteins, set forth in bold text, which in some aspects are used to cyclize the MPL, e.g., by peroxide or overnight with air:

(SEQ ID NO:58)
SCQFDLSTRRLKCGGGGSEVTIKVNLIFADGKIQTAEFKGTFEEATAEA

YRYAALLAKVNGEYTADLEDGGNHMNIKFAG.

In some embodiments, the meditope-Protein L (MPL) construct exhibits improved binding affinity for a meditope-enabled antibody as compared to meditope alone. For example, the improvement can be an at least or an at or about 10,000, 9000, 8000, 7000, 6000, 5000, 4000, 3000, 2000, 1000, 900, 800, 700, 600, 500, 400, 300, 200, 100, 90, 80, 70, 60, 50, 40, 30, 20, or 10-fold improvement in affinity, e.g., in dissociation constant, for the meditope-enabled antibody as compared with the corresponding meditope alone and/or with the Protein L alone. In one example, the binding constants for interactions between Protein L and the meditope alone with the meditope-enabled antibody are approximately 0.5 µM and 1 µM, respectively, whereas the binding constant for the MPL to the antibody is approximately 165 pM.

IV. Meditope-Agent Conjugates

In certain embodiments, the meditopes, including one or more meditope, meditope variants, multivalent meditopes, meditope-Protein L fusions (MPLs), multivalent tethering agents or multivalent meditope variant tethering agents are conjugated to one or more therapeutic or diagnostic agent, e.g., imaging agents, therapeutically effective agents or compounds in therapeutically effective amounts or both. Provided are such complexes containing the meditope and one or more agent.

In some aspects, the binding of the meditopes or variants thereof to one or more meditope-enabled antibody conjugated to a therapeutic or diagnostic (e.g., imaging) agent or compound is used to treat, prevent, diagnose or monitor a disease or condition. In one aspect, such conjugation of a meditope, such as a multivalent meditope, to an agent, when used in connection with meditope-enabled monoclonal antibodies, provides a highly versatile platform technology that will significantly improve mAb based therapeutics and imaging methods to treat and detect disease (see FIG. 8).

The diagnostic and therapeutic agents include any such agent, which are well-known in the relevant art. Among the imaging agents are fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. Enzymes that may be used as imaging agents in accordance with the embodiments of the disclosure include, but are not limited to, horseradish peroxidase, alkaline phosphatase, acid phoshatase, glucose oxidase, β-galactosidase, β-glucoronidase or β-lactamase. Such enzymes may be used in combination with a chromogen, a fluorogenic compound or a luminogenic compound to generate a detectable signal.

Radioactive substances that may be used as imaging agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Eu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the imaging agent is a radioactive metal or paramagnetic ion, the agent may be reacted with another long-tailed reagent having a long tail with one or more chelating groups attached to the long tail for binding to these ions. The long tail may be a polymer such as a polylysine, polysaccharide, or other derivatized or derivatizable chain having pendant groups to which the metals or ions may be added for binding. Examples of chelating groups that may be used according to the disclosure include, but are not limited to, ethylenediaminetetraacetic acid (EDTA), diethylenetriaminepentaacetic acid (DTPA), DOTA, NOTA, NETA, TETA, porphyrins, polyamines, crown ethers, bis-thiosemicarbazones, polyoximes, and like groups. The chelate is normally linked to the PSMA antibody or functional antibody fragment by a group, which enables the formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antibodies and carriers described herein. Macrocyclic chelates such as NOTA, DOTA, and TETA are of use with a variety of metals and radiometals including, but not limited to, radionuclides of gallium, yttrium and copper, respectively. Other ring-type chelates such as macrocyclic polyethers, which are of interest for stably binding nuclides, such as $^{223}$Ra for RAIT may be used. In certain embodiments, chelating moieties may be used to attach a PET imaging agent, such as an Al—$^{18}$F complex, to a targeting molecule for use in PET analysis.

Exemplary therapeutic agents include, but are not limited to, drugs, chemotherapeutic agents, therapeutic antibodies and antibody fragments, toxins, radioisotopes, enzymes (e.g., enzymes to cleave prodrugs to a cytotoxic agent at the site of the tumor), nucleases, hormones, immunomodulators, antisense oligonucleotides, RNAi molecules (e.g., siRNA or shRNA), chelators, boron compounds, photoactive agents and dyes. The therapeutic agent may also include a metal, metal alloy, intermetallic or core-shell nanoparticle bound to a chelator that acts as a radiosensitizer to render the targeted cells more sensitive to radiation therapy as compared to healthy cells. Further, the therapeutic agent may include paramagnetic nanoparticles for MRI contrast agents (e.g., magnetite or $Fe_3O_4$) and may be used with other types of therapies (e.g., photodynamic and hyperthermal therapies and imaging (e.g., fluorescent imaging (Au and CdSe)).

Chemotherapeutic agents are often cytotoxic or cytostatic in nature and may include alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that may be used as therapeutic agents in accordance with the embodiments of the disclosure include, but are not limited to, 13-cis-retinoic acid, 2-chlorodeoxyadenosine, 5-azacitidine, 5-fluorouracil, 6-mercaptopurine, 6-thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, bacillus calmette-guerin (BCG), bendamustine, bevacizumab, etanercept, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

Therapeutic antibodies and functional fragments thereof, that may be used as therapeutic agents in accordance with the embodiments of the disclosure include, but are not limited to, alemtuzumab, bevacizumab, cetuximab, edrecolomab, gemtuzumab, ibritumomab tiuxetan, panitumumab, rituximab, tositumomab, and trastuzumab and other antibodies associated with specific diseases listed herein.

Toxins that may be used as therapeutic agents in accordance with the embodiments of the disclosure include, but are not limited to, ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

Radioisotopes that may be used as therapeutic agents in accordance with the embodiments of the disclosure include, but are not limited to, $^{32}$P, $^{89}$Sr, $^{90}$Y. $^{99m}$Tc, $^{99}$Mo, $^{131}$I, $^{153}$Sm, $^{177}$Lu, $^{186}$Re, $^{213}$B, $^{223}$Ra and $^{225}$Ac.

E. Methods of Use and Compositions

Also provided are methods and uses of the meditopes, meditope-enabled antibodies, and complexes containing the same, including therapeutic and diagnostic uses, as well as other uses, including antibody purification. Also provided are pharmaceutical compositions containing the meditopes (including variant and multivalent meditopes and meditope fusion proteins) for use in such diagnostic and therapeutic methods.

I. Therapeutic and Diagnostic Uses and Pharmaceutical Compositions

In one embodiment, the specificity and binding of the meditopes, meditope variants, multivalent meditopes, MPLs, multivalent meditope tethering agents and multivalent meditope variant tethering agents, etc., are used to deliver therapeutic agents, diagnostic agents (e.g., imaging agents), or a combination thereof for treatment, diagnosis (e.g., imaging) a disease or condition, typically when administered in combination with (either simultaneously or separately) one or more meditope-enabled monoclonal antibodies.

In one example, meditopes, e.g., multivalent meditopes, are used for pre-targeted therapy or pre-targeted imaging, as described further below, by administering a meditope-enabled monoclonal antibody before administering the meditopes, meditope variants, multivalent meditope tethering agents or multivalent meditope variant tethering agents. Further, the use of multivalent meditopes can enhance selectivity and improve tumor detection as has been demonstrated for engineered scFvs or chemically conjugated mAbs, but avoids potential immunogenicity inherent in these non-human constructs.

Thus, the platform technology described herein has a broad impact on the mAb delivery field and provides useful methods for the treatment and diagnosis of various diseases and conditions, including cancers, such as those against which use of an antibody is indicated. For example, meditope-enabled antibodies directed against EGFR-positive cancers, including colorectal and squamous cell carcinoma head and neck cancers, would benefit from use of where cetuximab and a meditope. Additionally, modifying other therapeutic antibodies to generate meditope-enabled versions of such antibodies allows for the platform technology to be utilized in methods for the treatment and diagnosis of several other cancers, diseases and other conditions.

Use of the meditopes in such methods is advantageous, for example, by way of specificity, e.g., as compared to other means for binding or conjugation to antibodies. For example, PpL (Protein L) and SpA (Protein A) are not murine-specific or chimeric antibody-specific. PpL binds to ~66% of murine and ~50% of human IgG Kappa light chains and SpA binds to 12% of murine and 50% of human variable heavy chains (Graille et al., 2002). In contrast, as demonstrated herein, the interaction of meditopes with meditope-enabled antibodies is highly specific, which can avoid adverse effects, including off-target effects, e.g., avoiding binding of the therapeutic compound to immunoglobulins endogenous to the subject.

In some embodiments, a meditope administered in combination with a meditope enabled antibody, an antibody-meditope complex, a multivalent tethering agent administered in combination with a meditope enabled antibody, or a combination thereof may be conjugated to one or more imaging agent. In one aspect, an imaging agent may include, but is not limited to a fluorescent, luminescent, magnetic protein, or radionuclide protein, peptide or derivatives thereof (e.g., genetically engineered variants). Fluorescent proteins that may be expressed by the mRNA component include green fluorescent protein (GFP), enhanced GFP (EGFP), red, blue, yellow, cyan, and sapphire fluorescent proteins, and reef coral fluorescent protein. Luminescent proteins that may be expressed by the mRNA component include luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; Handbook of Fluorescent Probes and Research Products, Molecular Probes, 9.sup.th edition, 2002; and The Handbook—A Guide to Fluorescent Probes and Labeling Technologies, Invitrogen, 10th edition, available at the Invitrogen web site; both of which are hereby incorporated by reference as if fully set forth herein.)

In other aspects, the meditope administered in combination with a meditope enabled antibody, the antibody-meditope complex, the multivalent tethering agent administered in combination with a meditope enabled antibody, or a combination thereof may be further conjugated to or otherwise associated with a non-protein imaging agent or a delivery vehicle such as a nanoparticle, radioactive substances (e.g., radioisotopes, radionuclides, radiolabels or radiotracers), dyes, contrast agents, fluorescent compounds or molecules, bioluminescent compounds or molecules, enzymes and enhancing agents (e.g., paramagnetic ions). In addition, it should be noted that some nanoparticles, for example quantum dots and metal nanoparticles (described below) may also be suitable for use as an imaging agent or a therapeutic agent (e.g., using hyperthermal and photodynamic therapies as well as imaging agents through fluorescence and or MRI contrast).

The meditope-mAb technology allows for a system that may be used to generate an antibody-meditope complex that may be further conjugated to one or more meditope-enabled antibody, a therapeutic agent, an imaging agent or a combination thereof. Thus, a set of meditopes or high affinity meditope variants, each conjugated to a unique cytotoxic or imaging agent, would allow for the co-administration of a desired meditope conjugate and meditope-enabled mAb for treatment. The meditope conjugates are an improvement over the current antibody-drug conjugates, which have drawbacks such as a reduced specificity due to chemical modification or release of payload. A method for enhancing the binding affinity of a therapeutic antibody or functional fragment thereof is provided herein. Such a method may include administering to a subject a therapeutically effective amount of a pharmaceutical composition via any suitable route of administration. The pharmaceutical composition may include a meditope or meditope variant in combination with a meditope enabled antibody, a multivalent meditope or meditope variant tethering entity in combination with a meditope enabled antibody, a meditope-enabled therapeutic antibody or functional fragment thereof, a pharmaceutically acceptable carrier, and any combination thereof. The enhanced binding affinity of the multivalent meditope may be attributed to the multivalent cross-linking of IgGs bound to the cell surface. Crosslinking IgGs (through parental murine M425 antibody or using anti-IgG IgM) significantly affects signaling, receptor endocytosis and recycling, and cell death. Thus, multivalent peptides may act synergistically with a therapeutic monoclonal antibody to enhance its therapeutic efficacy.

In some embodiments, the meditope, alone or as part of the tethering entity, may contain a cysteine or other suitable alkylating agent that binds to a Fab cysteine at the binding site, thus creating a cysteine-cysteine interaction. Alternatively, the meditope may bind to the Fab at an unnatural amino acid (e.g., p-acetylphenylalanine). The Cys meditope is conjugated to any substance and directs the conjugate to the IgG.

An antibody-meditope complex may also be used in a method for directing treatment to a particular type of cell or population of cells in a disease or condition that can be targeted by a therapeutic antibody. Such a method of treatment may include administering a therapeutically effective amount of a pharmaceutical composition to a subject having the disease or condition via any suitable route of administration. The pharmaceutical composition may include a meditope or meditope variant in combination with a meditope enabled antibody, a multivalent meditope or meditope variant tethering entity in combination with a meditope enabled antibody, a meditope-enabled therapeutic antibody or functional fragment thereof.

In other embodiments, a method for imaging tumors or other tissues is provided. In such methods, an unmodified therapeutic antibody may be administered to target a tumor or other tissue that overexpress the corresponding antigen. Subsequently, a multivalent meditope tethering entity that is labeled with an imaging agent is administered via any suitable route of administration and will bind to the therapeutic antibodies that are bound to the target tumor or tissue. See FIG. 8. Examples of imaging agents include but are not limited to radiolabels (e.g., $^{3}$H, $^{14}$C, $^{35}$S, $^{90}$Y, $^{99m}$Tc, $^{125}$I, $^{131}$I, $^{177}$Lu, $^{166}$Ho, and $^{153}$Sm), metal or magnetic labels (e.g., gold, iron, gadolinium), biotin, chelating agents (e.g., 1,4,7,10-tetraazacyclododecane-N,N',N'',N'''-tetraacetic acid ("DOTA")) or any agent described above. In one embodiment, the imaging agent used with the method described herein is DOTA.

There are several advantages over known methods to the imaging or treatment methods described above. First, the bivalent character of a therapeutic monoclonal antibody enhances the selectivity to the tumor. As discussed further below, this enhanced selectivity is lost with the use of scFvs and is not entirely compensated for by enhanced affinity. Second, the mass of the labeled multivalent meditope tethering entity will be below the renal threshold for filtering (less than 60 kDa, may be as low as ~10 kDa), allowing it to be easily filtered out of the body. In contrast, direct labeling of a therapeutic antibody with an imaging agent or other therapeutic agent is typically avoided because it will circulate for extended periods (days to weeks) in the body. Thus, imaging of tumors or other diseased organs is often accomplished using less selective scFvs.

In further embodiments, the meditopes may be used to join two or more therapeutic molecules to form a pharmaceutical compound that may be administered, as part of a pharmaceutical composition, in a therapeutically effective amount to a subject for treatment of cancer, autoimmune disease or other conditions. The two or more therapeutic molecules may include, but are not limited to, functional antibody fragments (e.g., F(ab')$_2$ or Fab fragments), peptides or other small molecules that can target tumor or disease-specific receptors such as those described above. The therapeutic molecules may be two or more of the same therapeutic molecule or alternatively, may be two or more different molecules that target the same tumor or diseased tissue.

In some embodiments, the pharmaceutical compound or composition may include a proprietary antibody, or portion thereof, such as a CovX-Body™. In one example, the meditopes are used as linkers to join two or more therapeutic molecules to a specially designed CovX antibody. In one example, a small molecule, peptide or scFv associated with such a meditope is recognized by the meditope-binding site (e.g., framework binding interface) of the CovX antibody. When these components are combined, the resulting bivalent CovX-Body™ possesses the biologic actions of the small molecule, peptide or scFv while also retaining an extended half-life of the antibody.

In some embodiments, the provided meditopes, meditope-enabled antibodies, and complexes thereof, are used in treatment, diagnosis or imaging of a disease or condition, including any cancer, disease or other condition that may be treated or targeted using a therapeutic antibody. Cancers avoid immune surveillance by actively suppressing the immune system. One method envisioned for counteracting this immunosuppression is through vaccination using epitopes of antigens that are either uniquely expressed or overexpressed by the tumor cells. For example, monoclonal antibodies (mAbs) that block signaling pathways, sequester growth factor and/or induce an immune response have been successfully implemented in the clinic to treat cancer and other diseases.

Thus, the diseases and conditions include any cancer, as well as other diseases and conditions, such as those targeted using therapeutic mAbs, including, but not limited to, leukemia and lymphomas (which can be treated or imaged using, e.g., meditope-enabled versions of alemtuzumab, bectumomab, gemtuzumab, FBTA05, ibritumomab tiuzetan, ofatumumab, rituximab, tositumomab), breast cancer (which can be treated or imaged using, e.g., meditope-enabled versions of trastuzumab, adecatumumab, ertumaxomab) prostate cancer (which can be treated or imaged using, e.g., meditope-enabled versions of adecatumumab, capromab pendetide, etaracizumab), colorectal cancer (which can be treated or imaged using, e.g., meditope-enabled versions of labetuzumab, panitumumab, altumumab pentetate, votumumab), gastrointestinal cancers (which can be treated or imaged using, e.g., meditope-enabled versions of arcitumumab, catumaxomab), ovarian cancer (which can be treated or imaged using, e.g., meditope-enabled versions of abagovomab, catumaxomab, etaracizumab, igovomab, oregovomab), lung cancer (which can be treated or imaged using, e.g., meditope-enabled versions of anatumumab mafenatox), pancreatic cancer (which can be treated or imaged using, e.g., meditope-enabled versions of clivatuzumab tetraxetan), renal cancer (which can be treated or imaged using, e.g., meditope-enabled versions of girentuximab), melanoma cancer (which can be treated or imaged using, e.g., meditope-enabled versions of etaracizumab, ipilimumab, TRBS07), glioma (which can be treated or imaged using, e.g., meditope-enabled versions of nimotuzumab), bone metastases (which can be treated or imaged using, e.g., meditope-enabled versions of denosumab), head and neck cancer (which can be treated or imaged using, e.g., meditope-enabled versions of zalutumumab), cardiovascular disease (which can be treated or imaged using, e.g., meditope-enabled versions of abciximab), autoimmune disorders (which can be treated or imaged using, e.g., meditope-enabled versions of adalimumab, infliximab), rheumatoid arthritis (which can be treated or imaged using, e.g., meditope-enabled versions of atlizumab, golimumab, infliximab), transplant rejection (which can be treated or imaged using, e.g., meditope-enabled versions of basiliximab, daclizumab, muromonab-CD3), Crohn's disease (which can be treated or imaged using, e.g., meditope-enabled versions of certolizumab, fontolizumab, natalizumab, infliximab, visilizumab), hemoglobinuria (which can be treated or imaged using, meditope-enabled versions of eculizumab), psoriasis (which can be treated or imaged using, e.g., meditope-enabled versions of efalizumab, infliximab, ustekinumab), multiple sclerosis (which can be treated or imaged using, e.g., meditope-enabled versions of natalizumab, ustekinumab), asthma (which can be treated or imaged using, e.g., meditope-enabled versions of benralizumab, mepolizumab, omalizumab), respiratory syncytial virus (RSV) (which can be treated or imaged using, e.g., meditope-enabled versions of palivizumab), macular degeneration (which can be treated or imaged using, e.g., meditope-enabled versions of ranibizumab), appendicitis (which can be treated or imaged using, e.g., meditope-enabled versions of fanolesomab) and any other condition that may be targeted or treated with an antibody. The above-listed antibodies and related diseases or disorders are examples only and do not limit the platform.

In certain embodiments, one or more meditopes, meditope variants, multivalent meditope tethering agents or multivalent meditope variant tethering agents may be conjugated to one or more imaging agents, therapeutically effective agents or compounds in therapeutically effective amounts or both, such that the binding of the meditopes or variants thereof to one or more meditope-enabled antibody with the therapeutically effective compound may treat, prevent, diagnose or monitor a disease or condition. Such conjugation of a high affinity and/or multivalent meditope coupled to meditope-enabled mAbs provides a highly versatile platform technology that will significantly improve mAb based therapeutics and imaging methods to treat and detect disease (see FIG. 8).

III. Other Uses and Compositions

Also provided are methods and compositions for stabilization of scFv (single chain Fab variable) fragments. In general, scFv fragments (e.g., the scFv format of a given Fab) bind antigen with a substantially lower affinity than full-length mAbs and other fragments, such as the Fab itself. Such reduced affinity is attributed, at least in part, to absence of the Fab constant domain that directly affects the orientation, conformational fluctuations of the Fv domains, and possibly, to poor linker design. On the other hand, scFv and other smaller fragments can have other advantages, including better tissue, e.g., tumor penetration.

Figure 9:
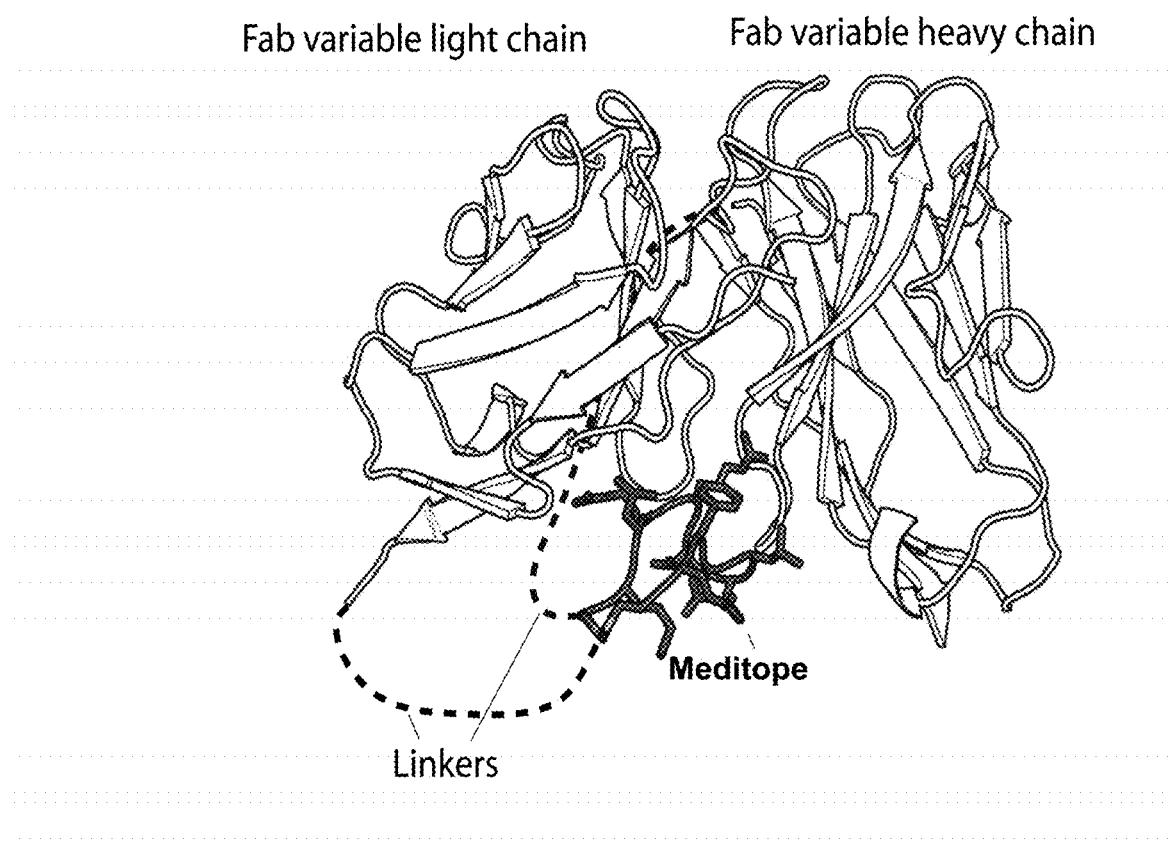
FIG. 9 shows an scFv-meditope linker. scFvs are created by fusing the light chain variable domain to the heavy chain variable domain (or vice versa) through a 12-20 amino acid linker (typically $\{GGGS\}_{3-5}$) (SEQ ID NOs:184-186). In this example, a portion of the flexible linker sequence can be replaced with the meditope sequence.

In some embodiments, provided is a method for improving the stability and affinity of scFv fragments. In one aspect, such methods are carried out by incorporating a meditope into an scFv fragment by facilitating its interaction with residues in the VH and VL regions corresponding to residues within the meditope binding site of the corresponding Fab or whole antibody, for example, by introducing a linker between the scFv and the meditope, to stabilize the scFv. Also provided are complexes containing the scFv bound to one or more meditopes, and compositions containing the same, and uses thereof in the provided methods. In some aspects, such methods will help to enforce the proper orientation of the variable domains and thus enhance the affinity (FIG. 9).

Figure 10:
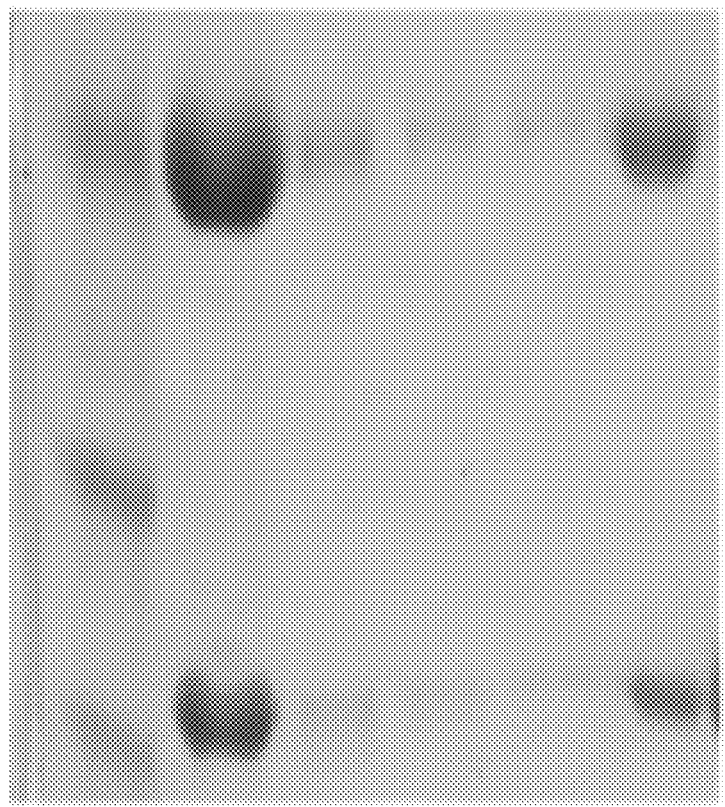
FIG. 10 shows results from an SDS-PAGE showing that the cQFD meditope coupled to beads could bind to cetuximab. Biotinylated cQFD peptide was added to avidin-coupled beads, thoroughly washed, and equilibrated in PBS. Cetuximab was then added to the beads (lane 1), washed (lanes 2-4), and then eluted (lane 5). The top band is the IgG heavy chain and bottom band is the IgG light chain.

Also provided are isolation and purification methods using the meditopes, including methods for purifying meditope-enabled antibodies and fragments thereof, and/or cells expressing such antibodies, and compositions and kits for use in the same. In one embodiment, such methods are carried out by coupling the meditope (e.g., any of the provided meditopes) to a solid support, such as a bead, e.g., magnetic bead, plate, column, or other solid support. See FIG. 10. In another example, a meditope having the sequence CQFDLSTRRLRCGGGSK (SEQ ID NO:187) was successfully linked through amine coupling to a solid support, and is useful, for example in biacore/surface plasmon resonance studies. See FIG. 29. Such biacore studies in certain embodiments are performed by flowing antibody over an amine coupled long meditope chip.

Methods for coupling proteins to solid supports are well known to those skilled in the art and can be used in connection with this embodiment. Meditope-enabled antibodies or cells expressing the same then can be exposed to the solid support, whereby they are isolated and purified.

There are several advantages to such purification methods compared to other available methods. For example, the provided meditopes are easily synthesized and can be readily added to common solid supports (including magnetic beads). Second, the affinity of the meditopes is easily modulated by point mutations, which enables the fine-tuning of the purification procedure and avoids harsh conditions such as low pH that is commonly used to elute antibodies from Protein A or Protein L. In some embodiments, these Protein A or Protein L resins usually contain the full length (e.g., wildtype) sequence where there are up to 5 domains. One or more of these domains are the same as Protein L and Protein A being used herein. In some examples, the meditopes are made bivalent or multivalent (such as those described in Example 7 below) for use in extracting meditope-enabled antibodies, such as intact meditope-enabled antibodies.

In some aspects, the provided purification and isolation methods have additional advantages over other purification methods using Protein A or Protein L, including reduction in the high cost associated with the production of Protein A or Protein L, improvement compared to the limited life cycle of these proteins, and avoidance of the risk of introducing extraneous biological material such as bacterial pathogens, associated with use of Protein L or A.

F. Modification and Screening of Meditopes and Meditope-Enabled Antibodies

I. Modification of Meditope-Enabled Antibodies

Also provided are methods for modifying meditope-enabled antibodies to alter one or more properties of the antibodies, such as binding affinity or specificity with respect to the meditope, and/or other properties. Also provided are modified antibodies produced by the methods and libraries for producing the same. In one embodiment, residues that line the meditope-binding site of a meditope-enabled antibody and/or that are otherwise important for binding of such an antibody to a meditope, are systematically or randomly altered (e.g., using degenerate libraries and selection), for example, to enhance and/or change the specificity of the meditope or meditope analogs (see, for example, Sheedy et al. 2007 and Akamatsu et al. 2007, hereby incorporated herein by reference, for methods of making alterations). In some aspects, the residues are substituted with natural or non-natural amino acids or both, in order to improve the affinity of the meditope interaction and/or alter another property of the meditope-antibody interaction. The incorporation of a non-natural amino acid in an antibody to generate a bi-specific antibody was described by Hutchins et al. 2011).

Residues of meditope-enabled antibodies that make contact with the meditope and/or are otherwise important, e.g., line the cavity, for example, residues within 8 Å of any atom of a bound meditope, that can be systematically or randomly changed to improve the meditope affinity through hydrogen bonding, ionic, electrostatic or steric interaction can include, but are not limited to, one or more light chain residues (e.g., P8, V9 or 19, I10 or L10, S14, E17, Q38, R39, T40, N41 G42, S43, P44, R45, D82, I83, A84, D85, Y86, Y87, G99, A100, G101, T102, K103, L104, E105, K107, R142, S162, V163, T164, E165, Q166, D167, S168, or Y173 of the light chain, based on Kabat numbering and with reference to cetuximab, meditope-enabled trastuzumab, or meditope-enabled M5A, or analogous residues in other meditope-enabled antibodies), and/or one or more heavy chain residues (e.g., Q6, P9, R38, Q39, S40, P41, G42, K43, G44, L45, S84, D86, T87, A88, I89, Y90, Y91, W103, G104, Q105, G106, T107, L108, V109, T110, V111, Y147, E150, P151, V152, T173, F174, P175, A176, V177, Y185, S186, or L187 of the heavy chain, based on Kabat numbering and with reference to cetuximab, meditope-enabled trastuzumab, or meditope-enabled M5A, or analogous residues in other meditope-enabled antibodies), or a combination thereof.

For example, in some aspects, one or more of P8, V9 or 19, I10 or L10, Q38, R39, T40, N41 G42, S43, P44, R45, D82, I83, A84, D85, Y86, Y87, G99, A100, G101, T102, K103, L104, E105, R142, S162, V163, T164, E165, Q166, D167, S168, and Y173 of the light chain, and/or one or more of Q6, P9, R38, Q39, S40, P41, G42, K43, G44, L45, S84, D86, T87, A88, I89, Y90, Y91, W103, G104, Q105, G106, T107, L108, V109, T110, V111, Y147, E150, P151, V152, T173, F174, P175, A176, V177, Y185, S186, and L187 (with reference to cetuximab, or analogous residues in other meditope-enabled antibodies) of the heavy chain are mutated.

Other residues within or in proximity to the meditope binding site may be mutated to allow a meditope group to hydrate it and bind with high affinity. For example, the Tyr87 of the light chain residue, the Tyr91 of the heavy chain residue, or both, may be used to form a hydrate with an aldehyde or boron containing compound originating from a meditope analog. In some aspects, as shown in the Examples herein, meditopes do not affect antigen binding and can be used to deliver drugs, daisy chain/crosslink antibodies, to increase the efficiency and/or efficacy of therapeutic antibodies, and in targeted diagnostic, e.g., imaging, methods, among other uses as described herein. Thus, in some embodiments, the meditope binding site of a provided meditope-enabled antibody is altered, for example, such that it can bind to a meditope with higher affinity and/or can bind with one or more variant meditopes, meditope analogs, and/or small molecules such as DOTA or a DOTA derivative (for radioactive delivery and/or pre-targeted imaging).

In some embodiments, alteration of the residues of the meditope binding site is by systematic alteration. In some aspects, mutating all sites would involve $>20^6$, potentially $>20^{16}$, combinations of mutations. Thus, in some aspects, desired mutations are efficiently identified using a library, in which mutations in the antibody are generated at the DNA level. In one aspect, the library contains individual members that collectively express each individual natural amino acid at one or more positions targeted for mutation. In one example, a DNA library is created using degenerate oligonucleotides at sites of interest (e.g., any one or more of the sites described herein, e.g., Ile89, Thr87, Leu108 and Thr110 of the heavy chain and Lys103 and Glu165 light chain), producing a library the members of which collectively encode all 20 naturally occurring amino acids at these sites.

In some aspects, an anchor, e.g., a GPI domain, is coupled to the antibody members of the library, such as to the C-terminus of the antibody (e.g., IgG) heavy chain, to facilitate selection of the expressed antibodies. The library can be transfected using standard methods and members of the library expressed.

Mutant antibodies of the library having one or more desired characteristics then can be selected. In some aspects, members of the library are selected for their ability to bind to an antigen, e.g., to select for mutations that do not affect antigen binding. In one example, cells expressing antibodies of the library that bind to a fluorescently labeled antigen (e.g., HER2, EGFR, IGFR, CLTA-4, etc) are selected, e.g., by FACS (FIG. 20). In some aspects (either after or instead of antigen-binding selection), cells expressing antibodies of the library are selected for another characteristic, such as binding to a specific meditope, meditope analog, or other molecule of interest (e.g., DOTA). In another example, two or more characteristics are simultaneously selected for.

Selected members of the library, e.g., cells expressing the antibodies, are evaluated and characterized, for example, to determine the desired mutation or combination of mutations for achieving a particular property. In one aspect, sorted cells are characterized by PCR to identify the resulting mutations that facilitate or enhance meditope/analog/small molecule binding.

In some aspects, the methods are carried out in an iterative fashion, for example, by repeating the mutation, selection, and characterization process, e.g., multiple times, to "evolve/optimize" the binding or other desired characteristic(s).

II. Meditope Analogs and Fragments

Also provided are meditope analogs, and methods for identifying, producing, and screening such analogs. Thus, in some embodiments, other molecules also bind to meditope binding sites of meditope-enabled antibodies, with functional characteristics similar to those of a meditope. Such molecules are called meditope analogs and include, but are not limited to, small molecules, aptamers, nucleic acid molecules, peptibodies and any other substance able to bind to the same binding interface as a meditope. In one example, the analog is a DOTA derivative.

In one embodiment, provided are screening methods for identifying such analogs, including small molecule analogs that mimic the meditopes. Such methods include fluorescence polarization assays, diffraction based and NMR based fragment screening, and tethering dynamic combinatorial methods.

In other embodiments, a fragment-based drug discovery approach is used to identify fragments, small molecules, such as chemical groups, that bind to the meditopes, meditope binding sites, and/or meditope-enabled antibodies near the meditope binding sites. See, for example, Erlanson, *Top Curr Chem* (2012) 317:1-32. In some examples, the identified fragments are coupled to the meditopes, for example, to improve their affinity or other properties of the interaction with the meditope binding site. In other examples, they are expanded and/or linked together to generate compounds for coupling to meditopes or meditope-enabled antibodies, or for use as meditope analogs. Methods for fragment and/or meditope analog discovery include, but are not limited to, the following. In some examples, the fragments are between about or at 100 and about or at 1000 Da.

Fluorescence Polarization Assays

In some aspects, the methods include fluorescence polarization assays and/or other competition-based assays. In one example, to identify alternative molecules that can bind at the meditope site and be used for similar functions, a fluorescent marker (e.g., Alexafluor, rhodamine, fluorescein) is conjugated to a meditope, e.g., using a suitable method (e.g., amines, sulfhydryl, carboxylate, sugars or other known methods), and allowed to interact with a meditope-enabled antibody. In general, interaction between the labeled meditope and meditope-enabled antibody causes a change in the fluorescence polarization/intensity of the fluorescent tag. Once established, test compounds (potential analogs), such as small molecule compounds (MW<1000 Da), are added and equilibrated, e.g., with fluorescent tagged meditope-antibody complex, and the fluorescence polarization is monitored. Test compounds that block the meditope-antibody interaction will alter the fluorescent polarization properties. Accordingly, another embodiment is a method of identifying compounds that can be optimized and used for target delivery. The analogs or potential analogs may be screened and further characterized, e.g., by crystallography or other methods described herein for characterization of the meditopes.

Diffraction Methods

Diffraction based methods to identify lead compounds are well established (Shuker et al. 1996; Erlanson et al. 2001; Hughes et al. 2011). Since cetuximab and other meditope-enabled Fabs diffract beyond 2.5 Å, this approach is used in certain embodiments to identify lead compounds or small molecule fragments that can be coupled to a meditope or used as analogs. For example, such compounds include fragments that are then linked together to form synthetic meditope analogs. In one example, a compound library is developed to soak into crystals of cetuximab or other meditope-enabled antibody. Diffraction data from these soaks are collected and data sets analyzed. Such methods can identify additional sites on meditope-enabled antibodies that are amendable for fragment growth and optimization.

The fragments, can be grown (chemically derivatized) to enhance their binding and specificity. The fragments can also be chemically tethered to the meditope. Optimization of this chemical coupling can significantly enhance the overall binding affinity of the meditope for the meditope binding site. Additionally, analogs found by diffraction methods can be optimized and used in lieu of the meditope for drug delivery, multivalent scaffolding and other functions. Further, mutations in the light and heavy chains may be made to change the specificity of the ligand (meditope) and that these diffraction methods (including fluorescence polarization, NMR screening, and phage display methods) can be used to optimized alternative ligands.

NMR Screening

NMR can also be used to identify analogs and fragments (e.g., peptide fragments, non-peptide based small molecules) that can be optimized and used as described herein. In one example, to identify such leads, one dimensional (1D) spectra of pools containing fragments, e.g., 15 to 20 fragments, are collected. In one embodiment, the fragments used are non-peptide based small molecules. Next, a meditope-enabled antibody is added to each pool and a second 1D spectra collected. Compounds that bind (transiently) to a meditope-enabled antibody undergo rapid magnetization transfer, resulting in a loss of intensity. Thus, in some aspects, comparing the spectra before and after meditope-enabled antibody binding and identifying peaks that are altered, indicates an interaction. These peaks can be pre-assigned to a specific compound and thus immediately known or the pools can be subdivided and the spectra recollected. After several rounds the exact identity of the compound is known. In these experiments, the precise position of the interaction is not known. The binding site can be determined by NMR or the fluorescence polarization assay. Alternatively, the Fab fragment can be labeled with NMR active and inactive nuclei (e.g., $^{13}$C, $^{15}$N and $^2$H), multiple NMR experiments performed to assign the spectrum, and then used with the fragment library to identify the binding position.

Virtual Ligand Screening

Virtual ligand screening is another method that can be used to identify lead meditope analogs, fragments, and other compounds. Using crystal structures, standard programs (e.g., Schroerdinger Glide) can define a "box" about a site of a macromolecule (the meditope binding site) and dock known ligands to this site. Potential lead compounds are scored by a select energy function and the top 50 to 200 compounds can be purchased. In our initial studies, approximately 100 lead compounds have been identified, and using crystallography, these lead compounds should be shown to demonstrate that they bind to the meditope site.

In one embodiment, a method of screening for meditopes or meditope analogs is provided herein. Such a method may include, but is not limited to, steps of contacting a library of putative meditopes or small molecules with a meditope-enabled antibody; determining whether the putative meditopes of small molecules bind the meditope-enabled antibody at a framework binding interface; identifying one or more candidate meditopes or meditope analogs; determining binding affinity of the one or more candidates; and identifying one or more of the candidates as a meditope or meditope analogs when the binding dissociation constant is less than 0.70 µM. In other contexts, a low affinity meditope is desired, such that a minimum dissociation constant is specified, for example, 0.70 µM. In some examples, the candidate is identified as a meditope or analog thereof if it exhibits binding constant of less than at or about 10 µM, less than at or about 5 µM, or less than at or about 2 µM, less than at or about 1 µM, less than at or about 500, 400, 300, 200, 100 nm, or less. In some cases, the dissociation constant, such as any of those listed herein, is that measured using a particular technique, such as SPR, Isothermal Titration calorimetry (ITC), fluorescence, fluorescence polarization, NMR, IR, calorimetry titrations; kinetic exclusion; circular dichroism, differential scanning calorimetry, or other known method. For example, in some cases, the analog or meditope exhibits a binding constant of less than at or about 10 µM, less than at or about 5 µM, or less than at or about 2 µM, less than at or about 1 µM, less than at or about 500, 400, 300, 200, 100 nm, or less, as measured by SPR or as measured by ITC or as measured by any of these methods.

Additionally, methods of screening for novel framework binding interfaces are also provided, and are described further in the examples below.

In another embodiment, provided is a method for identifying and optimizing fragments useful in connection with the meditopes, such as in building meditope analogs and/or in coupling to the meditopes to improve their function. Also provided are such analogs and fragments and compounds.

Having described the invention with reference to the embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLE 1

Determination of Meditope-Antibody Fab Crystal Structures

Meditopes were discovered that bind with high specificity and affinity within a central cavity of the Fab region and Fab fragment of cetuximab. These meditopes were bound to cetuximab Fabs and the structures determined crystalographically.

Materials and Methods

Reagents. An antigen binding fragment (Fab) of cetuximab was obtained by digestion of the cetuximab IgG with immobilized papain (Pierce), followed by reverse purification with Protein A and size exclusion chromatography (SEC) on a Superdex 75 column (GE Healthcare). The single chain variable fragment of cetuximab (scFvC225) was synthesized with a twenty amino acid linker between the light chain and heavy chain. ScFvC225 and soluble epidermal growth factor receptor domain III (sEGFRdIII) were expressed in Sf9 cells and purified as previously described (Donaldson, J. M., Kari, C., Fragoso, R. C., Rodeck, U. & Williams, J. C. Design and development of masked therapeutic antibodies to limit off-target effects: Application to anti-EGFR antibodies. *Cancer Biol Ther* 8 (2009)).

Meditopes CQFDLSTRRLKC (cQFD; SEQ ID NO:1) and CQYNLSSRALKC (cQYN; SEQ ID NO:2), isolated from a phage display biopanning experiment as described by Riemer, A. B. et al., Vaccination with cetuximab mimotopes and biological properties of induced anti-epidermal growth factor receptor antibodies, *J Natl Cancer Inst* 97, 1663-70 (2005), were synthesized, oxidized and purified at the City of Hope Synthetic and Polymer Chemistry Core Facility.

Crystallization and Diffraction Data. Cetuximab Fabs (5 mg/mL) were mixed with cQFD and cQYN meditopes at a 1:10 molar ratio and screened for crystal formation using the Qiagen JCSG Core Suites (IIV) at 20° C. Co-crystals that diffracted beyond 2.2 Å were grown in 100 mM sodium phosphate/citrate, pH 4.5, 2.5 M sodium/potassium phosphate and 1.6% w/v mesoerythritol. The crystals were wicked through 14% w/v mesoerythritol and flash frozen in liquid nitrogen. Crystallization trials and initial screening studies were carried out in the X-ray facility at City of Hope. Diffraction data were collected at the Stanford Synchrotron Radiation Lab, beam lines 9.1 and 11.1. The initial phases were determined by molecular replacement using the program Phaser (McCoy, A. J. et al. Phaser crystallographic software. *J Appl Crystallogr* 40, 658-674 (2007)) with the unliganded structure of cetuximab (pdb:1YY8—chains A and B) (Li, S. et al. Structural basis for inhibition of the epidermal growth factor receptor by cetuximab. *Cancer Cell* 7, 301-11 (2005)). Two Fabs were placed in the asymmetric unit with a Matthews Coefficient of 3.26 and solvent content of 62.4%. The Z scores (standard deviation of the solution over the mean) were 27 and 25 for the rotational search and 38 and 71 for the translational search. A third Fab fragment could not be placed (three Fabs in the asymmetric unit cell produces a reasonable Matthews coefficient of 2.18 at 43% solvent). The cQFD and cQYN meditopes were built into the density manually through multiple iterations using Coot (Emsley, P. & Cowtan, K. Coot: model-building tools for molecular graphics. *Acta Crystallogr D Biol Crystallogr* 60, 2126-32 (2004)) and Phenix (Adams, P. D. et al. PHENIX: building new software for automated crystallographic structure determination. *Acta Crystallogr D Biol Crystallogr* 58, 1948-54 (2002)).

Crystallization and Structure Determination

As noted above, cetuximab Fabs were generated and purified and mixed with cQFD meditope (cyclic peptide of SEQ ID NO: 1) at a 1:10 ratio; commercial factorials were used to screen for crystal formation. Crystals formed after 1 day at 20° C. Initial diffraction analysis of these crystals indicated that the unit cell dimensions and space group were similar to those for the cetuximab Fab already deposited in the Protein Data Bank (1YY8.pdb) (Li, S. et al. Structural basis for inhibition of the epidermal growth factor receptor by cetuximab. *Cancer Cell* 7, 301-11 (2005)). The observation that the CDR loops in the deposited structure make extensive crystal contacts could have suggested that the cQFD meditope was not present in the crystal. Nonetheless, the structure was solved by molecular replacement and the experimental maps were examined to identify unmodeled electron density consistent with the meditope. The initial Fo-Fc map clearly indicated an area in the middle of the Fab fragment as a potential binding site (FIG. 1). After an initial round of refinement using the Fab model only, a continuous stretch of unmodeled density consistent with the meditope was observed. The meditope was built into the density and the R and $R_{Free}$ dropped accordingly. Water molecules were added during refinement using Phenix (Adams, P. D. et al. PHENIX: building new software for automated crystallographic structure determination. *Acta Crystallogr D Biol Crystallogr* 58, 1948-54 (2002)). The diffraction data and refinement statistics are given in Table 5 below.

TABLE 5

Diffraction Data and Refinement Statistics for Meditope-Antibody Co-Crystals for Meditopes cQFD, cQYN

| | cQYD | cQYN |
|---|---|---|
| Data collection | | |
| Space group | $P2_12_12_1$ | $P2_12_12_1$ |
| Cell dimensions | | |
| a, b, c (Å) | 64.26, 82.59, 211.63 | 64.16, 82.52, 211.88 |
| α, β, γ (°) | 90.0, 90.0, 90.0 | 90.0, 90.0, 90.0 |
| Resolution (Å) | 19.85-2.24 (2.30-2.24)* | 29.61-2.20 (2.26-2.20)* |
| $R_{merge-F}$ | 0.078 (0.50) | 0.067 (0.26) |
| I/σI | 17.0 (3.1) | 25.5 (6.0) |
| Completeness (%) | 97.4 (83.3) | 99.9 (100) |
| Redundancy | 4.2 (3.2) | 7.9 (8.2) |
| Refinement | | |
| Resolution (Å) | 19.85-2.24 | 29.61-2.20 |
| No. reflections | 53791 | 58047 |
| $R_{work}/R_{free}$ | 18.2/22.6 | 17.4/22.2 |
| No. atoms | | |
| Protein | 6602 | 6528 |
| Ligand/ion | 200/15 | 188/15 |
| Water | 581 | 618 |
| B-factors | | |
| Protein | 31.4 | 32.0 |
| Ligand/ion | 50.3/67.4 | 64.0/44.2 |
| Water | 37.5 | 38.7 |
| R.m.s. deviations | | |
| Bond lengths (Å) | 0.004 | 0.007 |
| Bond angles (°) | 0.913 | 1.100 |

*values in parenthesis are for the highest resolution shell

Based on these observations and as a point of comparison, crystals of the cetuximab Fab bound to the meditope cQYN (SEQ ID NO: 2) were produced. As for the meditope of SEQ ID NO: 1, clear unmodeled electron density was observed in the center of the Fab. Using the first structure, the differences in sequences were modeled accordingly and multiple rounds of refinement were carried out. Representative electron density maps of both meditopes are shown in FIG. 1 B. The diffraction data and refinement statistics for the cQYN-Fab complex also are presented in Table 5, above.

EXAMPLE 2

Characterization of the Meditope Binding Site of Cetuximab Fab

The meditope binding site of cetuximab was characterized as discussed below. It was demonstrated that this meditope binding site is unique and has not been found to exist in the immunoglobulins examined to date.

Materials and Methods

In addition to those described in Example 1 above, the following materials and methods were used.

Meditopes and point mutations. As described in Example 1, CQFDLSTRRLKC (cQFD; SEQ ID NO:1) and CQYN-LSSRALKC (cQYN; SEQ ID NO:2), were synthesized, oxidized and purified at the City of Hope Synthetic and Polymer Chemistry Core Facility. Alanine point mutations in the cQFD meditope were generated at residues 3 (Phe3 to Ala), 5 (Leu5 to Ala), 8 (Arg8 to Ala) and 10 (Leu10 to Ala) and the mutants produced bacterially by encoding the peptides at the C-terminus of SMT3 (Mossessova, E. & Lima, C. D. Ulp1-SUMO crystal structure and genetic analysis reveal conserved interactions and a regulatory element essential for cell growth in yeast. *Mol Cell* 5, 865-76 (2000)). The peptides were oxidized by dialysis into buffer without DTT and purified by SEC to obtain monomers. Before surface plasmon resonance (SPR) analysis, ubiquitin-like protease (Ulp1) was added to the samples to release the peptides. Each of the biosynthesized mutant peptides contained an additional serine residue at the N-terminus due to the ULP1 cleavage site. Ulp1 and SMT3 were run as controls and did not interact with the cetuximab Fab.

Characterization of the meditope-Fab interface. Affinity analysis by SPR was performed as previously described (Donaldson et al., 2009; Li et al., 2005, supra). Briefly, scFvC225 or FabC225 (cetuximab Fab) was immobilized on a CM5 chip using amine chemistry. Peptide or sEGFRdIII affinities were assessed by equilibrium methods at 20° C. and fit to the equation RU={Rmax*[L]}/{[L]*$K_d$}+$R_{offset}$. SEC was performed using a Superdex 200 10/300 column (GE Healthcare). The proteins were mixed, incubated at room temperature for 20 min and applied to the column at 4° C.

The EGFR-expressing MDA-MB-468 cell line was used to test cetuximab binding in the presence of peptide meditope. Labeled cetuximab (AF488, Invitrogen) was added for 20 min with or without 60 μM cQFD peptide at 4° C. Labeled MOPS-21 was used as an isotype control. Cell fluorescence was determined using a FACS Calibur instrument (BD Biosciences).

Analysis of Meditope/Fab Interface

Figure 2:
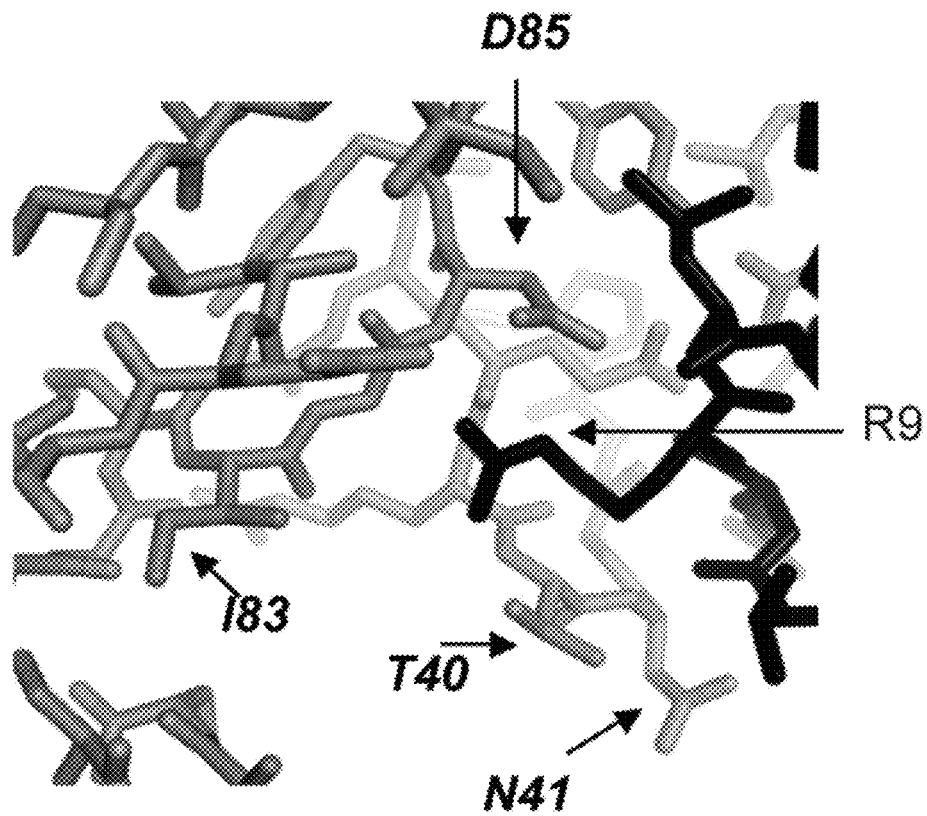
FIG. 2 shows certain embodiments of the cetuximab Fab binding interface. Cetuximab is a human-murine chimera and, therefore, has a mix of murine Ig variable domains and human constant Ig domains.

The interface of the binding site between the meditope (SEQ ID NO: 1) and the cetuximab Fab was determined to be formed by all four domains of the IgG Fab (e.g., the variable heavy and light chain domains, the light chain constant region, and the heavy chain CH1). Using the PISA server, the buried surface area at the cQFD or cQYN meditope-Fab interface was 904 (±28) Å2 and 787 (±42) Å2, respectively, and approximately equally distributed between the light and heavy chains. FIGS. 2, 35, and 36 show the residues and the loops from the Fab that were determined to contact the meditope.

Both meditopes (SEQ ID NOs: 1 and 2) were determined to make multiple hydrogen bonds and hydrophobic contacts with the cetuximab Fab. The amino acid sequences of cetuximab (murine chimeric IgG) were aligned with a chimeric monoclonal IgG (ch14.18) used as an isotype control in the phage display experiments that originally identified the meditopes of SEQ ID NOs: 1 and 2, and trastuzumab (a humanized monoclonal antibody that binds to ErbB2) (see FIG. 2A). The structure of trastuzumab Fab also was superimposed onto the structure of cetuximab Fab bound to the meditope of SEQ ID NO: 1. FIG. 2A shows amino acid differences between the residues within the central cavity meditope-binding interface of the cetuximab Fab (murine chimera IgG) and ch14.18 and trastuzumab.

Superposition of the humanized trastuzumab Fab (1NZ8.bdb) on the cetuximab Fab indicated that Arg9 of the cQFD meditope binds to a unique cavity created by the murine variable light chain. Specifically, Asp85, Ile83 and Thr40 of the murine variable light chain of cetuximab, based on Kabat numbering, were shown to be important with respect to binding to the Arg9 residue of the cQFD meditope (FIG. 2B). Asp85 in the murine framework region of the variable light chain was shown to make a salt bridge to the guanidinium group of Arg9 of the cQFD meditope ($d_{NE\ldots OD1}$=2.7 and 2.9 Å & $d_{NH2\ldots OD2}$=3.0 and 3.1 Å). The carboxyl group of Asp85 also was shown to make a hydrogen bond to the backbone amide nitrogen of Leu10 of the cQFD meditope ($d_{OD2\ldots HN}$=2.7 and 2.8 Å). The hydroxyl group of Thr40 from the light chain also was shown to make a hydrogen bond to guanidinium group of the meditope Arg9 ($d_{OG1\ldots NH1}$=3.2 Å for both). Superimposition of the structures also showed that the phenyl ring in Phe83 and the pyrrolidine ring of Pro40 found in the human variable light chain sequence (corresponding to Ile and Thr, respectively, in cetuximab) are positioned such that they would sterically occlude the side chain of Arg9 in the cQFD meditope.

Although the Arg9 side chain in the cQFD meditope mapped to the differences between the murine and human Fab sequences, the cQYN meditope encodes an alanine at the same position as Arg9 in the cQFD meditope, and thus could potentially have bound to the human Fab. Although the hydrogen bond to the guanidinium group of Arg9 of the cQFD meditope to Asp85 of the light chain was not present for the cQYN meditope, the carboxyl group of Asp85 of the light chain was shown to retain its hydrogen bond to the backbone amide nitrogen of Leu10 of the cQYN meditope. Differences between the cQFD and cQYN meditopes and their interaction with the cetuximab Fab were determined Superposition of the structures of the two meditopes (cQFD and cQYN) bound to cetuximab Fab (specifically of the Cα atoms of the heavy and light Fab chains) showed that the hydrophobic side chains of residues Phe/Tyr3, Leu5 and Leu10 of each meditope were positioned nearly identically, indicating that interaction of these residues with the antibody were important for binding (FIG. 2B). The phenyl ring was shown to pack against the conserved Gln39 of the heavy chain variable region (Kabat numbering); the Leu5 side chain was shown to pack against Ile 89 and Leu108 of the heavy chain variable region (Kabat numbering), as well as the phenyl ring from Phe3/Tyr3 of the meditopes. Leu10 of the meditopes was shown to bind to an exposed pocket located on the variable light chain.

The backbone traces of the cQFD and cQYN peptides, however, did deviate. Specifically, the Arg8 side chain structure of the cQFD meditope is extended and makes a strong backbone hydrogen bond to the backbone carbonyl of Gln105 of the Fab heavy chain ($d_{NH1\ldots O=C}$=2.6 and 2.8; $d_{NH2\ldots O=C}$=2.8 and 2.9 Å). The hydroxyl group of Tyr3 in the cQYN peptide, however, sterically interferes with the Arg8 side chain (FIG. 2B) and blocks the interaction between Arg8 of the cQYN meditope and Gln105 of the heavy chain. Consistent with this observation, both Arg8 side chains in the cQYN complex are poorly defined in the electron density map and takes on at least two different rotamers. (There are two Fab-meditope complexes in the asymmetric unit.) Concomitant with this change, a shift in the backbone hydrogen bond pattern was observed. The amide carbonyl of Thr7 in the cQFD meditope makes a hydrogen bond to the amide Asn41 in the cetuximab Fab light chain $d_{N-H\ldots O=C}$=2.7 and 2.8 Å). This hydrogen bond shifts to the carbonyl of the Arg8 backbone in the amide of backbone of Asn41 in the cQYN peptide ($d_{C=O\ldots H-N}$=3.0 and 3.1 Å).

The superposition indicated that the change from Pro40 and Gly41 in the human light chain sequence to Thr and Asn in the cetuximab light chain relieves a steric constraint and affords two additional points for forming hydrogen bonds to the meditopes. In the cQFD meditope-cetuximab Fab structure, the amide nitrogen of Fab Asn41 was shown to interact with the carbonyl of Thr7 ($d_{N-H \ldots O=C}$=2.7 and 2.8 Å) of the meditope and the side chain amide of Fab Asn41 was shown to interact with the carbonyl of Ser6 ($d_{ND2 \ldots O=C}$=3.2 and 3.2 Å) of the meditope. In the cQYN meditope-cetuximab Fab structure, the shift of the backbone results in a shift of the hydrogen bond pattern. The amide nitrogen of Fab Asn41 interacts with carbonyl of Arg8 of cQYN ($d_{N-H \ldots O=C}$=3.0 and 3.1 Å) but the side chain interaction with Fab Asn41 is lost.

In addition to these results, superposition of the molecular structure of trastuzumab (1N8Z; Cho et al., *Nature*, "Structure of the extracellular region of HER2 alone and in complex with the Herceptin Fab," 2003 Feb. 13; 421(6924): 756-60) and rituximab (2OSL; Du et al., *J Biol Chem*, 2007 May 18; 282(20):15073-80. Epub 2007 Mar. 29) Fabs on to the meditope bound cetuximab Fab structure further highlighted the uniqueness of the framework.

Collectively, these results suggest that the differences in the framework region of cetuximab and the control IgG (as opposed to the differences in the CDRs) accounted for the selection of the meditope to the central cavity of the Fab (i.e., cetuximab and the phage display control antibody differed in regions other than CDRs).

Meditopes do not Induce Large Conformational Changes in the Fab

Figure 6:
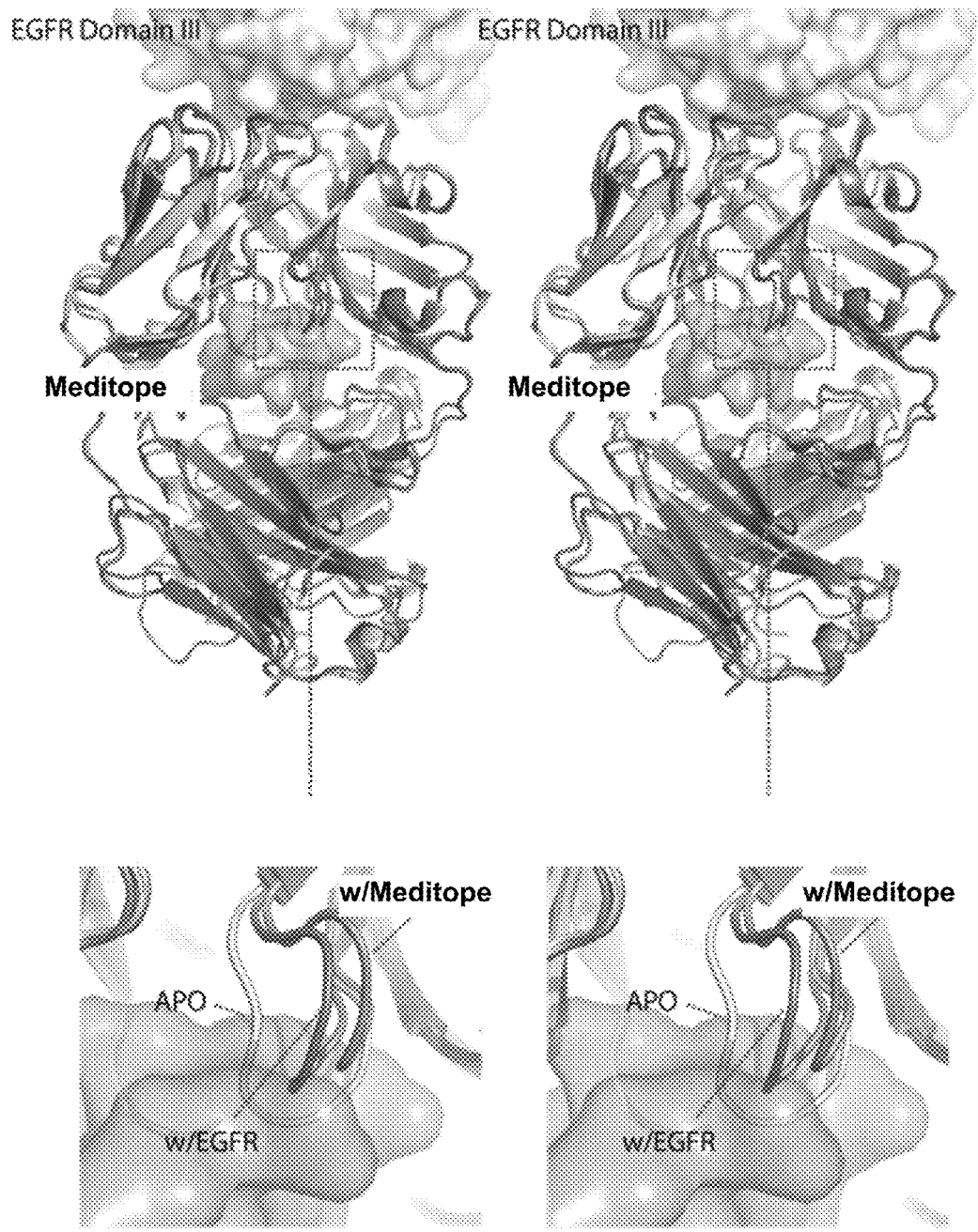
FIG. 6 shows how meditope and EGFR bind to distinct sites. The top images show superposition of the cQFD-Fab complex and the EGFR-Fab complex (1YY8) in stereo. The bottom images show that residues 39-46 of the heavy chain are flexible and accommodate the meditope.

Based on the location of the meditope-cetuximab Fab interface, it was determined whether the meditopes perturbed the relative orientation of the IgG domains to the unligated and/or ligated structure. First, the light and heavy chains within the asymmetric unit cell of both meditope complexes were compared and then each chain was compared to the unligated and EGFR-ligated structures. The variable domains of the light chains bound to either meditope were essentially identical to the unliganded structure of cetuximab (r.m.s.d. average: cQFD, 0.231±0.014 Å, cQYN, 0.18±0.01 Å). However, the variable domains of the heavy chain showed a greater divergence (r.m.s.d. average: cQFD, 0.85±0.01 Å, cQYN, 0.88±0.01 Å). This divergence mainly stemmed from the position of framework region 2 (residues 39-46), since deleting the residues in this region and recalculating the r.m.s.d. resulted in a much lower value: cQFD, 0.18±0.01 Å; cQYN, 0.31±0.01 Å) (FIG. 6). In addition, this region was also shown to be displaced in the Fab C225-EGFR (cetuximab Fab-antigen) co-crystal structure, and its relative B-factor value suggested that it is flexible (FIG. 6). Finally, the presence of the meditope did not result in significant changes to the CDR structure relative to the EGFR bound or unbound structure. Although the backbone of Tyr98 in the heavy chain CDR loop 3 of the EGFR-liganded structure was shown to be flipped as compared to the Fab structure bound to either meditope, this flip is also observed in the unliganded cetuximab Fab structure (Li et al., 2005, supra).

Contribution of Meditope Residues to Antibody Binding

Figure 3:
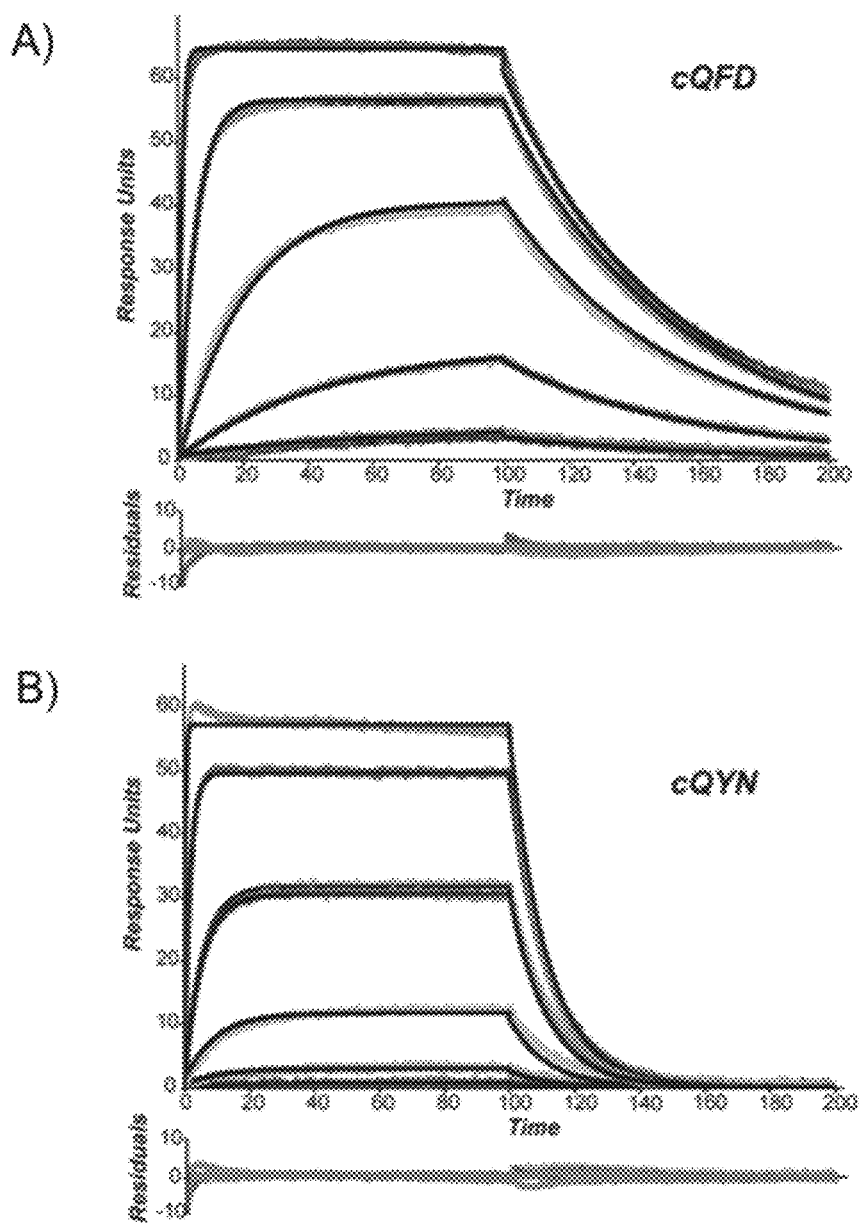
FIG. 3 shows surface plasmon resonance (SPR) traces of cQFD and cQYN with an immobilized Fab. The cetuximab Fab used for crystallographic studies was coupled to a CM5 chip at low densities. Traces at increasing concentrations of the cQFD (FIG. 3A) and cQYN (FIG. 3B) meditopes are shown. The series of traces are fit to a simple 1:1 Langmuir binding model. The residuals of the fit are shown below each.

Based on the structure of the cQFD meditope-Fab complex, as well as the sequence similarity of cQYN to cQFD, several point mutations in the cQFD meditope were generated (Phe3→Ala, Leu5→Ala, Arg8→Ala and Leu10→Ala) to characterize the role of these residues to the overall binding affinity of the meditope. To assess binding affinity, the cetuximab Fab fragment was coupled to a CM5 chip using standard amine chemistry and surface plasmon resonance (SPR) was used to measure the binding properties of the various meditopes. The affinities of the synthetic cQFD and cQYN meditopes to the cetuximab Fab were measured to be 950±30 nM and 3.5±0.1 µM, respectively (n=3). The binding kinetics were also measured (FIG. 3). The association constants, modeled as a bimolecular interaction, were 4.2 (±0.1)×10$^4$ M$^{-1}$s$^{-1}$ and 1.8 (±0.1)×10$^4$ M$^{-1}$s$^{-1}$ for cQFD and cQYN, respectively. The dissociation constants were 2.5 (±0.1)×10$^{-2}$ s$^{-1}$ and 8.6 (±0.1)×10$^{-2}$ s$^{-1}$ for cQFD and cQYN, respectively. The $K_D$ values based on these measurements, 430 (±30) nM for cQFD and 3.5 (±0.1) µM for cQYN, are in close agreement with the equilibrium measurements.

Next, the affinity of each mutated cQFD meditope was measured. The point mutation and wild type cQFD meditopes were generated as C-terminal fusions to SMT3 and cleaved with Ulp1 before the analysis. The biologically-produced, wild type cQFD meditope bound with an affinity of 770 nM, similar to the synthetically-produced cQFD, whereas the mutations Phe3→Ala, Leu5→Ala and Arg8→Ala significantly reduced the affinity for the cetuximab Fab (Table 6, below). In particular, the Arg8→Ala mutation resulted in an approximately 183-fold loss in binding affinity.

In Table 6, WT=cQFD (SEQ ID NO: 1), F3A=SEQ ID NO: 26 with an additional serine before the cysteine, L5A=SEQ ID NO: 27 with an additional serine before the cysteine, R8A=SEQ ID NO: 28 with an additional serine before the cysteine, and L10A=SEQ ID NO: 29 with an additional serine before the cysteine.

TABLE 6

Dissociation constants for "WT" (cQFD) and mutant meditopes
Dissociation constants of cQFD mimotope mutants

| Ligand | $K_D$ (µM) | ΔΔG (kcal/mol) |
|---|---|---|
| WT | 0.77 | — |
| F3A | 34 | 2.3 |
| L5A | 57 | 2.6 |
| R8A | 141 | 3.1 |
| L10A | 2.2 | 0.63 |

Finally, the Fab of trastuzumab, a humanized therapeutic monoclonal antibody, was coupled to a CM5 chip to characterize the affinity of the cQFD and cQYN meditopes to a human framework. Equilibrium measurements revealed that the dissociation constants for both meditopes exceed 150 µM.

EXAMPLE 3

Binding of Meditopes to Regions Other than CDRs

Materials and Methods

It was demonstrated that binding of the meditopes cQFD and cQYN, and others, to a meditope-enabled antibody (cetuximab), does not affect the ability of the antibody to bind to antigen, meaning that the meditope-enabled antibodies can bind to antigen and a meditope simultaneously.

In addition to those described in Examples 1 and 2 above, the following materials and methods were used.

Reagents. As described above, the single chain variable fragment of cetuximab (scFvC225) was synthesized with a twenty amino acid linker between the light chain and heavy chain. ScFvC225 and soluble epidermal growth factor receptor domain III (sEGFRdIII) were expressed in Sf9 cells and purified as previously described (Donaldson et al., 2009).

Meditopes and Point Mutations. As described above, CQFDLSTRRLKC (cQFD; SEQ ID NO:1) and CQYNLSSRALKC (cQYN; SEQ ID NO:2), were cyclized through the oxidation of the cysteines to create a disulfide bond and purified at the City of Hope Synthetic and Polymer Chemistry Core Facility. Alanine point mutations in the cQFD meditope were generated at residues 3 (Phe3 to Ala), 5 (Leu5 to Ala), 8 (Arg8 to Ala) and 10 (Leu10 to Ala) and were produced bacterially by encoding the peptides at the C-terminus of SMT3 (Mossessova et al., 2000). Before surface plasmon resonance (SPR) analysis, ubiquitin-like protease (Ulp1) was added to the samples to release the peptides. An N-terminal serine residue remained as a remnant of the protease cleavage site.

Simultaneous Binding of EGFR and Meditope to Fab

The cetuximab Fab was incubated with sEGFRdIII and cQFD and applied to an analytical SEC column. A peak at 13.9 mL was observed, indicating the formation of a heterotrimeric complex between these three components. Non-reducing SDS-PAGE of the peak showed the presence of all three components (FIG. 4B). In comparison, the individual components eluted at 15.2 mL (Fab C225), 15.6 mL (sEGFRdIII) and 16.3 mL (SMT-CQFDLSTRRLKC; SEQ ID NO:1). The results showed that the meditopes and EGFR could bind to cetuximab simultaneously, indicating that meditope binding did not occlude antigen binding by cetuximab.

In addition, Förster resonance energy transfer (FRET) measurements were used to confirm that the meditope did not affect antigen binding by cetuximab. The fluorescent signal emitted from Alexfluor 488-labeled cetuximab Fab was quenched upon binding of Alexafluor 555-labeled sEGFRdIII. Titration of labeled cetuximab with labeled sEGFRdIII afforded a binding constant of 20 nM, essentially the same value as was observed using SPR (data not shown). To test for allostery, labeled cetuximab Fab was incubated with sEGFRdIII at concentrations ranging from 5 to 1000 nM in the presence of the cQFD meditope (66 µM). The experiment was performed in triplicate. Similar to the SEC studies, no substantial change in the binding constant of the Fab-sEGFRdIII interaction was observed.

Taken together, these biochemical studies indicate that the meditope-Fab interaction does not substantially affect antigen binding. These observations are similar to results with Protein L and Protein A, which also bind to the Fab framework region without affecting antigen binding to Fab.

cQFD Meditope does not Bind to CDR Loops of Cetuximab

To further confirm that the meditopes did not bind to CDRs, binding between the cQFD meditope and the scFv fragment of cetuximab was assessed. In the scFv, the CDR loops remain intact, but the Fab variable domains are directly connected through a short peptide linker, eliminating the Fab constant domains. In other words, much of the meditope binding pocket is eliminated in the scFv, while the CDRs are minimally affected. SPR demonstrated that EGFR domain III and the cQFD meditope bound to cetuximab Fab tethered to a CM5 chip (See FIG. 4D). In addition, EGFR domain III bound with a minimal affinity loss to the scFv tethered to a second CM5 chip. However, relative to Fab binding, the cQFD meditope did not saturate the scFv at concentrations as high as 100 µM of meditope. This indicates minimal, if any, affinity of the meditope for the CDRs, consistent with the crystallographic studies.

cQFD Meditope Binding does not Affect Cetuximab Binding to EGFR-Expressing Cells As described above, the cetuximab Fab could bind to the cQFD meditope and EGFR domain III simultaneously. It was further shown that this meditope did not affect cetuximab (full IgG) binding to EGFR-expressing cells. FACS analysis was used to follow the binding of the IgG, as a function of meditope concentration, to MDA MB-468 cells, which overexpress EGFR. Cells were incubated with cetuximab in the presence of increasing cQFD meditope concentrations. Even with meditope concentrations greater than 60 µM, no significant changes in cetuximab binding to the cells were observed. This observation is consistent with the SEC studies described above, and indicates that the meditope does not act as an allosteric regulator of antigen binding.

Simultaneous binding to the Fab of EGFR domain III and the meditope is shown at concentrations significantly above the $K_D$ of the meditope. Like the cQFD and cQYN meditopes, superantigens SpA and PpL, bind to the Fab framework region and do not affect antigen binding (see Graille, M. et al. Crystal structure of a *Staphylococcus aureus* Protein A domain complexed with the Fab fragment of a human IgM antibody: structural basis for recognition of B-cell receptors and superantigen activity. *Proc Natl Acad Sci USA* 97, 5399-404 (2000)); Graille, M. et al. Complex between *Peptostreptococcus magnus* Protein L and a human antibody reveals structural convergence in the interaction modes of Fab binding proteins. *Structure* 9, 679-87 (2001); Young, W. W., Jr., Tamura, Y., Wolock, D. M. & Fox, J. W. Staphylococcal Protein A binding to the Fab fragments of mouse monoclonal antibodies. *J Immunol* 133, 3163-6 (1984); Graille, M. et al. Evidence for plasticity and structural mimicry at the immunoglobulin light chain-Protein L interface. *J Biol Chem* 277, 47500-6 (2002)).

Meditope Binding in Relation to Other Fab-Binding Proteins

The meditope binding site on the Fab is distinct from that of other proteins that bind to the framework region of a Fab. For example, domain D of Protein A, isolated from *Staphylococcus aureus*, binds to the framework of heavy chain ($V_H$) of human IgG; the $B_1$ domain of Protein L, isolated from *Peptostreptococcus magnus*, binds to the framework region of kappa light chain ($V_L$) of human IgG; and domain II of Protein G, isolated from a Streptococcal strain, binds to the framework of heavy chain ($V_C$) of human IgG. Unlike these interactions, in which the interface is predominantly confined to a single Fab domain that is solvent-exposed, the meditope-Fab interface was shown to be formed by all four domains (e.g., the variable and constant domains of the heavy and light chains).

The buried surface areas at the cQFD and cQYN meditope-cetuximab Fab interface were shown to be 904 (±28) Å$^2$ and 787 (±42) Å$^2$, respectively, and generally distributed equally between the light and heavy chains. These values are roughly similar to those for the interfaces of the Protein A, L and G domains bound to their Fab domains: 580 Å$^2$ (1DEE.pdb), 714 Å$^2$ (1HEZ.pdb), and 518 Å$^2$ (1QKZ.pdb), respectively. There are two unique interfaces between the variable region of the Fab and Protein L, which buries 646 Å$^2$, and a minor interaction between the constant region of the Fab and Protein G, which buries 184 Å$^2$.

Steric Mask

Figure 11:
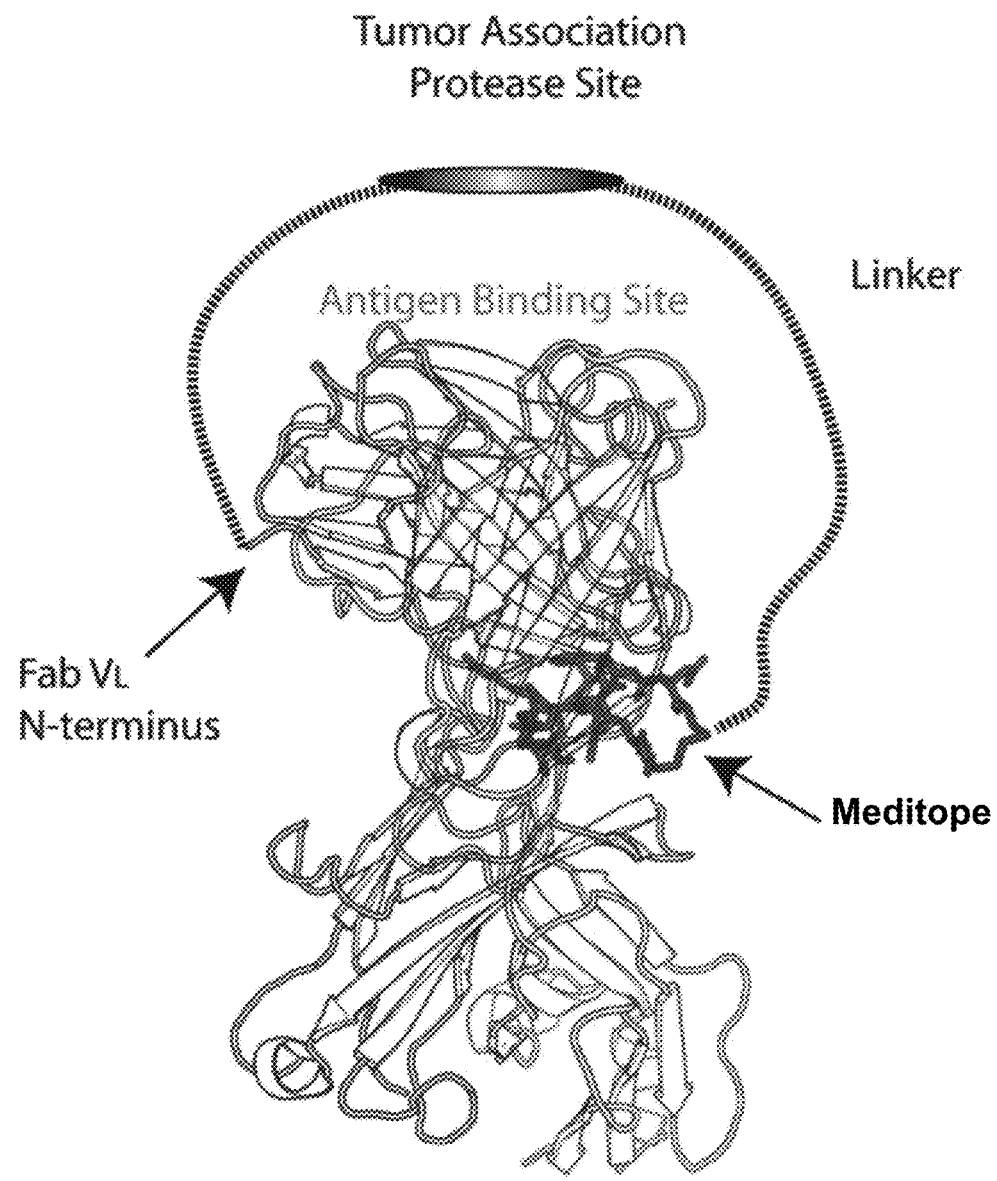
FIG. 11 is a depiction of an exemplary embodiment of a steric mask. In this exemplary embodiment, the meditope is fused to the N-terminus of the Fab light or heavy chain through a flexible linker containing a tumor associated protease site, to sterically occlude the antigen binding site.

The meditope can be tethered to the N-terminus of either the light chain or heavy chain N-terminus of a murine chimera or meditope-enabled human mAb through a flexible linker (FIG. 11). The N-termini of mAb IgGs are juxtaposed to the antigen binding site and the extension from the N-termini through the flexible linker will sterically interfere with antigen binding. By encoding a tumor specific protease site (e.g., MMP9, MMP14, prostate-specific antigen (PSA) serine protease or other suitable site) in the linker, the steric constraint of intramolecular "masked" IgG construct will be severed at the tumor site and permit antibody binding. This design principle would avoid binding of the intramolecularly 'masked' IgG to healthy tissues and avoid adverse side effects due to off-target binding. Off-rate determination for avidin-peptide mask on cetuximab showed that a multivalent meditope bound with higher affinity than a monovalent meditope, but did not mask.

EXAMPLE 4

Generation of Meditope-Enabled Antibodies

Based on structural information, additional meditope-enabled antibodies were generated.

A. Generation of Meditope-Enabled Trastuzumab by Mutation

A meditope-enabled HER2-binding antibody was generated by mutating trastuzumab. The sequence differences between the heavy and light chain variable region framework regions of a human IgG (trastuzumab—1N8Z.pdb) compared to those of cetuximab were mapped onto the crystal structure of cetuximab Fab bound to cQFD meditope. Residues in the human framework corresponding to residues lining the meditope binding site in cetuximab were mutated to contain the corresponding residues present in cetuximab; additionally, S9 and S10 of the light chain, according to Kabat numbering, were mutated to isoleucine and leucine, respectively. FIGS. 23A and 23C show nucleic acid sequences of a portion of the heavy chain (SEQ ID NO: 5) and the light chain (SEQ ID NO: 8), respectively, of the mutant (meditope-enabled) trastuzumab. FIGS. 23B and 23D show the amino acid sequences of a portion of the heavy chain (SEQ ID NO:6) and light chain (SEQ ID NO:9), respectively, of the meditope-enabled trastuzumab. FIGS. 23B and 23D also show a comparison of these amino acid sequences and those of a portion of the heavy and light chain of wild type trastuzumab (SEQ ID NO:7 and SEQ ID NO:10, respectively).

The nucleic acids encoding the heavy and light chains of this mutant, meditope-enabled trastuzumab were synthesized using standard methods and subcloned into a standard vector for mammalian expression. The meditope-enabled trastuzumab IgG was purified using standard methods and characterized for the ability to bind to HER2 and the cQFD meditope.

Meditope-Enabled Trastuzumab Binds to Antigen and Meditope and has Indistinguishable PK/PD Properties as Wild-Type Trastuzumab In one study, to characterize antigen binding, wild-type trastuzumab and meditope-enabled trastuzumab were labeled with Alexa 647 using standard protocols. A cQFD (SEQ ID NO: 1) meditope-Fc fusion protein (produced as described in Example 7 and shown in FIGS. 15 and 16) was labeled with Alexa488 using the same protocols. To show that the meditope-Fc binds to the meditope-enabled trastuzumab and not to the wild-type trastuzumab, SKBR3 cells ($0.5 \times 10^6$), which over-express HER2, were incubated with labeled wild-type and meditope-enabled trastuzumab for 30 minutes. Unbound antibody was washed and the cells were incubated with the meditope-Fc construct for 30 minutes. Antibody binding and meditope binding were analyzed by FACS analysis. The FACS data demonstrate that meditope-enabled trastuzumab binds to HER2 expressed on the SKBR3 cells (e.g., the meditope site can be grafted onto an antibody without loss of antigen specificity) (FIG. 22A), and that the meditope-Fc binds to the meditope-enabled trastuzumab, but not to wild-type trastuzumab (FIG. 22B).

In another study, wild-type and meditope-enabled trastuzumab were labeled with Alexafluor 488 using standard protocols. SKBR3 cells ($0.5 \times 10^6$) were trypsinized, washed once with 0.1% BSA, and incubated with 1, 10, or 100 nM wild-type or meditope-enabled trastuzumab, for 30 minutes. Unbound antibody was washed twice and analyzed by flow cytometry. The results are shown in FIG. 43, demonstrating that meditope-enabled trastuzumab had a similar affinity for antigen-expressing cells as did wild-type trastuzumab.

In another study, a cQFD (SEQ ID NO: 1) meditope-Protein L fusion protein (MPL) was labeled with Alexafluor 647 using the same standard protocols. SKBR3 cells were trypsinized, washed once with 0.1% BSA, and then pre-bound to wild-type trastuzumab (WTT) or meditope-enabled trastuzumab (TM) (by incubation for 30 minutes). The cells then were washed, followed by another 30 min incubation with 0.1 μM or 1 μM MPL (right). Cells were washed twice and analyzed by flow cytometry (FACS). Cells not pre-bound antibody (MPL (WT) only) were used as a negative control. The results are shown in FIG. 44. Histograms demonstrate that cells bound to meditope-enabled trastuzumab, but not unbound cells or cells bound to wild-type trastuzumab, bound to the meditope-Protein L fusion protein. Dot plots show percentage of cells in each quadrant relative to the MPL only control.

As shown in FIG. 45, the same results were obtained using a meditope-Protein L in which all but one lysine in the Protein L were mutated to Arg/Asn residues (MPL-5K).

These data demonstrate that meditope-enabled trastuzumab is able to bind to antigen to the same degree as the wild-type antibody, and that that the meditope-enabled trastuzumab (but not wild-type trastuzumab) binds to the meditope. Thus, these data confirm that binding of the meditopes to the meditope binding site of this antibody did not affect antigen binding in this study, demonstrating the tripartite interaction.

FIG. 50 (top panel) shows stick representations of the structures of meditope 18 (SEQ ID NO: 18, shown in Table 3, with a β,β'-diphenylalanine at position 5) bound to cetuximab (dark grey sticks), the same meditope (18) bound to meditope-enabled trastuzumab (white sticks), and wild-type trastuzumab (outline), superimposed. The bottom panel shows a ribbon cartoon comparing wild-type and meditope-enabled trastuzumab. The results demonstrate that the position of residues important for binding with the meditope are in nearly identical places in cetuximab and the meditope-enabled trastuzumab. The right panel of FIG. 50 shows a ribbon cartoon of wild-type and meditope-enabled trastuzumab, demonstrating little difference in structure.

Likewise, FIG. 51, in the upper-left panel, shows a superposition of the structures of trastuzumab and trastuzumab memAb (labeled "Meditope-enabled Memab") with certain residues involved in meditope-binding in the meditope-enabled antibody illustrated by sticks. The top right panel shows a superposition of the structures of meditope-enabled trastuzumab (memAb) and cetuximab, with the same residues labeled. As shown, Ile83 takes on two rotamers in the respective structures, which was determined not to be problematic, given that in the meditope bound meditope-enabled trastuzumab crystal structure, it assumes the same rotamer as observed in cetuximab. The bottom panel is a 'cartoon/ribbon diagram' figure of all three structures superimposed, demonstrating no significant differences overall.

Some differences in CDR loops were observed, as expected (given binding of these antibodies to different antigens).

Additionally, animal studies indicated that the biodistribution of the meditope-enabled trastuzumab and wild-type trastuzumab were indistinguishable.

These data demonstrate that antibodies can be effectively meditope-enabled, while retaining other functions, by mutating residues to correspond with those in the meditope-binding interface of cetuximab.

Meditope-Enabled Trastuzumab Binds to Meditope and Antigen, Whether Contacted Sequentially or Pre-Mixed with Meditope Another study demonstrated that meditope bound to meditope-enabled trastuzumab with similar efficiency whether the cells were pre-bound with antibody (sequential) or a pre-formed meditope-antibody complex (pre-mixed) was applied to cells. The results are shown in FIG. 46. In this study, SKBR3 cells were trypsinized, washed once with 0.1% BSA, then incubated with 10 nM meditope-enabled trastuzumab (TM) for 30 min, washed, and then incubated for another 30 min with 4, 20, or 100 nM MPL (left panel). Alternatively, 10 nM of TM was premixed with 4, 20, or 100 nM of MPL for 30 min on ice, followed by application of the mixture to the cells for 1 hr (right panel). Cells were washed twice and analyzed by FACS. Percentage of MPL-positive cells relative to no-treatment control is shown in the legend.

B. Generation of Meditope-Enabled HER2-Binding Antibody by CDR-Grafting

A meditope-enabled HER2-binding antibody was generated by grafting the CDRs of trastuzumab onto cetuximab.

Nucleic acid and amino acid sequences of a heavy chain of trastuzumab are shown in FIG. 25A (SEQ ID NOs: 11 and 12, respectively), with signal sequence and other sequences. Nucleic acid and amino acid sequence of a light chain of trastuzumab are shown in FIG. 25B (SEQ ID NOs: 13 and 14, respectively), with signal sequence and other sequences.

While the "boundaries" of the CDR loops of mAbs have been clearly defined by sequence homology structural methods in general, the crystal structure of trastuzumab was superimposed onto cetuximab and the position of each residue examined to address potential differences outside of the CDR loops that may have a secondary effect on the conformation of the CDR loops; based on this information, additional modifications beyond modifying the CDRs. The amino acid sequences of the light and heavy chains of the antibody designed to contain trastuzumab-like CDRs on a cetuximab-like framework were translated into DNA sequences and the genes encoding each were synthesized. The amino acid and nucleic acid sequences of the resulting heavy and light chains of antibodies containing trastuzumab-like CDRs grafted onto cetuximab-like framework are shown in FIG. 47. Specifically, FIG. 47A shows light chain nucleic acid (SEQ ID NO: 60) and light chain amino acid (SEQ ID NO: 61) sequences of a CDR-grafted meditope-enabled trastuzumab (with trastuzumab-like CDRs grafted onto a cetuximab-like framework), with the signal sequence and other residues shaded. FIG. 47B shows heavy chain nucleic acid (SEQ ID NO: 62) and heavy chain amino acid (SEQ ID NO: 63) of this antibody.

The genes were then subcloned in frame into the remaining IgG DNA sequence, confirmed by DNA sequencing and placed in individual expression vectors. The resulting expression vectors were transfected into NS0 cells for co-expression of the heavy and light chains. As the expressed full-length CDR-grafted IgG was secreted, the supernatant was clarified by centifugation, concentrated, and passed over a Protein A column IgG was eluted using a low pH solution and immediately neutralized. SDS-PAGE (poly acrylamide gel electrophoresis) was carried out on the full-length CDR-grafted IgG, under reducing conditions. The results indicated two protein bands with apparent masses consistent with the light and heavy chain. The position of the bands migrated at similar positions compared to wild-type cetuximab.

Figure 24:
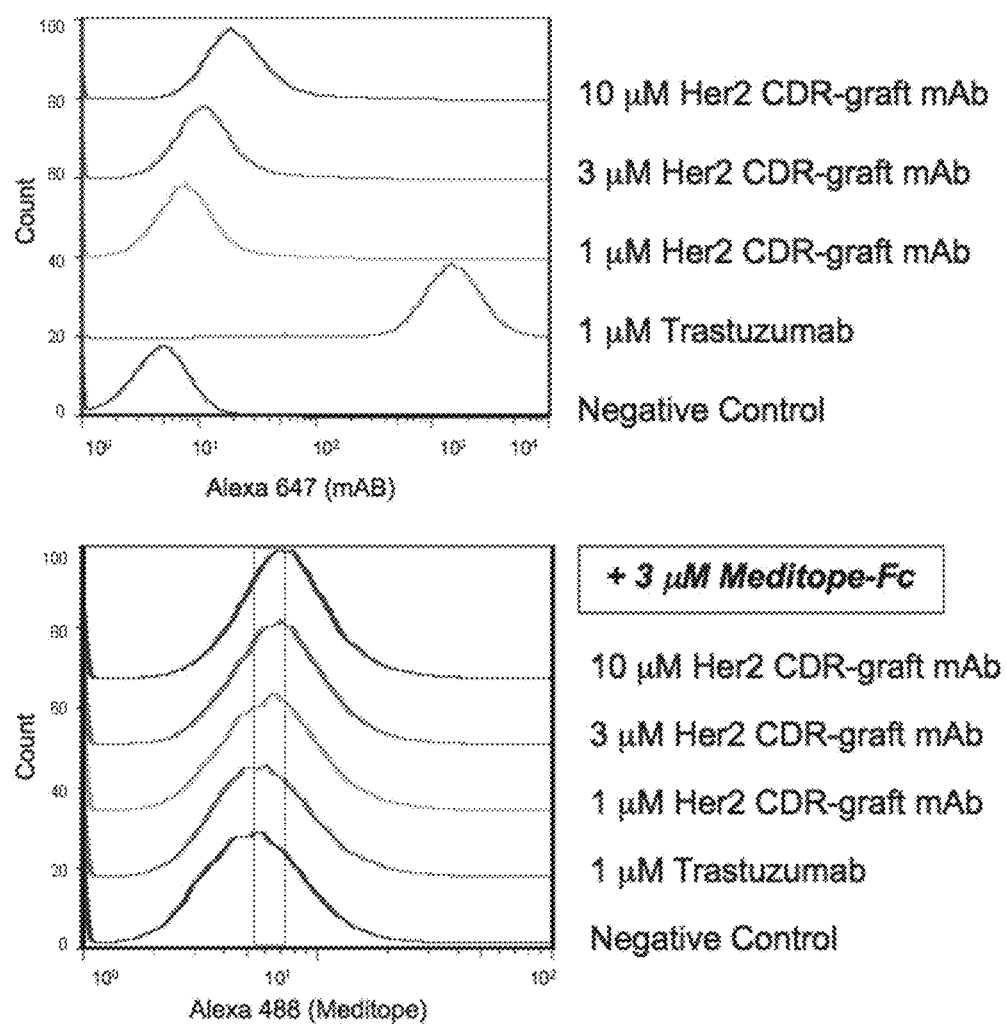
FIG. 24 shows that an antibody containing HER2-binding CDR loops grafted on cetuximab-like framework binds to HER2 and a meditope-Fc.

To characterize antigen binding, wild-type trastuzumab and the trastuzumab CDR-grafted, meditope-enabled mAb (memAb) were labeled with Alexafluor 647 using standard protocols. As described above, cQFD (SEQ ID NO: 1) meditope-Fc (produced as described in Example 7 and shown in FIGS. 15 and 16); Meditope-Fc was labeled with Alexafluor 488 using the same protocols. To show that the meditope-Fc binds to the trastuzumab CDR-grafted, meditope-enabled mAb and not to the wild-type trastuzumab, SKBR3 cells ($0.5 \times 10^6$) which over-express HER2, were incubated with labeled wild-type or CDR-grafted meditope-enabled trastuzumab as produced in this example, for 30 minutes. Unbound antibody was washed and the cells were incubated with the meditope-Fc construct for 30 minutes. Antibody binding and meditope binding were analyzed by FACS analysis. As an important component of the "CDR-grafting." The results are shown in FIG. 24. The FACS data showed that the trastuzumab CDR-grafted, meditope-enabled mAb bound to HER2 expressed on the SKBR3 cells, demonstrating that CDR loops of one antibody (trastuzumab) grafted onto a meditope-enabled antibody (cetuximab) framework retain the ability to bind to antigen (HER2) (FIG. 24A). The FACS data also showed that the meditope-Fc bound to the trastuzumab CDR-grafted, meditope-enabled mAb, but not to wild-type trastuzumab (FIG. 24B), demonstrating that a CDR-grafted meditope-enabled antibody binds to meditope.

It is noted that optimizing the production of the CDR-grafted meditope-enabled trastuzumab would produce more material for more rigorous/quantitative characterization. The low amount of material and thus less rigorous/quantitative characterization (e.g., uncertainty in the final concentration of the meditope-enabled trastuzumab and its labeling with Alexafluor 647) in this study likely accounted for the apparent reduced affinity. There are art-known methods to optimize antigen binding. The data show that the CDR-grafted meditope-enabled trastuzumab bind the trastuzumab antigen (i.e., bind to HER2 overexpressing SKBR3 cells)

and bind to the meditope of SEQ ID NO: 1 (i.e., antigen-expressing cells pretreated with the CDR-grafted meditope-enabled trastuzumab bind to the meditope).

C. Generation of Meditope-Enabled CEA-Binding Antibody (Meditope-Enabled M5A) by Mutation Additionally, an anti-CEA antibody (M5A) was meditope-enabled by mutation of residues to correspond to those of cetuximab. Specifically, as shown with shading in FIG. 56, eight point mutations were introduced in the light chain of the M5A antibody, allowing it to bind to meditopes. The wild-type heavy chain sequence and the meditope-enabled light chain sequence were cloned into a Lonza glutamine selection expression vector and transfected in NS0 cells. Two stable lines were obtained, expressing the meditope-enabled mAb at ~5 mg/L.

Binding of the meditope-enabled M5A to the M5A antigen (CEA) was demonstrated using LS174T cells by FACS. 500 nM of Alexa Fluor 488 labeled wild-type or meditope-enabled M5A was incubated with trypsinized cells and 9 µM of Alexa Fluor 647 labeled meditope-Protein L (see Example 10) for 30 min, room temperature. Cells were washed twice with 0.1% BSA and FACS analysis was performed. The results are shown in FIG. 57. Given that M5A is a humanized antibody with the same backbone as trastuzumab, results showed that the meditope-Protein L bound readily to the wild-type M5A. However, an enhanced binding was observed with the meditope-enabled M5A (M5A 8M), which is due to avidity gained from simultaneous binding of both the meditope and Protein L.

Additionally, SPR measurements were carried out as described herein using surface plasmon resonance, confirming binding of various meditope variants to this meditope-enabled antibody, including CQA (diphenyl)DLSTRRLKC (SEQ ID NO:17); CQFDA(diphenyl)STRRLKC (SEQ ID NO:18), meditope 31, and the cQYN meditope (FIG. 58).

EXAMPLE 5

Modification of the Meditope Binding Site

The residues lining the meditope-binding site of one or more of the provided meditope-enabled antibodies, such as cetuximab, are systematically or randomly altered, for example, using degenerate libraries and selection, to enhance and/or change the specificity of the meditope or meditope analogs (see Sheedy et al. 2007 and Akamatsu et al. 2007, for methods of making alterations). Residues at these positions are substituted with natural or non-natural amino acids or both, for example, to improve the affinity of the meditope interaction and/or alter another property of the meditope-antibody interaction.

Figure 21:
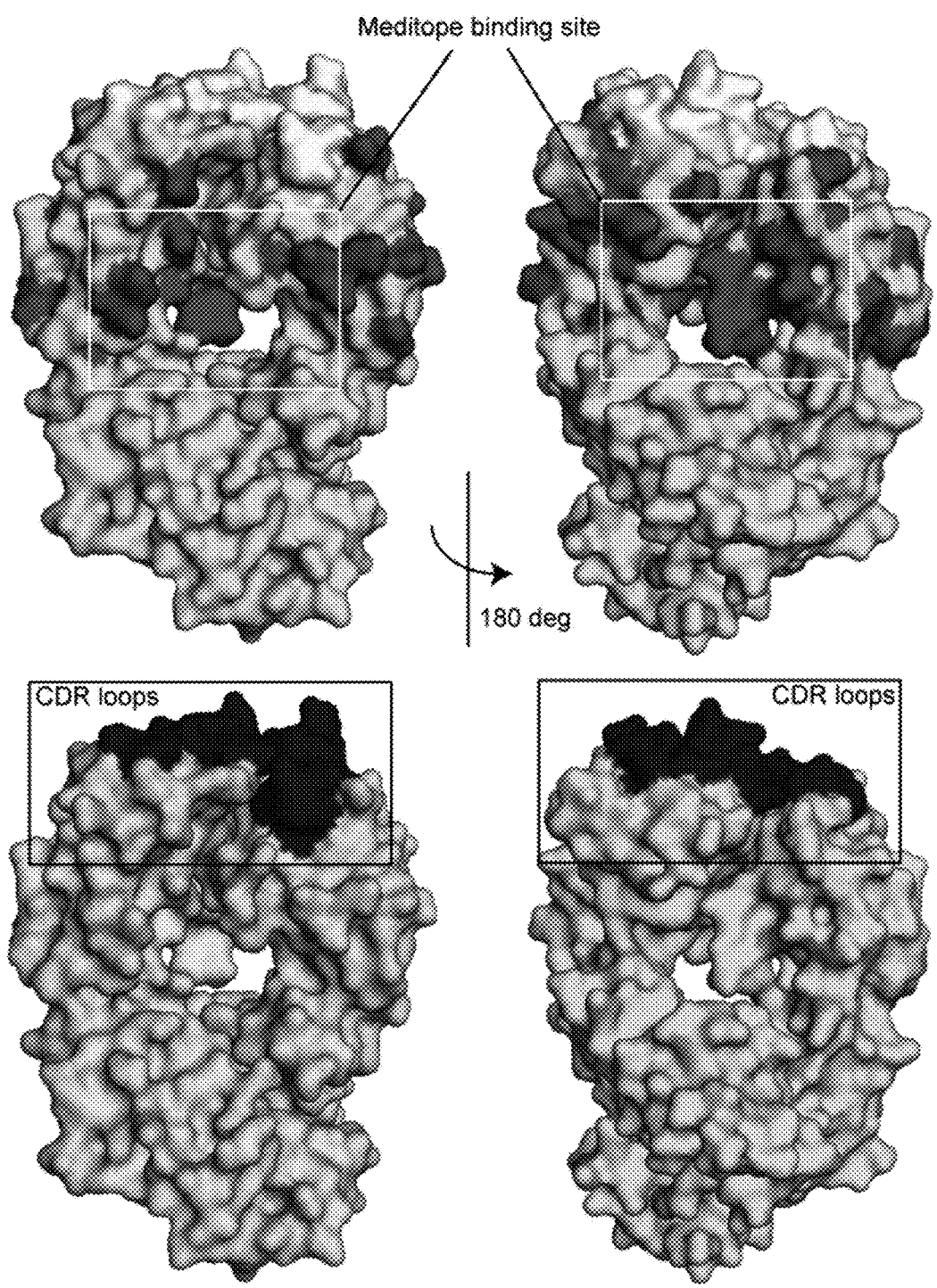
FIG. 21 shows surface representation of sequence differences of cetuximab and trastuzumab. The dark grey regions in the top panel indicate amino acid differences between cetuximab and the fully humanized trastuzumab framework. Certain residues inside the box have been mutated onto the trastuzumab framework. The CDR loops of trastuzumab have been identified (dark regions; bottom panel) and grafted onto the cetuximab framework.

Residues of meditope-enabled antibodies that make contact with the meditope, line the cavity, and/or are otherwise important (such as residues described for modification herein), are mutated. In one example, structural data, such as those obtained in the studies described above, are used to replace residues in the Fab, by mutagenesis, for example, to add additional hydrogen bonds, substitute amino acids for unnatural amino acids or alter the hydrophobic interface, for example, in ways that might better complement meditope binding. (See FIG. 21).

In one example, individual residues are systematically altered, followed by production and characterization of the mutant antibodies. In another example, a library of IgGs is generated at the DNA level using degenerate oligos at sites of interest to produce members that collectively encode all 20 naturally-occurring amino acids at the site or sites of interest, such that the library produces individual members of the library having each amino acid substituted at one or more given site.

A GPI domain was added, e.g., to the C-terminus of the Ig heavy chain, of the antibodies in the library. In one example, the library is transfected using standard methods; antibodies (e.g., IgGs) from the library are expressed.

To demonstrate binding to a GPI-linked meditope-enabled antibody according to these methods, a GPI-linked meditope-enabled trastuzumab was produced. FIG. 54 shows that this GPI-linked meditope-enabled trastuzumab bound to a meditope-Protein L (MPL), produced as described in Example 10, below. In this study, 1×10^6 cells/sample were used. Cells were removed from plates by gentle pipetting and were washed once with 0.1% BSA (w/v) in PBS. AF647 MPL was diluted to 10 nM in wash buffer and incubated with cells for 30 min at room temperature. Cells were washed twice and then analyzed by FACS.

Figure 20:
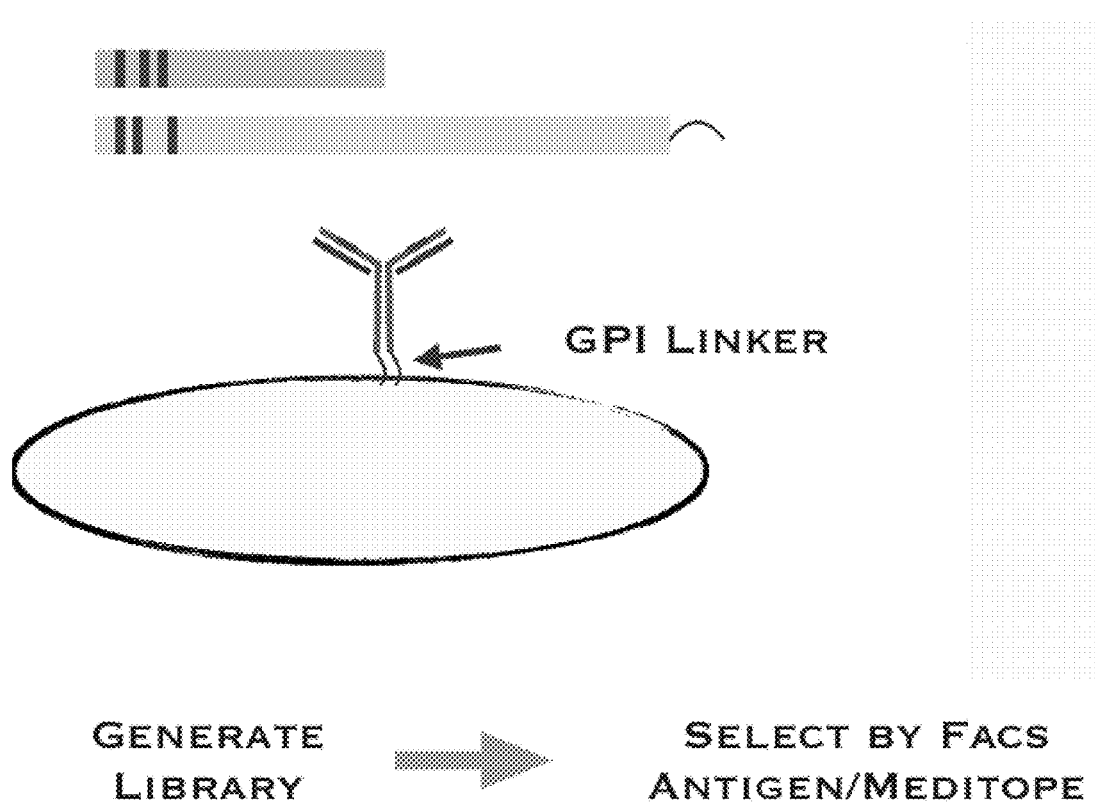
FIG. 20 illustrates exemplary steps to alter and/or enhance the binding affinity (or alter another property) of a mAb for a meditope or compound binding at the meditope site using a directed random library. Specifically, a gene library where codons for mAb residues that line the meditope binding site are replaced with NNK (where N is any nucleotide and K is a thymidine or guanosine) can be selected using FACS sorting (where the meditope and the antigen are labeled with distinct fluorophores). In another embodiment, the codons are substituted with NNN, where N is any nucleotide. The GPI linker can ensure the selected mAb remains associated with the cell transfected with vectors encoding the gene sequences. Sequencing the genes encoding the light and heavy chain from the selected cells will identify high affinity mAbs. The method can be repeated to select for higher affinity meditope or meditope analogs.

Antibodies produced from the library are screened for one or more desired traits. In one example, to select mutations that do not affect antigen binding, antibodies from the library (e.g., cells expressing the antibodies) that bind to a fluorescently labeled antigen to which the antibodies specifically bind (e.g., HER2, EGFR, IGFR, CLTA-4, etc.) are selected, e.g., by FACS (FIG. 20). In one example, antibodies selected for their antigen-binding capabilities are subjected to another round of selection, for example, to select for mutant antibodies that bind to a specific meditope, meditope analog, or other molecule of interest.

Following selection, the selected antibodies are characterized to determine the desired combination of mutations. In one example, following cell sorting, PCR is used to identify the resulting mutations that facilitate or enhance meditope/analog/small molecule binding. In one example, this process is repeated multiple times to 'evolve/optimize' the desired characteristic, e.g., binding, pH dependency, PK, and/or PD.

EXAMPLE 6

Variant Meditopes

Several variant meditopes were generated. For example, certain meditope variants in Tables 3 and 4 (above) were-synthesized, with demonstrated binding affinities to cetuximab. For the peptides in Table 3, a disulfide linkage was used to connect the C and N termini (except that meditope 31 contained an additional tail, meaning that the disulfide linkage is not between the two terminal residues). Meditopes 26, 27, 28, and 29 were biosynthesized and thus in this example, contained an additional serine before the first cysteine, i.e., position zero. Further, in some embodiments, meditope 31 may optionally include a GGSK linker. For the peptides in Table 4, a lactam bridge, a linkage other than disulfide (such as [3+2] cycloaddition), or no linkage was used as the connector. For example, meditope 55 is a linear peptide that binds within the meditope-binding site. Individual meditopes in these tables are discussed below.

As described above, the cyclic peptide cQFD (SEQ ID NO: 1) and cQYN (SEQ ID NO: 2) were identified and co-crystallized with cetuximab Fab, and shown to bind in a cavity created by the light and heavy chains of the Fab.

gen bond with the heavy chain carbonyl of Q105 of the meditope-enabled antibody heavy chain. The immediate area about this residue is hydrophobic, yet solvent-exposed (FIG. 33A).

Structural data indicated that incorporation of a modified Arg8 residue that maintains the guanidinium functionality for meditope-enabled antibody H-bonding, while simultaneously introducing a hydrophobic arm to partially fill the cavity, could produce significant gains in binding, due to entropic increases, as supported by ligand docking calculations.

A variant meditope was generated containing an n-butyl-arginine at position 8, meditope 54 (SEQ ID NO: 54, shown in Table 4), as follows:

Synthesis of Fmoc-N-Butyl Arg Derivative 3 (Meditope 54)

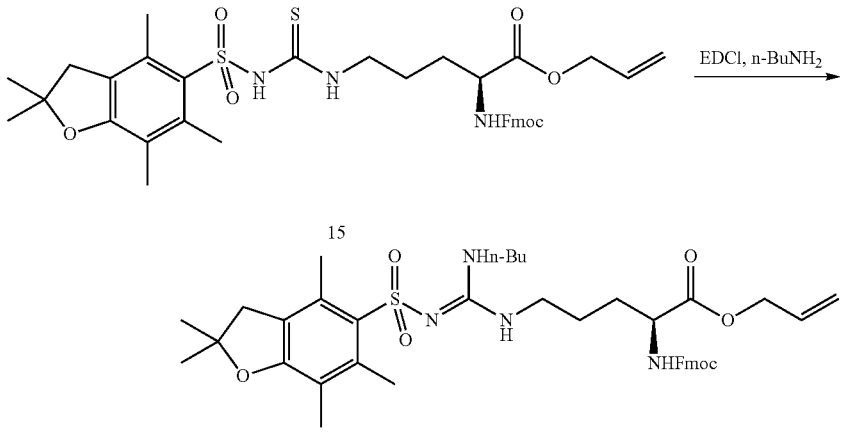

Biophysical and biochemical methods were used to characterize this interaction. Specifically, mutation of Phe3, Leu5, and Arg8 to alanine reduced the affinity of the meditope for the binding interface by 44-183-fold. See Tables 6 and 7.

Meditope Modification and Chemistry Design

Based on the structural and thermodynamic data, multiple positions within the provided meditopes were identified as targets for modification, e.g., with substitutions and/or non-natural amino acids, for example, to enhance the overall binding affinity and/or to alter another property. Modifications included generation of head-to-tail cyclic lactam peptides, modification of Arg8, modification of Phe3, modification of Leu5, modification of Leu10, and incorporation of hydratable carbonyl functionality (see FIG. 31).

Modification of Arg8.

Modifications were made to Arg8. Based on structural data, it was determined that Arg8 of the unmodified meditope (cQFD; SEQ ID NO: 1) is extended, making a hydro- To a stirred solution of 15, above, (23 mg, 0.03 mmol) in $CH_2Cl_2$ (0.6 mL) were added EDCI (12 mg, 0.06 mmol, 2 equiv) and n-butylamine (4.4 mg, 0.06 mmol, 2 equiv). After 5 min at room temperature (rt), the solvent was removed in vacuum. The residue was purified by silica gel column chromatography (40-50% EtOAc/Hex) to afford the product 16, above, (23 mg, 95%). $^1$H NMR (400 MHz, $CDCl_3$) δ 7.78-7.70 (m, 2H), 7.60-7.54 (m, 2H), 7.42-7.37 (m, 2H), 7.35-7.27 (m, 2H), 5.95-5.83 (m, 1H), 5.52-5.42 (m, 1H), 5.36-5.22 (m, 2H), 4.61 (d, J=5.4 Hz, 2H), 4.44-4.30 (m, 3H), 4.16 (t, J=6.4 Hz, 1H), 3.30-3.02 (m, 4H), 2.92 (s, 2H), 2.54 (s, 3H), 2.48 (s, 3H), 2.07 (s, 3H), 1.98-1.80 (m, 1H), 1.76-1.50 (m, 3H), 1.45 (s, 6H), 1.36-1.26 (m, 4H), 0.85 (t, J=7.2 Hz, 3H); $^{13}$C NMR (100 MHz, $CDC_3$) δ 171.9, 158.7, 156.4, 155.0, 144.0, 143.8, 141.5, 138.5, 133.8, 132.4, 131.5, 128.0, 127.3, 125.2, 124.6, 120.3, 119.6, 117.6, 86.5, 67.4, 66.5, 53.3, 47.3, 43.5, 41.5, 41.0, 30.9, 30.7, 28.8, 25.4, 20.2, 19.5, 18.2, 13.9, 12.7; HRMS $C_{41}H_{52}N_4O_7S$ [M+Na]$^+$ calc'd 767.3449. found. 767.3455.

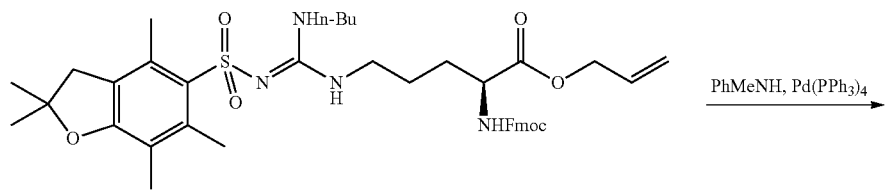

16

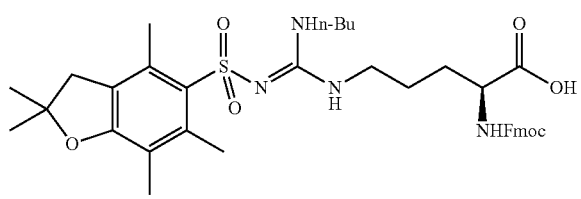

17

To a stirred solution of 16, above, (23 mg, 0.03 mmol) in THF (0.8 mL) were added N-methylaniline (10 mg, 0.09 mmol, 3 equiv) and Pd(PPh$_3$)$_4$ (2 mg, 0.0015 mmol, 0.05 equiv). After 45 min at rt, the solvent was removed in vacuum. The residue was purified by silica gel column chromatography (MeOH:CH$_2$Cl$_2$:HOAc=25:1:0.1) to afford the product 17, above, (20 mg, 90%). $^1$H NMR (400 MHz, CDCl$_3$) δ 7.78-7.70 (m, 2H), 7.60-7.54 (m, 2H), 7.40-7.34 (m, 2H), 7.30-7.24 (m, 2H), 5.95-5.83 (m, 1H), 4.48-4.10 (m, 5H), 3.30-3.02 (m, 4H), 2.90 (s, 2H), 2.58 (s, 3H), 2.50 (s, 3H), 2.07 (s, 3H), 2.00-1.86 (m, 1H), 1.86-1.74 (m, 1H), 1.72-1.60 (m, 2H), 1.45 (s, 6H), 1.30-1.22 (m, 4H), 0.82 (t, J=7.2 Hz, 3H); $^{13}$C NMR (100 MHz, CDCl$_3$) δ 174.9, 158.9, 156.6, 155.2, 144.0, 143.8, 141.5, 138.5, 133.3, 132.4, 129.3, 128.5, 128.0, 127.3, 125.3, 124.8, 120.2, 117.7, 86.6, 67.4, 53.4, 47.4, 43.4, 41.6, 41.1, 31.4, 29.9, 28.8, 25.2, 20.1, 19.5, 18.2, 13.9, 12.7;HRMS C$_{38}$H$_{48}$N$_4$O$_7$S [M+Na]$^+$ calc'd 727.3136. found. 727.3144.

See Martin, N. I., and Liskamp, R. M. *J. Org. Chem.* 2008, 73, 7849-7851.

Synthesis of Arg-Butyl Meditope 54.

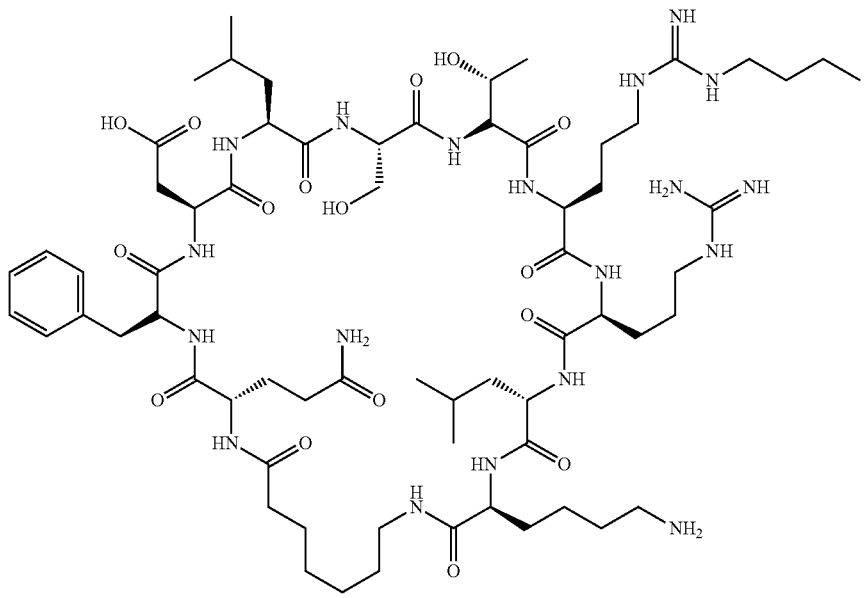

Additionally, meditope 54 ((SEQ ID NO: 54), in the above structure) was prepared as according to solid phase Fmoc synthesis protocol using Fmoc-N-butyl Arg derivative 17. FIG. 59 shows an HPLC trace and mass spectrum of meditope 54.

The structure of meditope 54 bound to a cetuximab Fab fragment (backside view) is shown in FIG. 48, with structures of the 5-position β,β'-diphenylalanine meditope (SEQ ID NO: 18, meditope 18) and cQFD (meditope 1, SEQ ID NO: 1) superimposed. As shown in Table 7, below, meditope 54 was determined by SPR to bind to cetuximab with an average $K_D$ of 745.2 nM.

In some examples, this meditope-enabled antibody binding pocket identified in these studies is explored as described herein for new contacts (meditopes or analogs) that may increase affinity of a meditope-meditope-enabled antibody interaction.

Modification of Phe3.

Figure 30:
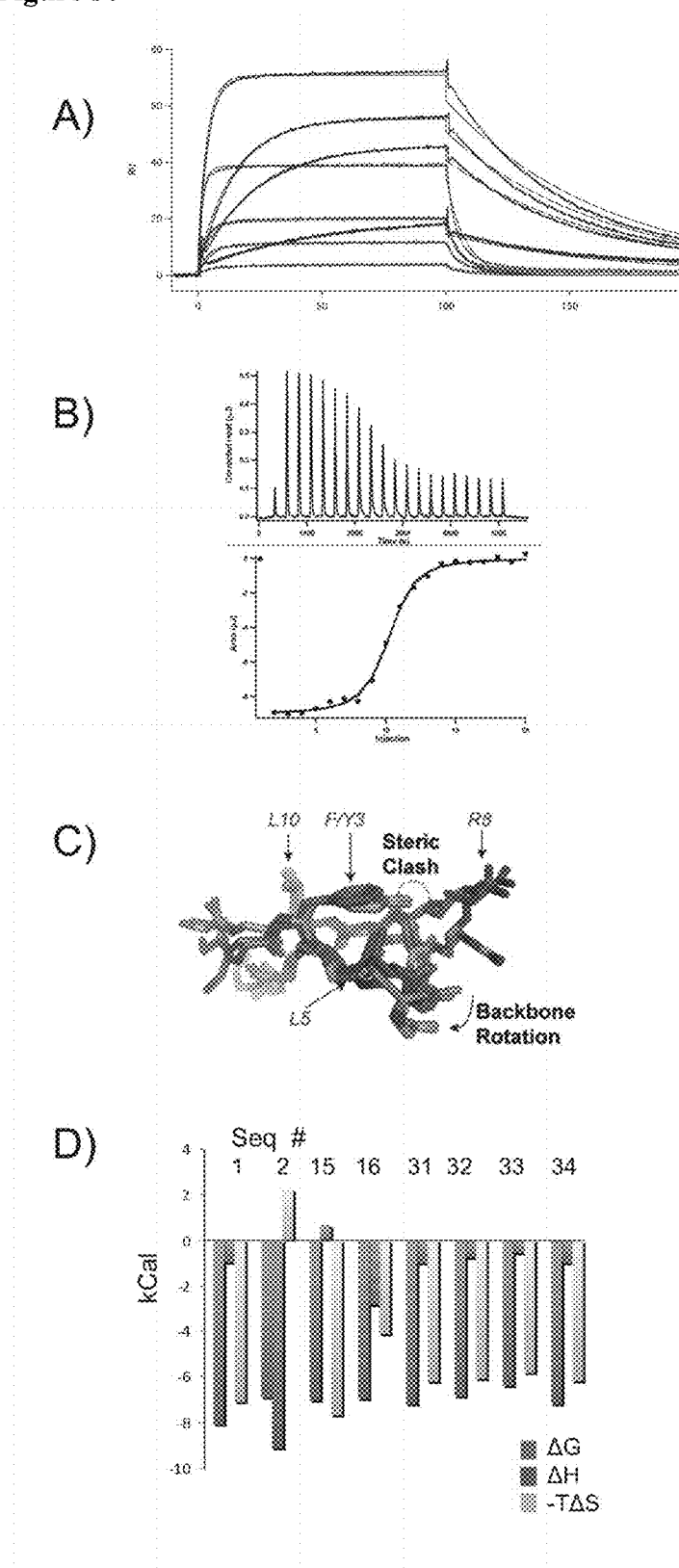
FIG. 30 shows biophysical data obtained for the meditopes.

Various modifications were made to Phe3 of cQFD. Structural data demonstrated that the hydroxyl group of the meditope variant Phe3Tyr cQYN (SEQ ID NO: 2) has an alteration in the extended conformation of the Arg8 side chain as compared to cQFD (meditope 1) (see FIGS. 30C and 35). SPR demonstrated that the overall affinity of this variant for the cetuximab Fab was reduced. ITC measurements indicated a significant decrease in entropy for this Phe3Tyr cQYN variant upon binding that was off-set by a favorable increase in enthalpy compared to unmodified meditope (SEQ ID NO: 1) (from −2.1 kCal/mol to −7.9 kCal/mol [n=3]) (FIG. 30D). Structural data suggested the formation of a favorable hydrogen bond network, with water bound to the Fab.

It was determined that when bound to a meditope-enabled antibody, the hydrophobic phenyl ring of Phe3 was surrounded by a fairly polar array of side chain residues of a meditope-enabled antibody (cetuximab) Fab (FIG. 35). It was desired to introduce one or more halogen atom onto the phenyl ring, which could participate in halogen bonding (relatively strong non-covalent bonding, similar to a hydrogen bond but involving the interaction of a halogen such as bromine or chlorine with an oxygen atom), such as by incorporation of an ortho-meta- and/or para-bromo phenyl substituent to favorably place a bromine atom for halogen bonding with Tyr87 (light chain), Gln39, and/or Tyr91 (heavy chain) of a meditope-enabled antibody, respectively. Meditopes 36 (SEQ ID NO: 36), 37 (SEQ ID NO: 37), and 38 (SEQ ID NO: 38) were generated, containing 2-bromo-L-phenylalanine, 3-bromo-L-phenylalanine, and 4-bromo-L-phenylalanine, respectively, in place of the Phe at position 3. These meditopes were co-crystallized with cetuximab Fab. These commercially available derivatives were incorporated by SPPS. Structures are shown in FIG. 39. Diffraction data are shown in FIG. 40. Affinities of some of these meditopes for the cetuximab Fab (average $K_D$ values) were determined by SPR and are listed in Table 7, below.

Additionally, based on the structural information for the meditope containing a Phe3His mutation (meditope 33, SEQ ID NO: 33), a meditope was synthesized with β,β'-diphenylalanine at position 3 (meditope 17, SEQ ID NO: 17). As shown in FIG. 41, a significant improvement in the binding affinity for cetuximab was observed by SPR, representing a roughly 4-fold increase compared to cQFD (increase in affinity by a factor of approximately 4 to 5 (~200 nM)).

Modification of Leu5 and Leu10.

Modifications were made to Leu5 and Leu10. It was determined that the Leu5 and Leu10 side chains make hydrophobic contacts to the meditope-enabled Fab (FIG. 36, right panel; Leu10). In one example, natural amino acids (Phe/Tyr/Trp) and/or non-natural analogs (e.g., β,β'-diphenylalanine, branched alkyl, extended aromatics such as napthyl, etc.) are systematically introduced via SPPS at one or both of these positions. The observation, above, that introduction of β,β'-diphenylalanine at position three increased the overall affinity for the cetuximab Fab (see FIGS. 41-42), demonstrated success by introducing such non-natural amino acids in the meditopes. Accordingly, a β,β'-diphenylalanine was introduced at position 5 and the average affinity of the resulting meditope (meditope 18, SEQ ID NO: 18) determined by SPR to be 687 nM (see Table 7, below). These data confirm that use of structural biology to identify regions for alteration and mutation of residues are useful to alter characteristics of the meditopes, such as to improve their binding kinetics. In another embodiment, the same modification may be made to Leu10.

Alternative Cyclization Strategies and Replacement of Disulfide Bridge

Alternative cyclization strategies were used to replace the disulfide bridge in cQFD and other meditopes. As shown in Table 4, various lactam cyclization strategies were used, including those involving natural and non-natural amino acids, generated based on different starting materials, including glycine, β-Ala, 7-aminoheptanoic acid, diaminopropionic acid, and isoaspartic acid, to produce different lactam ring sizes (see FIG. 31, left and middle boxes).

In one example, a 7-aminoheptanoic acid was used to replace the disulfide bridge of the original cQFD meditope, and the affinity of the resulting meditope for the cetuximab Fab fragment determined by SPR (meditope 42, SEQ ID NO: 42). The SPR data are shown in FIG. 41, bottom panel. Although the binding affinity was decreased compared to cQFD, these data indicate that modifications can be made to the meditope to address potential issues with pharmacokinetics, pharmacodynamics and toxicity in animal and human studies. It is noted that alternative linkers can be combined with unnatural amino acids at other positions within the meditope.

Other variant meditopes with lactam linkages were generated using glycine, 7-aminoheptanoic acid, iso-aspartic acid, β-alanine, and diaminopropionic acid (see meditopes 42, 43, 44, 45, 46, 49, 51, 52, 53, and 54, listed in Table 4 and others). Affinities for some of these meditope variants for cetuximab Fab are listed in Table 7.

An azide alkyne Huisgen cycloaddition was used to produce a triazole as a linkage in meditope 50, by incorporating propargylglycine at position 12 and beta-azidoalanine at position 1 and carrying out a cyclization between these termini.

Additional cyclization strategies, such as 'click' chemistry and olefin metathesis, also were used (FIG. 31, right boxes). For example, head-to-tail lactam peptides were designed and synthesized by solid phase peptide synthesis (SPPS) starting from Fmoc-Asp (Wang resin LL)-Oall (FIG. 31, lower left box & FIG. 32). One such variant, meditope 32 (SEQ ID NO: 32), with FITC conjugation, was shown to bind to cetuximab in a similar manner but with slightly reduced affinity compared to the unmodified meditope of SEQ ID NO: 1 (meditope 1). Other head-to-tail lactam variant meditopes produced include meditopes 33-47, 49, and 50-54 (see Tables 4 and 7). Meditope 48 in Table 4 was engineered with a disulfide linkage and a 4:11 lactam linkage.

Meditope 32 was conjugated with fluorescein for FACS analysis. In another example, this strategy is applied to conjugate the meditope with DOTA for in vivo PET imaging.

Structural data demonstrated that additional positions are amendable to cyclization, such as by cyclization between residues 3 and 11 or 4 and 11.

Meditope 55, a linear peptide, was produced and demonstrated to bind to the meditope-enabled antibody, cetuximab, albeit with reduced affinity.

Hydratable Carbonyl Functionality.

In another example, a meditope with hydratable carbonyl capabilities is developed to create a highly selective but irreversible interaction. Several Fab hydroxyl-bearing side chains in a meditope-enabled antibody that surround the meditope cavity are exploited through selective trapping, by formation of their corresponding hemi-acetal or -ketal, using a hydratable-enabled meditope. For example, Arg8 of the meditope extends in proximity to Ser43 of the light chain (3.5 Å) and Tyr91 of the heavy chain (3.8 and 4.0 Å) of the meditope-enabled antibody light chain, according to Kabat numbering (FIG. 36, left panel). In one example, incorporation of a hydratable carbonyl functionality at the end of Arg8 or Leu10 of the meditope allows selective formation of a serine or tyrosine hemi-acetal, which essentially affords irreversible binding. In another example, a residue containing boronic acid is integrated into the meditope as an alternative to a hydratable carbonyl group. Boronic acid plays an important role in the structural activity of bortezamib (Velcade®), which is used to treat multiple myeloma. Representative examples of such hydratable residues are also shown in FIG. 36 or 34, where R=—$CH_2CHO$ or —$CH_2B(OH)_2$. In some examples, such analogs are modified using SPPS (Duggan, P. J. and D. A. Offermann (2007). "The Preparation of Solid-Supported Peptide Boronic Acids Derived from 4-Borono-L-phenylalanine and their Affinity for Alizarin," *Australian Journal of Chemistry*, 60(11): 829-834.

Other Methods

In some examples, fluorescence polarization assays are used to identify meditope variants that can displace a given meditope, such as SEQ ID NO: 1. In other examples, the same technique is used to identify small molecules that can displace the meditope and then use these small molecules as templates to further improve the binding affinity of the meditopes.

Characterization of Meditopes

For characterization, variant meditope peptide lyophilized powders were suspended in 500 µL of 10 mM Tris pH 8.0 buffer and dialyzed 3 times into 1 L of $H_2O$ each time. The final volume after dialysis was carefully measured and absorbance measurements were taken to estimate the concentration (typically 1-10 mM). These stock solutions were used to make dilutions into HBS-EP buffer (10 mM Hepes pH 7.4, 150 mM NaCl, 3 mM EDTA and 0.05% v/v surfactant P20) for SPR measurements. SPR measurements were carried out on the GE Biacore T100 instrument using a CM5 chip with cetuximab IgG or cetuximab Fab ligand immobilized using amine coupling chemistry. Ligands were immobilized at low levels suitable for kinetic data. Typical kinetics SPR experiments were carried out at a flow rate of 30 µL/min using HBS-EP as both running and regeneration buffer. Kinetic parameters were calculated using the Biacore T100 evaluation software version 2.0.1.

Isothermal titration calorimetry experiments were performed in 100 mM Hepes, pH 7.4 at 25° C. using Nano ITC calorimeter (TA Instruments). In a typical experiment, 250 µl of protein (Fab or IgG) at 0.03-0.06 mM were loaded into the calorimeter cell (163 µl or 185 µl) and the titrant (meditope, at 0.3-0.8 mM) was loaded into a 50 µl syringe. The cell solution was stirred at 250 rpm and upon equilibration the titrant was added in 2-2.5 µl increments. Heat of the reaction was measured and the data was processed using NanoAnalyze software (TA Instruments). Background heat was subtracted by averaging the last four measurements or by subtracting heat of reaction obtained from titration of the meditope at the same concentration into buffer containing no protein.

A number of the meditope variants were co-crystallized with cetuximab Fab fragment. Meditopes were purified to >95% homogeneity and structurally characterized by mass spectrometry. Peptides were dialyzed in water. Their concentrations were measured, for example, in some cases, by UV-Vis and calibrated with elemental analysis, and diluted (>100×) into the appropriate buffer. The structures of some of these meditope variants, corresponding to SEQ ID NOs: 15-18, 22-25 and 31-40, are shown in FIG. 39.

Interactions of various meditopes with the meditope-enabled antibody cetuximab were characterized by X-Ray diffraction. Since the co-crystallization conditions of the cetuximab Fab fragment and the meditope of SEQ ID NO: 1 are well-established, diffraction quality crystals were typically obtained in 1 to 3 days, typically 1 day. Full data sets were collected in 8 to 12 hours with an in-house source (Rigaku 007-HF and an R-Axis IV++) and in less than 10 min at the Stanford Synchrotron Radiation Lightsource, which allows for rapid characterization of the interactions of the meditope variants with cetuximab.

Diffraction data were collected for various different meditope-Fab (cetuximab) complexes, including complexes containing the cQFD (SEQ ID NO: 1) and cQYN (SEQ ID NO: 2) meditopes and modified meditopes. X-ray diffraction data for several meditopes are shown in FIG. 40. Most of these co-crystal structures were shown to diffract beyond 2.4 Å and be well refined, with R and $R_{Free}$ less than 20 and 24%, respectively. All of these meditope variants have very good stereochemical values (Molprobity scores above $89^{th}$ percentile).

For SPR measurements, low density and high density chips were conjugated with the cetuximab Fab or full IgG. Each chip was first characterized using a soluble fragment of the entire extracellular domain of EGFR (residues 1-621). Similar kinetics and binding affinities were observed as previously reported. Using the low density chips, on and off rates were measured for the unmodified meditope and determined to be $k_{on}=9.2\times10^{-4}$ $M^{-1}$ $s^{-1}$ and $k_{off}=9.9\times10^{-3}$ $s^{-1}$, respectively. With meditopes of SEQ ID NO: 1 and 2, consistent with ITC, similar values for the Fab-conjugated chip and the IgG-conjugated chip were observed, demonstrating that either can be used for binding assessments.

Table 7, below, lists information on the average dissociation constants ($K_Ds$), which were determined by SPR, for several of the meditopes listed in Tables 3 and 4.

TABLE 7

Dissociation Constants Determined by SPR

| SEQ ID NO/ Meditope No. | Average $K_D$ (nM) |
|---|---|
| 1 | 898.8 |
| 2 | 3500 |
| 15 | 18300 |
| 16 | 2828 |
| 17 | 624.9 |
| 18 | 687 |
| 21 | 11180 |
| 22 | 54820 |
| 23 | 9460 |

TABLE 7-continued

Dissociation Constants Determined by SPR

| SEQ ID NO/ Meditope No. | Average $K_D$ (nM) |
|---|---|
| 24 | 14180 |
| 25 | 39340 |
| 26 | 34000 |
| 27 | 57000 |
| 28 | 140000 |
| 29 | 2200 |
| 31 | 102.5 |
| 32 | 5041 |
| 33 | No binding observed |
| 34 | No binding observed |
| 35 | No binding observed |
| 36 | 1791 |
| 37 | 29130 |
| 39 | 8186 |
| 40 | No binding observed |
| 41 | No binding observed |
| 42 | 1520 |
| 43 | 1619 |
| 44 | 16490 |
| 45 | 4634 |
| 46 | 5467 |
| 48 | 517.1** |
| 49 | 23800 |
| 50 | 21002 |
| 51 | 433.3 |
| 52 | 1264 |
| 53 | No binding observed |
| 54 | 745.2 |
| 55 | 8684 |

**In this study, meditope 48 hydrolyzed to the original meditope.

Binding of several meditopes to the meditope-enabled antibody cetuximab was rigorously characterized by ITC, SPR, X-ray diffraction and combinations thereof. ITC measurements were performed on a TA Instruments nanoITC, with as little as 1-2 mg of peptide per measurement. ITC, SPR and X-ray diffraction data, e.g., collectively, provide atomic detail to guide subsequent chemical modifications and ultimately improve the affinity of the meditopes and/or make other alterations to the meditopes. A calculation based on ΔG=−RT ln Ka shows that the difference between micromolar and nanomolar affinity of a meditope for cetuximab results from a change in free energy at 300 K of ~4 kCal/mol, which is on the order of a strong hydrogen bond. Thus, the loss of an ordered water molecule from a protein binding pocket or the reorientation of an amino acid residue-chain may be sufficient to alter binding by orders of magnitude.

The data in this example demonstrate that a large number of meditope permutations may be systematically and efficiently introduced, indicating that a large number of meditope variant permutations may be generated, for example, to produce altered meditope-meditope enabled antibody binding affinity, pharmacokinetics (PK), pharmacodynamics (PD), toxicity, and/or ability to bind or strength of binding under differing conditions, such as pH, e.g., pH dependence, for example, to produce high affinity meditopes.

In one example, after characterization by ITC, SPR and diffraction methods, the meditope with the highest affinity (or other desired property, e.g., pH dependence) is subsequently modified, e.g., to further improve the desired property (e.g., overall affinity or pH dependence).

EXAMPLE 7

Generation of Multivalent Meditopes

Bivalent and other multivalent meditopes were generated, e.g., for use in enhancing selectivity and/or binding affinity by "cross-linking" meditope-enabled antibodies on the surface of cells expressing antigen.

Bivalent Meditope-Fc

Figure 16:
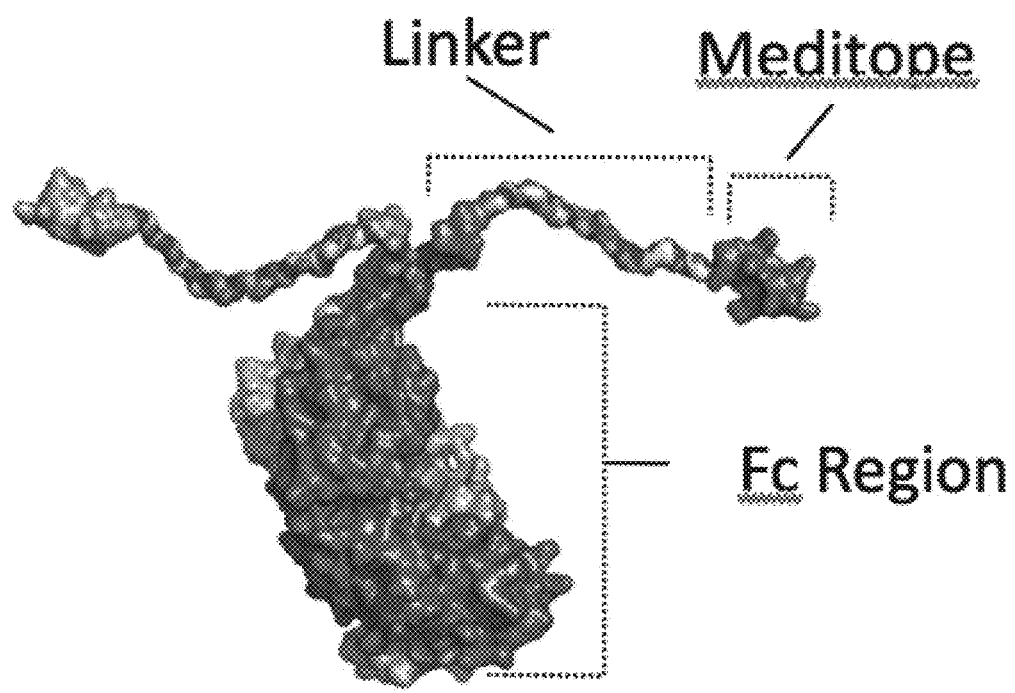
FIG. 16 shows an exemplary bivalent meditope. The meditope is directly fused to the N-terminus of a peptide linker that is directly fused to the Fc Region of an IgG. In this example, as the Fc is naturally homodimerized during expression, the end product from the meditope-Fc construct is bivalent.

The use of the Fc region to 'dimerize' ligands is established and described, for example, by Jazayeri J A & Carroll G J., "Fc-based cytokines: prospects for engineering superior therapeutics," *BioDrugs*, 22(1):11-26 (2008) To generate a bivalent meditope, the meditope cQFD (SEQ ID NO: 1) was fused to the N-terminus of the Fc region of an IgG through a flexible peptide linker of 17 amino acids in length, comprised of glycine and serines. The length of the linker was chosen to roughly match the distance between the Fabs of an IgG. The nucleic acid and amino acid sequences of the resulting "meditope-Fc" are shown in FIG. 15 (SEQ ID NO: 3 and 4, respectively). The structure of the meditope-Fc is shown in FIG. 16.

Figure 17:
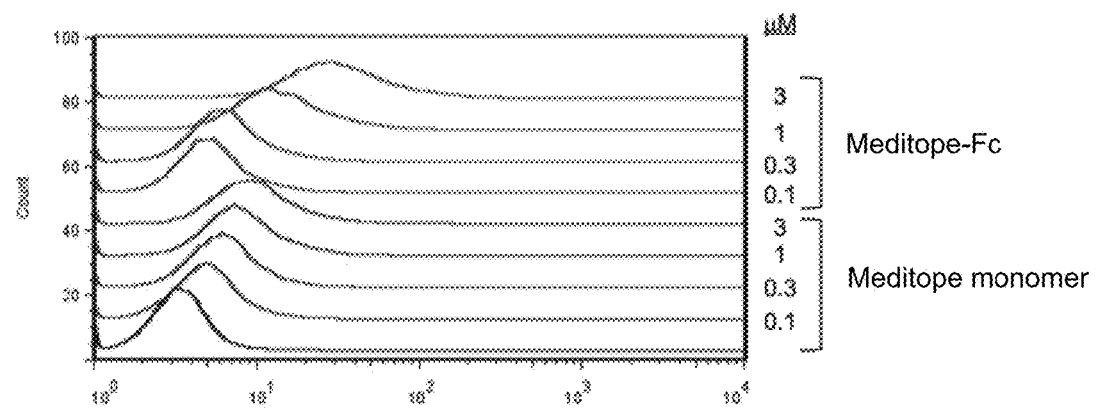
FIG. 17 shows the results of a series of exemplary FACS analyses monitoring binding of monovalent and bivalent meditopes to cetuximab pretreated EGFR-expressing cells. MDA-MB-468 cells that over-express EGFR were pre-treated with 10 nM of cetuximab for 30 minutes, rinsed, and then treated with either the meditope-Fc construct or the monomeric meditope at four concentrations. The bottom trace is a negative control (no antibody). The next four traces show that a monomeric meditope binds to cells pre-treated with cetuximab in a concentration dependent manner. The top four traces also show that the bivalent, meditope Fc binds to cells pre-treated with cetuximab in a concentration dependent manner, but with higher affinity (i.e., more shifted to the right). This is predicted and consistent with a multivalent interaction.

To demonstrate enhanced binding to antigen afforded by the multivalency of the meditope-Fc, $0.5 \times 10^6$ MDA-MB-468 cells were labeled with 10 nM cetuximab for 30 min at room temperature, washed, then incubated with 0.1, 0.3, 1 and 3 μM of bivalent meditope-Fc or monomeric meditope for 30 min at room temperature, washed, and then analyzed by FACS. As shown in FIG. 17, FACS analysis demonstrated that the meditope-Fc, corrected for the stoichiometry, bound to cells pre-treated with cetuximab with higher affinity compared to the meditope monomer. The interaction was demonstrated to be specific to the meditope-enabled mAb (cetuximab). These data demonstrate synergy using meditope-Fc, combined with a meditope enabled mAb, and thus that a bivalent meditope can be substituted for a second antibody to produce synergistic effects.

In another study, the meditope-Fc fusion protein was labeled with Alexa488 as described above. MDA-MB-468 cells were labeled with cetuximab or M425 (a murine anti-EGFR antibody) for 30 minutes. Unbound antibody was washed and the cells were incubated with the meditope-Fc (600 nM, 180 nM, or 60 nM) for 30 minutes. Antibody binding and meditope binding were analyzed by FACS analysis. The FACS data, shown in FIG. 49 demonstrate that the meditope-Fc bound to the cells incubated with cetuximab, but not to cells incubated with M425 or those not incubated with any antibody, with increasing signal at higher concentrations of meditope-Fc.

Similar to the FACS experiments described above, MDA-MB-468 cells were treated with Alexa 555-labeled cetuximab, washed, incubated with Alexa 488-labeled meditope-Fc, and washed. The cells were then imaged at 20× by microscopy (FIG. 61A). Strong surface-associated staining of Cetuximab was observed. The meditope-FC also localized to the cell surface and appeared to co-localize with cetuximab (FIG. 61A). Concomitant with this staining, we also observe the co-localization of the labeled meditope-Fc was observed (FIG. 61A, white arrows). This co-localization, however, was absent in cells which that were not pre-treated with cetuximab (FIG. 61B).

Taken together, these experiments show that the meditope binds to EGFR-expressing cells that are pre-treated with cetuximab, that using a multivalent scaffold affords creates a higher apparent affinity for cetuximab pre-treated cells, and that the apparent binding affinity, in this study, was more sensitive.

Figure 28:
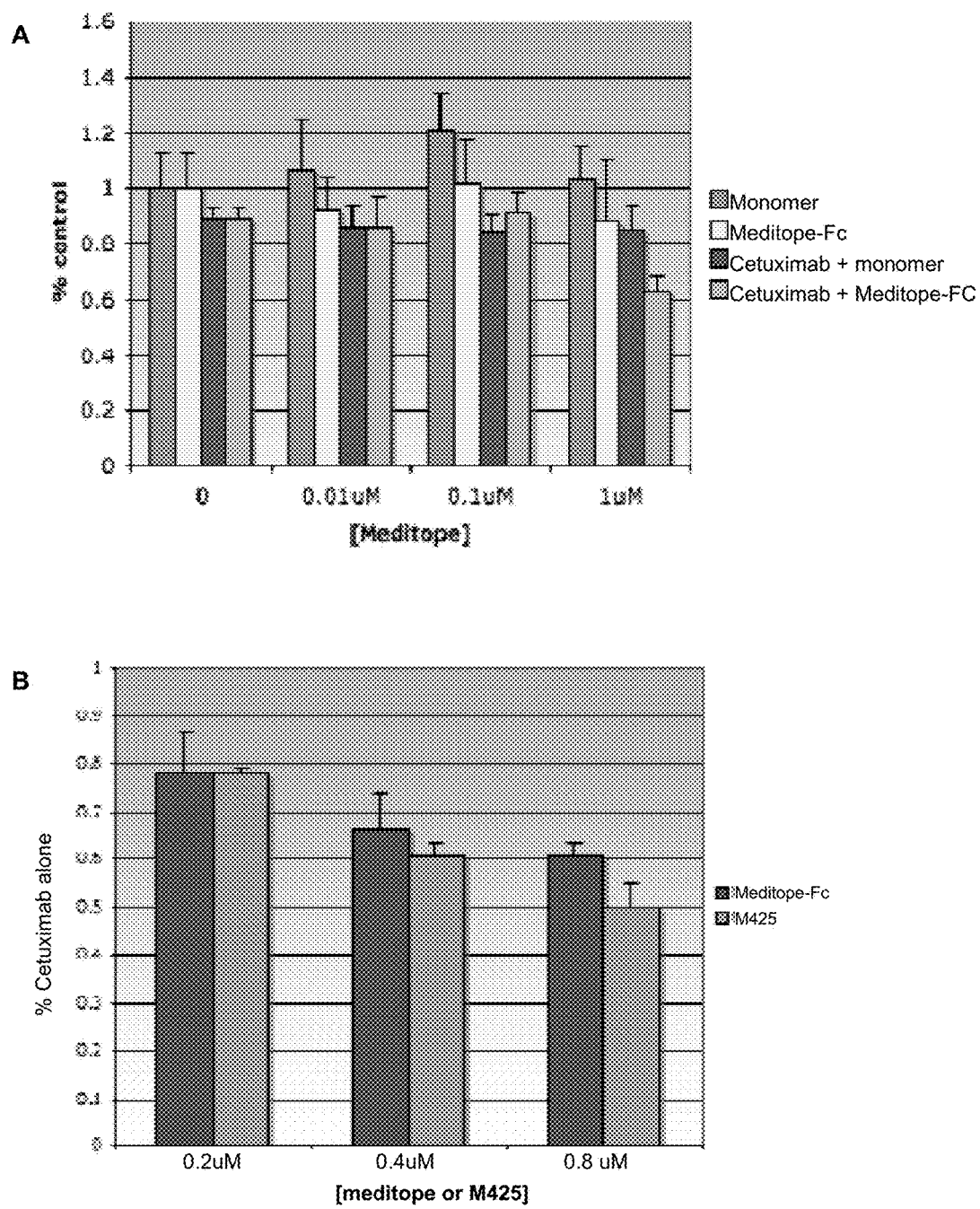
FIG. 28 illustrates the results of an MTT assay comparing the efficacy of a bivalent meditope-Fc to that of a monomeric meditope to inhibit MDA-MB-468 cell growth.

The ability of a bivalent meditope-Fc to induce cell death in conjunction with the meditope-enabled antibody, cetuximab, was confirmed using an MTT assay. 4000 MDA-MB-468 cells were placed in each well of a 96 well plate in 80 µl of medium. 10 µl of 1 µM cetuximab was added along with 10 µl of 0.1, 1 or 10 µM of monovalent meditope (cQFD—(control) or bivalent meditope-Fc (two cQFDs) to a final concentration of 0.1 µM cetuximab and 0.01, 0.1 and 1 µM meditope or meditope-Fc. Each component was also added alone with PBS as control. After a 48-hour incubation, 10 µl of MTT reagent was added and allowed to incubate for another 4 hours. The culture supernatant was then removed, 100 µl of MTT crystal dissolving reagent was added, and the plate was read at 630 nm. Neither addition of monovalent meditope (alone or with cetuximab), or meditope-Fc alone altered cell growth significantly. Addition of meditope-Fc together with cetuximab, however, inhibited cell growth, as shown in FIG. 28A.

The ability of the multivalent meditope-Fc to enhance cell killing by cetuximab to a degree comparable to a second anti-EGFR antibody was demonstrated by MTT assay. The assay compared the enhancement of cetuximab-mediated inhibition of antigen-expressing tumor cell growth by meditope-Fc and by M425 (a mouse anti-EGFR antibody). 4000 MDA-MB-468 cells were placed in each well of a 96 well plate in 80 µl of medium. 10 µl of 1 µM cetuximab was added, along with 10 µl of either 2, 4 or 8 µM of meditope-Fc or M425, to a final concentration of 0.1 µM cetuximab and either 0.2, 0.4 or 0.8 µM meditope-Fc or M425. cetuximab added with PBS alone was used as control. After a 48-hour incubation period, 10 µl MTT reagent was added and the mixture allowed to incubate for an additional 4 hours. The culture supernatant was removed, 100 µl of MTT crystal dissolving reagent added, and the plate read at 630 nm. As shown in FIG. 28B, meditope-Fc and M425 enhanced the cell-killing capacity of cetuximab to a similar degree.

In some examples, the composition of and the distance between the Fc and meditope are systematically explored to optimize affinity and specificity. In one example, each natural or unnatural residue is substituted at any position within the linker, for optimization. In another example, the linker is 'rigidified' to limit the radius of gyration and to enhance the affinity and specificity of the Fc-meditope. In one example, a coiled coil domain is placed between the meditope and the Fc (FIG. 18). In another example, inert protein domains (e.g., immunoglobulin folds) are substituted for the linker. In one example, multiple immunoglobulin folds are placed between the meditope and the Fc domain. In certain examples, the composition of the linker is of human origin, e.g., to mitigate potential antigenicity.

Multivalent Scaffolds

To address the receptor constraints on the linker, meditopes were coupled to multivalent scaffolds.

Figure 8:
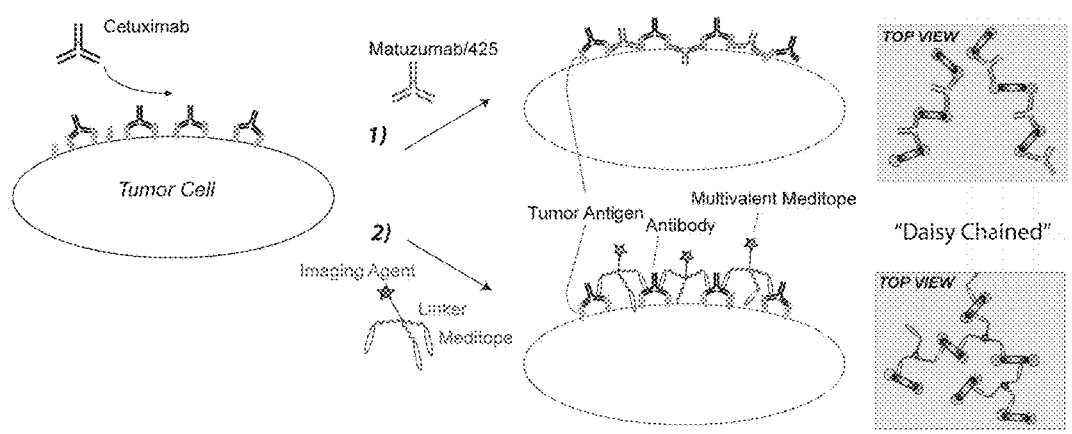
FIG. 8 illustrates a mechanism of action in one embodiment for enhancing tumor therapy. In the exemplified embodiment, bivalent antibodies bound to antigen (e.g., ErbB receptor family) overexpressed on tumor cells (left panel) and blocks receptor signaling, alters endocytosis and receptor recycling and/or elicits an immune response. The addition of an antibody such as matuzumab which recognizes a different domain of EGFR in combination with cetuximab can, in some cases be more effective due to daisy chaining of the surface receptor (right panel 1). A multivalent meditope (in this particular example, trivalent) tethers/cross-links the therapeutic mAb and can enhance its therapeutic potential (right). In addition, the multivalent meditope (shown here as a trivalent version) can also carry an imaging agent, which can allow for both enhanced therapeutics as well as imaging.

Multivalent meditopes were designed to "latch-on" to adjacent IgGs to form a "daisy-chain"-like array (see FIG. 8). Synthesis of a FITC-labeled bivalent meditope was developed using "Click" chemistry, using compound 2 (SEQ ID NO: 32). Templates 4 and 5 of FIG. 13, were used to form bi- and trivalent meditopes, respectively. A 30 Å PEG bifunctional arm was incorporated in the synthesis of a FITC-labeled bivalent meditope containing meditopes of SEQ ID NOs: 32 (meditopes 32), namely compound 13, shown in FIG. 13. As also shown in FIG. 13, a trivalent meditope (compound 14) also was successfully synthesized.

Figure 14:
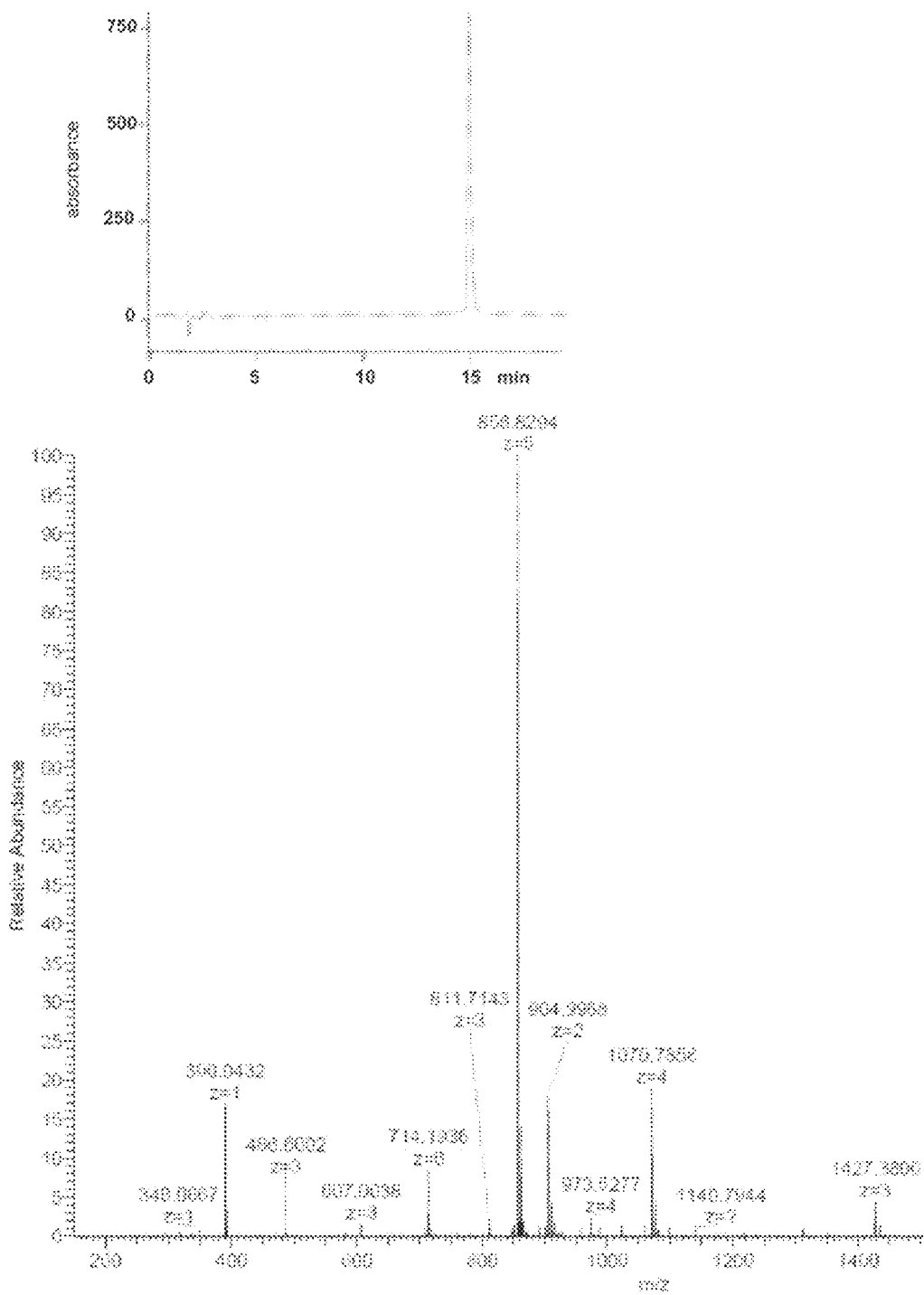
FIG. 14 illustrates the characterization of a fluorescein isothiacyanate (FITC)-labeled meditope dimer ("14" in FIG. 13), which contains two meditopes of SEQ ID NO: 32 (shown in both orientations), with an HPLC trace of final bivalent meditope and its mass spectrum.
Figure 14:
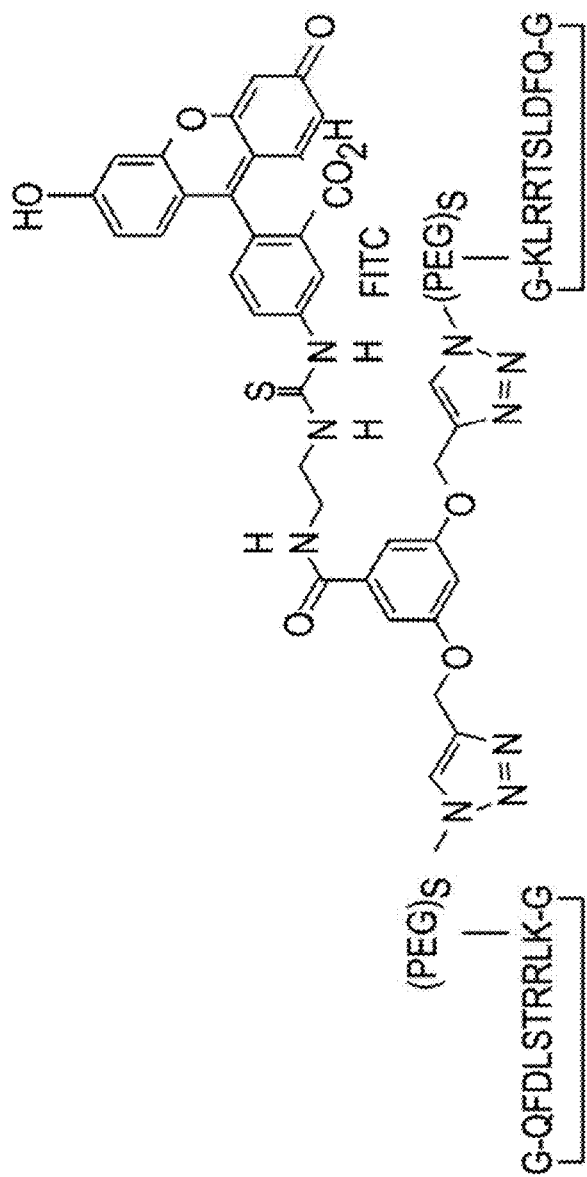

FIG. 14 illustrates the characterization of this fluorescein isothiocyanate (FITC)-labeled meditope compound 13.

In other examples, differing lengths of polyethylene glycol (PEG) (and other) linkers are used, for example, to optimize binding. In other examples, this synthetic approach is used to incorporate DOTA for radionuclide imaging. The distance between the CDR regions within an IgG is ~130 Å. End-to-end distances of commercially available PEGs extend to 90 Å (Pierce), which would exceed the IgG distance. In one example, the length of the PEG linker is systematically varied, bearing in mind this constraint.

In some examples, trivalent or higher valency scaffolds are used, with the goal of having more than one antibody "daisy chained". In some example, different scaffolds and linkers are used to generate high affinity multivalent meditopes. In one example, DNA is used as a more rigid scaffold.

Different scaffolds of biological and chemical origin also are used to achieve multivalency. This includes, but is not limited to, constructing a bivalent or trivalent scaffold, using streptavidin or collagen (see published U.S. patent application, Publication No.: US 20080176247), strepavidin as a tetravalent scaffold, unique scaffolds (see Hutchins et al., *J. Molecular. Biology*, 2011, 406(4), 595-603), Origami DNA (Hongzhou et al., *Nature Nanotechnology*, 2009, 4:245-248) and the like. A chemical scaffold may also be created using molecules including, but not limited to, DNA (single strand, duplex, Holliday junctions, aptamers and the like), RNA (single strand, hairpin, stem loop, aptamers and the like), PNA (peptide nucleic acids), DNA/PNA duplexes and triplexes for rigidity, inorganic or organic nanoparticles (directly coupled or coupled through organic polymers such as PEG), organic polymers that can form duplexes with themselves and/or with DNA or PNA.

Multivalent Meditope Characterization

In one example, the multivalent meditopes are characterized by SPR and ITC, to verify that conjugation to the multivalent scaffold does not affect the meditope-IgG interaction.

In other examples, FACS analysis, cell viability assays, and other assays are used. For example, cell viability assays are used as described above for meditope-Fc to quantify the effect of the multivalent meditope directly on cells that overexpress the antigen recognized by the meditope-enabled antibody of choice, such as EGFR when the meditope-enabled antibody is cetuximab. For example, MTT, 3-(4,5-Dimethylthiazol-2-yl)-2,5-diphenyltetrazolium bromide, is used to quantify the number or percentage of viable cells. In some examples, a shift at far lower concentrations than observed for the corresponding monovalent meditope and/or a relative increase in percentage of cells that shift, is observed.

In some examples, for multivalent meditopes that demonstrate activity in such assays, Western blot analysis is performed to follow other parameters, such as phosphorylation status of EGFR, AKT, and MAPK in the case of antibodies targeting the EGFR signaling pathway, such as cetuximab. In one example, the data are compared with data from antibody (e.g., cetuximab)-only treated cells and cells treated with inhibitors (e.g., tyrosine kinase inhibitors (AG1478)). An increase in cell death as a function of multivalent meditope concentration is observed.

In one example, to further confirm the additive effects of the multivalent meditope, the non-labeled, monovalent meditope is used to compete with the labeled multivalent meditope for the antigen-bound cetuximab.

EXAMPLE 8

Meditope Binding Affinity as a Function of pH

The composition of the meditope was altered to affect the binding affinity as a function of pH. As shown in FIG. 27, the binding affinity of three different meditope variants was measured as a function of buffer pH. The results demonstrated that cQYD (SEQ ID NO: 16, meditope 16) meditope variant had a marked decrease in affinity for the meditope-enabled antibody cetuximab at lower pH. Substitution of the aspartate to asparagine in the cQYN variant produced a flat pH dependence. The affinity of the cQFD meditope (SEQ ID NO: 1) was determined to be slightly greater at higher pHs. Collectively, these data demonstrate that the affinity of the meditope-memAb interaction can be tailored to pH, which is used, for example, to generate meditope variants for the specific release at low pH, such as in lysozymes for drug delivery, and/or to bind with higher affinity in a hypoxic environment, e.g., tumor stroma.

EXAMPLE 9

Meditope Analogs, Fragments, and Other Compounds

Screening methods were carried out to identify meditope analogs and compounds, such as small molecules, fragments, aptamers, nucleic acid molecules, peptibodies and/or other substances that bind meditope-enabled antibodies near meditope-binding sites and in some aspects can be linked to meditopes, for example, to improve their affinities for the meditope-binding sites.

Fluorescence Polarization Assays:

To identify compounds, including alternative molecules that could bind at the meditope binding site of meditope-enabled antibodies and thus be used for similar functions, a displacement assay was established. A cyclic meditope was synthesized and chemically attached to a fluorescein, generating a fluorescein-labeled meditope of the following sequence: AcCQFDLSTRRLRCGGGSK (SEQ ID NO: 31, cysteines form a disulfide linkage)-Fluorescein. This fluorescently-labeled peptide was then titrated with cetuximab and the fluorescence polarization measured. The interaction between the labeled meditope and mAb cause a change in the fluorescence polarization/intensity of the fluorescent tag. The dissociation constant, 1 µM, closely matched values obtained from surface plasmon resonance and isothermal titration calorimetry. A non-labeled meditope, AcCQFDLSTRRLRCGGGSK (SEQ ID NO: 31), was used to displace the fluorescein-label peptide pre-bound to cetuximab. The fluorescence polarization was monitored. Compounds that blocked the meditope-antibody interaction altered the fluorescent polarization properties. As shown in FIG. 37, a sigmoid curve indicative of a competition reaction was observed. Accordingly, this method is useful for identifying meditope analogs.

Based on these data, an initial screen to identify small molecules capable of displacing the meditope was carried out. In this study, 42 lead compounds at concentrations of 50 µM were identified from a library of 30,000 small molecule compounds. FIG. 38 shows five such lead compounds.

In another example, these compounds are characterized further, for example, by crystallography.

Diffraction Methods. Cetuximab Fab was shown to diffract beyond 2.5 Å, as shown above. Established diffraction-based methods (well-established for identifying lead compounds (Shuker et al. 1996; Erlanson et al. 2001; Hughes et al. 2011)) were used to identify candidate compounds, including compounds that can be coupled to a meditope, for example, to improve affinity for the meditope binding site. A library of small molecules was developed to soak into crystals of cetuximab. Diffraction data from these soaks was collected and several data sets analyzed. In these initial studies, two additional sites were identified on cetuximab that are amendable for fragment growth and optimization.

In another example, such fragments (small molecules that can serve as building blocks for larger entities), such as chemical groups, e.g., imidazole or other chemical group, are grown (chemically derivatized) to enhance their binding and specificity and/or are chemically tethered to the meditope. Optimization of this chemical coupling can significantly enhance the overall binding affinity.

NMR Screening: NMR was used to identify fragments for optimization of meditopes, e.g., by linkage to the meditope, and/or use in lieu of the meditope (i.e., as meditope analogs). To identify these leads, one dimensional (1D) spectra of pools containing 15 to 20 fragments were collected. Cetuximab was added to each pool and second 1D spectra were collected. Compounds that bound (transiently) with cetuximab underwent rapid magnetization transfer, resulting in a loss of intensity. The spectra were compared before and after addition of cetuximab and altered peaks identified, indicating interactions.

Figure 19:
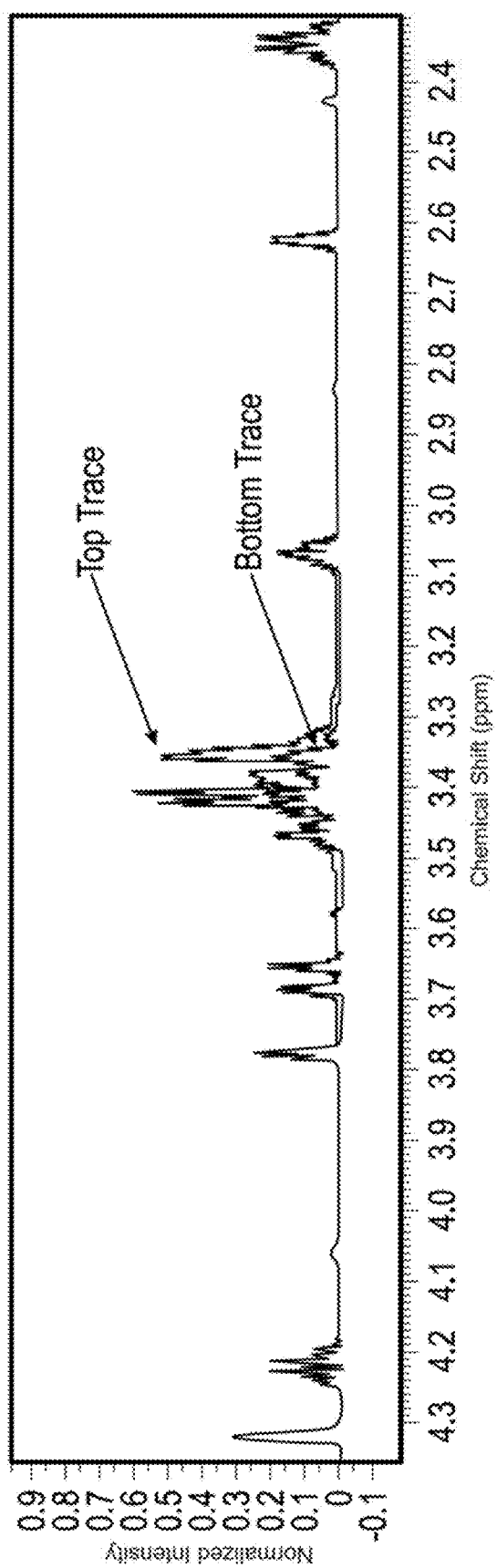
FIG. 19: Fragment screening by NMR. Representative NMR spectra of a fragment pool before (top trace) and after (bottom trace) cetuximab addition. Using this method, lead compounds (e.g., those shown herein) have been identified and the binding site is being determined using diffraction studies.

In one example, these peaks are pre-assigned to a specific compound, and thus immediately known. Alternatively, the pools are subdivided and the spectra recollected. After several rounds, the exact identity of the compound is known. In these experiments, the precise position of the interaction is not known. The binding site is determined by NMR or the fluorescence polarization assay. Alternatively, the Fab fragment is labeled with NMR active and inactive nuclei (e.g., $^{13}$C, $^{15}$N and $^{2}$H), followed by multiple NMR experiments performed to assign the spectrum, and use of the fragment library to identify the binding position. Using this procedure, a set of initial lead compounds has been identified (FIG. 19, bottom).

Virtual Ligand Screening: Virtual ligand screening was used to identify lead compounds to function as meditopes. Using crystal structure, standard programs (e.g., Schroerdinger Glide) were used to define a "box" about a site of the macromolecule (the meditope binding site); known ligands were docked to this site. Potential lead compounds were scored by a select energy function. In this study, approximately 100 lead compounds were identified.

In another example, additional analogs found by diffraction methods are optimized and used in lieu of the meditope for drug delivery, multivalent scaffolding and other functions.

In another example, mutations in the light and heavy chains are made to change the specificity of the ligand (meditope) and all the above-described methods (including fluorescence polarization, NMR screening, phage display, and diffraction methods are used to optimized alternative ligands.

EXAMPLE 10

Meditope-Protein L Fusion

Characterization by diffraction of the cQFD meditope-enabled Fab fragment bound to a meditope demonstrated that the N- and C-termini of the meditope were juxtaposed to the location of bound Protein L, a bacterial protein that binds to human IgGs. See FIG. 52, showing the crystal structure of meditope 18 (5-β,β'-diphenyl), Protein L (left), Protein A (right) and Fab (grey cartoon) and meditope-enabled trastuzumab Fab.

To generate a meditope that binds to meditope-enabled antibodies with greater affinity via energy additivity, a meditope-Protein L fusion polypeptide was produced. Based on structural data information, four glycines were introduced to link the C-terminus of the cQFD meditope and the N-terminus of Protein L. The coding sequence of a meditope-Protein L fusion protein is set forth in SEQ ID NO: 56.

The amino acid sequence of an encoded protein, including a His6-Smt3 tag (plain text), meditope (underlined), and Protein L (bold) is set forth below and in SEQ ID NO: 57:

(SEQ ID NO:57)
HHHHHHSSGLVPRGSHMASMSDSEVNQEAKPEVKPEVKPETHINLKVSD

GSSEIFFKIKKTTPLRRLMEAFAKRQGKEMDSLRFLYDGIRIQADQTPE

DLDMEDNDIIEAHREQIGGS<u>CQFDLSTRRLKC</u>GGGGSEVTIKVNLIFAD

GKIQTAEFKGTFEEATAEYRYAALLAKVNGEYTADLEDGGNHMNIKFAG

The amino acid sequence of the meditope-Protein L fusion protein, after cleavage of the tag, is set forth below (meditope underlined; two cysteins that are cyclized (e.g., by peroxide or overnight with air) set forth in bold text) SEQ ID NO: 58:

(SEQ ID NO:58)
<u>SCQFDLSTRRLKCGGGGSEVTIKVNLIFADGKIQTAEFKGTFEEATAEA

YRYAALLAKVNGEYTADLEDGGNHMNIKFAG.</u>

Binding constants for the interaction of this fusion protein (and separately, the interaction of each individual component) with meditope-enabled antibodytrastuzumab were measured by surface plasmon resonance (SPR). The binding constant for the interaction between Protein L and the meditope-enabled trastuzumab was approximately 0.5 µM. For the interaction between the meditope and the meditope-enabled trastuzumab Fab fragment, it was approximately 1 µM. The binding constant for the interaction between the meditope-Protein L fusion protein and the IgG, however, was 165 pM. FIG. 53 shows surface plasmon resonance (SPR) data for a meditope-Protein L fusion (MPL): The top panel shows the traces of MPL being added to the meditope-enabled trastuzumab at concentrations up to 10 nM. The fit data indicates a binding affinity of 165 pM. The bottom panel shows the traces of Protein L (only) added at the same concentrations to the meditope-enabled trastuzumab, showing that there was no binding at this concentration in this study. This result demonstrated far stronger binding between the fusion protein and meditope-enabled antibody compared to the individual interactions, indicating improved affinity via additivity.

Point mutations were created in Protein L and the meditope to ensure specificity. As expected, in both cases, the binding constant was reduced.

To facilitate conjugation of various molecules, such as therapeutic and diagnostic agents, e.g., cytotoxins, radionucleotides, for example, DOTA, proteins, solid supports, and other molecules, e.g., for drug delivery, imaging, or purification, all lysines in the Protein L-meditope fusion protein but one were mutated to arginine or another residue. The crystal structure shown in FIG. 52 was used to identify all lysines on Protein L and the meditope that, if conjugated, would sterically occlude the meditope-Protein L/meditope-enabled antibody interaction. Based on this information, the meditope-Protein L fusion (MPL) having the sequence set forth in SEQ ID NO: 59 (SCQFDLSTRRLRCGGGG-SEVTIRVNLIFADGNIQTAEFRGTFEEATAEAY-RYAALLA RVNGEYTADLEDGGNHMNIKFAG) was produced, in which certain lysines in Protein L/meditope (shown in black in FIG. 52—all but one lysine) were mutated to Arg or Asn. In the sequence shown above, the residues mutated from lysine to arginine/asparagine are shown in bold text. The lysine that was not mutated (underlined above) is pointed into the solvent. Thus, in the resulting meditope-Protein L fusion protein, the N-terminal amine and epsilon amine were left for conjugation, the latter being solvent exposed and likely more reactive.

In another example, this unique lysine residue in this mutant is used to PEGylate the MPL, e.g., to address potential antigenicity.

MPL-DOTA-NHS Conjugates

MPL having the sequence set forth in SEQ ID NO: 59 was conjugated to DOTA-NHS in a reaction carried out with various ratios (0.5:1, 2:1, 10:1, 30:1, 60:1, 120:1, 240:1) of starting material (DOTA-NHS:MPL) in phosphate buffer (80 mM) for 10 minutes at a pH=10, which favors conjugation to lysine as compared to N-terminal conjugation. The mono-DOTA-conjugate product increases with increasing DOTA-NHS. A significant amount of MPL-mono-DOTA-MPL was formed at a 60:1 ratio, and a significant amount of both MPL-mono-DOTA and MPL-di-DOTA formed at a 120:1 ratio (FIG. 60).

The foregoing examples and methods of the invention are illustrative only and are not intended to be limiting of the invention in any way. Those of ordinary skill in the art will recognize that various modifications of the foregoing are within the intended scope of the invention.

REFERENCES

All references below and cited in the specification above are hereby incorporated by reference in their entirety, as if fully set forth herein.
1. Accardi, L., and Di Bonito, P. (2010) Antibodies in single-chain format against tumour-associated antigens: present and future applications, Curr Med Chem 17, 1730-1755.
2. Adams, G. P., Schier, R., McCall, A. M., Simmons, H. H., Horak, E. M., Alpaugh, R. K., Marks, J. D., and Weiner, L. M. (2001) Cancer Res 61, 4750-4755.
3. Adams, J., Behnke, M., Chen, S., Cruickshank, A. A., Dick, L. R., Grenier, L., Klunder, J. M., Ma, Y. T., Plamondon, L., and Stein, R. L. (1998) Potent and selective inhibitors of the proteasome: dipeptidyl boronic acids, Bioorg Med Chem Lett 8, 333-338.
4. Adams, P. D., Grosse-Kunstleve, R. W., Hung, L. W., Ioerger, T. R., McCoy, A. J., Moriarty, N. W., Read, R. J., Sacchettini, J. C., Sauter, N. K., and Terwilliger, T. C. (2002) Acta Crystallogr D Biol Crystallogr 58, 1948-1954.
5. Adessi, C., and Soto, C. (2002) Converting a peptide into a drug: strategies to improve stability and bioavailability, Curr Med Chem 9, 963-978.
6. Akamatsu, Y., Pakabunto, K., Xu, Z., Zhang, Y., and Tsurushita, N. (2007) Whole
7. IgG surface display on mammalian cells: Application to isolation of neutralizing chicken monoclonal anti-IL-12 antibodies, J Immunol Methods 327, 40-52.

8. Alley, S. C., Okeley, N. M., and Senter, P. D. (2010) Antibody-drug conjugates: targeted drug delivery for cancer, Curr Opin Chem Biol 14, 529-537.
9. Auffinger, P., Hays, F. A., Westhof, E., and Ho, P. S. (2004) Halogen bonds in biological molecules, Proc Natl Acad Sci USA 101, 16789-16794.
10. Beck, A., Wurch, T., Bailly, C., and Corvaia, N. (2010) Strategies and challenges for the next generation of therapeutic antibodies, Nat Rev Immunol 10, 345-352.
11. Beck, A., Wagner-Rousset, E., Bussat, M. C., Lokteff, M., Klinguer-Hamour, C., Haeuw, J. F., Goetsch, L., Wurch, T., Van Dorsselaer, A., and Corvaia, N. (2008) Trends in glycosylation, glycoanalysis and glycoengineering of therapeutic antibodies and Fc-fusion proteins, Curr Pharm Biotechnol 9, 482-5001.
12. Bilgicer, B., Moustakas, D. T., and Whitesides, G. M. (2007) A synthetic trivalent hapten that aggregates anti-2,4-DNP IgG into bicyclic trimers, J Am Chem Soc 129, 3722-3728.
13. Bilgicer B, Thomas S W 3rd, Shaw B F, Kaufman G K, Krishnamurthy V M, Estroff L A, Yang J, Whitesides G M., A non-chromatographic method for the purification of a bivalently active monoclonal IgG antibody from biological fluids. J. Am. Chem. Soc. 2009 JUL 8; 131(26): 9361-7.
14. Bokemeyer, C., Bondarenko, I., Makhson, A., Hartmann, J. T., Aparicio, J., de Braud, F., Donea, S., Ludwig, H., Schuch, G., Stroh, C., Loos, A. H., Zubel, A., and Koralewski, P. (2009) Fluorouracil, leucovorin, and oxaliplatin with and without cetuximab in the first-line treatment of metastatic colorectal cancer, J Clin Oncol 27, 663-671.
15. Bretscher, L. E., Li, H., Poulos, T. L., and Griffith, O. W. (2003) Structural characterization and kinetics of nitric-oxide synthase inhibition by novel N5-(iminoalkyl)- and N5-(iminoalkenyl)-ornithines, J Biol Chem 278, 46789-46797.
16. Butlin, N. G., and Meares, C. F. (2006) Antibodies with infinite affinity: origins and applications, Acc Chem Res 39, 780-787.
17. Cardarelli, P. M., Quinn, M., Buckman, D., Fang, Y., Colcher, D., King, D. J., Bebbington, C., and Yarranton, G. (2002) Binding to CD20 by anti-B1 antibody or F(ab')(2) is sufficient for induction of apoptosis in B-cell lines, Cancer Immunol Immunother 51, 15-24.
18. Carson, K. R., Focosi, D., Major, E. O., Petrini, M., Richey, E. A., West, D. P., and Bennett, C. L. (2009) Lancet Oncol 10(8), 816-824
19. Chen, V. B., Arendall, W. B., 3rd, Headd, J. J., Keedy, D. A., Immormino, R. M., Kapral, G. J., Murray, L. W., Richardson, J. S., and Richardson, D. C. (2010) MolProbity: all-atom structure validation for macromolecular crystallography, Acta Crystallogr D Biol Crystallogr 66, 12-21.
20. Chih, H. W., Gikanga, B., Yang, Y., and Zhang, B. (2011) Identification of amino acid residues responsible for the release of free drug from an antibody-drug conjugate utilizing lysine-succinimidyl ester chemistry, J Pharm Sci 100, 2518-2525.
21. Chmura, A. J., Orton, M. S., and Meares, C. F. (2001) Antibodies with infinite affinity, Proc Natl Acad Sci USA 98, 8480-8484.
22. Cho, H. S., Mason, K., Ramyar, K. X., Stanley, A. M., Gabelli, S. B., Denney, D. W., Jr., and Leahy, D. J. (2003) Structure of the extracellular region of HER2 alone and in complex with the Herceptin Fab, Nature 421, 756-760.
23. Collis, A. V., Brouwer, A. P., and Martin, A. C. (2003) J Mol Biol 325, 337-354.
24. Dechant, M., Weisner, W., Berger, S., Peipp, M., Beyer, T., Schneider-Merck, T., Lammerts van Bueren, J. J., Bleeker, W. K., Parren, P. W., van de Winkel, J. G., and Valerius, T. (2008) Complement-dependent tumor cell lysis triggered by combinations of epidermal growth factor receptor antibodies, Cancer Res 68, 4998-5003.
25. Demarest, S. J., and Glaser, S. M. (2008) Antibody therapeutics, antibody engineering, and the merits of protein stability, Curr Opin Drug Discov Devel 11, 675-687.
26. DeNardo, G., and DeNardo, S. (2010) Dose intensified molecular targeted radiotherapy for cancer-lymphoma as a paradigm, Semin Nucl Med 40, 136-144.
27. Derksen, D. J., Stymiest, J. L., and Vederas, J. C. (2006) Antimicrobial leucocin analogues with a disulfide bridge replaced by a carbocycle or by noncovalent interactions of allyl glycine residues, J Am Chem Soc 128, 14252-14253.
28. Donaldson, J. M., Kari, C., Fragoso, R. C., Rodeck, U., and Williams, J. C. (2009) Design and development of masked therapeutic antibodies to limit off-target effects: application to anti-EGFR antibodies, Cancer Biol Ther 8, 2147-2152.
29. Doppalapudi, V. R., Huang, J., Liu, D., Jin, P., Liu, B., Li, L., Desharnais, J., Hagen, C., Levin, N. J., Shields, M. J., Parish, M., Murphy, R. E., Del Rosario, J., Oates, B. D., Lai, J. Y., Matin, M. J., Ainekulu, Z., Bhat, A., Bradshaw, C. W., Woodnutt, G., Lerner, R. A., and Lappe, R. W. (2010) Chemical generation of bispecific antibodies, Proc Natl Acad Sci USA 107, 22611-22616.
30. Doppalapudi, V. R., Tryder, N., Li, L., Aja, T., Griffith, D., Liao, F. F., Roxas, G., Ramprasad, M. P., Bradshaw, C., and Barbas, C. F., 3rd. (2007) Chemically programmed antibodies: endothelin receptor targeting CovX-Bodies, Bioorg Med Chem Lett 17, 501-506.
31. Dornan, D., Bennett, F., Chen, Y., Dennis, M., Eaton, D., Elkins, K., French, D., Go, M. A., Jack, A., Junutula, J. R., Koeppen, H., Lau, J., McBride, J., Rawstron, A., Shi, X., Yu, N., Yu, S. F., Yue, P., Zheng, B., Ebens, A., and Polson, A. G. (2009) Therapeutic potential of an anti-CD79b antibody-drug conjugate, anti-CD79b-vc-MMAE, for the treatment of non-Hodgkin lymphoma, Blood 114, 2721-2729.
32. Du, J., Wang, H., Zhong, C., Peng, B., Zhang, M., Li, B., Huo, S., Guo, Y., and Ding, J. (2007) Structural basis for recognition of CD20 by therapeutic antibody Rituximab, J Biol Chem 282, 15073-15080
33. Emsley, P., and Cowtan, K. (2004) Acta Crystallogr D Biol Crystallogr 60, 2126-2132.
34. Erlanson, D. A., Arndt, J. W., Cancilla, M. T., Cao, K., Elling, R. A., English, N., Friedman, J., Hansen, S. K., Hession, C., Joseph, I., Kumaravel, G., Lee, W. C., Lind, K. E., McDowell, R. S., Miatkowski, K., Nguyen, C., Nguyen, T. B., Park, S., Pathan, N., Penny, D. M., Romanowski, M. J., Scott, D., Silvian, L., Simmons, R. L., Tangonan, B. T., Yang, W., and Sun, L. (2011) Discovery of a potent and highly selective PDK1 inhibitor via fragment-based drug discovery, Bioorg Med Chem Lett 21, 3078-3083.
35. Ferenczy, G. G., and Keseru, G. M. (2010) Thermodynamics guided lead discovery and optimization, Drug Discov Today 15, 919-932.
36. Gencoglan, G., and Ceylan, C. (2007) Skin Pharmacol Physiol 20, 260-262.

37. Goodwin, D. A., and Meares, C. F. (1999) Pretargeted peptide imaging and therapy, Cancer Biother Radiopharm 14, 145-152.
38. Graille, M., Stura, E. A., Corper, A. L., Sutton, B. J., Taussig, M. J., Charbonnier, J. B., and Silverman, G. J. (2000) Proc Natl Acad Sci USA 97, 5399-5404.
39. Graille, M., Stura, E. A., Housden, N. G., Beckingham, J. A., Bottomley, S. P., Beale, D., Taussig, M. J., Sutton, B. J., Gore, M. G., and Charbonnier, J. B. (2001) Structure 9, 679-687.
40. Graille, M., Harrison, S., Crump, M. P., Findlow, S. C., Housden, N. G., Muller, B. H., Battail-Poirot, N., Sibai, G., Sutton, B. J., Taussig, M. J., Jolivet-Reynaud, C., Gore, M. G., and Stura, E. A. (2002) J Biol Chem 277, 47500-47506.
41. Green, D. J., Pagel, J. M., Pantelias, A., Hedin, N., Lin, Y., Wilbur, D. S., Gopal, A., Hamlin, D. K., and Press, O. W. (2007) Pretargeted radioimmunotherapy for B-cell lymphomas, Clin Cancer Res 13, 5598-5603.
42. Guay, D., Beaulieu, C., and Percival, M. D. (2010) Therapeutic utility and medicinal chemistry of cathepsin C inhibitors, Curr Top Med Chem 10, 708-716.
43. Hansel, T. T., Kropshofer, H., Singer, T., Mitchell, J. A., and George, A. J. (2010) The safety and side effects of monoclonal antibodies, Nat Rev Drug Discov 9, 325-338.
44. Hardegger, L. A., Kuhn, B., Spinnler, B., Anselm, L., Ecabert, R., Stihle, M., Gsell, B., Thoma, R., Diez, J., Benz, J., Plancher, J. M., Hartmann, G., Banner, D. W., Haap, W., and Diederich, F. (2011) Systematic investigation of halogen bonding in protein-ligand interactions, Angew Chem Int Ed Engl 50, 314-318.
45. Hartmann, C., Muller, N., Blaukat, A., Koch, J., Benhar, I., and Wels, W. S. (2010) Oncogene 29, 4517-4527.
46. Hernandes, M. Z., Cavalcanti, S. M., Moreira, D. R., de Azevedo Junior, W. F., and Leite, A. C. (2010) Halogen atoms in the modern medicinal chemistry: hints for the drug design, Curr Drug Targets 11, 303-314.
47. Hughes, S. J., Millan, D. S., Kilty, I. C., Lewthwaite, R. A., Mathias, J. P., O'Reilly, M. A., Pannifer, A., Phelan, A., Stuhmeier, F., Baldock, D. A., and Brown, D. G. (2011) Fragment based discovery of a novel and selective PI3 kinase inhibitor, Bioorg Med Chem Lett.
48. Hutchins, B. M., Kazane, S. A., Staflin, K., Forsyth, J. S., Felding-Habermann, B., Schultz, P. G., and Smider, V. V. (2011) Site-specific coupling and sterically controlled formation of multimeric antibody fab fragments with unnatural amino acids, J Mol Biol 406, 595-603.
49. Junutula, J. R., Raab, H., Clark, S., Bhakta, S., Leipold, D. D., Weir, S., Chen, Y., Simpson, M., Tsai, S. P., Dennis, M. S., Lu, Y., Meng, Y. G., Ng, C., Yang, J., Lee, C. C., Duenas, E., Gorrell, J., Katta, V., Kim, A., McDorman, K., Flagella, K., Venook, R., Ross, S., Spencer, S. D., Lee Wong, W., Lowman, H. B., Vandlen, R., Sliwkowski, M. X., Scheller, R. H., Polakis, P., and Mallet, W. (2008) Site-specific conjugation of a cytotoxic drug to an antibody improves the therapeutic index, Nat Biotechnol 26, 925-932.
50. Kamat, V., Donaldson, J. M., Kari, C., Quadros, M. R., Lelkes, P. I., Chaiken, I., Cocklin, S., Williams, J. C., Papazoglou, E., and Rodeck, U. (2008) Enhanced EGFR inhibition and distinct epitope recognition by EGFR antagonistic mAbs C225 and 425, Cancer Biol Ther 7, 726-733.
51. Kiessling, L. L., and Splain, R. A. (2010) Chemical approaches to glycobiology, Annu Rev Biochem 79, 619-653.
52. Ladbury, J. E., Klebe, G., and Freire, E. (2010) Adding calorimetric data to decision making in lead discovery: a hot tip, Nat Rev Drug Discov 9, 23-27.
53. Lazar, G. A., Dang, W., Karki, S., Vafa, O., Peng, J. S., Hyun, L., Chan, C., Chung, H. S., Eivazi, A., Yoder, S. C., Vielmetter, J., Carmichael, D. F., Hayes, R. J., and Dahiyat, B. I. (2006) Engineered antibody Fc variants with enhanced effector function, Proc Natl Acad Sci USA 103, 4005-4010.
54. Lesch, H. P., Kaikkonen, M. U., Pikkarainen, J. T., and Yla-Herttuala, S. (2010) Avidin-biotin technology in targeted therapy, Expert Opin Drug Deliv 7, 551-564.
55. Li, M., Yan, Z., Han, W., and Zhang, Y. (2006) Cell Immunol 239, 136-143.
56. Li, S., Schmitz, K. R., Jeffrey, P. D., Wiltzius, J. J., Kussie, P., and Ferguson, K. M. (2005) Structural basis for inhibition of the epidermal growth factor receptor by cetuximab, Cancer Cell 7, 301-311.
57. Liu, C. C., and Schultz, P. G. (2010) Adding new chemistries to the genetic code, Annu Rev Biochem 79, 413-444.
58. Lowe C R, Lowe A R, Gupta G. (2001) J. Biochem. Bioph. Meth. 49: 561-574.
59. Mammen, M., Choi, S.-K., and Whitesides, G. M. Polyvalent Interactions in Biological Systems: Implications for Design and Use of Multivalent Ligands and Inhibitors, (1998) Angew. Chem. Int. Ed. Engl., 37, 2749-2798.
60. McCoy, A. J., Grosse-Kunstleve, R. W., Adams, P. D., Winn, M. D., Storoni, L. C., and Read, R. J. (2007) J Appl Crystallogr 40, 658-674.
61. Meares, C. F. (2008) The chemistry of irreversible capture, Adv Drug Deliv Rev 60, 1383-1388.
62. Meira, D. D., Nobrega, I., de Almeida, V. H., Mororo, J. S., Cardoso, A. M., Silva, R. L., Albano, R. M., and Ferreira, C. G. (2009) Eur J Cancer 45, 1265-1273.
63. Melosky, B., Burkes, R., Rayson, D., Alcindor, T., Shear, N., and Lacouture, M. (2009) Curr Oncol 16(1), 16-26.
64. Meredith, R. F., and Buchsbaum, D. J. (2006) Pretargeted radioimmunotherapy, Int J Radiat Oncol Biol Phys 66, S57-59.
65. Milo, L. J., Lai, J. H., Wu, W., Liu, Y., Maw, H., Li, Y., Jin, Z., Shu, Y., Poplawski, S., Wu, Y., Sanford, D. G., Sudmeier, J. L., and Bachovchin, B. (2011) Chemical and Biological Evaluation of Dipeptidyl Boronic Acid Proteasome Inhibitors for Use in Pro- and Pro-soft Drugs Targeting Solid Tumors, J Med Chem (in press—DOI: 10.1021/jm200460q).
66. Molloy, E. S., and Calabrese, L. H. (2009) Nat Rev Rheumatol 5(8), 418-419.
67. Morse, L., and Calarese, P. (2006) Semin Oncol Nurs 22(3), 152-162.
68. Moss, L. S., Starbuck, M. F., Mayer, D. K., Harwood, E. B., and Glotzer, J. (2009) Oncol Nurs Forum 36, 676-685.
69. Mossessova, E., and Lima, C. D. (2000) Mol Cell 5, 865-876.
70. Muller, D., and Kontermann, R. E. (2010) Bispecific antibodies for cancer immunotherapy: Current perspectives, BioDrugs 24, 89-98.
71. Muller, S., Lange, S., Gautel, M., and Wilmanns, M. (2007) Rigid conformation of an immunoglobulin domain tandem repeat in the A-band of the elastic muscle protein titin, J Mol Biol 371, 469-480.
72. Nicola, G., Peddi, S., Stefanova, M., Nicholas, R. A., Gutheil, W. G., and Davies, C. (2005) Crystal structure of *Escherichia coli* penicillin-binding protein 5 bound to a 73. Pagel, J. M., Lin, Y., Hedin, N., Pantelias, A., Axworthy, D., Stone, O., Hamlin, D. K., Wilbur, D. S., and Press, 0. W. (2006) Comparison of a tetravalent single-chain antibody-streptavidin fusion protein and an antibody-streptavidin chemical conjugate for pretargeted anti-CD20 radioimmunotherapy of B-cell lymphomas, Blood 108, 328-336.
74. Pakkala, M., Weisell, J., Hekim, C., Vepsalainen, J., Wallen, E. A., Stenman, U. H., Koistinen, H., and Narvanen, A. (2010) Mimetics of the disulfide bridge between the N- and C-terminal cysteines of the KLK3-stimulating peptide B-2, Amino Acids 39, 233-242.
75. Pugashetti, R., and Koo, J. (2009) J Dermatolog Treat 20(3), 132-136.
76. Rao, J., Lahiri, J., Isaacs, L., Weis, R. M., and Whitesides, G. M. (1998) A trivalent system from vancomycin.D-ala-D-Ala with higher affinity than avidin.biotin, Science 280, 708-711.
77. Riemer, A. B., Klinger, M., Wagner, S., Bernhaus, A., Mazzucchelli, L., Pehamberger, H., Scheiner, O., Zielinski, C. C., and Jensen-Jarolim, E. (2004) J Immunol 173, 394-401.
78. Riemer, A. B., Kurz, H., Klinger, M., Scheiner, O., Zielinski, C. C., and Jensen-Jarolim, E. (2005) Vaccination with cetuximab mimotopes and biological properties of induced anti-epidermal growth factor receptor antibodies, J Natl Cancer Inst 97, 1663-1670.
79. Rivera, F., Garcia-Castano, A., Vega, N., Vega-Villegas, M. E., and Gutierrez-Sanz, L. (2009) Cetuximab in metastatic or recurrent head and neck cancer: the EXTREME trial, Expert Rev Anticancer Ther 9, 1421-1428.
80. Roe, E., Garcia Muret, M. P., Marcuello, E., Capdevila, J., Pallares, C., and Alomar, A. (2006) J Am Acad Dermatol 55(3), 429-437.
81. Rossi, E. A., Goldenberg, D. M., Cardillo, T. M., McBride, W. J., Sharkey, R. M., and Chang, C. H. (2006) Stably tethered multifunctional structures of defined composition made by the dock and lock method for use in cancer targeting, Proc Natl Acad Sci USA 103, 6841-6846.
82. Rudnick, S. I., and Adams, G. P. (2009) Cancer Biother Radiopharm 24, 155-161.
83. Scheuer W, Friess T, Burtscher H, Bossenmaier B, Endl J, Hasmann M., Strongly enhanced antitumor activity of trastuzumab and pertuzumab combination
84. treatment on HER2-positive human xenograft tumor models. Cancer Res. 2009 Dec. 15; 69(24):9330-6.
85. Schrag, D., Chung, K. Y., Flombaum, C., and Saltz, L. (2005) J Natl Cancer Inst 97(16), 1221-1224.
86. Seeman, N. C. (2003) DNA in a material world, Nature 421, 427-431.
87. Shaav, T., Wiesmuller, K. H., and Walden, P. (2007) Vaccine 25, 3032-3037.
88. Shan, D., Ledbetter, J. A., and Press, 0. W. (1998) Apoptosis of malignant human B cells by ligation of CD20 with monoclonal antibodies, Blood 91, 1644-1652.
89. Sharkey, R. M., Rossi, E. A., McBride, W. J., Chang, C. H., and Goldenberg, D. M. (2010) Recombinant bispecific monoclonal antibodies prepared by the dock-and-lock strategy for pretargeted radioimmunotherapy, Semin Nucl Med 40, 190-203.
90. Sheedy, C., MacKenzie, C. R., and Hall, J. C. (2007) Isolation and affinity maturation of hapten-specific antibodies, Biotechnol Adv 25, 333-352.
91. Shirasaki, Y., Nakamura, M., Yamaguchi, M., Miyashita, H., Sakai, O., and Inoue, J. (2006) Exploration of orally available calpain inhibitors 2: peptidyl hemiacetal derivatives, J Med Chem 49, 3926-3932.
92. Shuker, S. B., Hajduk, P. J., Meadows, R. P., and Fesik, S. W. (1996) Discovering high-affinity ligands for proteins: SAR by NMR, Science 274, 1531-1534.
93. Spangler, J. B., Neil, J. R., Abramovitch, S., Yarden, Y., White, F. M., Lauffenburger, D. A., and Wittrup, K. D. (2010) Combination antibody treatment down-regulates epidermal growth factor receptor by inhibiting endosomal recycling, Proc Natl Acad Sci USA 107, 13252-13257.
94. Stymiest, J. L., Mitchell, B. F., Wong, S., and Vederas, J. C. (2005) Synthesis of oxytocin analogues with replacement of sulfur by carbon gives potent antagonists with increased stability, J Org Chem 70, 7799-7809.
95. Teillaud, J. L. (2005) Engineering of monoclonal antibodies and antibody-based fusion proteins: successes and challenges, Expert Opin Biol Ther 5 Suppl 1, S15-27.
96. Thakur, A., and Lum, L. G. (2010) Cancer therapy with bispecific antibodies: Clinical experience, Curr Opin Mol Ther 12, 340-349.
97. Van Cutsem, E., Kohne, C. H., Hitre, E., Zaluski, J., Chang Chien, C. R., Makhson, A., D'Haens, G., Pinter, T., Lim, R., Bodoky, G., Roh, J. K., Folprecht, G., Ruff, P., Stroh, C., Tejpar, S., Schlichting, M., Nippgen, J., and Rougier, P. (2009) Cetuximab and chemotherapy as initial treatment for metastatic colorectal cancer, N Engl J Med 360, 1408-1417.
98. Wakankar, A. A., Feeney, M. B., Rivera, J., Chen, Y., Kim, M., Sharma, V. K., and Wang, Y. J. (2010) Physicochemical stability of the antibody-drug conjugate Trastuzumab-DM1: changes due to modification and conjugation processes, Bioconjug Chem 21, 1588-1595.
99. Young, W. W., Jr., Tamura, Y., Wolock, D. M., and Fox, J. W. (1984) J Immunol 133, 3163-3166.

What is claimed is:

1. A method comprising:
   administering to a subject having cancer, a meditope-enabled antibody or antigen-binding fragment thereof and a meditope comprising a peptide having the amino acid sequence selected from the group consisting of SEQ ID NO: 1, 2, 15, 16, 17, 18, 29, 31, 32, 36, 42, 43, 51, 54, and 55, wherein:
   said meditope-enabled antibody or antigen-binding fragment thereof comprises a heavy chain variable (VH) region; a heavy chain constant region (CH) or portion thereof; a light chain variable (VL) region comprising a threonine, serine, or aspartate at position 40, a residue other than glycine at position 41, a residue other than phenylalanine at position 83, and an aspartate or asparagine at position 85, according to Kabat numbering; and a light chain constant region (CL) or portion thereof;
   said meditope-enabled antibody or antigen-binding fragment thereof is a meditope-enabled variant of a human or humanized template antibody or antigen-binding fragment thereof, said variant comprising a plurality of framework region (FR) modifications, compared to the template antibody or antigen-binding fragment thereof, according to Kabat numbering, being only at positions selected from the group consisting of positions 8, 9, 10, 38, 39, 40, 41, 42, 43, 44, 45, 82, 83, 84, 85, 86, 87, 99, 100, 101, 102, 103, 104, and 105 of the VL of said template antibody or antigen-binding fragment thereof, and positions 6, 9, 38, 39, 40, 41, 42, 43, 44, 45, 84, 86, 87, 88, 89, 90, 91, 103, 104, 105, 106, 107, 108, 109, and 110 of the VH of said template antibody or antigen-binding fragment thereof;
   said meditope-enabled antibody or antigen-binding fragment thereof is capable of binding to an antigen expressed by the cancer, is capable of binding to a cyclic peptide comprising the amino acid sequence of SEQ ID NO 1 via a meditope binding site comprising residues 40, 41, 83, and 85 of the VL of the meditope-enabled antibody or antigen-binding fragment thereof, according to Kabat numbering, and/or residues 39, 89, 105, and 108 of the heavy chain VH of the meditope-enabled antibody or antigen-binding fragment thereof, according to Kabat numbering, and does not specifically bind to the epitope of EGFR that is specifically bound by cetuximab.

2. The method of claim 1, wherein:
   the meditope is coupled to a therapeutic agent selected from the group consisting of: chemotherapeutic agent, therapeutic antibody, toxin, radioisotope, enzyme, chelator, boron compound, photoactive agent, dye, metal, metal alloy, and nanoparticle; or
   the meditope is coupled to a diagnostic agent comprising an imaging agent selected from the group consisting of fluorescent substance, luminescent substance, dye, indicator, and radioactive substance.

3. The method of claim 1, wherein the meditope-enabled antibody or antigen-binding fragment thereof and the meditope are administered sequentially.

4. The method of claim 1, wherein the meditope-enabled antibody or antigen-binding fragment thereof and the meditope are administered simultaneously.

5. The method of claim 4, wherein the meditope-enabled antibody or antigen-binding fragment thereof and the meditope are administered as a complex comprising the meditope bound to the meditope binding site in the meditope-enabled antibody or antigen-binding fragment thereof.

6. The method of claim 1, wherein the meditope is coupled to a chemotherapeutic agent.

7. The method of claim 1, wherein the meditope is cyclic.

8. The method of claim 1, wherein the meditope comprises the amino acid sequence of SEQ ID NO: 1.

* * * * *